United States Patent
Pedram et al.

(10) Patent No.: US 8,580,811 B2
(45) Date of Patent: Nov. 12, 2013

(54) ANDROGEN RECEPTOR MODULATOR METHODS

(75) Inventors: Bijan Pedram, San Diego, CA (US); Cornelis Arjan Van Oeveren, San Diego, CA (US); Lin Zhi, San Diego, CA (US); Shuo Zhao, San Diego, CA (US); Yixing Shen, San Diego, CA (US)

(73) Assignee: Ligand Pharmaceuticals Incorporated, La Jolla, CA (US)

( * ) Notice: Subject to any disclaimer, the term of this patent is extended or adjusted under 35 U.S.C. 154(b) by 0 days.

(21) Appl. No.: 13/385,802

(22) Filed: Mar. 6, 2012

(65) Prior Publication Data

US 2012/0165362 A1    Jun. 28, 2012

Related U.S. Application Data

(62) Division of application No. 11/883,247, filed as application No. PCT/US2006/023111 on Jun. 12, 2006, now Pat. No. 8,193,357.

(60) Provisional application No. 60/691,891, filed on Jun. 17, 2005.

(51) Int. Cl.
*A61K 31/4745* (2006.01)
*A61P 1/00* (2006.01)
*A61P 1/02* (2006.01)
*A61P 1/04* (2006.01)
*A61P 3/00* (2006.01)
*A61P 3/04* (2006.01)

(52) U.S. Cl.
USPC .............. 514/285; 514/292; 435/29; 530/402

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. | 424/424 |
| 3,847,988 A | 11/1974 | Gold | 562/802 |
| 3,919,238 A | 11/1975 | Spencer et al. | 544/361 |
| RE28,819 E | 5/1976 | Thompson | 514/174 |
| 4,044,126 A | 8/1977 | Cook et al. | 514/180 |
| 4,097,578 A | 6/1978 | Perronnet et al. | 514/389 |
| 4,328,245 A | 5/1982 | Yu et al. | 514/530 |
| 4,358,603 A | 11/1982 | Yu | 560/2 |
| 4,364,923 A | 12/1982 | Cook et al. | 424/46 |
| 4,409,239 A | 10/1983 | Yu | 514/530 |
| 4,410,545 A | 10/1983 | Yu et al. | 514/530 |
| 4,414,209 A | 11/1983 | Cook et al. | 514/180 |
| 4,522,811 A | 6/1985 | Eppstein et al. | 514/2.4 |
| 4,636,505 A | 1/1987 | Tucker | 514/256 |
| 4,981,784 A | 1/1991 | Evans et al. | 435/6 |
| 5,033,252 A | 7/1991 | Carter | 53/425 |
| 5,052,558 A | 10/1991 | Carter | 206/439 |
| 5,071,773 A | 12/1991 | Evans et al. | 436/501 |
| 5,323,907 A | 6/1994 | Kalvelage | 206/531 |
| 5,576,324 A | 11/1996 | Kyotani et al. | 514/291 |
| 5,688,810 A | 11/1997 | Jones et al. | 514/311 |
| 5,693,646 A | 12/1997 | Jones et al. | 514/285 |
| 5,693,647 A | 12/1997 | Jones et al. | 514/285 |
| 5,696,130 A | 12/1997 | Jones et al. | 514/291 |
| 5,696,133 A | 12/1997 | Jones et al. | 514/314 |
| 6,017,924 A | 1/2000 | Edwards et al. | 514/292 |
| 6,180,794 B1 | 1/2001 | Edwards et al. | 546/152 |
| 6,380,207 B2 | 4/2002 | Coghlan et al. | 514/285 |
| 6,462,038 B1 | 10/2002 | Higuchi et al. | 514/224.5 |
| 6,506,766 B1 | 1/2003 | Coghlan et al. | 514/285 |
| 6,566,372 B1 | 5/2003 | Zhi et al. | 514/312 |
| 6,569,896 B2 | 5/2003 | Dalton et al. | 514/493 |
| 6,673,799 B1 | 1/2004 | Taniguchi et al. | 514/253.01 |
| 6,777,427 B2 | 8/2004 | Miyakawa et al. | 514/311 |
| 6,964,973 B2 | 11/2005 | Zhi et al. | 514/312 |
| 7,026,484 B2 | 4/2006 | Zhi et al. | 546/80 |
| 7,037,919 B1 | 5/2006 | Hanada et al. | 514/290 |
| 7,214,690 B2 | 5/2007 | Higuchi et al. | 514/314 |
| 7,696,246 B2 | 4/2010 | Zhi et al. | 514/457 |
| 7,727,980 B2 | 6/2010 | Zhi et al. | 514/215 |
| 7,816,372 B2 | 10/2010 | Zhi et al. | 514/312 |
| 2002/0183314 A1 | 12/2002 | Higuchi et al. | 514/224.5 |
| 2002/0183346 A1* | 12/2002 | Zhi et al. | 514/291 |
| 2003/0055094 A1 | 3/2003 | Sun et al. | 514/379 |
| 2003/0186970 A1 | 10/2003 | Higuchi et al. | 514/224.2 |
| 2004/0186132 A1 | 9/2004 | Jones et al. | 514/312 |
| 2005/0288350 A1 | 12/2005 | Zhi et al. | 514/397 |
| 2006/0128740 A1 | 6/2006 | Zhi et al. | 514/291 |
| 2007/0066650 A1 | 3/2007 | Zhi et al. | 514/312 |
| 2007/0072849 A1 | 3/2007 | Higuchi et al. | 514/224.5 |

(Continued)

FOREIGN PATENT DOCUMENTS

DE    24 27 409    1/1975
EP    0 638 571    2/1995

(Continued)

OTHER PUBLICATIONS

Dong et al, Androgen Receptor Function During Undernutrition, 6(4) J. Neuroendocrinol 397-402 (1994).*
Akhvlediani et al., "Chichibabin reaction in a series of angular pyrroloquinolines," Zh. Org. Khim. 17(7):1542-1546 (1981) [Chemical Abstracts Accession No. 96:66161].
Ansel, H., "*Introduction to Pharmaceutical Dosage Forms*," Fourth Edition, Lea and Febiger, Philadelphia, PA, p. 126 (1985).
Bains, W. and R. Tacke, "Silicon chemistry as a novel source of chemical diversity in drug design," Curr. Opin. Drug Discov. Devel. 6:526-543 (2003).

(Continued)

*Primary Examiner* — Janet Andres
*Assistant Examiner* — Timothy R Rozof
(74) *Attorney, Agent, or Firm* — Knobbe Martens Olson & Bear, LLP

(57) ABSTRACT

Provided herein are compounds that bind to androgen receptors and/or modulate activity of androgen receptors, and to methods for making and using such compounds. Also provided are compositions including such compounds and methods for making and using such compositions.

14 Claims, No Drawings

(56) References Cited

U.S. PATENT DOCUMENTS

| | | | |
|---|---|---|---|
| 2007/0167445 | A1 | 7/2007 | Higuchi et al. ............. 514/230.5 |
| 2007/0254875 | A1 | 11/2007 | Zhi et al. .................... 514/230.5 |
| 2007/0293528 | A9 | 12/2007 | Zhi et al. ........................ 514/291 |
| 2008/0300241 | A9 | 12/2008 | Higuchi et al. ............. 514/224.5 |
| 2009/0203725 | A1 | 8/2009 | Van Oeveren et al. ........ 514/285 |
| 2009/0227571 | A1 | 9/2009 | Loren et al. ................. 514/228.5 |
| 2009/0264455 | A9 | 10/2009 | Pedram et al. ................ 514/285 |
| 2010/0069379 | A1 | 3/2010 | Zhi et al. .................... 514/230.5 |
| 2010/0210678 | A1 | 8/2010 | Zhi et al. ........................ 514/285 |
| 2010/0256129 | A1 | 10/2010 | Zhi ............................. 514/229.8 |
| 2011/0112084 | A9 | 5/2011 | Zhi et al. .................... 514/230.5 |
| 2012/0004220 | A9 | 1/2012 | Zhi ............................. 514/229.8 |

FOREIGN PATENT DOCUMENTS

| | | |
|---|---|---|
| JP | 2004-524309 | 8/2004 |
| SU | 548608 | 2/1977 |
| WO | WO 96/19458 | 6/1996 |
| WO | WO 00/12502 | 3/2000 |
| WO | WO 01/16108 | 3/2001 |
| WO | WO 01/27086 | 4/2001 |
| WO | WO 02/22585 | 3/2002 |
| WO | WO 02/066475 | 8/2002 |
| WO | WO 02/068427 | 9/2002 |
| WO | WO 03/037905 | 5/2003 |
| WO | WO 2005/090282 | 9/2005 |
| WO | WO 2006/138347 | 12/2006 |
| WO | WO 2007/005887 | 1/2007 |
| WO | WO 2007/075884 | 7/2007 |

OTHER PUBLICATIONS

Berger et al., "Interaction of glucocorticoid analogues with the human glucocorticoid receptor," J. Steroid Biochem. Mol. Biol. 41(3-8):733-738 (1992).
Chapman et al., "Some substitution reactions of thieno[3,2-f]quinoline," J. Chem. Soc. C 17:2334-2339 (1970).
Cheng, Y. and W. Prusoff, "Relationship between the inhibition constant (K1) and the concentration of inhibitor which causes 50 per cent inhibition (I50) of an enzymatic reaction," Biochem. Pharmacol. 22(23):3099-3108 (1973).
Chengalvala et al., "Selective androgen receptor modulators," Expert Opin. Ther. Patents 13(1):59-66 (2003).
Derwent English abstract for Russian patent SU 548608, published Aug. 25, 1977, entitled: "Pyrrolo-quinoline derivatives used in preparation of medicines- obtained by reacting the parent amino-indole with corresponding beta-diketone and cyclization," Dialog File No. 351, Accession No. 1501343, 3 pages.
Derwent English abstract for Japanese patent WO 01/27086, published Apr. 19, 2001, entitled: "New tetrahydroquinoline derivatives useful as androgen receptor binding agents for treating e.g. males sexual dysfunction," Dialog File No. 351, Accession No. 13797739, 3 pages.
Edwards et al., "New nonsteroidal androgen receptor modulators based on 4-(trifluoromethyl)-2(1H)-pyrrolidino[3,2-g]quinolinone," Bioorg. Med. Chem. Lett. 8:745-750 (1998).
El-Desoky et al., "Synthesis of pyrrolo-, thienopyrrolo-, and benzothienopyrroloquinolines as well as of triazoloindole derivates," Z. Naturforsch. Pt. B 53(10):1612-1222 (1998) [Chemical Abstracts No. 130:13934].
Evans et al., "The steroid and thyroid hormone receptor superfamily," Science 240:889-895 (1988).
Ferlin et al., "Pyrrolo-quinoline derivatives as potential antineoplastic drugs," Bioorg. Med. Chem. 8(6):1415-1422 (2000).
Fingl et al., "The Pharmacological Basis of Therapeutics", Ch. 1 p. 1 (1975).
Gryanznov et al., "Reactivity of 1H-pyrrolo[2.3-f]-3H-pyrrolo[3.2-f] quinolines and their derivatives," Izvestiya Timiryazevskoi Sel 'skokhozyaistvennoi Akademii 3:185-190 (1988) [Article in Russian, Chemical Abstracts No. 110:75273].
Hamann et al., "Synthesis and biological activity of a novel series of nonsteroidal, peripherally selective androgen receptor antagonists derived from 1,2-dihydropyridono[5,6-g]quinolines," J. Med. Chem. 41(4):623-639 (1998).

Majumdar et al., "Studies on the amine oxide rearrangements: regioselective synthesis of pyrrolo[3,2-f]quinolin-7-ones," J. Chem. Res. S. 9:310-311 (1997).
Mulwad et al., "Synthesis of some pyrrolobenzopyrans," Ind. J. Het. Chem. 7(2):151-152 (1997) [Chemical Abstracts No. 128:114932].
Nogrady, M., "*Medicinal Chemistry: A Biochemical Approach*," Oxford University Press, New York, NY, pp. 388-392 (1985).
Pathirana et al., "Nonsteroidal human progesterone receptor modulators from the marine alga *Cymopolia barbata*," Mol. Pharmacol. 47(3):630-635 (1995).
Pooley et al., "Discovery and preliminary SAR studies of a novel, nonsteriodal progesterone receptor antagonist pharmacophore," J. Med. Chem. 41(18):3461-3466 (1998).
Rodbard, D., "Mathematics and statistics of ligand assays: an illustrated guide," In: *Ligand Assay*, Langon, J. and J. Clapp, eds., Masson Publishing U.S.A., Inc., New York, Chapter 3, pp. 45-99 (1981).
Tacke et al., "Sila-substitution: a useful strategy for drug design?" Endeavour, New Series, 10(4):191-197 (1986).
Yamashkin et al., "Reactivities of 5-, 6-, and 7-(enamino)indoles in the synthesis of pyrroloquinolines," Chem. Heterocyc. Cmpd. 34(9):1050-1065 (1998).
Yamashkin et al., "Synthesis of pyrroloquinolones," Khimiya Geterotsiklicheskikh Soedinenii 4:493-497 (1983) [Chemical Abstracts No. 99:38395].
Yin et al., "Key structural features of nonsteroidal ligands for binding and activation of the androgen receptor," Mol. Pharmacol. 63(1): 211-223 (2003).
Yoshikawa, "Synthesis of 4,6-diaminoquinoline derivatives. I. Synthesis of pyrrolo[f]quinoline derivatives," Yakuga. Zasshi 8:1317-1322 (1961) [Chemical Abstracts No. 56:38406 (1962)].
Yudin et al., "Nitropyrroloquinolines," Khim. Geterotsikl. Soedin. 10:1381-1385 (1979) [Chemical Abstracts No. 92:146650].
Zhi et al., "Switching androgen receptor antagonists to agonists by modifying C-ring substituents on an piperidino[3,2-g]quinolinone," Bioorg. Med. Chem. Lett. 9(7):1009-1012 (1999).
Zhi et al., "Nonsteroidal progesterone receptor antagonists based on 6-thiophenehydroquinolines," Bioorg. Med. Chem. Lett. 10(5):415-418 (2000).
Zhi et al., "Chapter 17: Selective androgen receptor modulators (SARMs)," Annual Reports in Medicinal Chemistry 36:169-180 (2001).
International Search Report, issued Jan. 12, 2007, in connection with corresponding International Patent Application No. PCT/US2006/23111, 2 pages.
International Preliminary Report on Patentability and Written Opinion, issued Dec. 17, 2007, in connection with corresponding International Patent Application No. PCT/US2006/23111, 12 pages.
Examination Report, issued Aug. 4, 2008, in connection with corresponding European Patent Application No. 06773124.0, 4 pages.
Response to Examination Report, filed Feb. 16, 2009, in connection with corresponding European Patent Application No. 06773124.0, 4 pages.
Official Action, issued Apr. 30, 2010, in connection with corresponding Chinese Patent Application No. 200680007699.8, 6 pages.
Notice of Acceptance, issued Oct. 8, 2010, in connection with corresponding New Zealand Patent Application No. 560354, 4 pages.
Official Action, issued Jan. 14, 2011, in connection with corresponding Australian Patent Application No. 2006259474, 2 pages.
Examination Report, issued Mar. 9, 2011, in connection with corresponding European Patent Application No. 06773124.0, 4 pages.
Office Action, issued Jun. 30, 2011, in connection with corresponding U.S. Appl. No. 11/883,247, 11 pages.
Response to Examination Report, submitted Sep. 15, 2011, in connection with corresponding European Patent Application No. 06773124.0, 20 pages.
Examination Report, issued Sep. 26, 2011, in connection with corresponding European Patent Application No. 06773124.0, 4 pages.
Notice of Acceptance, issued Oct. 27, 2011, in connection with corresponding Australian Patent Application No. 2006259474, 4 pages.
Official Action, issued Dec. 7, 2011, in connection with corresponding Mexican Patent Application No. MX/a/2007/009784, 6 pages.

(56) References Cited

OTHER PUBLICATIONS

Official Action, issued Jan. 24, 2012, in connection with corresponding Japanese Patent Application No. 2008-517047, 3 pages.
Official Action, issued Feb. 14, 2012, in connection with corresponding Israeli Patent Application No. 185003, 7 pages.
Response to Examination Report, submitted Mar. 26, 2012, in connection with corresponding European Patent Application No. 06773124.0, 31 pages.
Higuchi et al., "Novel series of potent, nonsteroidal, selective androgen receptor modulators based on 7H-[1,4]oxazino[3,2-g]quinolin-7-ones," J. Med. Chem. 50(10):2486-2496 (2007).
Long et al., "Selective androgen receptor modulators based on a series of 7H-[1,4]oxazino[3,2-g]quinolin-7-ones with improved in vivo activity," Bioorg. Med. Chem. Lett. 18(9):2967-2671 (2008).
van Oeveren et al., "Discovery of an androgen receptor modulator pharmacophore based on 2-quinolinones," Bioorg. Med. Chem. Lett. 17(6):1523-1526 (2007).

* cited by examiner

ANDROGEN RECEPTOR MODULATOR METHODS

RELATED APPLICATIONS

This application is a divisional of allowed U.S. patent application Ser. No. 11/883,247, filed May 15, 2008, now U.S. Pat. No. 8,193,357, entitled "ANDROGEN RECEPTOR MODULATOR COMPOUNDS AND METHODS, which is the National Stage of International Application. No. PCT/US2006/023111, filed 12 Jun. 2006, which claims benefit of priority under 35 U.S.C. §119(e) to U.S. provisional patent application Ser. No. 60/691,891, filed Jun. 17, 2005, entitled "ANDROGEN RECEPTOR MODULATOR COMPOUNDS AND METHODS." The disclosure of each of the above-referenced applications is incorporated herein by reference in its entirety.

FIELD

Provided herein are compounds that bind to androgen receptors and/or modulate activity of androgen receptors, and to methods for making and using such compounds. Also provided are compositions comprising such compounds and methods for making and using such compositions.

BACKGROUND

Certain intracellular receptors (IRs) have been shown to regulate transcription of certain genes. See e.g., R. M. Evans, Science, 240, 889 (1988). Certain of such IRs are steroid receptors, such as androgen receptors, estrogen receptors, mineralocorticoid receptors, and progesterone receptors. Gene regulation by such receptors typically involves binding of an IR by a ligand.

In certain instances, a ligand binds to an IR, forming a receptor/ligand complex. Such a receptor/ligand complex may then translocate to the nucleus of a cell, where it may bind to the DNA of one or more gene regulatory regions. Once bound to the DNA of a particular gene regulatory region, a receptor/ligand complex may modulate the production of the protein encoded by that particular gene. In certain instances, an androgen receptor/ligand complex regulates expression of certain proteins. In certain instances, an androgen receptor/ligand complex may interact directly with the DNA of a particular gene regulatory region. In certain instances, an androgen receptor/ligand complex may interact with other transcription factors, such as activator protein-1 (AP-1) or nuclear factor κB (NFκB). In certain instances, such interactions result in modulation of transcriptional activation.

SUMMARY

Compounds that modulate the activity of androgen receptors are provided. In certain embodiments, the compounds provided herein are agonists of androgen receptor. In certain embodiments, the compounds provided herein are antagonists of androgen receptor.

In certain embodiments, provided herein are compounds having a structure selected from among Formula I or Formula II:

wherein:

$R^1$ and $R^3$ are each independently selected from hydrogen, optionally substituted $C_1$-$C_4$ alkyl, $C_1$-$C_4$ heteroalkyl, $C_1$-$C_4$ haloalkyl, optionally substituted heteroaryl, and optionally substituted aryl; or $R^1$ and $R^3$ taken together form a $C_3$-$C_8$ carbocyclic ring;

$R^2$ and $R^4$ are each hydrogen; or $R^2$ and $R^4$ taken together form a bond;

$R^5$ is selected from hydrogen, $C_1$-$C_8$ alkyl, $C_1$-$C_8$ haloalkyl, $C_1$-$C_8$ heteroalkyl, $C_7$-$C_{10}$ arylalkyl, and $C_2$-$C_8$ heteroarylalkyl;

$R^6$ is hydrogen, or F;

$R^7$ is selected from hydrogen, $C_1$-$C_4$ alkyl, $C_1$-$C_4$ haloalkyl, optionally substituted heteroaryl, and optionally substituted aryl;

$R^8$ and $R^9$ are each independently selected from hydrogen, F, and hydroxyl;

$R^{10}$ is selected from hydroxyl, Cl, Br, $C_1$-$C_3$ fluoroalkyl, $C_1$-$C_3$ heteroalkyl, $C_2$-$C_4$ alkenyl, $C_2$-$C_4$ alkynyl;

and pharmaceutically acceptable salts and prodrugs thereof.

In certain embodiments, provided herein are compounds having a structure of Formula II:

wherein:

$R^2$ and $R^4$ are each hydrogen; or $R^2$ and $R^4$ taken together form a bond;

$R^6$ is hydrogen, or F;

$R^7$ is selected from hydrogen, $C_1$-$C_4$ alkyl, $C_1$-$C_4$ haloalkyl, optionally substituted heteroaryl, and optionally substituted aryl;

$R^8$ and $R^9$ are each independently selected from hydrogen, F, and hydroxyl;

$R^{10}$ is selected from hydroxyl, Cl, Br, $C_1$-$C_3$ fluoroalkyl, optionally substituted $C_1$-$C_5$ heteroalkyl, $C_2$-$C_4$ alkenyl and $C_2$-$C_4$ alkynyl, wherein if $R^{10}$ is a $C_2$-$C_4$ alkynyl, then $R^8$ and $R^9$ do not exist;

and pharmaceutically acceptable salts and prodrugs thereof.

In certain embodiments, provided herein are compounds having a structure of Formula III:

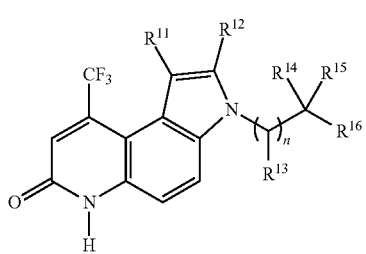

wherein:

$R^{11}$ is $C_1$-$C_4$ alkyl;

$R^{12}$ is selected from hydrogen, $C_1$-$C_4$ alkyl, $C_1$-$C_4$ haloalkyl, hydroxymethyl, optionally substituted heteroaryl, and optionally substituted aryl; or $R^{11}$ and $R^{12}$ taken together form a $C_3$-$C_8$ carbocyclic ring; wherein if $R^{11}$ and $R^{12}$ taken together form a $C_3$-$C_8$ carbocyclic ring, then $R^{16}$ is not Cl or F $R^{14}$ is selected from among hydrogen, F, hydroxyl and $C_1$-$C_3$ alkyl;

$R^{15}$ is selected from among hydrogen, F, hydroxyl and $C_1$-$C_3$ alkyl;

$R^{13}$ is hydrogen; or $R^{13}$ and $R^{16}$ taken together form a bond; wherein if $R^{13}$ and $R^{16}$ taken together form a bond then $R^{14}$ and $R^{15}$ are each $C_1$-$C_4$ alkyl;

$R^{16}$ is selected from hydroxyl, Cl, F, Br, $C_1$-$C_3$ fluoroalkyl, $C_1$-$C_3$ heteroalkyl, $C_2$-$C_4$ alkenyl, and $C_2$-$C_4$ alkynyl; wherein if $R^{13}$ is F, then $R^{12}$ is hydroxymethyl or $C_1$-$C_4$ haloalkyl;

n is 0 or 1; wherein if n is 0, then $R^{16}$ is $C_2$-$C_4$ alkenyl or $C_2$-$C_4$ alkynyl;

and pharmaceutically acceptable salts and prodrugs thereof.

In certain embodiments, $R^{11}$ is methyl.

In certain embodiments, $R^{11}$ and $R^{12}$ together form a cyclopentene.

In certain embodiments, $R^{12}$ is selected from among methyl, hydroxymethyl and trifluoromethyl.

In certain embodiments, $R^{14}$ is selected from among hydrogen, F, hydroxyl or methyl.

In certain embodiments, $R^{15}$ is selected from among hydrogen, F, hydroxyl or methyl.

In certain embodiments, $R^{16}$ is selected from among F, vinyl, 1-methylvinyl, ethynyl and trifluoromethyl.

In certain embodiments, provided herein is a compound selected from:

9-Chloro-1,2-dimethyl-3,6-dihydropyrrolo[3,2-f]quinolin-7-one (Compound 105);

9-Chloro-2-ethyl-1-methyl-3,6-dihydropyrrolo[3,2-f]quinolin-7-one (Compound 106);

9-Chloro-1,2-trimethylene-3,6-dihydropyrrolo[3,2-f]quinolin-7-one (Compound 107);

9-Chloro-1-methyl-2-trifluoromethyl-3,6-dihydropyrrolo[3,2-f]quinolin-7-one (Compound 108);

9-Chloro-2-methyl-1-ethyl-3,6-dihydropyrrolo[3,2-f]quinolin-7-one (Compound 109);

9-Chloro-1-methyl-2-phenyl-3,6-dihydropyrrolo[3,2-f]quinolin-7-one (Compound 110);

9-Chloro-1-methyl-7-oxo-6,7-dihydro-3H-pyrrolo[3,2-f]quinoline-2-carboxylic acid ethyl ester (Compound 111);

9-Chloro-2-methyl-3,6-dihydropyrrolo[3,2-f]quinolin-7-one (Compound 112);

9-Chloro-1,2-tetramethylene-3,6-dihydropyrrolo[3,2-f]quinolin-7-one (Compound 113);

9-Chloro-1-methyl-3,6-dihydropyrrolo[3,2-f]quinolin-7-one (Compound 114);

9-Chloro-2-(4-methoxy-phenyl)-1-methyl-3,6-dihydro-pyrrolo[3,2-f]quinolin-7-one (Compound 115);

9-Chloro-2-(4-fluorophenyl)-1-methyl-3,6-dihydropyrrolo[3,2-f]quinolin-7-one (Compound 116);

9-Chloro-2-(2,4-difluorophenyl)-1-methyl-3,6-dihydropyrrolo[3,2-f]quinolin-7-one (Compound 117);

9-Chloro-2-(4-chlorophenyl)-1-methyl-3,6-dihydropyrrolo[3,2-f]quinolin-7-one (Compound 118);

9-Chloro-2-(2-fluorophenyl)-1-methyl-3,6-dihydropyrrolo[3,2-f]quinolin-7-one (Compound 119);

9-Chloro-1-methyl-2-thien-2-yl-3,6-dihydropyrrolo[3,2-f]quinolin-7-one (Compound 120);

2-Acetyl-9-chloro-1-methyl-3,6-dihydropyrrolo[3,2-f]quinolin-7-one (Compound 121);

(9-Chloro-2-methyl-7-oxo-6,7-dihydro-3H-pyrrolo[3,2-f]quinolin-1-yl)-acetic acid (Compound 122);

9-Chloro-1-ethyl-2-thien-2-yl-3,6-dihydropyrrolo[3,2-f]quinolin-7-one (Compound 123);

9-Chloro-2-methyl-1-propyl-3,6-dihydropyrrolo[3,2-f]quinolin-7-one (Compound 124);

9-Chloro-1-ethyl-2-phenyl-3,6-dihydropyrrolo[3,2-f]quinolin-7-one (Compound 125);

(±)-9-Chloro-3-(2,2,2-trifluoroethyl)-1,2-trimethylene-1,2,3,6-tetrahydropyrrolo-[3,2-f]-quinolin-7-one (Compound 126);

(±)-9-Chloro-1,2-dimethyl-3-(2,2,2-trifluoroethyl)-1,2,3,6-tetrahydro-pyrrolo[3,2-f]-quinolin-7-one (Compound 127);

(±)-9-Chloro-2-ethyl-1-methyl-3-(2,2,2-trifluoroethyl)-1,2,3,6-tetrahydropyrrolo-[3,2-f]-quinolin-7-one (Compound 128);

(±)-9-Chloro-1-ethyl-2-methyl-3-(2,2,2-trifluoroethyl)-1,2,3,6-tetrahydropyrrolo-[3,2-f]-quinolin-7-one (Compound 129)

(±)-9-Chloro-1-methyl-2-phenyl-3-(2,2,2-trifluoroethyl)-1,2,3,6-tetrahydro-pyrrolo[3,2-f]-quinolin-7-one (Compound 130);

(±)-9-Chloro-2-methyl-3-(2,2,2-trifluoroethyl)-1,2,3,6-tetrahydropyrrolo[3,2-f]-quinolin-7-one (Compound 131);

(±)-9-Chloro-1-methyl-3-(2,2,2-trifluoroethyl)-1,2,3,6-tetrahydropyrrolo[3,2-f]-quinolin-7-one (Compound 132);

(±)-9-Chloro-1,2-tetramethylene-3-(2,2,2-trifluoroethyl)-1,2,3,6-tetrahydro-pyrrolo[3,2-f]-quinolin-7-one (Compound 133);

(±)-9-Chloro-3-ethyl-1-methyl-1,2,3,6-tetrahydro-pyrrolo[3,2-f]quinolin-7-one (Compound 134);

(±)-9-Chloro-1,2-dimethyl-3-ethyl-1,2,3,6-tetrahydropyrrolo[3,2-f]quinolin-7-one (Compound 135);

(±)-9-Chloro-1,2,3-trimethyl-1,2,3,6-tetrahydropyrrolo[3,2-f]quinolin-7-one (Compound 136);

(±)-9-Chloro-1,2-dimethyl-3-propyl-1,2,3,6-tetrahydropyrrolo[3,2-f]quinolin-7-one (Compound 137);

(±)-9-Chloro-3-(2-chloro-2,2-difluoroethyl)-1,2-dimethyl-1,2,3,6-tetrahydro-pyrrolo[3,2-f]-quinolin-7-one (Compound 138);

(±)-9-Chloro-1,2-dimethyl-3-(2-hydroxyethyl)-1,2,3,6-tetrahydro-pyrrolo[3,2-f]-quinolin-7-one (Compound 139);

(±)-9-Chloro-1,2-dimethyl-1,2,3,6-tetrahydropyrrolo quinolin-7-one (Compound 140);

(±)-9-Chloro-1,2-dimethyl-3-(2,2-dimethylpropyl)-1,2,3,6-tetrahydro-pyrrolo[3,2-f]-quinolin-7-one (Compound 141);

(±)-9-Chloro-1,2-dimethyl-3-(2-thien-2-ylethyl)-1,2,3,6-tetrahydro-pyrrolo[3,2-f]-quinolin-7-one (Compound 142);

(±)-9-Chloro-3-(2,2-difluoroethyl)-1,2-dimethyl-1,2,3,6-tetrahydropyrrolo[3,2-f]-quinolin-7-one (Compound 143);

(±)-9-Chloro-1,2-dimethyl-3-phenylmethyl-1,2,3,6-tetrahydropyrrolo[3,2-f]-quinolin-7-one (Compound 144);

(±)-9-Chloro-1,2-dimethyl-3-(3,3,3-trifluoropropyl)-1,2,3,6-tetrahydropyrrolo-[3,2-f]-quinolin-7-one (Compound 145);

(±)-9-Chloro-2-(3-chlorophenyl)-1-methyl-3-(2,2,2-trifluoroethyl)-1,2,3,6-tetrahydropyrrolo[3,2-f]quinolin-7-one (Compound 146);

(±)-9-Chloro-1-methyl-2-(4-trifluoromethyl-phenyl)-3-(2,2,2-trifluoroethyl)-1,2,3,6-tetrahydropyrrolo[3,2-f]quinolin-7-one (Compound 147);

(±)-9-Chloro-2-(4-methoxy-phenyl)-1-methyl-3-(2,2,2-trifluoroethyl)-1,2,3,6-tetrahydro-pyrrolo[3,2-f]quinolin-7-one (Compound 148);

(±)-9-Chloro-2-(4-fluoro-phenyl)-1-methyl-3-(2,2,2-trifluoroethyl)-1,2,3,6-tetrahydro-pyrrolo[3,2-f]quinolin-7-one (Compound 149);

(±)-9-Chloro-2-(2,4-difluorophenyl)-1-methyl-3-(2,2,2-trifluoroethyl)-1,2,3,6-tetrahydro-pyrrolo[3,2-f]quinolin-7-one (Compound 150);

(±)-9-Chloro-1,2-dimethyl-5-fluoro-3-(2,2,2-trifluoroethyl)-1,2,3,6-tetrahydro-pyrrolo[3,2-f]quinolin-7-one (Compound 151);

(±)-9-Chloro-2-(4-chlorophenyl)-1-methyl-3-(2,2,2-trifluoroethyl)-1,2,3,6-tetrahydro-pyrrolo[3,2-f]quinolin-7-one (Compound 152);

(±)-2-(3-Bromophenyl)-9-chloro-1-methyl-3-(2,2,2-trifluoroethyl)-1,2,3,6-tetrahydro-pyrrolo[3,2-f]quinolin-7-one (Compound 153);

(±)-9-Chloro-1-methyl-2-(3-nitrophenyl)-3-(2,2,2-trifluoroethyl)-1,2,3,6-tetrahydro-pyrrolo[3,2-f]quinolin-7-one (Compound 154);

(±)-9-Chloro-2-(4-hydroxyphenyl)-1-methyl-3-(2,2,2-trifluoroethyl)-1,2,3,6-tetrahydro-pyrrolo[3,2-f]quinolin-7-one (Compound 155);

(±)-9-Chloro-2-(2-fluorophenyl)-1-methyl-3-(2,2,2-trifluoroethyl)-1,2,3,6-tetrahydro-pyrrolo[3,2-f]quinolin-7-one (Compound 156);

(±)-9-Chloro-2-(3,4-dichlorophenyl)-1-methyl-3-(2,2,2-trifluoroethyl)-1,2,3,6-tetrahydro-pyrrolo[3,2-f]quinolin-7-one (Compound 157);

(±)-9-Chloro-2-(3,5-bis(trifluoromethyl)phenyl)-1-methyl-3-(2,2,2-trifluoroethyl)-1,2,3,6-tetrahydro-pyrrolo[3,2-f]quinolin-7-one (Compound 158);

(±)-9-Chloro-1-methyl-3-(2,2,2-trifluoroethyl)-2-(3-trifluoromethylphenyl)-1,2,3,6-tetrahydro-pyrrolo[3,2-f]quinolin-7-one (Compound 159);

(±)-9-Chloro-1-ethyl-2-phenyl-3-(2,2,2-trifluoroethyl)-1,2,3,6-tetrahydro-pyrrolo[3,2-f]-quinolin-7-one (Compound 160);

(±)-9-Chloro-1-methyl-2-(thien-2-yl)-3-(2,2,2-trifluoroethyl)-1,2,3,6-tetrahydro-pyrrolo[3,2-f]quinolin-7-one (Compound 161);

(+)-9-Chloro-3-(2,2,2-trifluoro-ethyl)-1,2-trimethylene-1,2,3,6-tetrahydro-pyrrolo[3,2-f]-quinolin-7-one (Compound 162);

(−)-9-Chloro-3-(2,2,2-trifluoro-ethyl)-1,2-trimethylene-1,2,3,6-tetrahydro-pyrrolo[3,2-f]-quinolin-7-one (Compound 163);

(±)-9-Chloro-1-ethyl-2-(thien-2-yl)-3-(2,2,2-trifluoroethyl)-1,2,3,6-tetrahydro-pyrrolo[3,2-f]-quinolin-7-one (Compound 164);

(±)-9-Chloro-2-methyl-1-propyl-3-(2,2,2-trifluoroethyl)-1,2,3,6-tetrahydro-pyrrolo[3,2-f]-quinolin-7-one (Compound 165);

(±)-9-Chloro-2,3-diethyl-1-methyl-1,2,3,6-tetrahydro-pyrrolo[3,2-f]quinolin-7-one (Compound 166);

(±)-9-Chloro-1,2-dimethyl-3-(2,2,3,3,3-pentafluoropropyl)-1,2,3,6-tetrahydro-pyrrolo[3,2-f]quinolin-7-one (Compound 167);

(±)-9-Chloro-1,2-dimethyl-3-(2,2,3,3,4,4,4-heptafluorobutyl)-1,2,3,6-tetrahydro-pyrrolo[3,2-f]quinolin-7-one (Compound 168);

(±)-9-Chloro-1-methyl-2-phenyl-3-(3,3,3-trifluoropropyl)-1,2,3,6-tetrahydro-pyrrolo[3,2-f]-quinolin-7-one (Compound 169);

(±)-9-Chloro-2-ethyl-1-methyl-3-(3,3,3-trifluoropropyl)-1,2,3,6-tetrahydro-pyrrolo[3,2-f]-quinolin-7-one (Compound 170);

(±)-9-Chloro-1-methyl-3-(2,2,3,3,3-pentafluoropropyl)-2-phenyl-1,2,3,6-tetrahydro-pyrrolo[3,2-f]quinolin-7-one (Compound 171);

(±)-9-Chloro-1-methyl-2-phenyl-1,2,3,6-tetrahydropyrrolo[3,2-f]quinolin-7-one (Compound 172);

(±)-1,2-Dimethyl-3-(2,2,3,3,3-pentafluoropropyl)-9-trifluoromethyl-1,2,3,6-tetrahydro-pyrrolo[3,2-f]quinolin-7-one (Compound 173);

(±)-1,2-Dimethyl-9-trifluoromethyl-3-(3,3,3-trifluoropropyl)-1,2,3,6-tetrahydro-pyrrolo[3,2-f]quinolin-7-one (Compound 174);

(±)-3-(2-Chloro-2,2-difluoroethyl)-1,2-dimethyl-9-trifluoromethyl-1,2,3,6-tetrahydro-pyrrolo[3,2-f]quinolin-7-one (Compound 175);

(±)-9-Chloro-3-(2-Chloro-2,2-difluoroethyl)-2-ethyl-1-methyl-1,2,3,6-tetrahydro-pyrrolo[3,2-f]quinolin-7-one (Compound 176);

(±)-9-Chloro-2-ethyl-1-methyl-3-(2,2,3,3,3-pentafluoropropyl)-1,2,3,6-tetrahydro-pyrrolo[3,2-f]quinolin-7-one (Compound 177);

(±)-3-(2-Chloro-2,2-difluoroethyl)-2-ethyl-1-methyl-9-trifluoromethyl-1,2,3,6-tetrahydro-pyrrolo[3,2-f]quinolin-7-one (Compound 178);

(±)-2-Ethyl-1-methyl-3-(2,2,3,3,3-pentafluoropropyl)-9-trifluoromethyl-1,2,3,6-tetrahydro-pyrrolo[3,2-f]quinolin-7-one (Compound 179);

(±)-2-Ethyl-1-methyl-9-trifluoromethyl-3-(3,3,3-trifluoropropyl)-1,2,3,6-tetrahydro-pyrrolo[3,2-f]quinolin-7-one (Compound 180);

(±)-2-Ethyl-1-methyl-3-(4,4,4-trifluorobutyl)-9-trifluoromethyl-1,2,3,6-tetrahydro-pyrrolo[3,2-f]quinolin-7-one (Compound 181);

(±)-1,2-Dimethyl-3-(4,4,4-trifluorobutyl)-9-trifluoromethyl-1,2,3,6-tetrahydro-pyrrolo[3,2-f]quinolin-7-one (Compound 182);

9-Chloro-2-ethyl-1-methyl-3-(2,2,2-trifluoroethyl)-3,6-dihydro-pyrrolo[3,2-f]quinolin-7-one (Compound 183);

9-Chloro-1,2-dimethyl-3-(2,2,2-trifluoroethyl)-3,6-dihydro-pyrrolo[3,2-f]quinolin-7-one (Compound 184);

9-Chloro-1-ethyl-2-methyl-3-(2,2,2-trifluoroethyl)-3,6-dihydro-pyrrolo[3,2-f]-quinolin-7-one (Compound 185);

9-Chloro-2-methyl-3-(2,2,2-trifluoroethyl)-3,6-dihydro-pyrrolo[3,2-f]quinolin-7-one (Compound 186);

9-Chloro-1-methyl-2-phenyl-3-(2,2,2-trifluoroethyl)-3,6-dihydro-pyrrolo[3,2-f]-quinolin-7-one (Compound 187);

3-Benzyl-9-chloro-2-methyl-7-oxo-6,7-dihydro-3H-pyrrolo[3,2-f]quinoline-1-carbaldehyde (Compound 188);

9-Chloro-1,2-dimethyl-3-(2-thien-2-yl-ethyl)-3,6-dihydro-pyrrolo[3,2-f]quinolin-7-one (Compound 189);

9-Chloro-3-(2-hydroxy-ethyl)-1,2-dimethyl-3,6-dihydro-pyrrolo[3,2-f]quinolin-7-one (Compound 190);

9-Chloro-3-(2,2-difluoroethyl)-1,2-dimethyl-3,6-dihydro-pyrrolo[3,2-f]quinolin-7-one (Compound 191);

9-Chloro-3-(2-hydroxy-ethyl)-2-methyl-7-oxo-6,7-dihydro-3H-pyrrolo[3,2-f]-quinoline-1-carbaldehyde (Compound 192);

9-Chloro-3-ethyl-1-methyl-3,6-dihydro-pyrrolo[3,2-f]quinolin-7-one (Compound 193);

9-Chloro-2-(4-fluorophenyl)-1-methyl-3-(2,2,2-trifluoroethyl)-3,6-dihydro-pyrrolo[3,2-f]-quinolin-7-one (Compound 194);

9-Chloro-1,2-dimethyl-5-fluoro-3-(2,2,2-trifluoroethyl)-3,6-dihydro-pyrrolo[3,2-f]-quinolin-7-one (Compound 195);

9-Chloro-1,2-dimethyl-3-ethyl-3,6-dihydro-pyrrolo[3,2-f]quinolin-7-one (Compound 196);

9-Chloro-2-(4-methoxyphenyl)-1-methyl-3-(2,2,2-trifluoroethyl)-3,6-dihydro-pyrrolo[3,2-f]quinolin-7-one (Compound 197);

2-(3-Bromophenyl)-9-Chloro-1-methyl-3-(2,2,2-trifluoroethyl)-3,6-dihydro-pyrrolo[3,2-f]-quinolin-7-one (Compound 198);

9-Chloro-2-(2-fluorophenyl)-1-methyl-3-(2,2,2-trifluoroethyl)-3,6-dihydro-pyrrolo[3,2-f]-quinolin-7-one (Compound 199);

9-Chloro-2-(2,4-difluorophenyl)-1-methyl-3-(2,2,2-trifluoroethyl)-3,6-dihydro-pyrrolo[3,2-f]quinolin-7-one (Compound 200);

9-Chloro-1-methyl-2-(3-trifluoromethylphenyl)-3-(2,2,2-trifluoroethyl)-3,6-dihydro-pyrrolo[3,2-f]quinolin-7-one (Compound 201);

9-Chloro-1-methyl-2-(4-trifluoromethylphenyl)-3-(2,2,2-trifluoroethyl)-3,6-dihydro-pyrrolo[3,2-f]quinolin-7-one (Compound 202);

9-Chloro-1-ethyl-2-phenyl-3-(2,2,2-trifluoroethyl)-3,6-dihydro-pyrrolo[3,2-f]-quinolin-7-one (Compound 203);

9-Chloro-1-methyl-2-(4-methylphenyl)-3-(2,2,2-trifluoroethyl)-3,6-dihydro-pyrrolo[3,2-f]-quinolin-7-one (Compound 204);

9-Chloro-1-methyl-2-(3-nitrophenyl)-3-(2,2,2-trifluoroethyl)-3,6-dihydropyrrolo-[3,2-f]-quinolin-7-one (Compound 205);

9-Chloro-2(4-chlorophenyl)-1-methyl-3-(2,2,2-trifluoroethyl)-3,6-dihydro-pyrrolo[3,2-f]-quinolin-7-one (Compound 206);

9-Chloro-1-methyl-2-thien-2-yl-3-(2,2,2-trifluoroethyl)-3,6-dihydro-pyrrolo[3,2-f]-quinolin-7-one (Compound 207);

9-Chloro-1,2,3-trimethyl-3,6-dihydro-pyrrolo[3,2-f]quinolin-7-one (Compound 208);

9-Chloro-1-ethyl-2-thien-2-yl-3-(2,2,2-trifluoroethyl)-3,6-dihydro-pyrrolo[3,2-f]-quinolin-7-one (Compound 209);

9-Chloro-2-methyl-1-propyl-3-(2,2,2-trifluoroethyl)-3,6-dihydro-pyrrolo[3,2-f]-quinolin-7-one (Compound 210);

9-Chloro-1-methyl-3-(2,2,2-trifluoroethyl)-3,6-dihydro-pyrrolo[3,2-f]quinolin-7-one (Compound 211);

9-Chloro-3-(2-chloro-2,2-difluoroethyl)-1,2-dimethyl-3,6-dihydro-pyrrolo[3,2-f]-quinolin-7-one (Compound 212);

9-Chloro-1,2-dimethyl-3-(3,3,3-trifluoropropyl)-3,6-dihydro-pyrrolo[3,2-f]-quinolin-7-one (Compound 213);

9-Chloro-1,2-dimethyl-3-(2,2,3,3,4,4,4-heptafluorobutyl)-3,6-dihydropyrrolo[3,2-f]quinolin-7-one (Compound 214);

9-Chloro-1,2-dimethyl-3-(2,2,3,3,3-pentafluoropropyl)-3,6-dihydropyrrolo[3,2-f]-quinolin-7-one (Compound 215);

9-Chloro-2-ethyl-1-methyl-3-(3,3,3-trifluoropropyl)-3,6-dihydropyrrolo[3,2-f]-quinolin-7-one (Compound 216);

9-Chloro-1-methyl-2-phenyl-3-(3,3,3-trifluoropropyl)-3,6-dihydro-pyrrolo[3,2-f]-quinolin-7-one (Compound 217);

9-Chloro-1-methyl-3-(2,2,3,3,3-pentafluoropropyl)-2-phenyl-3,6-dihydropyrrolo-[3,2-f]-quinolin-7-one (Compound 218);

1,2-Dimethyl-3-(2,2,3,3,3-pentafluoropropyl)-9-trifluoromethyl-3,6-dihydro-pyrrolo[3,2-f]-quinolin-7-one (Compound 219);

1,2-Dimethyl-3-(2-chloro-2,2-difluoroethyl)-9-trifluoromethyl-3,6-dihydro-pyrrolo[3,2-f]-quinolin-7-one (Compound 220);

1,2-Dimethyl-9-trifluoromethyl-3-(3,3,3-trifluoropropyl)-3,6-dihydropyrrolo[3,2-f]-quinolin-7-one (Compound 221);

9-Chloro-3-(2-chloro-2,2-difluoroethyl)-2-ethyl-1-methyl-3,6-dihydropyrrolo[3,2-f]-quinolin-7-one (Compound 222);

9-Chloro-2-ethyl-1-methyl-3-(2,2,3,3,3-pentafluoropropyl)-3,6-dihydropyrrolo-[3,2-f]-quinolin-7-one (Compound 223);

3-(2-Chloro-2,2-difluoroethyl)-2-ethyl-1-methyl-9-trifluoromethyl-3,6-dihydro-pyrrolo[3,2-f]quinolin-7-one (Compound 224);

2-Ethyl-1-methyl-3-(2,2,3,3,3-pentafluoropropyl)-9-trifluoromethyl-3,6-dihydro-pyrrolo[3,2-f]quinolin-7-one (Compound 225);

2-Ethyl-1-methyl-9-trifluoromethyl-3-(3,3,3-trifluoropropyl)-3,6-dihydropyrrolo-[3,2-f]-quinolin-7-one (Compound 226);

1,2-Dimethyl-3-(4,4,4-trifluorobutyl)-9-trifluoromethyl-3,6-dihydro-pyrrolo[3,2-f]-quinolin-7-one (Compound 227);

2-Ethyl-1-methyl-3-(4,4,4-trifluorobutyl)-9-trifluoromethyl-3,6-dihydropyrrolo-[3,2-f]-quinolin-7-one (Compound 228);

9-Chloro-1-methyl-3-(2,2,2-trifluoro-ethyl)-2-trifluoromethyl-3,6-dihydro-pyrrolo-[3,2-f]-quinolin-7-one (Compound 229);

9-Chloro-2-hydroxymethyl-1-methyl-3-(2,2,2-trifluoroethyl)-3,6-dihydropyrrolo-[3,2-f]-quinolin-7-one (Compound 230);

(±)-9-Chloro-1,2-dimethyl-3-(3,3,3-trifluoro-2-hydroxypropyl)-3,6-dihydropyrrolo-[3,2-f]-quinolin-7-one (Compound 231);

(±)-9-Chloro-2-ethyl-1-methyl-3-(3,3,3-trifluoro-2-hydroxy-propyl)-3,6-dihydro-pyrrolo[3,2-f]quinolin-7-one (Compound 232);

(±)-9-Chloro-1-methyl-3-(3,3,3-trifluoro-2-hydroxypropyl)-2-trifluoromethyl-3,6-dihydropyrrolo[3,2-f]quinolin-7-one (Compound 233);

1-Methyl-3-(2,2,2-trifluoro-ethyl)-2,9-bis-trifluoromethyl-3,6-dihydro-pyrrolo[3,2-f]-quinolin-7-one (Compound 234);

2-Hydroxymethyl-1-methyl-3-(2,2,2-trifluoro-ethyl)-9-trifluoromethyl-3,6-dihydro-pyrrolo[3,2-f]quinolin-7-one (Compound 235);

3-Allyl-1,2-dimethyl-9-trifluoromethyl-3,6-dihydro-pyrrolo[3,2-f]quinolin-7-one (Compound 236);

1,2-Dimethyl-3-(2-methyl-allyl)-9-trifluoromethyl-3,6-dihydro-pyrrolo[3,2-f]-quinolin-7-one (Compound 237);

1,2-Dimethyl-3-(2-methylprop-1-enyl)-9-trifluoromethyl-3,6-dihydro-pyrrolo[3,2-f]-quinolin-7-one (Compound 238);

3-(3-Hydroxy-3-methyl-butyl)-1,2-dimethyl-9-trifluoromethyl-3,6-dihydro-pyrrolo[3,2-f]-quinolin-7-one (Compound 239);

1,2-Dimethyl-3-(2-hydroxyethyl)-9-trifluoromethyl-3,6-dihydro-pyrrolo[3,2-f]-quinolin-7-one (Compound 240);

3-(2-Acetoxyethyl)-1,2-Dimethyl-9-trifluoromethyl-3,6-dihydro-pyrrolo[3,2-f]-quinolin-7-one (Compound 241);

1,2-Dimethyl-3-(prop-2-ynyl)-9-trifluoromethyl-3,6-dihydro-pyrrolo[3,2-f]-quinolin-7-one (Compound 242);

(±)-1,2-Dimethyl-3-(3,3,3-trifluoro-2-hydroxy-propyl)-9-trifluoromethyl-3,6-dihydro-pyrrolo[3,2-f]quinolin-7-one (Compound 243);

(+)-1,2-Dimethyl-3-(3,3,3-trifluoro-2-hydroxy-propyl)-9-trifluoromethyl-3,6-dihydro-pyrrolo[3,2-f]quinolin-7-one (Compound 244);

(−)-1,2-Dimethyl-3-(3,3,3-trifluoro-2-hydroxy-propyl)-9-trifluoromethyl-3,6-dihydro-pyrrolo[3,2-f]quinolin-7-one (Compound 245);

(±)-3-(3,3,3-Trifluoro-2-hydroxy-propyl)-9-trifluoromethyl-1,2-trimethylene-3,6-dihydro-pyrrolo[3,2-f]quinolin-7-one (Compound 246);

(±)-2-Ethyl-1-methyl-3-(3,3,3-Trifluoro-2-hydroxy-propyl)-9-trifluoromethyl-3,6-dihydro-pyrrolo[3,2-f]quinolin-7-one (Compound 247);

1,2-Dimethyl-3-(3-fluoropropyl)-9-trifluoromethyl-3,6-dihydropyrrolo[3,2-f]-quinolin-7-one (Compound 248);

1,2-Dimethyl-3-(3-hydroxypropyl)-9-trifluoromethyl-3,6-dihydropyrrolo[3,2-f]-quinolin-7-one (Compound 249);

3-(3-Acetoxypropyl)-1,2-dimethyl-9-trifluoromethyl-3,6-dihydropyrrolo[3,2-f]-quinolin-7-one (Compound 250);

and pharmaceutically acceptable salts and prodrugs thereof.

These compounds modulate the activity of androgen receptors. Among these compounds are those that have a chlorine at position 9 (for example, Formula I). Tested compounds among these compounds exhibit increased activity compared to corresponding compounds having a hydrogen or trifluoromethyl group at the 9 position.

Provided herein are methods for modulating an activity of an androgen receptor by contacting an androgen receptor with at least one compound provided herein. In certain such embodiments, the androgen receptor is in a cell.

Provided herein are methods for identifying a compound that is capable of modulating an activity of an androgen receptor, by contacting a cell expressing an androgen receptor with a compound provided herein and monitoring an effect of the compound upon the cell.

Provided herein are methods for treating a patient by administering to the patient a compound provided herein. In certain embodiments, the methods provided herein are for increase or maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondro-dysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyper-insulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasias of the prostate (e.g., advanced metastatic prostate cancer) and malignant tumor cells including the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome;

counteracting preeclampsia, eclampsia of pregnancy and pre-term labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

In certain of such embodiments, the patient has a condition selected from acne, male-pattern baldness, wasting diseases, hirsutism, hypogonadism, osteoporoses, infertility, impotence, and cancer.

Provided herein are methods for stimulating hematopoiesis. In certain embodiments, the methods provided herein are for contraception. In certain embodiments, the methods provided herein are for improving athletic performance.

Provided herein are compounds that are selective androgen receptor modulators. In certain embodiments, the compounds provided herein are selective androgen receptor agonists. In certain embodiments, the compounds provided herein are selective androgen receptor antagonists. In certain embodiments, the compounds provided herein are androgen receptor partial agonists. In certain embodiments, the compounds provided herein are selective androgen receptor binding compounds. In certain embodiment, compounds provided herein are tissue specific selected androgen modulators.

Provided herein are methods for modulating at least one activity of an androgen receptor. Certain of such methods are effected by contacting an androgen receptor with one or more compounds provided herein.

Provided herein are methods for treating a patient by administering to the patient a compound provided herein. In certain embodiments, the methods provided herein are for treating a condition including, but not limited to, acne, male-pattern baldness, wasting diseases, hirsutism, hypogonadism, osteoporoses, infertility, impotence, and cancer.

Pharmaceutical compositions formulated for administration by an appropriate route and means including effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by androgen receptor activity, or in which androgen receptor activity is implicated, are also provided. The effective amounts and concentrations are effective for ameliorating any of the symptoms of any of the diseases or disorders.

In certain embodiments, provided herein is a pharmaceutical composition including: i) a physiologically acceptable carrier, diluent, and/or excipient; and ii) one or more compounds provided herein.

Articles of manufacture including packaging material, within the packaging material a compound or composition, or pharmaceutically acceptable derivative thereof, which is effective for modulating the activity of androgen receptor, or for treatment, prevention or amelioration of one or more symptoms of androgen receptor mediated diseases or disorders, or diseases or disorders in which androgen receptor activity is implicated, and a label that indicates that the compound or composition, or pharmaceutically acceptable derivative thereof, is used for modulating the activity of androgen receptor, or for treatment, prevention or amelioration of one or more symptoms of androgen receptor mediated diseases or disorders, or diseases or disorders in which androgen receptor activity is implicated, are provided.

DETAILED DESCRIPTION

A. Definitions

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that both the foregoing general description and the following detailed description are exemplary and explanatory only and are not restrictive of the subject matter claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

As used herein, the term "selective binding compound" refers to a compound that selectively binds to any portion of one or more target receptors.

As used herein, the term "selective androgen receptor binding compound" refers to a compound that selectively binds to any portion of an androgen receptor.

As used herein, the term "selectively binds" refers to the ability of a selective binding compound to bind to a target receptor with greater affinity than it binds to a non-target receptor. In certain embodiments, specific binding refers to binding to a target with an affinity that is at least 10, 50, 100, 250, 500, 1000 or more times greater than the affinity for a non-target.

As used herein, the term "target receptor" refers to a molecule or a portion of a receptor capable of being bound by a selective binding compound. In certain embodiments, a target receptor is a androgen receptor.

As used herein, the terms "treating" or "treatment" encompass either or both responsive and prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "selective modulator" refers to a compound that selectively modulates a target activity.

As used herein, the term "selective androgen receptor modulator" refers to a compound that selectively modulates at least one activity associated with an androgen receptor.

As used herein, the term "selectively modulates" refers to the ability of a selective modulator to modulate a target activity to a greater extent than it modulates a non-target activity. In certain embodiments the target activity is selectively modulated by, for example about 2 fold up to more that about 500 fold, in some embodiments, about 2, 5, 10, 50, 100, 150, 200, 250, 300, 350, 400, 450 or more than 500 fold.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "receptor mediated activity" refers any biological activity that results, either directly or indirectly, from binding of a ligand to a receptor.

As used herein, the term "agonist" refers to a compound, the presence of which results in a biological activity of a receptor that is the same as the biological activity resulting from the presence of a naturally occurring ligand for the receptor.

As used herein, the term "partial agonist" refers to a compound the presence of which results in a biological activity of a receptor that is of the same type as that resulting from the presence of a naturally occurring ligand for the receptor, but of a lower magnitude.

As used herein, the term "antagonist" refers to a compound, the presence of which results in a decrease in the magnitude of a biological activity of a receptor. In certain embodiments, the presence of an antagonist results in complete inhibition of a biological activity of a receptor.

As used herein, the $IC_{50}$ refers to an amount, concentration or dosage of a particular test compound that achieves a 50% inhibition of a maximal response, such as modulation of androgen receptor activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, $C_1$-$C_x$ includes $C_1$-$C_2$, $C_1$-$C_3$ ... $C_1$-$C_x$.

As used herein, the term "alkyl" alone or in combination refers to a straight, branched, or cyclic chain including at least one carbon atom. An alkyl group can be a "saturated alkyl," which means that it does not include any alkene or alkyne groups. An alkyl group can be an "unsaturated alkyl," which means that it includes at least one alkene or alkyne group. In certain embodiments, alkyls are optionally substituted.

In certain embodiments, an alkyl includes 1 to 20 carbon atoms (whenever it appears herein, a numerical range such as "1 to 20" refers to each integer in the given range; e.g., "1 to 20 carbon atoms" means that an alkyl group can include only 1 carbon atom, 2 carbon atoms, 3 carbon atoms, etc., up to and including 20 carbon atoms, although the term "alkyl" also includes instances where no numerical range of carbon atoms is designated). An alkyl can be designated as "$C_1$-$C_4$ alkyl" or similar designations. By way of example only, "$C_1$-$C_4$ alkyl" indicates an alkyl having one, two, three, or four carbon atoms, i.e., the alkyl is selected from among methyl, ethyl, propyl, iso-propyl, n-butyl, iso-butyl, sec-butyl, and t-butyl. Thus $C_1$-$C_4$ includes $C_1$-$C_2$ and $C_1$-$C_3$ alkyl. Alkyls can be substituted or unsubstituted. Alkyls include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like, each of which can be optionally substituted.

As used herein, the term "alkenyl" alone or in combination refers to an alkyl group including at least one carbon-carbon double bond. In certain embodiments, alkenyls are optionally substituted.

As used herein, the term "alkynyl" alone or in combination refers to an alkyl group including at least one carbon-carbon triple bond. In certain embodiments, alkynyls are optionally substituted.

As used herein, the term "non-cyclic alkyl" refers to an alkyl that is not cyclic (i.e., a straight or branched chain including at least one carbon atom). Non-cyclic alkyls may be fully saturated or may include non-cyclic alkenes and/or alkynes. Non-cyclic alkyls may be optionally substituted.

As used herein, the term "haloalkyl" alone or in combination refers to an alkyl in which at least one hydrogen atom is replaced with a halogen atom. In certain of the embodiments in which two or more hydrogen atom are replaced with halogen atoms, the halogen atoms are all the same as one another. In certain of such embodiments, the halogen atoms are not all the same as one another. Certain haloalkyls are saturated haloalkyls, which do not include any carbon-carbon double bonds or any carbon-carbon triple bonds. Certain haloalkyls are haloalkenes, which include one or more carbon-carbon double bonds. Certain haloalkyls are haloalkynes, which include one or more carbon-carbon triple bonds. In certain embodiments, haloalkyls are optionally substituted As used herein, the term "heteroalkyl" alone or in combination refers to a group including an alkyl and one or more heteroatoms. Certain heteroalkyls are saturated heteroalkyls, which do not include any carbon-carbon double bonds or any carbon-carbon triple bonds. Certain heteroalkyls are heteroalkenes, which include at least one carbon-carbon double bond. Certain heteroalkyls are heteroalkynes, which include at least one carbon-carbon triple bond. Certain heteroalkyls are acylalkyls, in which the one or more heteroatoms are within an alkyl chain. Examples of heteroalkyls include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3C(=O)CH_2-$, $CH_3NHCH_2-$, and the like. In certain embodiments, heteroalkyls are optionally substituted.

As used herein, the term "heterohaloalkyl" alone or in combination refers to a heteroalkyl in which at least one hydrogen atom is replaced with a halogen atom. In certain embodiments, heteroalkyls are optionally substituted.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings can be optionally substituted. Rings can form part of a ring system.

As used herein, the term "ring system" refers to two or more rings, wherein two or more of the rings are fused. The term "fused" refers to structures in which two or more rings share one or more bonds.

As used herein, the term "carbocycle" refers to a ring, wherein each of the atoms forming the ring is a carbon atom. Carbocyclic rings can be formed by three, four, five, six, seven, eight, nine, or more than nine carbon atoms. Carbocycles can be optionally substituted.

As used herein, the term "heterocycle" refers to a ring wherein at least one atom forming the ring is a carbon atom and at least one atom forming the ring is a heteroatom. Heterocyclic rings may be formed by three, four, five, six, seven, eight, nine, or more than nine atoms. Any number of those atoms may be heteroatoms (i.e., a heterocyclic ring may include one, two, three, four, five, six, seven, eight, nine, or more than nine heteroatoms, provided that at least one atom in the ring is a carbon atom). Herein, whenever the number of carbon atoms in a heterocycle is indicated (e.g., $C_1$-$C_6$ heterocycle), at least one other atom (i.e., the heteroatom) must be present in the ring. Designations such as "$C_1$-$C_6$ heterocycle" refer only to the number of carbon atoms in the ring and do not refer to the total number of atoms in the ring. It is understood that the heterocyclic ring will have additional heteroatoms in the ring. Designations such as "4-6 membered heterocycle" refer to the total number of atoms that are in the ring (i.e., a four, five, or six membered ring, in which at least one atom is a carbon atom, at least one atom is a heteroatom and the remaining two to four atoms are either carbon atoms or heteroatoms). In heterocycles including two or more heteroatoms, those two or more heteroatoms may be the same or different from one another. Heterocycles may be optionally substituted. Binding to a heterocycle can be at a heteroatom or via a carbon atom. Examples of heterocycles include, but are not limited to the following:

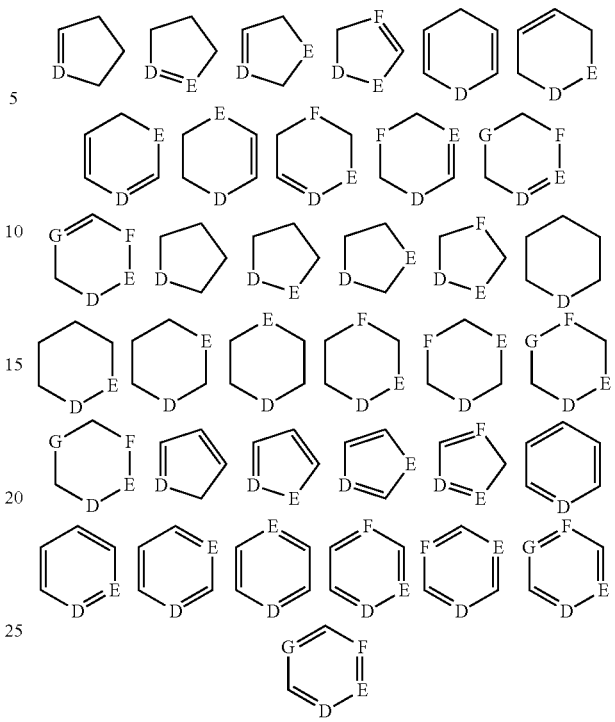

wherein D, E, F, and G independently represent a heteroatom. Each of D, E, F, and G may be the same or different from one another.

As used herein, the term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms can all be the same as one another, or some or all of the two or more heteroatoms can each be different from the others.

As used herein, the term "aromatic" refers to a planar ring having a delocalized π-electron system including 4 n+2 π electrons, where n is an integer. Aromatic rings may be formed by three, four, five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_1$-$C_6$ alkoxy, a $C_1$-$C_6$ alkyl, a hydroxy-$C_1$-$C_6$alkyl, an amino $C_1$-$C_6$alkyl, a $C_1$-$C_6$ alkylamino, an $C_1$-$C_6$ alkylsulfenyl, an $C_1$-$C_6$ alkylsulfinyl, an $C_1$-$C_6$ alkylsulfonyl, an sulfamoyl, or a trifluoromethyl. In certain embodiments, an aromatic group is substituted at one or more of the para, meta, and/or ortho positions. Examples of aromatic groups including substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethyl-phenyl, naphthyl, hydroxynaphthyl, hydroxymethylphenyl, (trifluoromethyl)phenyl, alkoxyphenyl, 4-(morpholin-4-yl)phenyl, 4-(pyrrolidin-1-yl)phenyl, 4-pyrazolylphenyl, 4-triazolylphenyl, and 4-(2-oxopyrrolidin-1-yl)phenyl.

As used herein, the term "aryl" refers to an aromatic ring wherein each of the atoms forming the ring is a carbon atom. Aryl rings can be formed by three, four, five, six, seven, eight, nine, or more than nine carbon atoms. Aryl groups can be optionally substituted.

As used herein, the term "heteroaryl" refers to an aromatic ring in which at least one atom forming the aromatic ring is a heteroatom. Heteroaryl rings can be formed by three, four, five, six, seven, eight, nine and more than nine atoms. Heteroaryl groups can be optionally substituted. Examples of heteroaryl groups include, but are not limited to, aromatic $C_3$-$C_8$ heterocyclic groups including one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_1$-$C_6$-alkoxy, $C_1$-$C_6$-alkyl, hydroxy-$C_1$-$C_6$-alkyl, amino-$C_1$-$C_6$-alkyl, $C_1$-$C_6$-alkylamino, $C_1$-$C_6$ alkylsulfenyl, $C_1$-$C_6$ alkylsulfinyl, $C_1$-$C_6$ alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_1$-$C_6$-alkyl, $C_1$-$C_6$-alkyl, hydroxy-$C_1$-$C_6$-alkyl, and amino-$C_1$-$C_6$-alkyl.

As used herein, the term "non-aromatic ring" refers to a ring that does not have a delocalized 4 n+2 π-electron system.

As used herein, the term "cycloalkyl" refers to a group including a non-aromatic ring wherein each of the atoms forming the ring is a carbon atom. Cycloalkyls can be formed by three, four, five, six, seven, eight, nine, or more than nine carbon atoms. Cycloalkyls can be optionally substituted. In certain embodiments, a cycloalkyl includes one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

As used herein, the term "non-aromatic heterocycle" refers to a non-aromatic ring wherein one or more atoms forming the ring is a heteroatom. Non-aromatic heterocyclic rings can be formed by three, four, five, six, seven, eight, nine, or more than nine atoms. Non-aromatic heterocycles can be optionally substituted. In certain embodiments, non-aromatic heterocycles include one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

As used herein, the term "arylalkyl" alone or in combination, refers to an alkyl substituted with an aryl that may be optionally substituted.

As used herein, the term "heteroarylalkyl" alone or in combination, refers to an alkyl substituted with a heteroaryl that may be optionally substituted.

As used herein, the substituent "R" appearing by itself and without a number designation refers to a substituent selected from alkyl, cycloalkyl, aryl, heteroaryl (bonded through a ring carbon) and non-aromatic heterocycle (bonded through a ring carbon).

As used herein, the term "O-carboxy" refers to a group of formula RC(=O)O—.

As used herein, the term "C-carboxy" refers to a group of formula —C(=O)OR.

As used herein, the term "acetyl" refers to a group of formula —C(=O)CH$_3$.

As used herein, the term "trihalomethanesulfonyl" refers to a group of formula X$_3$CS(=O)$_2$— where X is a halogen.

As used herein, the term "cyano" refers to a group of formula —CN.

As used herein, the term "isocyanato" refers to a group of formula —NCO.

As used herein, the term "thiocyanato" refers to a group of formula —CNS.

As used herein, the term "isothiocyanato" refers to a group of formula —NCS.

As used herein, the term "sulfinyl" refers to a group of formula —S(=O)—R.

As used herein, the term "S-sulfonamido" refers to a group of formula —S(=O)$_2$NR$_2$.

As used herein, the term "N-sulfonamido" refers to a group of formula RS(=O)$_2$NH—.

As used herein, the term "trihalomethanesulfonamido" refers to a group of formula X$_3$CS(=O)$_2$NR—.

As used herein, the term "O-carbamyl" refers to a group of formula —OC(=O)—NR$_2$.

As used herein, the term "N-carbamyl" refers to a group of formula ROC(=O)NH—.

As used herein, the term "O-thiocarbamyl" refers to a group of formula —OC(=S)—NR$_2$.

As used herein, the term "N-thiocarbamyl" refers to a group of formula ROC(=S)NH—.

As used herein, the term "C-amido" refers to a group of formula —C(=O)—NR$_2$.

As used herein, the term "N-amido" refers to a group of formula RC(=O)NH—.

As used herein, the term "ester" refers to a chemical moiety with formula —(R)$_n$—COOR', where R and R' are independently selected from alkyl, cycloalkyl, aryl, heteroaryl (bonded through a ring carbon) and non-aromatic heterocycle (bonded through a ring carbon), where n is 0 or 1.

As used herein, the term "amide" refers to a chemical moiety with formula —(R)$_n$—C(O)NHR' or —(R)$_n$—NHC(O)R', where R and R' are independently selected from alkyl, cycloalkyl, aryl, heteroaryl (bonded through a ring carbon) and heteroalicyclic (bonded through a ring carbon), where n is 0 or 1. In certain embodiments, an amide can be an amino acid or a peptide.

As used herein, the terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

As used herein, the term "linked to form a ring" refers to instances where two atoms that are bound either to a single atom or to atoms that are themselves ultimately bound, are each bound to a linking group, such that the resulting structure forms a ring. That resulting ring includes the two atoms that are linked to form a ring, the atom (or atoms) that previously linked those atoms, and the linker. For example, if A and B below are "linked to form a ring"

the resulting ring includes A, B, C, and a linking group. Unless otherwise indicated, that linking group may be of any length and may be optionally substituted. Referring to the above example, resulting structures include, but are not limited to:

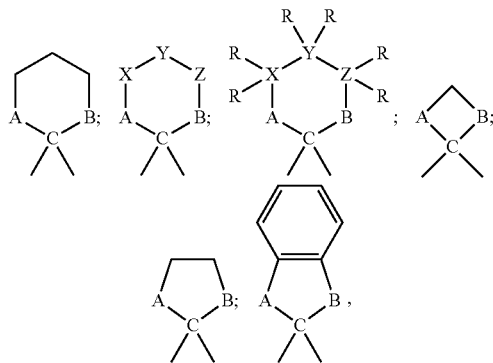

and the like.

In certain embodiments, the two substituents that together form a ring are not immediately bound to the same atom. For example, if A and B, below, are linked to form a ring:

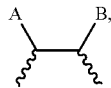

the resulting ring includes A, B, the two atoms that already link A and B and a linking group. Examples of resulting structures include, but are not limited to:

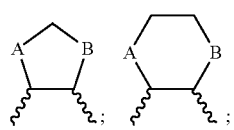

and the like.

In certain embodiments, the atoms that together form a ring are separated by three or more atoms. For example, if A and B, below, are linked to form a ring:

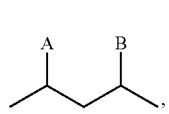

the resulting ring includes A, B, the 3 atoms that already link A and B, and a linking group. Examples of resulting structures include, but are not limited to:

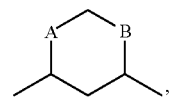

and the like.

As used herein, the term "together form a bond" refers to the instance in which two substituents to neighboring atoms are null and the bond between the neighboring atoms becomes a double bond. For example, if A and B below "together form a bond"

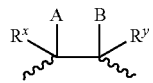

the resulting structure is:

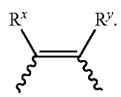

Unless otherwise indicated, the term "optionally substituted," refers to a group in which none, one, or more than one of the hydrogen atoms has been replaced with one or more group(s) individually and independently selected from: cycloalkyl, aryl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono and di-substituted amino groups, and the protected derivatives of amino groups. Such protective derivatives (and protecting groups that can form such protective derivatives) are known to those of skill in the art and can be found in references such as Greene and Wuts, above. In embodiments in which two or more hydrogen atoms have been substituted, the substituent groups can together form a ring.

Throughout the specification, groups and substituents thereof can be chosen by one skilled in the field to provide stable moieties and compounds.

A pyrrolo[3,2-f]quinolin-7-one is numbered by the following structure:

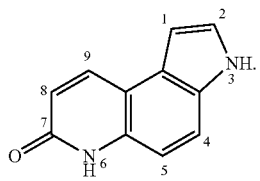

As used herein, the term "carrier" refers to a compound that facilitates the incorporation of another compound into cells or tissues. For example, dimethyl sulfoxide (DMSO) is a commonly used carrier for improving incorporation of certain organic compounds into cells or tissues.

As used herein, the term "pharmaceutical composition" refers to a chemical compound or composition capable of inducing a desired therapeutic effect in a patient. In certain embodiments, a pharmaceutical composition includes an active agent, which is the agent that induces the desired therapeutic effect. In certain embodiments, a pharmaceutical composition includes a prodrug. In certain embodiments, a pharmaceutical composition includes inactive ingredients such as carriers and excipients.

As used herein, the term "therapeutically effective amount" refers to an amount of a pharmaceutical composition sufficient to achieve a desired therapeutic effect.

As used herein, a "prodrug" refers to a compound that is converted from a less active form into a corresponding more active form in vivo. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

As used herein, the term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein can include chiral centers. Such chiral centers can be of either the (R) or (S) configuration, or can be a mixture thereof. Thus, the compounds provided herein can be enantiomerically pure, or be stereoisomeric or diastereomeric mixtures.

As used herein, the term "substantially pure" means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Thus, substantially pure object species (e.g., compound) is the predominant species present (i.e., on a molar basis it is more abundant than any other individual species in the composition). In certain embodiments, a substantially purified fraction is a composition wherein the object species includes at least about 50 percent (on a molar basis) of all species present. In certain embodiments, a substantially pure composition will include more than about 50%, 60%, 70%, 80%, 85%, 90%, 95%, or 99% of all species present in the composition. In certain embodiments, a substantially pure composition will include more than about 80%, 85%, 90%, 95%, or 99% of all species present in the composition. Methods for purification of the compounds to produce substantially chemically pure compounds are known to those of skill in the art. A substantially chemically pure compound can, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers can be prepared using chiral synthons or chiral reagents, or resolved using conventional techniques, such as reverse phase HPLC. When the compounds described herein include olefinic double bonds or other centers of geometric asymmetry, and unless specified otherwise, it is intended that the compounds include both E and Z geometric isomers. Likewise, all tautomeric forms are also intended to be included.

As used herein, the term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

As used herein, the term "subject" is an animal, typically a mammal, including human.

As used herein, the term "patient" includes human and animal subjects.

As used herein, the term "tissue-selective" refers to the ability of a compound to modulate a biological activity in one tissue to a greater or lesser degree than it modulates a biological activity in another tissue. The biological activities in the different tissues can be the same or they can be different. The biological activities in the different tissues can be mediated by the same type of target receptor. For example, in certain embodiments, a tissue-selective compound can modulate an androgen receptor mediated biological activity in one tissue and fail to modulate, or modulate to a lesser degree, an androgen receptor mediated biological activity in another tissue type.

As used herein, the term "monitoring" refers to observing an effect or absence of any effect. In certain embodiments, one monitors cells after contacting those cells with a compound provided herein. Examples of effects that can be monitored include, but are not limited to, changes in cell phenotype, cell proliferation, androgen receptor activity, or the interaction between an androgen receptor and a natural binding partner.

As used herein, the term "cell phenotype" refers to physical or biological characteristics. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

As used herein, the term "contacting" refers to bringing two or more materials into close enough proximity that they can interact. In certain embodiments, contacting can be accomplished in a vessel such as a test tube, a petri dish, or the like. In certain embodiments, contacting can be performed in the presence of additional materials. In certain embodiments, contacting can be performed in the presence of cells. In certain of such embodiments, one or more of the materials that are being contacted can be inside a cell. Cells can be alive or can be dead. Cells can or cannot be intact.

B. Compounds

Certain compounds that bind to androgen receptors and/or modulate an activity of such receptors play a role in health (e.g., normal growth, development, and/or absence of disease). In certain embodiments, selective androgen receptor modulators and/or binding compounds are useful for treating any of a variety of diseases or conditions.

Certain compounds have been previously described as receptor modulators or as possible receptor modulators. See e.g., U.S. Pat. Nos. 6,462,038; 5,693,646; 6,380,207; 6,506,766; 5,688,810; 5,696,133; 6,569,896, 6,673,799; 4,636,505; 4,097,578; 3,847,988; U.S. application Ser. No. 10/209,461 (Pub. No. US 2003/0055094); WO 01/27086; WO 02/22585; Zhi, et al. *Bioorganic & Medicinal Chemistry Letters* 2000, 10, 415-418; Pooley, et. al., *J. Med. Chem.* 1998, 41, 3461; Hamann, et al. *J. Med. Chem.* 1998, 41(4), 623; and Yin, et al., *Molecular Pharmacology*, 2003, 63 (1), 211-223 the entire disclosures of which are incorporated in their entirety.

In certain embodiments, the compounds provided herein are selective androgen receptor modulators. In certain embodiments, the compounds provided herein are selective androgen receptor binding agents. In certain embodiments, provided herein are methods of making and methods of using androgen receptor modulators and/or androgen binding agents provided herein. In certain embodiments, selective androgen modulators are agonists, partial agonists, and/or antagonists for the androgen receptor.

In certain embodiments, the compounds provided herein have a structure selected from Formula I or Formula II:

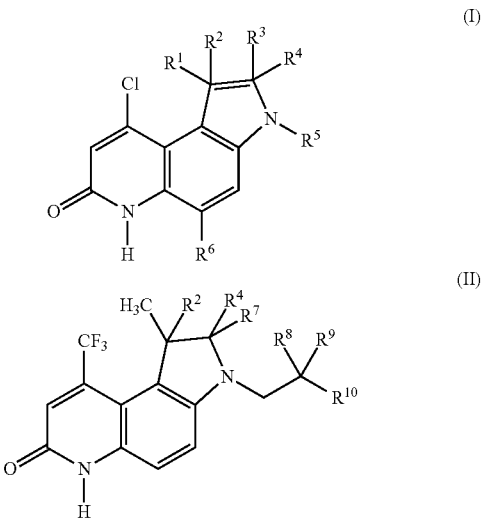

In certain embodiments, $R^1$ is selected from hydrogen, optionally substituted $C_1$-$C_4$ alkyl, $C_1$-$C_4$ heteroalkyl, $C_1$-$C_4$ haloalkyl, optionally substituted heteroaryl, and optionally substituted aryl. In certain embodiments, $R^1$ is selected from hydrogen, fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl. In certain embodiments, $R^1$ selected from hydrogen, $C_2$-$C_4$ alkenyl, $C_2$-$C_4$ heteroalkenyl, $C_2$-$C_4$ haloalkenyl, optionally substituted heteroaryl, and optionally substituted aryl. In certain embodiments, $R^1$ selected from hydrogen, $C_2$-$C_4$ alkynyl, $C_2$-$C_4$ heteroalkynyl, $C_2$-$C_4$ haloalkynyl, optionally substituted heteroaryl, and optionally substituted aryl.

In certain embodiments, $R^1$ is selected from optionally substituted $C_1$-$C_4$ alkyl, $C_1$-$C_4$ heteroalkyl, $C_1$-$C_4$ haloalkyl, optionally substituted heteroaryl, and optionally substituted aryl. In certain embodiments, $R^1$ is selected from fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl. In certain embodiments, $R^1$ is selected from $C_2$-$C_4$ alkenyl, $C_2$-$C_4$ heteroalkenyl, $C_2$-$C_4$ haloalkenyl, optionally substituted heteroaryl, and optionally substituted aryl. In certain embodiments, $R^1$ is selected from $C_2$-$C_4$ alkynyl, $C_2$-$C_4$ heteroalkynyl, $C_2$-$C_4$ haloalkynyl, optionally substituted heteroaryl, and optionally substituted aryl.

In certain embodiments, $R^1$ is selected from hydrogen, optionally substituted $C_1$-$C_4$ alkyl, $C_1$-$C_4$ heteroalkyl, and $C_1$-$C_4$ haloalkyl. In certain embodiments, $R^1$ is selected from hydrogen, fully saturated $C_1$-$C_4$ alkyl, fully saturated $C_1$-$C_4$ heteroalkyl, and fully saturated $C_1$-$C_4$ haloalkyl. In certain embodiments, $R^1$ is selected from hydrogen, $C_2$-$C_4$ alkenyl, $C_2$-$C_4$ heteroalkenyl, and $C_2$-$C_4$ haloalkenyl. In certain embodiments, $R^1$ is selected from hydrogen, $C_2$-$C_4$ alkynyl, $C_2$-$C_4$ heteroalkynyl, and $C_2$-$C_4$ haloalkynyl.

In certain embodiments, $R^1$ is selected from optionally substituted $C_1$-$C_4$ alkyl, $C_1$-$C_4$ heteroalkyl, and $C_1$-$C_4$ haloalkyl. In certain embodiments, $R^1$ is selected from fully saturated $C_1$-$C_4$ alkyl, fully saturated $C_1$-$C_4$ heteroalkyl, and fully saturated $C_1$-$C_4$ haloalkyl. In certain embodiments, $R^1$ is selected from $C_2$-$C_4$ alkenyl, $C_2$-$C_4$ heteroalkenyl, and $C_2$-$C_4$ haloalkenyl. In certain embodiments, $R^1$ is selected from $C_2$-$C_4$ alkynyl, $C_2$-$C_4$ heteroalkynyl, and $C_2$-$C_4$ haloalkynyl.

In certain embodiments, $R^1$ is selected from hydrogen, methyl, ethyl, propyl, acetic acid and formyl.

In certain embodiments, $R^1$ is selected from methyl, ethyl, propyl, acetic acid and formyl.

In certain embodiments, $R^3$ is selected from hydrogen, $C_1$-$C_4$ alkyl, $C_1$-$C_4$ heteroalkyl, $C_1$-$C_4$ haloalkyl, optionally substituted heteroaryl, and optionally substituted aryl. In certain embodiments, $R^3$ is selected from hydrogen, fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl. In certain embodiments, $R^3$ is selected from hydrogen, $C_2$-$C_4$ alkenyl, $C_2$-$C_4$ heteroalkenyl, $C_2$-$C_4$ haloalkenyl, optionally substituted heteroaryl, and optionally substituted aryl. In certain embodiments, $R^3$ is selected from hydrogen, $C_2$-$C_4$ alkynyl, $C_2$-$C_4$ heteroalkynyl, $C_2$-$C_4$ haloalkynyl, optionally substituted heteroaryl, and optionally substituted aryl.

In certain embodiments, $R^3$ is selected from $C_1$-$C_4$ alkyl, $C_1$-$C_4$ heteroalkyl, $C_1$-$C_4$ haloalkyl, optionally substituted heteroaryl, and optionally substituted aryl. In certain embodiments, $R^3$ is selected from fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl. In certain embodiments, $R^3$ is selected from $C_2$-$C_4$ alkenyl, $C_2$-$C_4$ heteroalkenyl, $C_2$-$C_4$ haloalkenyl, optionally substituted heteroaryl, and optionally substituted aryl. In certain embodiments, $R^3$ is selected from $C_2$-$C_4$ alkynyl, $C_2$-$C_4$ heteroalkynyl, $C_2$-$C_4$ haloalkynyl, optionally substituted heteroaryl, and optionally substituted aryl.

In certain embodiments, $R^3$ is selected from hydrogen, methyl, ethyl, hydroxymethyl, trifluoromethyl, phenyl, ethylcarboxylate, acetyl, 4-methoxyphenyl, 4-fluorophenyl, 2,4-difluorophenyl, 2-fluorophenyl, 4-chlorophenyl, 3-chlorophenyl, 3-bromophenyl, 3-nitrophenyl, 4-hydroxyphenyl, 3,4-dichlorophenyl, 3,5-bistrifluoromethylphenyl, 3-trifluoromethylphenyl, thien-2-yl, 4-trifluoromethylphenyl, and 4-methylphenyl.

In certain embodiments, $R^3$ is selected from methyl, ethyl, hydroxymethyl, trifluoromethyl, phenyl, ethylcarboxylate, acetyl, 4-methoxyphenyl, 4-fluorophenyl, 2,4-difluorophenyl, 2-fluorophenyl, 4-chlorophenyl, 3-chlorophenyl, 3-bromophenyl, 3-nitrophenyl, 4-hydroxyphenyl, 3,4-dichlorophenyl, 3,5-bistrifluoromethylphenyl, 3-trifluoromethylphenyl, thien-2-yl, 4-trifluoromethylphenyl, and 4-methylphenyl.

In certain embodiments, $R^3$ is selected from hydrogen, methyl, ethyl, hydroxymethyl, and trifluoromethyl.

In certain embodiments, $R^3$ is selected from methyl, ethyl, hydroxymethyl, and trifluoromethyl.

In certain embodiments, $R^1$ and $R^3$ taken together form a $C_3$-$C_8$ carbocyclic ring. In certain embodiments, $R^1$ and $R^3$ taken together form a $C_3$-$C_8$ aryl ring. In certain embodiments, $R^1$ and $R^3$ taken together form a $C_3$-$C_8$ cycloalkyl.

In certain embodiments $R_1$ and $R_3$ taken together form a cyclopentane, cyclopentene, cyclohexane or cyclohexene. In certain embodiments $R_1$ and $R_3$ taken together form a cyclopentane. In certain embodiments $R_1$ and $R_3$ taken together form a cyclopentene. In certain embodiments $R_1$ and $R_3$ taken together form a cyclohexane. In certain embodiments $R_1$ and $R_3$ taken together form a cyclohexene.

In certain embodiments, $R^2$ and $R^4$ are each hydrogen. In certain embodiments, $R^2$ and $R^4$ together form a bond.

In certain embodiments, $R^5$ is selected from hydrogen, $C_1$-$C_8$ alkyl, $C_1$-$C_8$ haloalkyl, $C_1$-$C_8$ heteroalkyl, $C_7$-$C_{10}$ arylalkyl, and $C_2$-$C_8$ heteroarylalkyl. In certain embodiments, $R^5$ is selected from hydrogen, fully saturated $C_1$-$C_8$ alkyl, fully saturated $C_1$-$C_8$ haloalkyl, fully saturated $C_1$-$C_8$ heteroalkyl, $C_7$-$C_{10}$ arylalkyl, and $C_2$-$C_8$ heteroarylalkyl. In certain embodiments, $R^5$ is selected from hydrogen, $C_1$-$C_8$ alkenyl, $C_1$-$C_8$ haloalkenyl, $C_1$-$C_8$ heteroalkenyl, $C_7$-$C_{10}$ arylalkyl, and $C_2$-$C_8$ heteroarylalkyl. In certain embodiments, $R^5$ is selected from hydrogen, $C_1$-$C_8$ alkynyl, $C_1$-$C_8$ haloalkynyl, $C_1$-$C_8$ heteroalkynyl, $C_7$-$C_{10}$ arylalkyl, and $C_2$-$C_8$ heteroarylalkyl.

In certain embodiments, $R^5$ is selected from $C_1$-$C_8$ alkyl, $C_1$-$C_8$ haloalkyl, $C_1$-$C_8$ heteroalkyl, $C_7$-$C_{10}$ arylalkyl, and $C_2$-$C_8$ heteroarylalkyl. In certain embodiments, $R^5$ is selected from fully saturated $C_1$-$C_8$ alkyl, fully saturated $C_1$-$C_8$ haloalkyl, fully saturated $C_1$-$C_8$ heteroalkyl, $C_7$-$C_{10}$ arylalkyl, and $C_2$-$C_8$ heteroarylalkyl. In certain embodiments, $R^5$ is selected from $C_2$-$C_8$ alkenyl, $C_2$-$C_8$ haloalkenyl, $C_2$-$C_8$ heteroalkenyl, $C_7$-$C_{10}$ arylalkyl, and $C_2$-$C_8$ heteroarylalkyl. In certain embodiments, $R^5$ is selected from $C_2$-$C_8$ alkynyl, $C_2$-$C_8$ haloalkynyl, $C_2$-$C_8$ heteroalkynyl, $C_7$-$C_{10}$ arylalkyl, and $C_2$-$C_8$ heteroarylalkyl.

In certain embodiments, $R^5$ is selected from hydrogen, methyl, ethyl, propyl, 2,2,2-trifluoroethyl, 2-chloro-2,2-difluoroethyl, 2-hydroxyethyl, 2,2-dimethylpropyl, 2-thiophen-2-yl-ethyl, 2,2-difluoroethyl, phenylmethyl, 3,3,3-trifluoropropyl, 2,2,2-trifluoroethyl, 2,2,3,3,3-pentafluoropropyl, 2,2,3,3,4,4,4-heptafluorobutyl, 3,3,3-trifluoropropyl, methylphenyl, 2-thien-2-ylethyl, 2-hydroxy-ethyl, and 2-hydroxy-3,3,3-trifluoropropyl.

In certain embodiments, $R^5$ is selected from methyl, ethyl, propyl, 2,2,2-trifluoroethyl, 2-chloro-2,2-difluoroethyl, 2-hydroxyethyl, 2,2-dimethylpropyl, 2-thiophen-2-yl-ethyl, 2,2-difluoroethyl, phenylmethyl, 3,3,3-trifluoropropyl, 2,2,2-trifluoroethyl, 2,2,3,3,3-pentafluoropropyl, 2,2,3,3,4,4,4-heptafluorobutyl, 3,3,3-trifluoropropyl, methylphenyl, 2-thien-2-ylethyl, 2-hydroxy-ethyl, and 2-hydroxy-3,3,3-trifluoropropyl.

In certain embodiments, $R^6$ is hydrogen. In certain embodiments, $R^6$ is F.

In certain embodiments, $R^7$ is selected from hydrogen, $C_1$-$C_4$ alkyl, $C_1$-$C_4$ haloalkyl, optionally substituted heteroaryl, and optionally substituted aryl. In certain embodiments, $R^7$ is selected from hydrogen, fully saturated $C_1$-$C_4$ alkyl, fully saturated $C_1$-$C_4$ haloalkyl, optionally substituted heteroaryl, and optionally substituted aryl. In certain embodiments, $R^7$ is selected from hydrogen, $C_2$-$C_4$ alkenyl, $C_2$-$C_4$ haloalkenyl, optionally substituted heteroaryl, and optionally substituted aryl. In certain embodiments, $R^7$ is selected from hydrogen, $C_2$-$C_4$ alkynyl, $C_2$-$C_4$ haloalkynyl, optionally substituted heteroaryl, and optionally substituted aryl.

In certain embodiments, $R^7$ is selected from $C_1$-$C_4$ alkyl, $C_1$-$C_4$ haloalkyl, optionally substituted heteroaryl, and optionally substituted aryl. In certain embodiments, $R^7$ is selected from fully saturated $C_1$-$C_4$ alkyl, fully saturated $C_1$-$C_4$ haloalkyl, optionally substituted heteroaryl, and optionally substituted aryl. In certain embodiments, $R^7$ is selected from $C_2$-$C_4$ alkenyl, $C_2$-$C_4$ haloalkenyl, optionally substituted heteroaryl, and optionally substituted aryl. In certain embodiments, $R^7$ is selected from $C_2$-$C_4$ alkynyl, $C_2$-$C_4$ haloalkynyl, optionally substituted heteroaryl, and optionally substituted aryl.

In certain embodiments, $R^7$ is selected from hydrogen and $C_1$-$C_4$ alkyl.

In certain embodiments, $R^7$ is selected from hydrogen and $C_1$-$C_4$ alkyl.

In certain embodiments, $R^7$ is selected from methyl and ethyl.

In certain embodiments, $R^8$ is selected from hydrogen, F, and hydroxyl.

In certain embodiments, $R^8$ is selected from F and hydroxyl.

In certain embodiments, $R^9$ is selected from hydrogen, F, and hydroxyl.

In certain embodiments, $R^9$ is selected from F and hydroxyl.

In certain embodiments, $R^{10}$ is selected from hydroxyl, Cl, Br, $C_1$-$C_3$ fluoroalkyl, $C_1$-$C_3$ heteroalkyl, $C_2$-$C_4$ alkenyl, $C_2$-$C_4$ alkynyl. In certain embodiments, $R^{10}$ is selected from hydroxyl, Cl, Br, $C_1$-$C_3$ fluoroalkyl, fully saturated $C_1$-$C_3$ heteroalkyl, $C_2$-$C_4$ alkenyl, $C_2$-$C_4$ alkynyl.

In certain embodiments, $R^{10}$ is selected from hydroxyl, Cl, Br, $C_1$-$C_3$ fluoroalkyl, optionally substituted $C_1$-$C_5$ heteroalkyl, $C_2$-$C_4$ alkenyl and $C_2$-$C_4$ alkynyl, where if $R^{10}$ is a $C_2$-$C_4$ alkynyl, then $R^8$ and $R^9$ do not exist. In certain embodiments, $R^{10}$ is a substituted $C_1$-$C_5$ heteroalkyl. In certain embodiments, $R^{10}$ is a $C_1$-$C_5$ heteroalkyl substituted with a hydroxy group.

In certain embodiments, $R^{10}$ is selected from hydroxyl, $C_1$, $C_1$-$C_3$ fluoroalkyl, and $C_1$-$C_3$ heteroalkyl.

In certain embodiments, $R^{10}$ is selected from hydroxy, chloro, trifluoromethyl, 2,2,2-trifluoroethyl, 2-hydroxyprop-2-yl, acetoxy, fluoromethyl, hydroxymethyl, and acetoxymethyl.

In certain embodiments, a compound of Formula I or Formula II is a selective androgen receptor modulator. In certain embodiments, a compound of Formula I or Formula II is a selective androgen receptor agonist. In certain embodiments, a compound of Formula I or Formula II is a selective androgen receptor antagonist. In certain embodiments, a compound of Formula I or Formula II is a selective androgen receptor partial agonist. In certain embodiments, a compound of Formula I or Formula II is a tissue-specific selective androgen modulator. In certain embodiments, a compound of Formula I or Formula II is a gene-specific selective androgen modulator. In certain embodiments, a compound of Formula I or Formula II is a selective androgen receptor binding compound.

In certain embodiments, the compounds provided herein have a structure of Formula III:

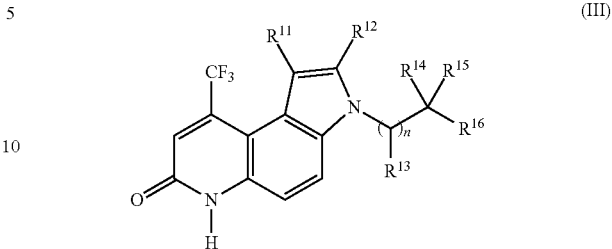

wherein:
$R^{11}$ is $C_1$-$C_4$ alkyl;
$R^{12}$ is selected from hydrogen, $C_1$-$C_4$ alkyl, $C_1$-$C_4$ haloalkyl, hydroxymethyl, optionally substituted heteroaryl, and optionally substituted aryl; or
$R^{11}$ and $R^{12}$ taken together form a $C_3$-$C_8$ carbocyclic ring; wherein if $R^{11}$ and $R^{12}$ taken together form a $C_3$-$C_8$ carbocyclic ring, then $R^{16}$ is not Cl or F
$R^{14}$ is selected from among hydrogen, F, hydroxyl and $C_1$-$C_3$ alkyl;
$R^{15}$ is selected from among hydrogen, F, hydroxyl and $C_1$-$C_3$ alkyl;
$R^{13}$ is hydrogen; or
$R^{13}$ and $R^{16}$ taken together form a bond; wherein if $R^{13}$ and $R^{16}$ taken together form a bond then $R^{14}$ and $R^{15}$ are each $C_1$-$C_4$ alkyl;
$R^{16}$ is selected from hydroxyl, Cl, F, Br, $C_1$-$C_3$ fluoroalkyl, $C_1$-$C_3$ heteroalkyl, $C_2$-$C_4$ alkenyl, and $C_2$-$C_4$ alkynyl; wherein if $R^{13}$ is F, then $R^{12}$ is hydroxymethyl or $C_1$-$C_4$ haloalkyl;
n is 0 or 1; wherein if n is 0, then $R^{16}$ is $C_2$-$C_4$ alkenyl or $C_2$-$C_4$ alkynyl;
and pharmaceutically acceptable salts and prodrugs thereof.
In certain embodiments, $R^{11}$ is methyl.
In certain embodiments, $R^{11}$ and $R^{12}$ together form a cyclopentene.
In certain embodiments, $R^{12}$ is selected from among methyl, hydroxymethyl and trifluoromethyl.
In certain embodiments, $R^{14}$ is selected from among hydrogen, F, hydroxyl or methyl.
In certain embodiments, $R^{15}$ is selected from among hydrogen, F, hydroxyl or methyl.
In certain embodiments, $R^{16}$ is selected from among F, vinyl, 1-methylvinyl, ethynyl and trifluoromethyl.
In certain embodiments, provided herein is a compound selected from:
9-Chloro-1,2-dimethyl-3,6-dihydro-pyrrolo[3,2-f]quinolin-7-one (Compound 105);
9-Chloro-2-ethyl-1-methyl-3,6-dihydro-pyrrolo[3,2-f]quinolin-7-one (Compound 106);
9-Chloro-1,2-trimethylene-3,6-dihydro-pyrrolo[3,2-f]quinolin-7-one (Compound 107);
9-Chloro-1-methyl-2-trifluoromethyl-3,6-dihydro-pyrrolo[3,2-f]quinolin-7-one (Compound 108);
9-Chloro-2-methyl-1-ethyl-3,6-dihydro-pyrrolo[3,2-f]quinolin-7-one (Compound 109);
9-Chloro-1-methyl-2-phenyl-3,6-dihydro-pyrrolo[3,2-f]quinolin-7-one (Compound 110);
9-Chloro-1-methyl-7-oxo-6,7-dihydro-3H-pyrrolo[3,2-f]quinoline-2-carboxylic acid ethyl ester (Compound 111);
9-Chloro-2-methyl-3,6-dihydro-pyrrolo[3,2-f]quinolin-7-one (Compound 112);
9-Chloro-1,2-tetramethylene-3,6-dihydro-pyrrolo[3,2-f]quinolin-7-one (Compound 113);

9-Chloro-1-methyl-3,6-dihydro-pyrrolo[3,2-f]quinolin-7-one (Compound 114);
9-Chloro-2-(4-methoxy-phenyl)-1-methyl-3,6-dihydro-pyrrolo[3,2-f]quinolin-7-one (Compound 115);
9-Chloro-2-(4-fluorophenyl)-1-methyl-3,6-dihydro-pyrrolo[3,2-f]quinolin-7-one (Compound 116);
9-Chloro-2-(2,4-difluorophenyl)-1-methyl-3,6-dihydro-pyrrolo[3,2-f]quinolin-7-one (Compound 117);
9-Chloro-2-(4-chlorophenyl)-1-methyl-3,6-dihydro-pyrrolo[3,2-f]quinolin-7-one (Compound 118);
9-Chloro-2-(2-fluorophenyl)-1-methyl-3,6-dihydro-pyrrolo[3,2-f]quinolin-7-one (Compound 119);
9-Chloro-1-methyl-2-thien-2-yl-3,6-dihydro-pyrrolo[3,2-f]quinolin-7-one (Compound 120);
2-Acetyl-9-chloro-1-methyl-3,6-dihydro-pyrrolo[3,2-f]quinolin-7-one (Compound 121);
(9-Chloro-2-methyl-7-oxo-6,7-dihydro-3H-pyrrolo[3,2-f]quinolin-1-yl)-acetic acid (Compound 122);
9-Chloro-1-ethyl-2-thien-2-yl-3,6-dihydro-pyrrolo[3,2-f]quinolin-7-one (Compound 123);
9-Chloro-2-methyl-1-propyl-3,6-dihydro-pyrrolo[3,2-f]quinolin-7-one (Compound 124);
9-Chloro-1-ethyl-2-phenyl-3,6-dihydro-pyrrolo[3,2-f]quinolin-7-one (Compound 125);
(±)-9-Chloro-3-(2,2,2-trifluoro-ethyl)-1,2-trimethylene-1,2,3,6-tetrahydro-pyrrolo[3,2-f]-quinolin-7-one (Compound 126);
(±)-9-Chloro-1,2-dimethyl-3-(2,2,2-trifluoro-ethyl)-1,2,3,6-tetrahydro-pyrrolo[3,2-f]-quinolin-7-one (Compound 127);
(±)-9-Chloro-2-ethyl-1-methyl-3-(2,2,2-trifluoro-ethyl)-1,2,3,6-tetrahydro-pyrrolo[3,2-f]-quinolin-7-one (Compound 128);
(±)-9-Chloro-1-ethyl-2-methyl-3-(2,2,2-trifluoro-ethyl)-1,2,3,6-tetrahydro-pyrrolo[3,2-f]-quinolin-7-one (Compound 129)
(±)-9-Chloro-1-methyl-2-phenyl-3-(2,2,2-trifluoro-ethyl)-1,2,3,6-tetrahydro-pyrrolo[3,2-f]-quinolin-7-one (Compound 130);
(±)-9-Chloro-2-methyl-3-(2,2,2-trifluoro-ethyl)-1,2,3,6-tetrahydro-pyrrolo[3,2-f]-quinolin-7-one (Compound 131);
(±)-9-Chloro-1-methyl-3-(2,2,2-trifluoro-ethyl)-1,2,3,6-tetrahydro-pyrrolo[3,2-f]-quinolin-7-one (Compound 132);
(±)-9-Chloro-1,2-tetramethylene-3-(2,2,2-trifluoro-ethyl)-1,2,3,6-tetrahydro-pyrrolo[3,2-f]-quinolin-7-one (Compound 133);
(t)-9-Chloro-3-ethyl-1-methyl-1,2,3,6-tetrahydro-pyrrolo[3,2-f]quinolin-7-one (Compound 134);
(±)-9-Chloro-1,2-dimethyl-3-ethyl-1,2,3,6-tetrahydro-pyrrolo[3,2-f]quinolin-7-one (Compound 135);
(±)-9-Chloro-1,2,3-trimethyl-1,2,3,6-tetrahydro-pyrrolo[3,2-f]quinolin-7-one (Compound 136);
(±)-9-Chloro-1,2-dimethyl-3-propyl-1,2,3,6-tetrahydro-pyrrolo[3,2-f]quinolin-7-one (Compound 137);
(±)-9-Chloro-3-(2-chloro-2,2-difluoro-ethyl)-1,2-dimethyl-1,2,3,6-tetrahydro-pyrrolo[3,2-f]-quinolin-7-one (Compound 138);
(±)-9-Chloro-1,2-dimethyl-3-(2-hydroxyethyl)-1,2,3,6-tetrahydro-pyrrolo[3,2-f]quinolin-7-one (Compound 139);
(±)-9-Chloro-1,2-dimethyl-1,2,3,6-tetrahydro-pyrrolo[3,2-f]quinolin-7-one (Compound 140);
(±)-9-Chloro-1,2-dimethyl-3-(2,2-dimethylpropyl)-1,2,3,6-tetrahydro-pyrrolo[3,2-f]-quinolin-7-one (Compound 141);
(±)-9-Chloro-1,2-dimethyl-3-(2-thien-2-yl-ethyl)-1,2,3,6-tetrahydro-pyrrolo[3,2-f]-quinolin-7-one (Compound 142);
(±)-9-Chloro-3-(2,2-difluoroethyl)-1,2-dimethyl-1,2,3,6-tetrahydro-pyrrolo[3,2-f]-quinolin-7-one (Compound 143);
(±)-9-Chloro-1,2-dimethyl-3-phenylmethyl-1,2,3,6-tetrahydro-pyrrolo[3,2-f]-quinolin-7-one (Compound 144);
(±)-9-Chloro-1,2-dimethyl-3-(3,3,3-trifluoropropyl)-1,2,3,6-tetrahydropyrrolo-[3,2-f]-quinolin-7-one (Compound 145);
(±)-9-Chloro-2-(3-chlorophenyl)-1-methyl-3-(2,2,2-trifluoroethyl)-1,2,3,6-tetrahydro-pyrrolo[3,2-f]quinolin-7-one (Compound 146);
(±)-9-Chloro-1-methyl-2-(4-trifluoromethyl-phenyl)-3-(2,2,2-trifluoroethyl)-1,2,3,6-tetrahydro-pyrrolo[3,2-f]quinolin-7-one (Compound 147);
(±)-9-Chloro-2-(4-methoxy-phenyl)-1-methyl-3-(2,2,2-trifluoroethyl)-1,2,3,6-tetrahydro-pyrrolo[3,2-f]quinolin-7-one (Compound 148);
(±)-9-Chloro-2-(4-fluoro-phenyl)-1-methyl-3-(2,2,2-trifluoroethyl)-1,2,3,6-tetrahydro-pyrrolo[3,2-f]quinolin-7-one (Compound 149);
(±)-9-Chloro-2-(2,4-difluorophenyl)-1-methyl-3-(2,2,2-trifluoroethyl)-1,2,3,6-tetrahydro-pyrrolo[3,2-f]quinolin-7-one (Compound 150);
(±)-9-Chloro-1,2-dimethyl-5-fluoro-3-(2,2,2-trifluoroethyl)-1,2,3,6-tetrahydro-pyrrolo[3,2-f]quinolin-7-one (Compound 151);
(±)-9-Chloro-2-(4-chlorophenyl)-1-methyl-3-(2,2,2-trifluoroethyl)-1,2,3,6-tetrahydropyrrolo[3,2-f]quinolin-7-one (Compound 152);
(±)-2-(3-Bromophenyl)-9-chloro-1-methyl-3-(2,2,2-trifluoroethyl)-1,2,3,6-tetrahydro-pyrrolo[3,2-f]quinolin-7-one (Compound 153);
(±)-9-Chloro-1-methyl-2-(3-nitrophenyl)-3-(2,2,2-trifluoroethyl)-1,2,3,6-tetrahydro-pyrrolo[3,2-f]quinolin-7-one (Compound 154);
(±)-9-Chloro-2-(4-hydroxyphenyl)-1-methyl-3-(2,2,2-trifluoroethyl)-1,2,3,6-tetrahydropyrrolo[3,2-f]quinolin-7-one (Compound 155);
(±)-9-Chloro-2-(2-fluorophenyl)-1-methyl-3-(2,2,2-trifluoroethyl)-1,2,3,6-tetrahydro-pyrrolo[3,2-f]quinolin-7-one (Compound 156);
(±)-9-Chloro-2-(3,4-dichlorophenyl)-1-methyl-3-(2,2,2-trifluoroethyl)-1,2,3,6-tetrahydropyrrolo[3,2-f]quinolin-7-one (Compound 157);
(±)-9-Chloro-2-(3,5-bis(trifluoromethyl)phenyl)-1-methyl-3-(2,2,2-trifluoroethyl)-1,2,3,6-tetrahydropyrrolo[3,2-f]quinolin-7-one (Compound 158);
(±)-9-Chloro-1-methyl-3-(2,2,2-trifluoroethyl)-2-(3-trifluoromethylphenyl)-1,2,3,6-tetrahydropyrrolo[3,2-f]quinolin-7-one (Compound 159);
(±)-9-Chloro-1-ethyl-2-phenyl-3-(2,2,2-trifluoroethyl)-1,2,3,6-tetrahydro-pyrrolo[3,2-f]quinolin-7-one (Compound 160);
(±)-9-Chloro-1-methyl-2-(thien-2-yl)-3-(2,2,2-trifluoroethyl)-1,2,3,6-tetrahydro-pyrrolo[3,2-f]quinolin-7-one (Compound 161);
(+)-9-Chloro-3-(2,2,2-trifluoro-ethyl)-1,2-trimethylene-1,2,3,6-tetrahydro-pyrrolo[3,2-f]quinolin-7-one (Compound 162);
(−)-9-Chloro-3-(2,2,2-trifluoro-ethyl)-1,2-trimethylene-1,2,3,6-tetrahydro-pyrrolo[3,2-f]quinolin-7-one (Compound 163);
(±)-9-Chloro-1-ethyl-2-(thien-2-yl)-3-(2,2,2-trifluoroethyl)-1,2,3,6-tetrahydro-pyrrolo[3,2-f]quinolin-7-one (Compound 164);
(±)-9-Chloro-2-methyl-1-propyl-3-(2,2,2-trifluoroethyl)-1,2,3,6-tetrahydro-pyrrolo[3,2-f]quinolin-7-one (Compound 165);

(±)-9-Chloro-2,3-diethyl-1-methyl-1,2,3,6-tetrahydro-pyrrolo[3,2-f]quinolin-7-one (Compound 166);
(±)-9-Chloro-1,2-dimethyl-3-(2,2,3,3,3-pentafluoropropyl)-1,2,3,6-tetrahydro-pyrrolo[3,2-f]quinolin-7-one (Compound 167);
(±)-9-Chloro-1,2-dimethyl-3-(2,2,3,3,4,4,4-heptafluorobutyl)-1,2,3,6-tetrahydro-pyrrolo[3,2-f]quinolin-7-one (Compound 168);
(±)-9-Chloro-1-methyl-2-phenyl-3-(3,3,3-trifluoropropyl)-1,2,3,6-tetrahydro-pyrrolo[3,2-f]-quinolin-7-one (Compound 169);
(±)-9-Chloro-2-ethyl-1-methyl-3-(3,3,3-trifluoropropyl)-1,2,3,6-tetrahydro-pyrrolo[3,2-f]-quinolin-7-one (Compound 170);
(±)-9-Chloro-1-methyl-3-(2,2,3,3,3-pentafluoropropyl)-2-phenyl-1,2,3,6-tetrahydro-pyrrolo[3,2-f]quinolin-7-one (Compound 171);
(±)-9-Chloro-1-methyl-2-phenyl-1,2,3,6-tetrahydro-pyrrolo[3,2-f]quinolin-7-one (Compound 172);
(±)-1,2-Dimethyl-3-(2,2,3,3,3-pentafluoropropyl)-9-trifluoromethyl-1,2,3,6-tetrahydro-pyrrolo[3,2-f]quinolin-7-one (Compound 173);
(±)-1,2-Dimethyl-9-trifluoromethyl-3-(3,3,3-trifluoropropyl)-1,2,3,6-tetrahydro-pyrrolo[3,2-f]quinolin-7-one (Compound 174);
(±)-3-(2-Chloro-2,2-difluoroethyl)-1,2-dimethyl-9-trifluoromethyl-1,2,3,6-tetrahydro-pyrrolo[3,2-f]quinolin-7-one (Compound 175);
(±)-9-Chloro-3-(2-Chloro-2,2-difluoroethyl)-2-ethyl-1-methyl-1,2,3,6-tetrahydro-pyrrolo[3,2-f]quinolin-7-one (Compound 176);
(±)-9-Chloro-2-ethyl-1-methyl-3-(2,2,3,3,3-pentafluoropropyl)-1,2,3,6-tetrahydro-pyrrolo[3,2-f]quinolin-7-one (Compound 177);
(±)-3-(2-Chloro-2,2-difluoroethyl)-2-ethyl-1-methyl-9-trifluoromethyl-1,2,3,6-tetrahydro-pyrrolo[3,2-f]quinolin-7-one (Compound 178);
(±)-2-Ethyl-1-methyl-3-(2,2,3,3,3-pentafluoropropyl)-9-trifluoromethyl-1,2,3,6-tetrahydro-pyrrolo[3,2-f]quinolin-7-one (Compound 179);
(±)-2-Ethyl-1-methyl-9-trifluoromethyl-3-(3,3,3-trifluoropropyl)-1,2,3,6-tetrahydro-pyrrolo[3,2-f]quinolin-7-one (Compound 180);
(±)-2-Ethyl-1-methyl-3-(4,4,4-trifluorobutyl)-9-trifluoromethyl-1,2,3,6-tetrahydro-pyrrolo[3,2-f]quinolin-7-one (Compound 181);
(±)-1,2-Dimethyl-3-(4,4,4-trifluorobutyl)-9-trifluoromethyl-1,2,3,6-tetrahydro-pyrrolo[3,2-f]quinolin-7-one (Compound 182);
9-Chloro-2-ethyl-1-methyl-3-(2,2,2-trifluoroethyl)-3,6-dihydro-pyrrolo[3,2-f]-quinolin-7-one (Compound 183);
9-Chloro-1,2-dimethyl-3-(2,2,2-trifluoroethyl)-3,6-dihydropyrrolo[3,2-f]quinolin-7-one (Compound 184);
9-Chloro-1-ethyl-2-methyl-3-(2,2,2-trifluoroethyl)-3,6-dihydro-pyrrolo[3,2-f]-quinolin-7-one (Compound 185);
9-Chloro-2-methyl-3-(2,2,2-trifluoroethyl)-3,6-dihydro-pyrrolo[3,2-f]quinolin-7-one (Compound 186);
9-Chloro-1-methyl-2-phenyl-3-(2,2,2-trifluoroethyl)-3,6-dihydro-pyrrolo[3,2-f]quinolin-7-one (Compound 187);
3-Benzyl-9-chloro-2-methyl-7-oxo-6,7-dihydro-3H-pyrrolo[3,2-f]quinoline-1-carbaldehyde (Compound 188);
9-Chloro-1,2-dimethyl-3-(2-thien-2-yl-ethyl)-3,6-dihydro-pyrrolo[3,2-f]quinolin-7-one (Compound 189);
9-Chloro-3-(2-hydroxy-ethyl)-1,2-dimethyl-3,6-dihydro-pyrrolo[3,2-f]quinolin-7-one (Compound 190);
9-Chloro-3-(2,2-difluoroethyl)-1,2-dimethyl-3,6-dihydro-pyrrolo[3,2-f]quinolin-7-one (Compound 191);
9-Chloro-3-(2-hydroxy-ethyl)-2-methyl-7-oxo-6,7-dihydro-3H-pyrrolo[3,2-f]-quinoline-1-carbaldehyde (Compound 192);
9-Chloro-3-ethyl-1-methyl-3,6-dihydro-pyrrolo[3,2-f]quinolin-7-one (Compound 193);
9-Chloro-2-(4-fluorophenyl)-1-methyl-3-(2,2,2-trifluoroethyl)-3,6-dihydro-pyrrolo[3,2-f]-quinolin-7-one (Compound 194);
9-Chloro-1,2-dimethyl-5-fluoro-3-(2,2,2-trifluoroethyl)-3,6-dihydro-pyrrolo[3,2-f]-quinolin-7-one (Compound 195);
9-Chloro-1,2-dimethyl-3-ethyl-3,6-dihydro-pyrrolo[3,2-f]quinolin-7-one (Compound 196);
9-Chloro-2-(4-methoxyphenyl)-1-methyl-3-(2,2,2-trifluoroethyl)-3,6-dihydro-pyrrolo[3,2-f]quinolin-7-one (Compound 197);
2-(3-Bromophenyl)-9-Chloro-1-methyl-3-(2,2,2-trifluoroethyl)-3,6-dihydropyrrolo-[3,2-f]-quinolin-7-one (Compound 198);
9-Chloro-2-(2-fluorophenyl)-1-methyl-3-(2,2,2-trifluoroethyl)-3,6-dihydro-pyrrolo[3,2-f]-quinolin-7-one (Compound 199);
9-Chloro-2-(2,4-difluorophenyl)-1-methyl-3-(2,2,2-trifluoroethyl)-3,6-dihydro-pyrrolo[3,2-f]quinolin-7-one (Compound 200);
9-Chloro-1-methyl-2-(3-trifluoromethylphenyl)-3-(2,2,2-trifluoroethyl)-3,6-dihydropyrrolo[3,2-f]quinolin-7-one (Compound 201);
9-Chloro-1-methyl-2-(4-trifluoromethylphenyl)-3-(2,2,2-trifluoroethyl)-3,6-dihydropyrrolo[3,2-f]quinolin-7-one (Compound 202);
9-Chloro-1-ethyl-2-phenyl-3-(2,2,2-trifluoroethyl)-3,6-dihydro-pyrrolo[3,2-f]-quinolin-7-one (Compound 203);
9-Chloro-1-methyl-2-(4-methylphenyl)-3-(2,2,2-trifluoroethyl)-3,6-dihydro-pyrrolo[3,2-f]-quinolin-7-one (Compound 204);
9-Chloro-1-methyl-2-(3-nitrophenyl)-3-(2,2,2-trifluoroethyl)-3,6-dihydropyrrolo-[3,2-f]-quinolin-7-one (Compound 205);
9-Chloro-2(4-chlorophenyl)-1-methyl-3-(2,2,2-trifluoroethyl)-3,6-dihydro-pyrrolo[3,2-f]-quinolin-7-one (Compound 206);
9-Chloro-1-methyl-2-thien-2-yl-3-(2,2,2-trifluoroethyl)-3,6-dihydro-pyrrolo[3,2-f]-quinolin-7-one (Compound 207);
9-Chloro-1,2,3-trimethyl-3,6-dihydro-pyrrolo[3,2-f]quinolin-7-one (Compound 208);
9-Chloro-1-ethyl-2-thien-2-yl-3-(2,2,2-trifluoroethyl)-3,6-dihydro-pyrrolo[3,2-f]quinolin-7-one (Compound 209);
9-Chloro-2-methyl-1-propyl-3-(2,2,2-trifluoroethyl)-3,6-dihydro-pyrrolo[3,2-f]-quinolin-7-one (Compound 210);
9-Chloro-1-methyl-3-(2,2,2-trifluoroethyl)-3,6-dihydro-pyrrolo[3,2-f]quinolin-7-one (Compound 211);
9-Chloro-3-(2-chloro-2,2-difluoroethyl)-1,2-dimethyl-3,6-dihydro-pyrrolo[3,2-f]-quinolin-7-one (Compound 212);
9-Chloro-1,2-dimethyl-3-(3,3,3-trifluoropropyl)-3,6-dihydro-pyrrolo[3,2-f]-quinolin-7-one (Compound 213);
9-Chloro-1,2-dimethyl-3-(2,2,3,3,4,4,4-heptafluorobutyl)-3,6-dihydropyrrolo[3,2-f]-quinolin-7-one (Compound 214);
9-Chloro-1,2-dimethyl-3-(2,2,3,3,3-pentafluoropropyl)-3,6-dihydropyrrolo[3,2-f]-quinolin-7-one (Compound 215);
9-Chloro-2-ethyl-1-methyl-3-(3,3,3-trifluoropropyl)-3,6-dihydropyrrolo[3,2-f]-quinolin-7-one (Compound 216);
9-Chloro-1-methyl-2-phenyl-3-(3,3,3-trifluoropropyl)-3,6-dihydropyrrolo[3,2-f]-quinolin-7-one (Compound 217);

9-Chloro-1-methyl-3-(2,2,3,3,3-pentafluoropropyl)-2-phenyl-3,6-dihydro-pyrrolo[3,2-f]-quinolin-7-one (Compound 218);
1,2-Dimethyl-3-(2,2,3,3,3-pentafluoropropyl)-9-trifluoromethyl-3,6-dihydro-pyrrolo[3,2-f]-quinolin-7-one (Compound 219);
1,2-Dimethyl-3-(2-chloro-2,2-difluoroethyl)-9-trifluoromethyl-3,6-dihydro-pyrrolo[3,2-f]-quinolin-7-one (Compound 220);
1,2-Dimethyl-9-trifluoromethyl-3-(3,3,3-trifluoropropyl)-3,6-dihydropyrrolo[3,2-f]-quinolin-7-one (Compound 221);
9-Chloro-3-(2-chloro-2,2-difluoroethyl)-2-ethyl-1-methyl-3,6-dihydropyrrolo[3,2-f]-quinolin-7-one (Compound 222);
9-Chloro-2-ethyl-1-methyl-3-(2,2,3,3,3-pentafluoropropyl)-3,6-dihydro-pyrrolo[3,2-f]-quinolin-7-one (Compound 223);
3-(2-Chloro-2,2-difluoroethyl)-2-ethyl-1-methyl-9-trifluoromethyl-3,6-dihydro-pyrrolo[3,2-f]quinolin-7-one (Compound 224);
2-Ethyl-1-methyl-3-(2,2,3,3,3-pentafluoropropyl)-9-trifluoromethyl-3,6-dihydro-pyrrolo[3,2-f]quinolin-7-one (Compound 225);
2-Ethyl-1-methyl-9-trifluoromethyl-3-(3,3,3-trifluoropropyl)-3,6-dihydro-pyrrolo[3,2-f]-quinolin-7-one (Compound 226);
1,2-Dimethyl-3-(4,4,4-trifluorobutyl)-9-trifluoromethyl-3,6-dihydropyrrolo[3,2-f]-quinolin-7-one (Compound 227);
2-Ethyl-1-methyl-3-(4,4,4-trifluorobutyl)-9-trifluoromethyl-3,6-dihydro-pyrrolo[3,2-f]-quinolin-7-one (Compound 228);
9-Chloro-1-methyl-3-(2,2,2-trifluoro-ethyl)-2-trifluoromethyl-3,6-dihydro-pyrrolo[3,2-f]-quinolin-7-one (Compound 229);
9-Chloro-2-hydroxymethyl-1-methyl-3-(2,2,2-trifluoroethyl)-3,6-dihydro-pyrrolo[3,2-f]-quinolin-7-one (Compound 230);
(±)-9-Chloro-1,2-dimethyl-3-(3,3,3-trifluoro-2-hydroxy-propyl)-3,6-dihydro-pyrrolo[3,2-f]-quinolin-7-one (Compound 231);
(±)-9-Chloro-2-ethyl-1-methyl-3-(3,3,3-trifluoro-2-hydroxy-propyl)-3,6-dihydro-pyrrolo[3,2-f]quinolin-7-one (Compound 232);
(±)-9-Chloro-1-methyl-3-(3,3,3-trifluoro-2-hydroxypropyl)-2-trifluoromethyl-3,6-dihydropyrrolo[3,2-f]quinolin-7-one (Compound 233);
1-Methyl-3-(2,2,2-trifluoro-ethyl)-2,9-bis-trifluoromethyl-3,6-dihydropyrrolo[3,2-f]-quinolin-7-one (Compound 234);
2-Hydroxymethyl-1-methyl-3-(2,2,2-trifluoro-ethyl)-9-trifluoromethyl-3,6-dihydro-pyrrolo[3,2-f]quinolin-7-one (Compound 235);
3-Allyl-1,2-dimethyl-9-trifluoromethyl-3,6-dihydro-pyrrolo[3,2-f]quinolin-7-one (Compound 236);
1,2-Dimethyl-3-(2-methyl-allyl)-9-trifluoromethyl-3,6-dihydropyrrolo[3,2-f]-quinolin-7-one (Compound 237);
1,2-Dimethyl-3-(2-methylprop-1-enyl)-9-trifluoromethyl-3,6-dihydro-pyrrolo[3,2-f]-quinolin-7-one (Compound 238);
3-(3-Hydroxy-3-methyl-butyl)-1,2-dimethyl-9-trifluoromethyl-3,6-dihydro-pyrrolo[3,2-f]-quinolin-7-one (Compound 239);
1,2-Dimethyl-3-(2-hydroxyethyl)-9-trifluoromethyl-3,6-dihydropyrrolo[3,2-f]-quinolin-7-one (Compound 240);
3-(2-Acetoxyethyl)-1,2-Dimethyl-9-trifluoromethyl-3,6-dihydropyrrolo[3,2-f]-quinolin-7-one (Compound 241);
1,2-Dimethyl-3-(prop-2-ynyl)-9-trifluoromethyl-3,6-dihydropyrrolo[3,2-f]-quinolin-7-one (Compound 242);
(±)-1,2-Dimethyl-3-(3,3,3-trifluoro-2-hydroxy-propyl)-9-trifluoromethyl-3,6-dihydro-pyrrolo[3,2-f]quinolin-7-one (Compound 243);
(+)-1,2-Dimethyl-3-(3,3,3-trifluoro-2-hydroxy-propyl)-9-trifluoromethyl-3,6-dihydro-pyrrolo[3,2-f]quinolin-7-one (Compound 244);
(−)-1,2-Dimethyl-3-(3,3,3-trifluoro-2-hydroxy-propyl)-9-trifluoromethyl-3,6-dihydro-pyrrolo[3,2-f]quinolin-7-one (Compound 245);
(±)-3-(3,3,3-Trifluoro-2-hydroxy-propyl)-9-trifluoromethyl-1,2-trimethylene-3,6-dihydro-pyrrolo[3,2-f]quinolin-7-one (Compound 246);
(±)-2-Ethyl-1-methyl-3-(3,3,3-Trifluoro-2-hydroxy-propyl)-9-trifluoromethyl-3,6-dihydro-pyrrolo[3,2-f]quinolin-7-one (Compound 247);
1,2-Dimethyl-3-(3-fluoropropyl)-9-trifluoromethyl-3,6-dihydropyrrolo[3,2-f]-quinolin-7-one (Compound 248);
1,2-Dimethyl-3-(3-hydroxypropyl)-9-trifluoromethyl-3,6-dihydropyrrolo[3,2-f]-quinolin-7-one (Compound 249);
3-(3-Acetoxypropyl)-1,2-dimethyl-9-trifluoromethyl-3,6-dihydropyrrolo[3,2-f]-quinolin-7-one (Compound 250);
and pharmaceutically acceptable salts and prodrugs thereof.

In certain embodiments, provided herein is a compound selected from:
9-Chloro-2-(3-fluorophenyl)-1-methyl-3-(2,2,2-trifluoroethyl)-3,6-dihydro-pyrrolo[3,2-f]quinolin-7-one (Compound 251);
9-Chloro-1-methyl-2-(1,3-thiazol-2-yl)-3-(2,2,2-trifluoroethyl)-3,6-dihydro-pyrrolo[3,2-f]quinolin-7-one (Compound 252);
9-Chloro-1-methyl-2-(3-pyridyl)-3-(2,2,2-trifluoroethyl)-3,6-dihydropyrrolo[3,2-f]quinolin-7-one (Compound 253);
9-Chloro-1-methyl-2-(4-pyridyl)-3-(2,2,2-trifluoroethyl)-3,6-dihydropyrrolo[3,2-f]quinolin-7-one (Compound 254);
9-Chloro-1-methyl-2-(pentafluoroethyl)-3-(2,2,2-trifluoroethyl)-3,6-dihydro-pyrrolo[3,2-f]quinolin-7-one (Compound 255);
9-Chloro-1-methyl-2-(5-methyl-2-furyl)-3-(2,2,2-trifluoroethyl)-3,6-dihydro-pyrrolo[3,2-f]quinolin-7-one (Compound 256);
9-Chloro-1-methyl-2-(2-oxazolyl)-3-(2,2,2-trifluoroethyl)-3,6-dihydropyrrolo[3,2-f]quinolin-7-one (Compound 257);
9-Chloro-1-methyl-2-(5-methyl-2-thiophenyl)-3-(2,2,2-trifluoroethyl)-3,6-dihydro-pyrrolo[3,2-f]quinolin-7-one (Compound 258);
9-Chloro-1-methyl-3-(2,2,3,3,3-pentafluoropropyl)-2-thiophen-2-yl-3,6-dihydro-pyrrolo[3,2-f]quinolin-7-one (Compound 259);
9-Chloro-1-methyl-3-(2,2,3,3,3-pentafluoropropyl)-2-(trifluoromethyl)-3,6-dihydropyrrolo[3,2-f]quinolin-7-one (Compound 260);
9-Chloro-1-methyl-2-(2-furyl)-3-(2,2,3,3,3-pentafluoropropyl)-3,6-dihydropyrrolo-[3,2-f]-quinolin-7-one; (Compound 261);
9-Chloro-1-methyl-3-(2,2,3,3,3-pentafluoropropyl)-2-(1,3-thiazol-2-yl)-3,6-dihydropyrrolo[3,2-f]quinolin-7-one (Compound 262);
9-Chloro-1-methyl-3-(2,2,3,3,3-pentafluoropropyl)-2-(4-pyridyl)-3,6-dihydro-pyrrolo[3,2-f]quinolin-7-one (Compound 263);
9-Chloro-1-methyl-3-(2,2,3,3,3-pentafluoropropyl)-2-(3-pyridyl)-3,6-dihydro-pyrrolo[3,2-f]quinolin-7-one (Compound 264);

9-Chloro-1-methyl-3-(2,2,3,3,3-pentafluoropropyl)-2-(2-pyridyl)-3,6-dihydro-pyrrolo[3,2-f]quinolin-7-one (Compound 265);
9-Chloro-1-methyl-2-(oxazol-2-yl)-3-(2,2,3,3,3-pentafluoropropyl)-3,6-dihydro-pyrrolo[3,2-f]quinolin-7-one (Compound 266);
9-Chloro-1-methyl-2-(5-methylfuran-2-yl)-3-(2,2,3,3,3-pentafluoropropyl)-3,6-dihydro-pyrrolo[3,2-f]quinolin-7-one (Compound 267);
9-Chloro-1-methyl-2-(5-methylthiophen-2-yl)-3-(2,2,3,3,3-pentafluoropropyl)-3,6-dihydro-pyrrolo[3,2-f]quinolin-7-one (Compound 268);
9-Chloro-1-(3-chloropropyl)-2-methyl-3-(2,2,3,3,3-pentafluoropropyl)-3,6-dihydro-pyrrolo[3,2-f]quinolin-7-one (Compound 269);
9-Chloro-1-(3-iodopropyl)-2-methyl-3-(2,2,3,3,3-pentafluoropropyl)-3,6-dihydro-pyrrolo[3,2-f]quinolin-7-one (Compound 270);
(S)-9-Chloro-1-methyl-2-phenyl-3-(3,3,3-trifluoro-2-hydroxy-propyl)-3,6-dihydro-pyrrolo[3,2-f]quinolin-7-one (Compound 271);
(S)-9-Chloro-1-methyl-2-thiophen-2-yl-3-(3,3,3-trifluoro-2-hydroxypropyl)-3,6-dihydro-pyrrolo[3,2-f]quinolin-7-one (Compound 272);
(S)-9-Chloro-1-methyl-2-(4-pyridyl)-3-(3,3,3-trifluoro-2-hydroxypropyl)-3,6-dihydropyrrolo[3,2-f]quinolin-7-one (Compound 273);
(S)-9-Chloro-1-methyl-2-(3-pyridyl)-3-(3,3,3-trifluoro-2-hydroxypropyl)-3,6-dihydro-pyrrolo[3,2-f]quinolin-7-one (Compound 274);
(S)-9-Chloro-1-methyl-2-(2-pyridyl)-3-(3,3,3-trifluoro-2-hydroxypropyl)-3,6-dihydro-pyrrolo[3,2-f]quinolin-7-one (Compound 275);
(S)-9-Chloro-1-methyl-2-(1,3-thiazol-2-yl)-3-(3,3,3-trifluoro-2-hydroxypropyl)-3,6-dihydropyrrolo[3,2-f]quinolin-7-one (Compound 276);
(S)-9-Chloro-2-(2-furyl)-1-methyl-3-(3,3,3-trifluoro-2-hydroxypropyl)-3,6-dihydropyrrolo[3,2-f]quinolin-7-one (Compound 277);
(R)-9-Chloro-1,2-dimethyl-3-(3,3,3-trifluoro-2-hydroxypropyl)-3,6-dihydro-pyrrolo[3,2-f]-quinolin-7-one (Compound 278);
rac-9-Chloro-1,2-dimethyl-3-(3,3,3-trifluoro-2-hydroxypropyl)-3,6-dihydro-pyrrolo[3,2-f]-quinolin-7-one (Compound 279);
9-Chloro-1-methyl-2-phenyl-3-(3,3,3-trifluoro-2-hydroxypropyl)-3,6-dihydro-pyrrolo[3,2-f]-quinolin-7-one (Compound 280);
(R)-9-Chloro-2-ethyl-1-methyl-3-(3,3,3-trifluoro-2-hydroxypropyl)-3,6-dihydro-pyrrolo[3,2-f]-quinolin-7-one (Compound 281);
(R)-9-Chloro-1-methyl-2-thiophen-2-yl-3-(3,3,3-trifluoro-2-hydroxy-propyl)-3,6-dihydropyrrolo[3,2-f]quinolin-7-one (Compound 282);
(R)-9-Chloro-1-methyl-2-(4-pyridyl)-3-(3,3,3-trifluoro-2-hydroxy-propyl)-3,6-dihydropyrrolo[3,2-f]quinolin-7-one (Compound 283);
(R)-9-Chloro-1-methyl-2-(5-methylfuran-2-yl)-3-(3,3,3-trifluoro-2-hydroxy-propyl)-3,6-dihydropyrrolo[3,2-f]quinolin-7-one (Compound 284);
(R)-9-Chloro-1-methyl-2-(5-methylthiophen-2-yl)-3-(3,3,3-trifluoro-2-hydroxy-propyl)-3,6-dihydropyrrolo[3,2-f]quinolin-7-one (Compound 285);
2-Ethyl-3-(3-hydroxypropyl)-1-methyl-3,6-dihydro-pyrrolo[3,2-f]quinolin-7-one (Compound 286);
9-Chloro-1,2-dimethyl-3-(3-hydroxypropyl)-3,6-dihydropyrrolo[3,2-f]quinolin-7-one (Compound 287);

3-(3-Bromopropyl)-1,2-dimethyl-9-trifluoromethyl-3,6-dihydropyrrolo[3,2-f]-quinolin-7-one (Compound 288);
1,2-Dimethyl-3-[3-(2-hydroxy-ethylamino)-propyl]-9-trifluoromethyl-3,6-dihydro-pyrrolo[3,2-f]quinolin-7-one (Compound 289);
9-Chloro-3-(2,3-dihydroxypropyl)-1,2-dimethyl-3,6-dihydropyrrolo[3,2-f]-quinolin-7-one (Compound 290);
(S)-9-Chloro-3-(2,3-dihydroxypropyl)-1,2-dimethyl-3,6-dihydropyrrolo[3,2-f]-quinolin-7-one (Compound 291);
(R)-9-Chloro-3-(2,3-dihydroxypropyl)-1,2-dimethyl-3,6-dihydropyrrolo[3,2-f]-quinolin-7-one (Compound 292);
3-(2,3-dihydroxypropyl)-1,2-dimethyl-9-trifluoromethyl-3,6-dihydropyrrolo[3,2-f]-quinolin-7-one (Compound 293);
3-(3-chloro-2-hydroxypropyl)-1,2-dimethyl-9-trifluoromethyl-3,6-dihydro-pyrrolo[3,2-f]-quinolin-7-one (Compound 294);
(S)-3-(2,3-dihydroxypropyl)-1,2-dimethyl-9-trifluoromethyl-3,6-dihydro-pyrrolo[3,2-f]-quinolin-7-one (Compound 295);
(R)-3-(2,3-dihydroxypropyl)-1,2-dimethyl-9-trifluoromethyl-3,6-dihydro-pyrrolo[3,2-f]-quinolin-7-one (Compound 296);
9-Chloro-3-(2,3-dihydroxypropyl)-2-ethyl-1-methyl-3,6-dihydropyrrolo[3,2-f]-quinolin-7-one (Compound 297);
3-{2-[2-(2-Hydroxy-ethoxy)-ethoxy]-ethyl}-1,2-dimethyl-9-trifluoromethyl-3,6-dihydropyrrolo[3,2-f]quinolin-7-one (Compound 298);

and pharmaceutically acceptable salts and prodrugs thereof.

Certain compounds provided herein can exist as stereoisomers including optical isomers. The present disclosure is intended to include all stereoisomers and both the racemic mixtures of such stereoisomers as well as the individual enantiomers that can be separated according to methods that are known in the art.

C. Preparation of the Compounds

In certain embodiments, of the compounds provided herein can be synthesized using the following synthesis schemes. In each of the Schemes the R groups correspond to the definitions described above.

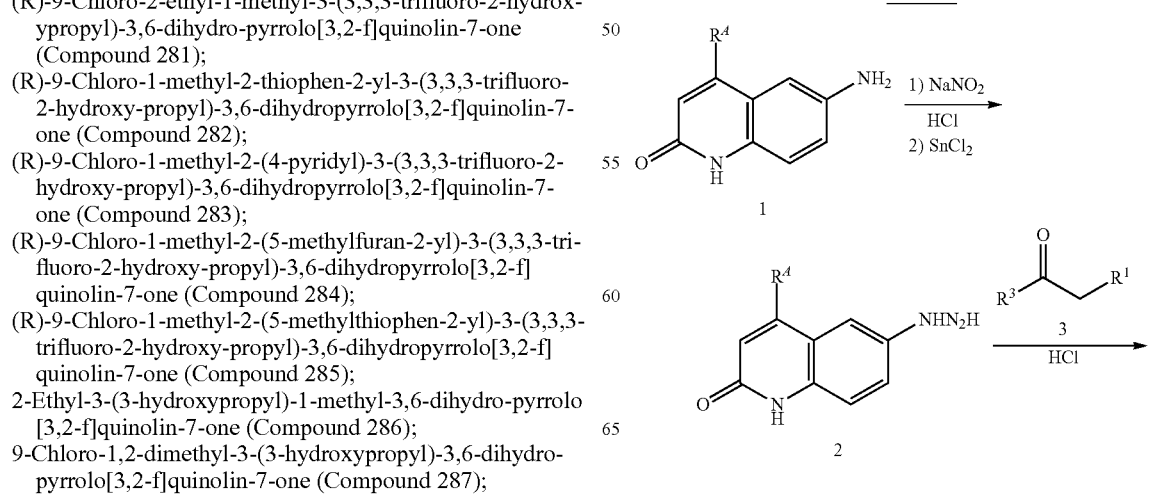

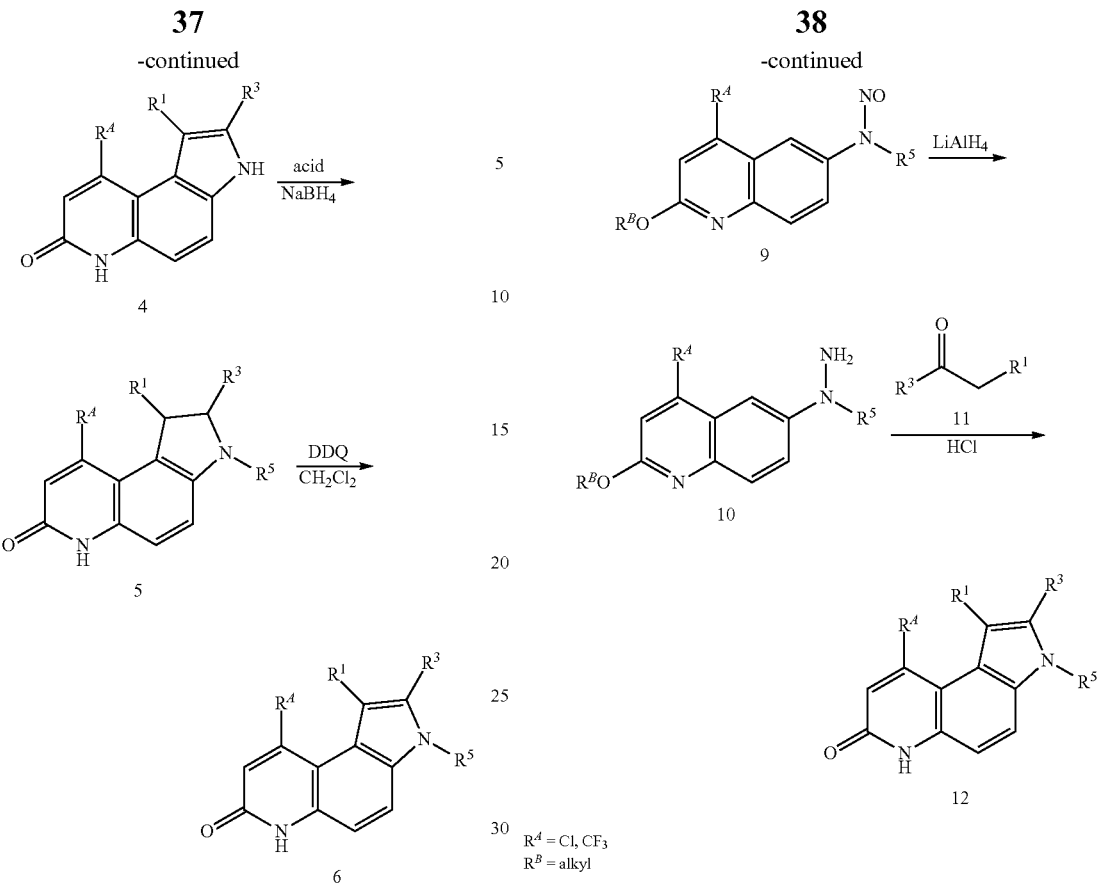

Scheme I describes the synthesis of angular and linear indole/indoline analogues of structure 6. Treatment of 6-amino-2-quinolinones of structure 1 with $NaNO_2$ in strongly acidic conditions such as concentrated HCl followed by reduction of the diazonium salt generates hydrazines of structure 2. Reaction of compound of structure 2 with a ketone such as structure 3 in acidic conditions affords pyrroloquinolinones of structures 4. Reductive alkylation of the indole nitrogen atom in structure 4 with an acid in the presence of a reducing agent such as $NaBH_4$ results in the formation of the reduced and alkylated products of structure 5. Oxidation of structure 5 provides analogues of structure 6.

Scheme II describes the synthesis of angular and linear indole/indoline analogues of structure 12. Treatment of protected 6-amino-2-quinolinones of structure 7 with alkylating agents generates alkylated amines of structure 8. Reaction of compound of structure 8 with $NaNO_2$ under acidic conditions affords the N-nitroso compounds of structure 9. Reduction of the N-nitroso compounds with $LiAlH_4$ generates hydrazines of structure 10. Treatment with a ketone such as structure 11 in acidic conditions affords pyrroloquinolinones of structures 12.

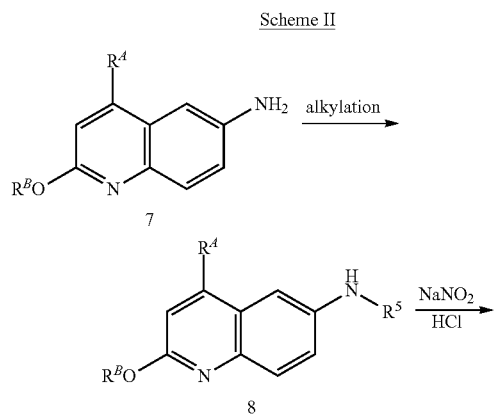

Scheme II

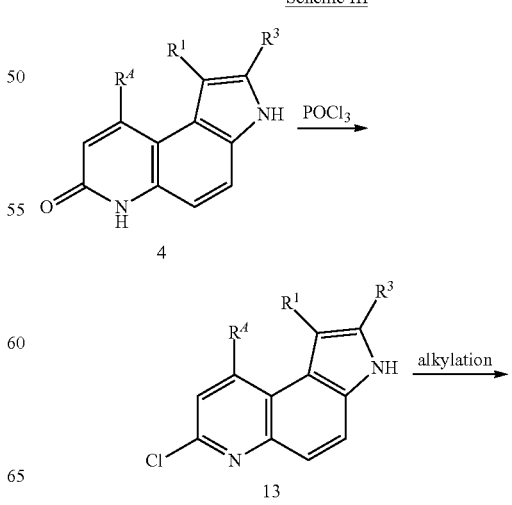

Scheme III

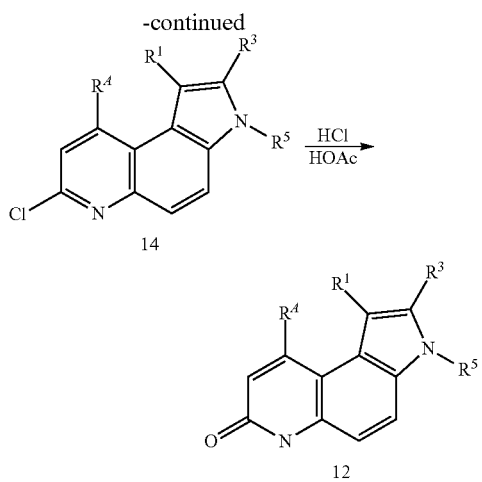

$R^4 = Cl, CF_3$

Scheme III describes another alternative synthetic route of compounds of structure 12. Treatment of the angular pyrroloquinolones of structure 4 with POCl₃ provides the chloroquinolines of structure 13. Alkylation of the intermediates 13 to introduce R⁵ gives products of structure 14. Hydrolysis of the chloroquinoline 14 generates final compounds of structure 12.

In certain embodiments, provided herein is a salt corresponding to any of the compounds provided herein. In certain embodiments, the salt corresponding to a selective androgen receptor modulator or selective androgen binding agent is provided herein. In certain embodiments, a salt is obtained by reacting a compound with an inorganic acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)-methylamine, and salts with amino acids such as arginine, lysine, etc.

In certain embodiments, one or more carbon atoms of a compound provided herein is replaced with silicon. See e.g., WO 03/037905A1; Tacke and Zilch, Endeavour, New Series, 10, 191-197 (1986); Bains and Tacke, Curr. Opin. Drug Discov. Devel. July:6(4):526-43 (2003). In certain embodiments, compounds provided herein including one or more silicon atoms possess certain desired properties, including, but not limited to, greater stability and/or longer half-life in a patient, when compared to the same compound in which none of the carbon atoms have been replaced with a silicon atom.

D. Formulation of Pharmaceutical Compositions

The pharmaceutical compositions provided herein include therapeutically effective amounts of one or more of the androgen receptor activity modulators provided herein that are useful in the prevention, treatment, or amelioration of one or more of the symptoms of diseases or disorders associated with androgen receptor activity. Such prevention, treatment, or amelioration of diseases or disorders include, but are not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteo-genesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neuro-degenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasias of the prostate (e.g., advanced metastatic prostate cancer) and malignant tumor cells including the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

The compositions include one or more compounds provided herein. The compounds are formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In certain embodiments, a pharmaceutical composition including one or more compounds provided herein is prepared using known techniques, including, but not limited to mixing, dissolving, granulating, dragee-making, levigating, emulsifying, encapsulating, entrapping or tabletting processes.

In the compositions, effective concentrations of one or more compounds or pharmaceutically acceptable derivatives is (are) mixed with a suitable pharmaceutical carrier or vehicle. The compounds can be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with androgen activity or in which androgen activity is implicated. Such prevention, treatment, or amelioration diseases or disorders include, but are not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasias of the prostate (e.g., advanced metastatic prostate cancer) and malignant tumor cells including the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds can be formulated as the sole pharmaceutically active ingredient in the composition or can be combined with other active ingredients. Liposomal suspensions, including tissue-targeted liposomes, such as tumor-targeted liposomes, can also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) can be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with androgen activity or in which androgen activity is implicated, as described herein.

The effective amount of a compound of provided herein can be determined by one of ordinary skill in the art, and includes exemplary dosage amounts for a mammal of from about 0.05 to 100 mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The active ingredient can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the compounds, compositions, methods and other subject matter provided herein.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with androgen receptor activity or in which androgen receptor activity is implicated, as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally in form of capsules, tablets, granules, powders or liquid formulations including syrups; parenterally, such as subcutaneously, intravenously, intramuscularly, with intersternal injection or infusion techniques (as sterile injectable aq. or non-aq. solutions or suspensions); nasally such as by inhalation spray; topically, such as in the form of a cream or ointment; rectally such as in the form of suppositories; liposomally; and locally. The compositions can be in liquid, semi-liquid or solid form and are formulated in a manner suitable for each route of administration. In certain embodiments, administration of the formulation include parenteral and oral modes of administration. In one embodiment, the compositions are administered orally.

In certain embodiments, the pharmaceutical compositions provided herein including one or more compounds provided herein is a solid (e.g., a powder, tablet, and/or capsule). In certain of such embodiments, a solid the pharmaceutical composition including one or more compounds provided herein is prepared using ingredients known in the art, including, but not limited to, starches, sugars, diluents, granulating agents, lubricants, binders, and disintegrating agents.

In certain embodiments, a pharmaceutical composition including one or more compounds provided herein is formulated as a depot preparation. Certain of such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition including one or more compounds provided herein includes a delivery system. Examples of delivery systems include, but are not limited to, liposomes and emulsions. Certain delivery systems are useful for preparing certain pharmaceutical compositions including those including hydrophobic compounds. In certain embodiments, certain organic solvents such as dimethylsulfoxide are used.

In certain embodiments, a pharmaceutical composition including one or more compounds provided herein includes one or more tissue-specific delivery molecules designed to deliver the pharmaceutical composition to specific tissues or cell types. For example, in certain embodiments, pharmaceutical compositions include liposomes coated with a tissue-specific antibody.

In certain embodiments, a pharmaceutical composition including one or more compounds provided herein includes a co-solvent system. Certain of such co-solvent systems include, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co solvent system, which is a solution of absolute ethanol including 3% w/v benzyl alcohol, 8% w/v of the nonpolar surfactant Polysorbate™, and 65% w/v polyethylene glycol 300. The proportions of such co solvent systems may be varied considerably without significantly altering their solubility and toxicity characteristics. Furthermore, the identity of co solvent components may be varied: for example, other surfactants may be used instead of Polysorbate™; the fraction size of polyethylene glycol may be varied; other biocompatible polymers may replace polyethylene glycol, e.g., polyvinyl pyrrolidine; and other sugars or polysaccharides may substitute for dextrose.

In certain embodiments, solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds can be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds can also be used in formulating effective pharmaceutical compositions.

In certain embodiments, a pharmaceutical composition including one or more compounds provided herein includes a sustained release system. A non-limiting example of such a sustained-release system is a semipermeable matrix of solid hydrophobic polymers. In certain embodiments, sustained release systems may, depending on their chemical nature, release compounds over a period of hours, days, weeks or months.

In certain embodiments, upon mixing or addition of the compound(s), the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions including suitable quantities of the compounds or pharmaceutically acceptable derivatives thereof. The pharmaceutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose includes a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can include along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia, gelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also include minor amounts of nontoxic auxiliary substances such as wetting agents, emulsifying agents, or solubilizing agents, pH buffering agents and the like, for example, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15$^{th}$ Edition, 1975. The composition or formulation to be administered will, in any event, include a quantity of the active compound in an amount sufficient to alleviate the symptoms of the treated subject.

Dosage forms or compositions including active ingredient in the range of 0.005% to 100% with the balance made up from non-toxic carrier can be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and micro-encapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions can include 0.001%-100% active ingredient, in one embodiment 0.1-85%, in another embodiment 75-95%.

In certain embodiments, the compounds can be administered in a form suitable for immediate release or extended release. Immediate release or extended release can be achieved with suitable pharmaceutical compositions or, particularly in the case of extended release, with devices such as subcutaneous implants or osmotic pumps. Exemplary compositions for topical administration include a topical carrier such as PLASTIBASE® (mineral oil gelled with polyethylene).

In certain embodiments, compounds used in the pharmaceutical compositions may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, the pharmaceutical compositions include a compound provided herein in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

The compositions can include other active compounds to obtain desired combinations of properties. The compounds provided herein, or pharmaceutically acceptable derivatives thereof as described herein, can also be advantageously administered for therapeutic or prophylactic purposes together with another pharmacological agent known in the general art to be of value in treating one or more of the diseases or medical conditions referred to hereinabove, such as diseases or disorders associated with androgen receptor activity or in which androgen receptor activity is implicated. It is to be understood that such combination therapy constitutes a further aspect of the compositions and methods of treatment provided herein.

In certain embodiments, a pharmaceutical composition including one or more compounds provided herein is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid including compound is the corresponding active form. In certain embodiments, a prodrug includes a short peptide (polyaminoacid) bound to an acid group. In certain of such embodiments, the peptide is metabolized to form the corresponding active form.

In certain embodiments, a pharmaceutical composition including one or more compounds provided herein is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical compositions are administered to achieve local rather than systemic exposures. For example, pharmaceutical compositions may be injected directly in the area of desired effect (e.g., in the renal or cardiac area). In certain embodiments in which the pharmaceutical composition is administered locally, the dosage regimen is adjusted to achieve a desired local concentration of a compound provided herein.

In certain embodiments, a pharmaceutical composition including one or more compounds provided herein is administered in the form of a dosage unit (e.g., tablet, capsule, bolus, etc.). In certain embodiments, such dosage units include a selective androgen receptor modulator in a dose from about 1 μg/kg of body weight to about 50 mg/kg of body weight. In certain embodiments, such dosage units include a selective androgen receptor modulator in a dose from about 2 μg/kg of body weight to about 25 mg/kg of body weight. In certain embodiments, such dosage units include a selective androgen receptor modulator in a dose from about 10 μg/kg of body weight to about 5 mg/kg of body weight. In certain embodiments, pharmaceutical compositions are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical composition.

In certain embodiments, a pharmaceutical composition provided herein is administered for a period of continuous therapy. For example, a pharmaceutical composition provided herein may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound provided herein at an amount sufficient to achieve a desired effect. In certain of such embodiments the plasma concentration is maintained above the minimal effective concentration (MEC). In certain embodiments, pharmaceutical compositions provided herein are administered with a dosage regimen designed to maintain a concentration above the MEC for 10-90% of the time, between 30-90% of the time, or between 50-90% of the time.

1. Compositions for Oral Administration

In certain embodiments, oral pharmaceutical dosage forms are either solid, gel or liquid. The solid dosage forms are tablets, capsules, granules, and bulk powders. Types of oral tablets include compressed, chewable lozenges and tablets which can be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms, preferably capsules or tablets. The tablets, pills, capsules, troches and the like can include any of the following ingredients, or compounds of a similar nature: a binder; a diluent; a disintegrating agent; a lubricant; a glidant; a sweetening agent; and a flavoring agent.

In certain embodiments, pharmaceutical compositions for oral administration are push fit capsules made of gelatin. Certain of such push fit capsules include one or more compounds provided herein in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more compounds provided are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

Examples of binders for use in the compositions provided herein include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, sodium alginate, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can include, in addition to material of the above type, a liquid carrier such as a fatty oil. In addition, dosage unit forms can include various other materials which modify the physical form of the dosage unit, for example, coatings of sugar and other enteric agents. The compounds can also be administered as a component of an elixir, suspension, syrup, wafer, sprinkle, chewing gum or the like. A syrup can include, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient can be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents can also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and can include a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, xanthan gum, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those including a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations can be coated as known by those of skill in the art in order to modify or sustain dissolution of the active ingredient. Thus, for example, they can be coated with a conventional enterically digestible coating, such as phenylsalicylate, waxes and cellulose acetate phthalate.

Exemplary compositions can include fast-dissolving diluents such as mannitol, lactose, sucrose, and/or cyclodextrins. Also included in such formulations can be high molecular weight excipients such as celluloses (AVICEL®), xanthan gum (KELTROL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers can also be added for ease of fabrication and use.

In certain of such embodiments, a pharmaceutical composition for oral administration is formulated by combining one or more compounds provided herein with one or more pharmaceutically acceptable carriers. Certain of such carriers enable compounds provided herein to be formulated as tablets, pills, dragees, capsules, liquids, gels, syrups, slurries, suspensions and the like, for oral ingestion by a patient. In certain embodiments, pharmaceutical compositions for oral use are obtained by mixing one or more compounds provided herein and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally include gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, a daily dosage regimen for a patient includes an oral dose of between 0.1 mg and 2000 mg of a compound provided herein. In certain embodiments, a daily dosage regimen is administered as a single daily dose. In certain embodiments, a daily dosage regimen is administered as two, three, four, or more than four doses.

2. Injectables, Solutions and Emulsions

In certain embodiments, the pharmaceutical composition is prepared for transmucosal administration. In certain of such embodiments penetrants appropriate to the barrier to be permeated are used in the formulation. Such penetrants are generally known in the art.

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol, mannitol, 1,3-butanediol, Ringer's solution, an isotonic sodium chloride solution or ethanol. In addition, if desired, the pharmaceutical compositions to be administered can also include minor amounts of non-toxic auxiliary substances such as wetting or emulsifying agents, pH buffering agents, stabilizers, solubility enhancers, and other such agents, such as for example, mono- or diglycerides, fatty acids, such as oleic acid, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound included in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions including thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, xanthan gum, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution including an active compound is an effective mode of administration. Another embodiment is a sterile aqueous or oily solution or suspension including an active material injected as necessary to produce the desired pharmacological effect.

Injectables are designed for local and systemic administration. Typically a therapeutically effective dosage is formulated to include a concentration of at least about 0.1% w/w up to about 90% w/w or more, preferably more than 1% w/w of the active compound to the treated tissue(s). The active ingredient can be administered at once, or can be divided into a number of smaller doses to be administered at intervals of time. It is understood that the precise dosage and duration of treatment is a function of the tissue being treated and can be determined empirically using known testing protocols or by extrapolation from in vivo or in vitro test data. It is to be noted that concentrations and dosage values can also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of formulations provided herein.

The compounds can be formulated in any suitable vehicle or form. For example, they can be in micronized or other suitable form and/or can be derivatized to produce a more soluble active product or to produce a prodrug or for other purposes. The form of the resulting mixture depends upon a number of factors, including, for example, an intended mode of administration and the solubility of the compound in the selected carrier or vehicle. The effective concentration is sufficient for ameliorating the symptoms of the condition and can be empirically determined.

In certain embodiments, a pharmaceutical composition is prepared for administration by injection wherein the pharmaceutical composition includes a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampules or in multi dose containers. Certain pharmaceutical compositions for injection are suspensions, solutions or emulsions in oily or aqueous vehicles, and may include formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may include substances that increase the viscosity of the suspension, such as sodium carboxymethyl cellulose, sorbitol, or dextran. Optionally, such suspensions may also include suitable stabilizers or agents that increase the solubility of the compounds to allow for the preparation of highly concentrated solutions.

In certain embodiments, the pharmaceutical composition is prepared for administration by inhalation. Certain of such pharmaceutical compositions for inhalation are prepared in the form of an aerosol spray in a pressurized pack or a nebulizer. Certain of such pharmaceutical compositions include a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations include a powder mixture of a compound provided herein and a suitable powder base such as lactose or starch.

In certain embodiments, the pharmaceutical compositions provided are administered by continuous intravenous infusion. In certain of such embodiments, from 0.1 mg to 500 mg of the composition is administered per day.

3. Lyophilized Powders

Of interest herein are also lyophilized powders, which can be reconstituted for administration as solutions, emulsions and other mixtures. They can also be reconstituted and formulated as solids or gels.

The sterile, lyophilized powder is prepared by dissolving a compound provided herein, or a pharmaceutically acceptable derivative thereof, in a suitable solvent. The solvent can include an excipient which improves the stability or other pharmacological component of the powder or reconstituted solution, prepared from the powder. Excipients that can be used include, but are not limited to, dextrose, sorbitol, fructose, corn syrup, xylitol, glycerin, glucose, sucrose or other suitable agent. The solvent can also include a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will include a single dosage 10-1000 mg, in one embodiment, 100-500 mg or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture can be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

In certain embodiments, the pharmaceutical compositions for inhalation are prepared in the form of an aerosol spray in a pressurized pack or a nebulizer. Certain of such pharmaceutical compositions include a propellant, e.g., dichlorodifluoromethane, trichlorofluoromethane, dichlorotetrafluoroethane, carbon dioxide or other suitable gas. In certain embodiments using a pressurized aerosol, the dosage unit can be determined with a valve that delivers a metered amount. In certain embodiments, capsules and cartridges for use in an inhaler or insufflator can be formulated. Certain of such formulations include a powder mixture of a compound provided herein and a suitable powder base such as lactose or starch.

Exemplary compositions for nasal aerosol or inhalation administration include solutions which can include, for example, benzyl alcohol or other suitable preservatives, absorption promoters to enhance absorption and/or bioavailability, and/or other solubilizing or dispersing agents such as those known in the art.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, can be formulated as 0.01%-10% isotonic solutions, pH about 5-7, with appropriate salts. In certain embodiments in which the compositions is administered locally, the dosage regimen is adjusted to achieve a desired local concentration of a compound provided herein.

In certain embodiments, the pharmaceutical composition is prepared for topical administration. Certain of such pharmaceutical compositions include bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for the pharmaceutical composition provided herein can be chosen in view of a particular patient's condition. (See e.g., Fingl et al. 1975, in "The Pharmacological Basis of Therapeutics", Ch. 1 p. 1). In certain embodiments, the pharmaceutical composition is administered as a single dose. In certain embodiments, a pharmaceutical composition is administered as a series of two or more doses administered over one or more days.

5. Compositions for Other Routes of Administration

Other routes of administration, such as topical application, transdermal patches, and rectal administration are also contemplated herein.

In certain embodiments, the pharmaceutical composition is prepared for topical administration such as rectal administration. The pharmaceutical dosage forms for rectal administration include, but are not limited to rectal suppositories, capsules and tablets for systemic effect. In certain embodiments, a pharmaceutical agent is prepared for rectal administration, such as a suppositories or retention enema. Certain of such pharmaceutical agents include known ingredients, such as cocoa butter and/or other glycerides. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases can be used. In certain embodiments, the pharmaceutical compositions include bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.). Agents to raise the melting point of suppositories include spermaceti and wax. Rectal suppositories can be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives can be packaged as articles of manufacture including packaging material, within the packaging material a compound or pharmaceutically acceptable derivative thereof provided herein, which is effective for modulating the activity of androgen receptor, or for treatment, prevention or amelioration of one or more symptoms of androgen receptor mediated diseases or disorders, or diseases or disorders in which androgen receptor activity is implicated, and a label that indicates that the compound or composition, or pharmaceutically acceptable derivative thereof, is used for modulating the activity of androgen receptor or for treatment, prevention or amelioration of one or more symptoms of androgen receptor mediated diseases or disorders, or diseases or disorders in which androgen receptor activity is implicated.

The articles of manufacture provided herein include packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which androgen receptor activity is implicated as a mediator or contributor to the symptoms or cause.

In certain embodiments, the pharmaceutical compositions can be presented in a pack or dispenser device which can include one or more unit dosage forms including a compound provided herein. The pack can for example include metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions including a compound provided herein formulated in a compatible pharmaceutical carrier can also be prepared, placed in an appropriate container, and labeled for treatment of an indicated condition.

E. Evaluation of the Activity of the Compounds

Standard physiological, pharmacological and biochemical procedures are available for testing the compounds provided herein to identify those that possess activity as androgen receptor modulators. In vitro and in vivo assays known in the art can be used to evaluate the activity of the compounds provided herein as androgen receptor modulators. Exemplary assays include, but are not limited to fluorescence polarization assay, luciferase assay, co-transfection assay. In certain embodiments, the compounds provided herein are capable of modulating activity of androgen receptor in a "co-transfection" assay (also called a "cis-trans" assay), which is known in the art. See e.g., Evans et al., *Science,* 240:889-95 (1988); U.S. Pat. Nos. 4,981,784 and 5,071,773; Pathirana et al., "Nonsteroidal Human Progesterone Receptor Modulators from the Marie Alga Cymopolia Barbata," *Mol. Pharm.* 47:630-35 (1995)). Modulating activity in a co-transfection assay has been shown to correlate with in vivo modulating activity. Thus, in certain embodiments, such assays are predictive of in vivo activity. See, e.g., Berger et al., *J. Steroid Biochem. Molec. Biol.* 41:773 (1992).

In certain co-transfection assays, two different co-transfection plasmids are prepared. In the first co-transfection plasmid, cloned cDNA encoding an intracellular receptor (e.g., androgen receptor) is operatively linked to a constitutive promoter (e.g., the SV 40 promoter). In the second co-transfection plasmid, cDNA encoding a reporter protein, such as firefly luciferase (LUC), is operatively linked to a promoter that is activated by a receptor-dependant activation factor. Both co-transfection plasmids are co-transfected into the same cells. Expression of the first co-transfection plasmid results in production of the intracellular receptor protein. Activation of that intracellular receptor protein (e.g., by binding of an agonist) results in production of a receptor-dependant activation factor for the promoter of the second co-transfection plasmid. That receptor-dependant activation factor in turn results in expression of the reporter protein encoded on the second co-transfection plasmid. Thus, reporter protein expression is linked to activation of the receptor. Typically, that reporter activity can be conveniently measured (e.g., as increased luciferase production).

Certain co-transfection assays can be used to identify agonists, partial agonists, and/or antagonists of intracellular receptors. In certain embodiments, to identify agonists, co-transfected cells are exposed to a test compound. If the test compound is an agonist or partial agonist, reporter activity is expected to increase compared to co-transfected cells in the absence of the test compound. In certain embodiments, to identify antagonists, the cells are exposed to a known agonist (e.g., androgen for the androgen receptor) in the presence and absence of a test compound. If the test compound is an antagonist, reporter activity is expected to decrease relative to that of cells exposed only to the known agonist.

In certain embodiments, compounds provided herein are used to detect the presence, quantity and/or state of receptors in a sample. In certain of such embodiments, samples are obtained from a patient. In certain embodiments, compounds are radio- or isotopically-labeled. For example, compounds provided herein that selectively bind androgen receptors may be used to determine the presence of such receptors in a sample, such as cell homogenates and lysates.

F. Methods of Use of the Compounds and Compositions

Methods of use of the compounds and compositions provided herein also are provided. The methods include in vitro and in vivo uses of the compounds and compositions for altering androgen receptor activity and for treatment, prevention, or amelioration of one or more symptoms of diseases or disorder that are modulated by androgen receptor activity, or in which androgen receptor activity, is implicated. In certain embodiments, provided herein are methods of treating a patient by administering a compound provided herein. In certain embodiments, such patient exhibits symptoms or signs of a androgen receptor mediated condition. In certain embodiments, a patient is treated prophylactically to reduce or prevent the occurrence of a condition.

The compounds provided herein can be used in the treatment of a variety of conditions including, but not limited to, maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olfaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colitis; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasias of the prostate (e.g., advanced metastatic prostate cancer) and malignant tumor cells including the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and pre-term labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength. The term treatment is also intended to include prophylactic treatment.

In certain embodiments, the compounds provided herein are used to treat acne, male-pattern baldness, wasting diseases, hirsutism, hypogonadism, osteoporoses, infertility, impotence, obesity, and cancer. In certain embodiments, one or more compounds provided herein are used to stimulate hematopoiesis. In certain embodiments, one or more compounds provided herein are used for contraception.

In certain embodiments, one or more compounds provided herein are used to treat cancer. Certain exemplary cancers include, but are not limited to, breast cancer, colorectal cancer, gastric carcinoma, glioma, head and neck squamous cell carcinoma, papillary renal carcinoma, leukemia, lymphoma, Li-Fraumeni syndrome, malignant pleural mesothelioma, melanoma, multiple myeloma, non-small cell lung cancer, synovial sarcoma, thyroid carcinoma, transitional cell carcinoma of urinary bladder, and prostate cancer, including, but not limited to prostatic hyperplasia.

In certain embodiments, one or more compounds provided herein are used to improve athletic performance. In certain such embodiments, one or more compounds provided herein are used, for example to shorten the time normally needed to recover from physical exertion or to increase muscle strength. Athletes to whom one or more compounds provided herein can be administered include, but are not limited to, horses, dogs, and humans. In certain embodiments, one or more compounds provided herein are administered to an athlete engaged in a professional or recreational competition, including, but not limited to weight-lifting, body-building, track and field events, and any of various team sports.

In certain embodiments, provided are methods for treating a patient by administering one or more selective androgen receptor agonists and/or partial agonists. Exemplary conditions that can be treated with such selective androgen receptor agonists and/or partial agonist include, but are not limited to, hypogonadism, wasting diseases, cancer cachexia, frailty, infertility, and osteoporosis. In certain embodiments, a selective androgen receptor agonist or partial agonist is used for male hormone replacement therapy. In certain embodiments, one or more selective androgen receptor agonists and/or partial agonists are used to stimulate hematopoiesis. In certain embodiments, a selective androgen receptor agonist or partial agonist is used as an anabolic agent. In certain embodiments, a selective androgen receptor agonist and/or partial agonist is used to improve athletic performance.

In certain embodiments, provided herein are methods for treating a patient by administering one or more selective androgen receptor antagonists and/or partial agonists. Exemplary conditions that may be treated with such one or more selective androgen receptor antagonists and/or partial agonists include, but are not limited to, hirsutism, acne, male-pattern baldness, prostatic hyperplasia, and cancer, including, but not limited to, various hormone-dependent cancers, including, without limitation, prostate and breast cancer.

G. Combination Therapies

In certain embodiments, one or more compounds or compositions provided herein can be co-administered with one or more other pharmaceutical agents. In certain embodiments, such one or more other pharmaceutical agents are designed to treat the same disease or condition as the one or more compounds or pharmaceutical compositions provided herein. In certain embodiments, such one or more other pharmaceutical agents are designed to treat a different disease or condition as the one or more compounds or compositions provided herein. In certain embodiments, such one or more other pharmaceutical agents are designed to treat an undesired effect of one or more compounds or compositions provided herein. In certain embodiments, one or more compounds or compositions provided herein is co-administered with another pharmaceutical agent to treat an undesired effect of that other pharmaceutical agent.

In certain embodiments, compounds or compositions provided herein and one or more other pharmaceutical agents are administered at the same time. In certain embodiments, compounds or compositions provided herein and one or more other pharmaceutical agents are administered at the different times. In certain embodiments, compounds or compositions provided herein and one or more other pharmaceutical agents are prepared together in a single formulation. In certain embodiments, compounds or compositions provided herein and one or more other pharmaceutical agents are prepared separately.

Examples of pharmaceutical agents that may be co-administered with compounds or compositions provided herein include, but are not limited to, analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In other embodiments, pharmaceutical agents that may be co-administered with compounds or compositions provided herein include, but are not limited to, other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phosphodiesterase inhibitors; protein tyrosine kinase inhibitors; thyroid mimetics (including thyroid receptor agonists); anabolic agents; HIV or AIDS therapies; therapies used in the treatment of Alzheimer's and other cognitive disorders; therapies used in the treatment of sleeping disorders; anti-proliferative agents; and anti-tumor agents.

EXAMPLES

The following examples, including experiments and results achieved, are provided for illustrative purposes only and are not to be construed as limiting the claimed subject matter.

Example 1

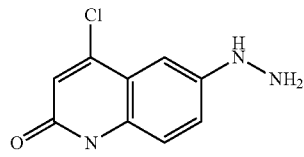 [SMILES: NNc1ccc2[nH]c(=O)cc(Cl)c2c1]

4-Chloro-6-hydrazino-quinolin-2(1H)-one
(Compound 104, Structure 2 of Scheme I, where
$R^A$=chloro)

In a 250 mL round bottomed flask a suspension of 6-amino-4-chloroquinolin-2(1H)-one (structure 1 of Scheme I, where $R^A$=chloro) (1.94 g, 10 mmol) in 10 mL conc. HCl was cooled to −1° C. and a solution of $NaNO_2$ (0.40 g, 12 mmol) in water (5 mL) was added dropwise over 20 min. The resulting dark yellow suspension was stirred at −1° C. for 2 hours and then a solution of $SnCl_2.2H_2O$ (5.2 g, 15 mmol) in concentrated HCl (10 mL) was added dropwise over 10 minutes. The resulting light yellow suspension of the hydrazine was stirred at −1° C. for 2 hours and then used directly or stored in a refrigerator at −1° C. until it was used (the crude compound can be stored for at least one month without decomposition).

Example 2

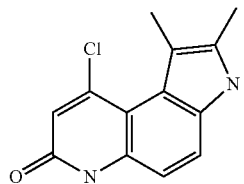 [SMILES: Cc1[nH]c2ccc3[nH]c(=O)cc(Cl)c3c2c1C]

9-Chloro-1,2-dimethyl-3,6-dihydro-pyrrolo[3,2-f]quinolin-7-one (Compound 105, Structure 4 of Scheme I, where $R^3=R^1$=methyl, $R^4$=chloro)

To the crude suspension of compound 104 (Example 1) (~0.4 M) in aqueous HCl was added a solution of a ketone (structure 3 of Scheme I) (2-5 eq.) in an equal volume of EtOH and the mixture was refluxed for 2 hours. Then the mixture was diluted with an equal volume of water while still hot and allowed to cool to room temperature. The resulting precipitate from that mixture was filtered and washed with water to give the indole as a mixture of regioisomers. The ratio of angular and linear isomers was determined by $^1$H NMR. The mixture of regioisomers could be separated by chromatography (Silica gel, hex/EtOAc 1:1 to 0:1 gradient). Spectra data for compound 105: $^1$H NMR (500 MHz, DMSO-$d_6$) δ 11.91 (s, 1H), 11.41 (s, 1H), 7.57 (d, J=8.6 Hz, 1H), 7.07 (d, J=8.6 Hz, 1H), 6.60 (s, 1H), 2.74 (q, J=7.6 Hz, 2H), 2.43 (s, 3H), 1.22 (t, J=7.6 Hz, 3H).

Example 3

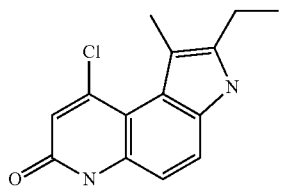 [SMILES: CCc1[nH]c2ccc3[nH]c(=O)cc(Cl)c3c2c1C]

9-Chloro-2-ethyl-1-methyl-3,6-dihydro-pyrrolo[3,2-f]quinolin-7-one (Compound 106, Structure 4 of Scheme I, where $R^4$=chloro, $R^1$=methyl, $R^3$=ethyl)

This compound was prepared using the method described in Example 2 from compound 104 and 2-butanone. Spectral data for compound 106: $^1$H NMR (500 MHz, DMSO-$d_6$) δ 11.91 (s, 1H), 11.44 (s, 1H), 7.55 (d, J=8.5 Hz, 1H), 7.06 (d, J=8.5 Hz, 1H), 6.60 (s, 1H), 2.42 (s, 3H), 2.35 (s, 3H).

Example 4

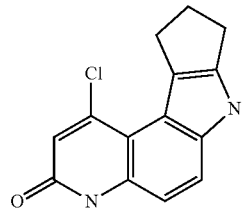 [SMILES: O=c1cc(Cl)c2c(ccc3[nH]c4c(c32)CCC4)[nH]1]

9-Chloro-1,2-trimethylene-3,6-dihydro-pyrrolo[3,2-f]quinolin-7-one (Compound 107, Structure 4 of Scheme I, where $R^4$=chloro, $R^1$, $R^3$=—CH$_2$CH$_2$CH$_2$—)

This compound was prepared using the method described in Example 2 from compound 104 and cyclopentanone. Spectral data for compound 107: $^1$H NMR (500 MHz, DMSO-$d_6$) δ 11.95 (s, 1H), 11.53 (s, 1H), 7.59 (d, J=8.8 Hz, 1H), 7.09 (d, J=8.8 Hz, 1H), 6.63 (s, 1H), 3.15 (t, J=7.2 Hz, 2H), 2.88 (t, J=7.2 Hz, 2H), 2.40 (qn, J=7.2 Hz, 2H).

Example 5

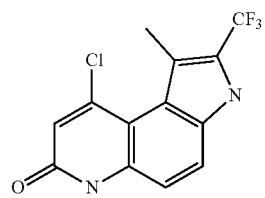 [SMILES: Cc1c(C(F)(F)F)[nH]c2ccc3[nH]c(=O)cc(Cl)c3c12]

9-Chloro-1-methyl-2-trifluoromethyl-3,6-dihydro-pyrrolo[3,2-f]quinolin-7-one (Compound 108, Structure 4 of Scheme I, where $R^4$=chloro, $R^1$=methyl, $R^3$=trifluoromethyl)

This compound was prepared using the method described in Example 2 from compound 104 and 1,1,1-trifluorobutan-2-one. Spectral data for compound 108: $^1$H NMR (500 MHz, DMSO-$d_6$) δ 12.61 (s, 1H), 12.17 (s, 1H), 7.73 (d, J=8.9 Hz, 1H), 7.35 (d, J=8.9 Hz, 1H), 6.74 (s, 1H), 2.61 (q, J=1.6 Hz, 3H).

Example 6

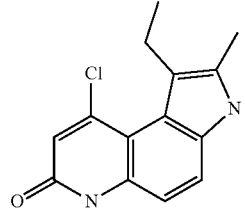 [SMILES: CCc1c(C)[nH]c2ccc3[nH]c(=O)cc(Cl)c3c12]

9-Chloro-2-methyl-1-ethyl-3,6-dihydro-pyrrolo[3,2-f]quinolin-7-one (Compound 109, Structure 4 of Scheme I, where $R^4$=chloro $R^1$=ethyl, $R^3$=methyl)

This compound was prepared using the method described in Example 2 from compound 104 and 2-pentanone. Spectral data for compound 109: $^1$H NMR (500 MHz, DMSO-d$_6$) δ 11.94 (s, 1H), 11.47 (s, 1H), 7.56 (d, J=8.5 Hz, 1H), 7.07 (d, J=8.5 Hz, 1H), 6.64 (s, 1H), 2.99 (q, J=7.3 Hz, 2H), 2.39 (s, 3H), 1.08 (t, J=7.3 Hz, 3H).

Example 7

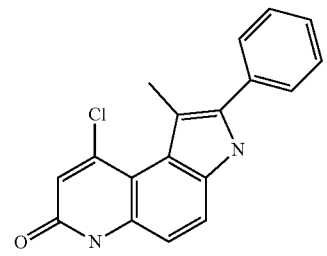 [SMILES: Cc1c(-c2ccccc2)[nH]c2ccc3[nH]c(=O)cc(Cl)c3c12]

9-Chloro-1-methyl-2-phenyl-3,6-dihydro-pyrrolo[3,2-f]quinolin-7-one (Compound 110, Structure 4 of Scheme I, where $R^4$=chloro, $R^1$=methyl, $R^3$=phenyl)

This compound was prepared using the method described in Example 2 from compound 104 and propiophenone. Spectral data for compound 110: $^1$H NMR (500 MHz, DMSO-d$_6$) δ 12.05 (s, 1H), 11.91 (s, 1H), 11.41 (s, 1H), 7.71 (d, J=8.3 Hz, 1H), 7.67 (d, J=7.3 Hz, 2H), 7.56 (t, J=7.8 Hz, 2H), 7.45 (t, J=7.3 Hz, 1H), 7.22 (d, J=8.8 Hz, 3H), 6.70 (s, 1H), 2.60 (s, 3H).

Example 8

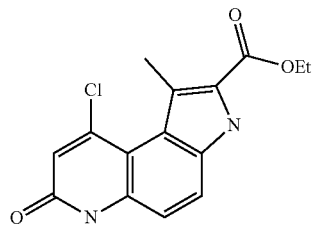 [SMILES: CCOC(=O)c1[nH]c2ccc3[nH]c(=O)cc(Cl)c3c2c1C]

9-Chloro-1-methyl-7-oxo-6,7-dihydro-3H-pyrrolo[3,2-f]quinoline-2-carboxylic acid ethyl ester (Compound 111, Structure 4 of Scheme I, where $R^4$=chloro, $R^1$=methyl, $R^3$=ethylcarboxylate)

This compound was prepared using the method described in Example 2 from compound 104 and 2-oxobutyric acid. Spectral data for compound 111: $^1$H NMR (500 MHz, DMSO-d$_6$) δ 12.23 (s, 1H), 12.19 (s, 1H), 11.41 (s, 1H), 7.76 (d, J=8.8 Hz, 1H), 7.36 (d, J=8.8 Hz, 1H), 6.75 (s, 1H), 4.40 (q, J=7.2 Hz, 2H), 2.80 (s, 3H), 1.38 (t, J=7.1 Hz, 3H).

Example 9

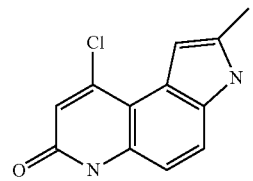 [SMILES: Cc1cc2c(ccc3[nH]c(=O)cc(Cl)c32)[nH]1]

9-Chloro-2-methyl-3,6-dihydro-pyrrolo[3,2-f]quinolin-7-one (Compound 112, Structure 4 of Scheme I, where $R^4$=chloro, $R^1$=H, $R^3$=methyl)

This compound was prepared using the method described in Example 2 from compound 104 and methylthioacetone. Spectral data for compound 112: $^1$H NMR (500 MHz, DMSO-d$_6$) δ 11.96 (s, 1H), 11.54 (s, 1H), 7.62 (d, J=8.3 Hz, 1H), 7.11 (d, J=8.3 Hz, 1H), 7.02 (s, 1H), 6.67 (s, 1H), 2.46 (s, 3H).

Example 10

9-Chloro-1,2-tetramethylene-3,6-dihydro-pyrrolo[3,2-f]quinolin-7-one (Compound 113, Structure 4 of Scheme I, where $R^4$=chloro, $R^1$, $R^3$=—CH$_2$CH$_2$CH$_2$CH$_2$—)

This compound was prepared using the method described in Example 2 from compound 104 and cyclohexanone. Spectral data for compound 113: $^1$H NMR (500 MHz, DMSO-d$_6$) δ 11.94 (s, 1H), 11.41 (s, 1H), 7.59 (d, J=8.3 Hz, 1H), 7.10 (d, J=8.3 Hz, 1H), 6.64 (s, 1H), 3.03 (t, J=5.8 Hz, 2H), 2.82 (t, J=5.8 Hz, 2H), 1.88-1.82 (m, 2H), 1.76-1.68 (m, 3H).

Example 11

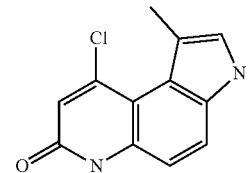 [SMILES: Cc1c[nH]c2ccc3[nH]c(=O)cc(Cl)c3c12]

9-Chloro-1-methyl-3,6-dihydro-pyrrolo[3,2-f]quinolin-7-one (Compound 114, Structure 4 of Scheme I, where $R^4$=chloro, $R^1$=methyl, $R^3$=H)

This compound was prepared using the method described in Example 2 from compound 104 and 1,1,1-trifluorobutan-2-one. Spectral data for compound 114: $^1$H NMR (500 MHz, DMSO-$d_6$) δ 12.62 (s, 1H), 12.20 (s, 1H), 7.76 (d, J=9.3 Hz, 1H), 7.37 (d, J=9.3 Hz, 1H), 6.77 (s, 1H), 2.64 (s, 3H).

Example 12

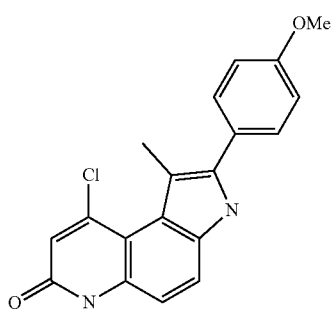 [SMILES: COc1ccc(-c2[nH]c3ccc4[nH]c(=O)cc(Cl)c4c3c2C)cc1]

9-Chloro-2-(4-methoxy-phenyl)-1-methyl-3,6-dihydro-pyrrolo[3,2-f]quinolin-7-one (Compound 115, Structure 4 of Scheme I, where $R^4$=chloro, $R^1$=methyl, $R^3$=4-methoxyphenyl)

This compound was prepared using the method described in Example 2 from compound 104 and 4-methoxypropiophenone. Spectral data for compound 115: $^1$H NMR (500 MHz, DMSO-$d_6$) δ 12.03 (s, 1H), 11.82 (s, 1H), 7.68 (d, J=8.8 Hz, 1H), 7.60 (d, J=8.8 Hz, 2H), 7.19 (d, J=8.8 Hz, 1H), 7.13 (d, J=8.8 Hz, 2H), 6.68 (s, 1H), 3.85 (s, 3H), 2.57 (s, 3H).

Example 13

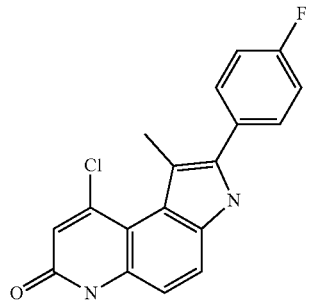 [SMILES: Cc1c(-c2ccc(F)cc2)[nH]c2ccc3[nH]c(=O)cc(Cl)c3c12]

9-Chloro-2-(4-fluorophenyl)-1-methyl-3,6-dihydro-pyrrolo[3,2-f]quinolin-7-one (Compound 116, Structure 4 of Scheme I, where $R^4$=chloro, $R^1$=methyl, $R^3$=4-fluorophenyl)

This compound was prepared using the method described in Example 2 from compound 104 and 4-fluoropropiophenone. Spectral data for compound 116: $^1$H NMR (500 MHz, DMSO-$d_6$) δ 12.06 (s, 1H), 11.93 (s, 1H), 7.70 (d, J=8.8 Hz, 2H), 7.69 (d, J=8.8 Hz, 1H), 7.41 (t, J=8.8 Hz, 2H), 7.22 (d, J=8.8 Hz, 1H), 6.70 (s, 1H), 2.57 (s, 3H).

Example 14

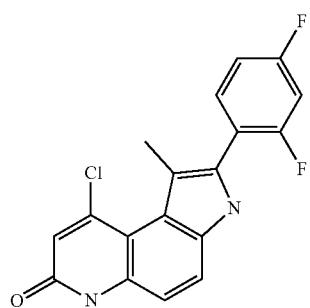 [SMILES: Cc1c(-c2ccc(F)cc2F)[nH]c2ccc3[nH]c(=O)cc(Cl)c3c12]

9-Chloro-2-(2,4-difluorophenyl)-1-methyl-3,6-dihydro-pyrrolo[3,2-f]quinolin-7-one (Compound 117, Structure 4 of Scheme I, where $R^4$ chloro, $R^1$=methyl, $R^3$=2,4-difluorophenyl)

This compound was prepared using the method described in Example 2 from compound 104 and 2,4-difluoropropiophenone. Spectral data for compound 117: $^1$H NMR (500 MHz, DMSO-$d_6$) δ 12.11 (s, 1H), 11.98 (s, 1H), 7.72 (d, J=8.8 Hz, 1H), 7.66 (td, J=8.5, 6.6 Hz, 1H), 7.50 (td, J=9.9, 2.5 Hz, 1H), 7.31 (td, J=8.5, 2.5 Hz, 1H), 7.25 (d, J=8.8 Hz, 1H), 6.72 (s, 1H), 2.44 (d, J=1.5 Hz, 3H).

Example 15

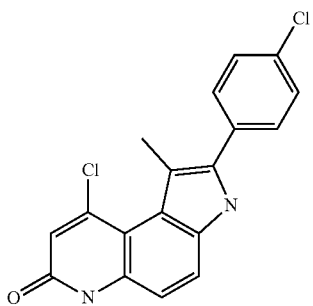 [SMILES: Cc1c(-c2ccc(Cl)cc2)[nH]c2ccc3[nH]c(=O)cc(Cl)c3c12]

9-Chloro-2-(4-chlorophenyl)-1-methyl-3,6-dihydro-pyrrolo[3,2-f]quinolin-7-one (Compound 118, Structure 4 of Scheme I, where $R^4$=chloro, $R^1$=methyl, $R^3$=4-chlorophenyl)

This compound was prepared using the method described in Example 2 from compound 104 and 4-chloropropiophenone. Spectral data for compound 118: $^1$H NMR (500 MHz, DMSO-$d_6$) δ 12.10 (s, 1H), 12.00 (s, 1H), 7.72 (d, J=8.8 Hz, 1H), 7.69 (d, J=8.8 Hz, 2H), 7.63 (d, J=8.8 Hz, 2H), 7.24 (d, J=8.8 Hz, 1H), 6.71 (s, 1H), 2.59 (s, 3H).

Example 16

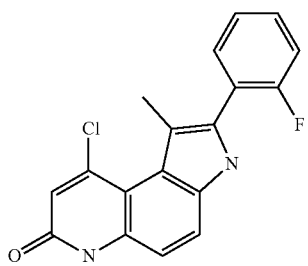 [SMILES: Cc1c(-c2ccccc2F)[nH]c2ccc3[nH]c(=O)cc(Cl)c3c12]

9-Chloro-2-(2-fluorophenyl)-1-methyl-3,6-dihydro-pyrrolo[3,2-f]quinolin-7-one (Compound 119, Structure 4 of Scheme I, where $R^4$=chloro, $R^1$=methyl, $R^3$=2-fluorophenyl)

This compound was prepared using the method described in Example 2 from compound 104 and 2-fluoropropiophenone. Spectral data for compound 119: $^1$H NMR (500 MHz, DMSO-$d_6$) δ 12.08 (s, 1H), 11.95 (s, 1H), 7.72 (d, J=8.8 Hz, 1H), 7.60 (m, 1H), 7.56 (m, 1H), 7.43 (m, 1H), 7.40 (m, 1H), 7.24 (d, J=8.8 Hz, 1H), 6.71 (s, 1H), 2.46 (d, J=2.0 Hz, 3H).

Example 17

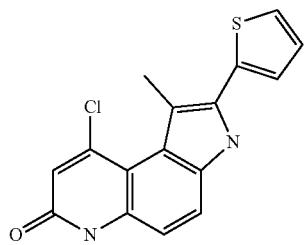 [SMILES: Cc1c(-c2cccs2)[nH]c2ccc3[nH]c(=O)cc(Cl)c3c12]

9-Chloro-1-methyl-2-thien-2-yl-3,6-dihydro-pyrrolo[3,2-f]quinolin-7-one (Compound 120, Structure 4 of Scheme I, where $R^4$=chloro, $R^1$=methyl, $R^3$=2-thienyl)

This compound was prepared using the method described in Example 2 from compound 104 and 2-propionylthiophene. Spectral data for compound 120: $^1$H NMR (500 MHz, DMSO-$d_6$) δ 12.06 (s, 1H), 11.96 (s, 1H), 7.73 (dd, J=5.0, 1.1 Hz, 1H), 7.69 (d, J=8.7 Hz, 1H), 7.49 (dd, J=3.5, 1.1 Hz, 1H), 7.27 (dd, J=5.0, 3.5 Hz, 1H), 7.22 (d, J=8.7 Hz, 1H), 6.70 (s, 1H), 2.67 (s, 3H).

Example 18

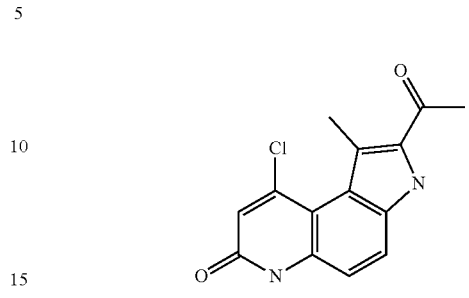

2-Acetyl-9-chloro-1-methyl-3,6-dihydro-pyrrolo[3,2-f]quinolin-7-one (Compound 121, Structure 4 of Scheme I, where $R^4$=chloro $R^1$=methyl, $R^3$=acetyl)

This compound was prepared using the method described in Example 2 from compound 104 and 2,3-pentanedione. Spectral data for compound 121: $^1$H NMR (500 MHz, DMSO-$d_6$) δ 12.19 (s, 2H), 7.77 (d, J=8.8 Hz, 1H), 7.37 (d, J=8.8 Hz, 1H), 6.75 (s, 1H), 2.79 (s, 3H), 2.63 (s, 3H).

Example 19

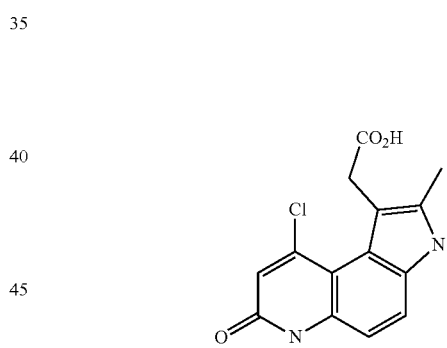

(9-Chloro-2-methyl-7-oxo-6,7-dihydro-3H-pyrrolo[3,2-f]quinolin-1-yl)-acetic acid (Compound 122, Structure 4 of Scheme I, where $R^4$=chloro, $R^1$=acetic acid, $R^3$=methyl)

This compound was prepared using the method described in Example 2 from compound 104 and 4-oxopentanoic acid. Spectral data for compound 122: $^1$H NMR (500 MHz, DMSO-$d_6$) δ 12.09 (s, 1H), 11.95 (s, 1H), 11.62 (s, 1H), 7.61 (d, J=8.6 Hz, 1H), 7.12 (d, J=8.6 Hz, 1H), 6.62 (s, 1H), 3.95 (s, 2H), 2.37 (s, 3H).

Example 20

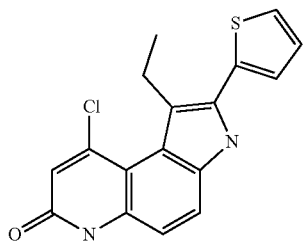 [SMILES: CCc1c(-c2cccs2)[nH]c2ccc3[nH]c(=O)cc(Cl)c3c12]

9-Chloro-1-ethyl-2-thien-2-yl-3,6-dihydro-pyrrolo[3,2-f]quinolin-7-one (Compound 123, Structure 4 of Scheme I, where $R^A$=chloro, $R^1$=ethyl, $R^3$=2-thienyl)

This compound was prepared using the method described in Example 2 from compound 104 and 2-butyroylthiophene. Spectral data for compound 123: $^1$H NMR (500 MHz, acetone-$d_6$) δ 11.19 (s, 1H), 11.03 (s, 1H), 7.75 (d, J=8.8 Hz, 1H), 7.63 (dd, J=5.1, 1.2 Hz, 1H), 7.41 (dd, J=3.7, 1.2 Hz, 1H), 7.32 (d, J=8.8 Hz, 1H), 7.22 (dd, J=5.1, 3.7 Hz, 1H), 6.73 (s, 1H), 3.38 (q, J=7.3 Hz, 2H), 1.13 (t, J=7.3 Hz, 3H).

Example 21

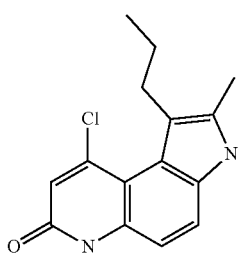 [SMILES: CCCc1c(C)[nH]c2ccc3[nH]c(=O)cc(Cl)c3c12]

9-Chloro-2-methyl-1-propyl-3,6-dihydro-pyrrolo[3,2-f]quinolin-7-one (Compound 124, Structure 4 of Scheme I, where $R^A$=chloro, $R^1$=propyl, $R^3$=methyl)

This compound was prepared using the method described in Example 2 from compound 104 and 2-hexanone. Spectral data for compound 124: $^1$H NMR (500 MHz, acetone-$d_6$) δ 11.02 (s, 1H), 10.63 (s, 1H), 7.63 (d, J=8.7 Hz, 1H), 7.17 (d, J=8.7 Hz, 1H), 6.65 (s, 1H), 3.03 (t, J=7.8 Hz, 2H), 2.47 (s, 3H), 1.58 (m, 2H), 1.19 (t, J=7.1 Hz, 3H).

Example 22

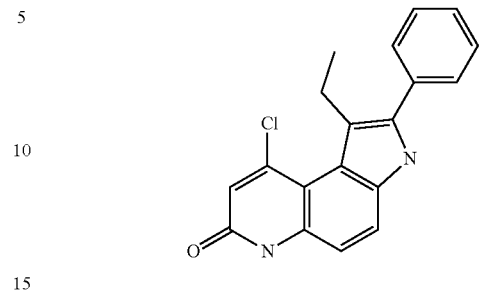

9-Chloro-1-ethyl-2-phenyl-3,6-dihydro-pyrrolo[3,2-f]quinolin-7-one (Compound 125, Structure 4 of Scheme I, where $R^A$=chloro, $R^1$=ethyl, $R^3$=phenyl)

This compound was prepared using the method described in Example 2 from compound 104 and 2-hexanone. Spectral data for compound 124: $^1$H NMR (500 MHz, DMSO-$d_6$) δ 12.06 (s, 1H), 11.86 (s, 1H), 7.69 (d, J=8.7 Hz, 1H), 7.61 (d, J=7.6 Hz, 2H), 7.56 (t, J=7.6 Hz, 2H), 7.47 (t, J=7.6 Hz, 1H), 7.21 (d, J=8.7 Hz, 1H), 6.72 (s, 1H), 3.19 (q, J=7.3 Hz, 2H), 0.98 (t, J=7.3 Hz, 3H).

Example 23

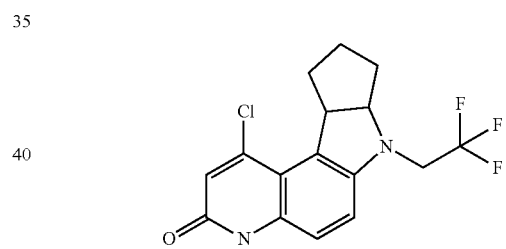

(±)-9-Chloro-3-(2,2,2-trifluoro-ethyl)-1,2-trimethylene-1,2,3,6-tetrahydro-pyrrolo[3,2-f]-quinolin-7-one (Compound 126, Structure 5 of Scheme I, where $R^A$=chloro, $R^1$, $R^3$=—$(CH_2)_3$—, $R^5$=2,2,2-trifluoroethyl)

To a solution of compound 107 (Example 4; 0.26 g, 1.0 mmol) in TFA (10 mL) in a 100 mL round bottomed flask was added a pellet (~0.75 g, 22 mmol) of NaBH$_4$. One more pellet of NaBH$_4$ was added after 30 minutes and the mixture was stirred at room temperature for 16 hours until the starting material was consumed. Water was carefully added (~50 mL) and the resulting yellow precipitate was filtered and washed with water. The yellow solid was purified by column chromatography (Silica gel, hex:EtOAc, 7:3) to give compound 126 (0.27 g, 79%) as a yellow solid: $^1$H NMR (500 MHz, acetone-$d_6$) δ 11.71 (s, 1H), 7.13 (d, J=8.8 Hz, 1H), 6.94 (d, J=8.8 Hz, 1H), 6.67 (s, 1H), 4.38 (td, J=8.9, 3.2 Hz, 1H), 4.28 (m, 1H), 4.02 (dq, J=16.4, 10.0 Hz, 1H), 3.94 (dq, J=16.4, 9.6 Hz, 1H), 2.14 (m, 1H), 2.01 (m, 1H), 1.73-1.58 (m, 3H), 1.44 (m, 1H).

Example 24

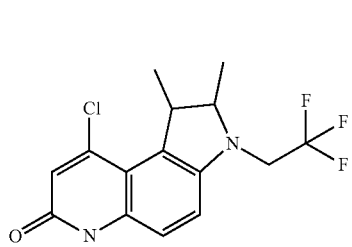 [SMILES: CC1c2c(ccc3[nH]c(=O)cc(Cl)c23)N(CC(F)(F)F)C1C]

(±)-9-Chloro-1,2-dimethyl-3-(2,2,2-trifluoro-ethyl)-1,2,3,6-tetrahydro-pyrrolo[3,2-f]quinolin-7-one (Compound 127, Structure 5 of Scheme I, where $R^4$=chloro, $R^1$=methyl, $R^3$=methyl, $R^5$=2,2,2-trifluoroethyl)

This compound was prepared using the method described in Example 23 from compound 105. Spectral data for compound 127: $^1$H NMR (500 MHz, acetone-$d_6$) δ 10.60 (s, 1H), 7.32 (d, J=8.8 Hz, 1H), 7.08 (d, J=8.8 Hz, 1H), 6.70 (s, 1H), 4.12-4.08 (m, 1H), 4.02-3.92 (m, 1H), 3.88-3.74 (m, 2H), 1.41 (d, J=6.8 Hz, 3H), 1.14 (d, J=6.8 Hz, 3H).

Example 25

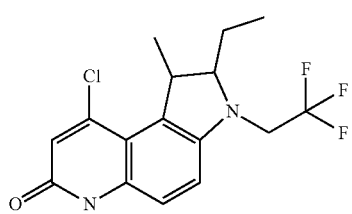 [SMILES: CCC1C(C)c2c(ccc3[nH]c(=O)cc(Cl)c23)N1CC(F)(F)F]

(±)-9-Chloro-2-ethyl-1-methyl-3-(2,2,2-trifluoro-ethyl)-1,2,3,6-tetrahydro-pyrrolo[3,2-f]quinolin-7-one (Compound 128, Structure 5 of Scheme I, where $R^4$=chloro, $R^1$=methyl, $R^3$=ethyl, $R^5$=2,2,2-trifluoroethyl)

This compound was prepared using the method described in Example 23 from compound 106. Spectral data for compound 128: $^1$H NMR (500 MHz, acetone-$d_6$) δ 10.64 (s, 1H), 7.31 (d, J=8.8 Hz, 1H), 7.08 (d, J=8.8 Hz, 1H), 6.68 (s, 1H), 4.22-4.16 (m, 1H), 4.02-3.92 (m, 1H), 3.88-3.78 (m, 1H), 3.50-3.46 (m, 1H), 2.03-1.95 (m, 1H), 1.79-1.69 (m, 1H), 1.14 (d, J=6.8 Hz, 3H), 1.07 (t, J=7.6 Hz, 3H).

Example 26

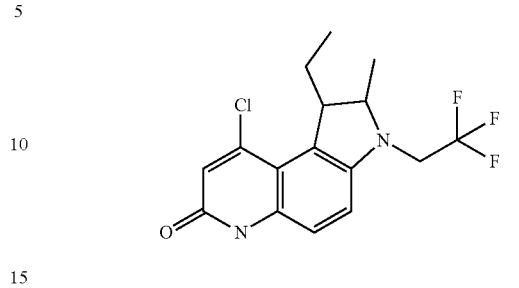

(±)-9-Chloro-1-ethyl-2-methyl-3-(2,2,2-trifluoro-ethyl)-1,2,3,6-tetrahydropyrrolo[3,2-f]-quinolin-7-one (Compound 129, Structure 5 of Scheme I, where $R^4$=chloro, $R^1$=ethyl, $R^3$=methyl, $R^5$=2,2,2-trifluoroethyl)

This compound was prepared using the method described in Example 23 from compound 109. Spectral data for compound 129: $^1$H NMR (500 MHz, acetone-$d_6$) δ 10.70 (s, 1H), 7.36 (d, J=8.3 Hz, 1H), 7.09 (d, J=8.3 Hz, 1H), 6.71 (s, 1H), 4.08-4.04 (m, 1H), 4.02-3.94 (m, 1H), 3.88-3.78 (m, 2H), 1.95-1.89 (m, 1H), 1.70-1.60 (m, 1H), 1.52 (d, J=6.4 Hz, 3H), 0.88 (t, J=7.1 Hz, 3H).

Example 27

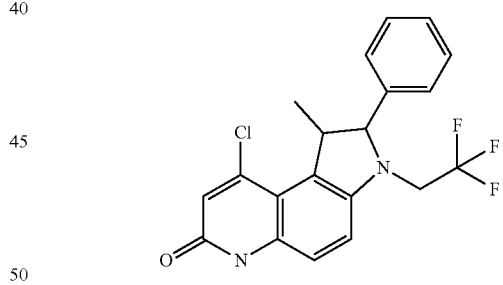

(±)-9-Chloro-1-methyl-2-phenyl-3-(2,2,2-trifluoro-ethyl)-1,2,3,6-tetrahydro-pyrrolo[3,2-f]-quinolin-7-one Compound 130 Structure 5 of Scheme I where $R^4$=chloro $R^1$=methyl, $R^3$=phenyl, $R^5$=2,2,2-trifluoroethyl)

This compound was prepared using the method described in Example 23 from compound 110. Spectral data for compound 130: $^1$H NMR (500 MHz, DMSO-$d_6$) δ 11.88 (s, 1H), 7.49-7.43 (m, 4H), 7.41-7.37 (m, 1H), 7.34 (d, J=8.8 Hz, 1H), 7.29 (d, J=8.8 Hz, 1H), 6.76 (s, 1H), 4.98 (d, J=7.80 Hz, 1H), 4.34-4.20 (m, 2H), 3.70-3.60 (m, 1H), 0.74 (d, J=6.8 Hz, 3H).

Example 28

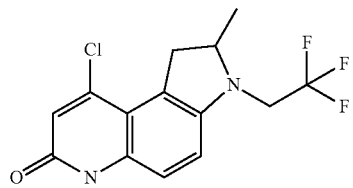 [SMILES: CC1Cc2c(ccc3[nH]c(=O)cc(Cl)c23)N1CC(F)(F)F]

(±)-9-Chloro-2-methyl-3-(2,2,2-trifluoro-ethyl)-1,2,3,6-tetrahydropyrrolo[3,2-f]quinolin-7-one (Compound 131, Structure 5 of Scheme I, where $R^4$=chloro, $R^1$=hydrogen, $R^3$=methyl, $R^5$=2,2,2-trifluoroethyl)

This compound was prepared using the method described in Example 23 from compound 112. Spectral data for compound 131: $^1$H NMR (500 MHz, acetone-$d_6$) δ 10.70 (s, 1H), 7.31 (d, J=8.8 Hz, 1H), 7.04 (d, J=8.8 Hz, 1H), 6.67 (s, 1H), 4.04 (dd, J=16.6 Hz, 9.3 Hz, 1H), 3.98-3.88 (m, 2H), 3.95 (dd, J=9.8 Hz, 1.5 Hz, 1H), 3.16 (ddd, J=16.6 Hz, 9.8 Hz, 1.0 Hz, 1H), 1.45 (d, J=5.9 Hz, 3H).

Example 29

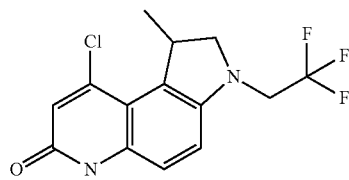 [SMILES: CC1CN(CC(F)(F)F)c2ccc3[nH]c(=O)cc(Cl)c3c21]

(±)-9-Chloro-1-methyl-3-(2,2,2-trifluoro-ethyl)-1,2,3,6-tetrahydro-pyrrolo[3,2-f]quinolin-7-one (Compound 132, Structure 5 of Scheme I, where $R^4$=chloro, $R^1$=methyl, $R^3$=hydrogen, $R^5$=2,2,2-trifluoroethyl)

This compound was prepared using the method described in Example 23 from compound 114. Spectral data for compound 132: $^1$H NMR (500 MHz, DMSO-$d_6$) δ 11.80 (s, 1H), 7.22 (d, J=8.8 Hz, 1H), 7.16 (d, J=8.8 Hz, 1H), 6.64 (s, 1H), 4.29-4.20 (m, 1H), 4.16-4.10 (m, 1H), 3.86-3.76 (m, 1H), 3.52 (t, J=8.3 Hz, 1H), 3.41 (d, J=8.3 Hz, 3H), 1.22 (d, J=6.8 Hz, 3H).

Example 30

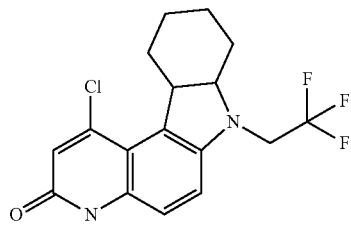 [SMILES: O=c1cc(Cl)c2c3c(ccc2[nH]1)N(CC(F)(F)F)C1CCCCC31]

(±)-9-Chloro-1,2-tetramethylene-3-(2,2,2-trifluoro-ethyl)-1,2,3,6-tetrahydro-pyrrolo[3,2-f]quinolin-7-one (Compound 133, Structure 5 of Scheme I, where $R^4$=chloro, $R^1$, $R^3$=—CH$_2$CH$_2$CH$_2$CH$_2$—, $R^5$=2,2,2-trifluoroethyl)

This compound was prepared using the method described in Example 23 from compound 113. Spectral data for compound 133: $^1$H NMR (500 MHz, acetone-$d_6$) δ 11.00 (s, 1H), 7.92 (d, J=9.3 Hz, 1H), 7.36 (d, J=9.3 Hz, 1H), 6.72 (s, 1H), 5.17 (q, J=9.3 Hz, 2H), 4.12-4.04 (m, 1H), 4.00-3.92 (m, 1H), 3.15 (t, J=6.1 Hz, 2H), 2.96 (t, J=6.1 Hz, 2H), 2.02 (m, 2H), 1.80 (m, 2H).

Example 31

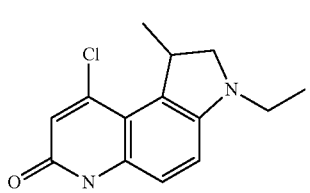 [SMILES: CCN1CC(C)c2c1ccc1[nH]c(=O)cc(Cl)c21]

(±)-9-Chloro-3-ethyl-1-methyl-1,2,3,6-tetrahydro-pyrrolo[3,2-f]quinolin-7-one (Compound 134, Structure 5 of Scheme I, where $R^4$=chloro, $R^1$=methyl, $R^3$=hydrogen, $R^5$=ethyl)

This compound was prepared using the method described in Example 23 from compound 114 and acetic acid. Spectral data for compound 134: $^1$H NMR (500 MHz, acetone-$d_6$) δ 10.72 (s, 1H), 7.29 (d, J=8.3 Hz, 1H), 6.98 (d, J=8.3 Hz, 1H), 6.67 (s, 1H), 4.08-3.98 (m, 2H), 3.72-3.66 (m, 1H), 3.47 (dq, 7.3, 14.6 Hz, 1H), 3.22 (dq, 7.3, 14.6 Hz, 1H), 1.14 (d, J=6.3 Hz, 3H), 1.04 (t, J=7.3 Hz, 3H).

Example 32

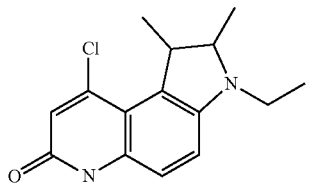 [SMILES: CCN1c2ccc3[nH]c(=O)cc(Cl)c3c2C(C)C1C]

(±)-9-Chloro-1,2-dimethyl-3-ethyl-1,2,3,6-tetrahydro-pyrrolo[3,2-f]quinolin-7-one (Compound 135, Structure 5 of Scheme I, where $R^4$=chloro, $R^1$=methyl, $R^3$=methyl, $R^5$=ethyl)

This compound was prepared using the method described in Example 23 from compound 105 and acetic acid. Spectral data for compound 135: $^1$H NMR (500 MHz, acetone-$d_6$) δ 10.72 (s, 1H), 7.28 (d, J=8.3 Hz, 1H), 6.98 (d, J=8.3 Hz, 1H), 6.67 (s, 1H), 4.04 (dq, J=14.2 Hz, 7.0 Hz, 1H), 3.69 (dq, J=14.2 Hz, 7.0 Hz, 1H), 3.46 (dq, J=15.1 Hz, 7.3 Hz, 1H), 3.22 (dq, J=15.1 Hz, 7.3 Hz, 1H), 1.35 (d, J=6.4 Hz, 3H), 1.14 (d, J=6.4 Hz, 3H), 1.05 (t, J=7.1 Hz, 3H).

Example 33

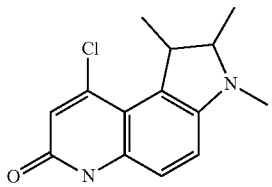 [SMILES: CC1c2c(ccc3[nH]c(=O)cc(Cl)c23)N(C)C1C]

(±)-9-Chloro-1,2,3-trimethyl-1,2,3,6-tetrahydro-pyrrolo[3,2-f]quinolin-7-one (Compound 136, Structure 5 of Scheme I, where $R^4$=chloro, $R^1$=$R^3$=$R^5$=methyl)

This compound was prepared using the method described in Example 23 from compound 105 and formic acid. Spectral data for compound 136: $^1$H NMR (500 MHz, CDCl$_3$) δ 12.56 (s, 1H), 7.31 (d, J=8.3 Hz, 1H), 6.90 (d, J=8.3 Hz, 1H), 6.87 (s, 1H), 4.04 (dq, J=14.2 Hz, 7.0 Hz, 1H), 3.32 (dq, J=J=14.2 Hz, 7.0 Hz, 1H), 2.74 (s, 3H), 1.38 (d, J=6.8 Hz, 3H), 1.18 (d, J=6.8 Hz, 3H).

Example 34

(±)-9-Chloro-1,2-dimethyl-3-propyl-1,2,3,6-tetrahydro-pyrrolo[3,2-f]quinolin-7-one (Compound 137, Structure 5 of Scheme I, where $R^4$=chloro, $R^1$=$R^3$=methyl, $R^5$=propyl)

This compound was prepared using the method as described in Example 23 from compound 105 and propionic acid. Spectral data for compound 137: $^1$H NMR (500 MHz, CDCl$_3$) δ 12.16 (s, 1H), 7.22 (d, J=8.8 Hz, 1H), 6.84 (s, 1H), 6.82 (d, J=8.8 Hz, 1H), 4.04 (dq, J=14.2 Hz, 7.0 Hz, 1H), 3.67 (dq, J=14.2 Hz, 7.0 Hz, 1H), 3.22-3.14 (m, 1H0, 3.10-3.02 (m, 1H), 1.60-1.46 (m, 2H), 1.35 (d, J=6.4 Hz, 1H), 1.16 (d, J=6.4 Hz, 3H), 0.98 (t, J=7.1 Hz, 3H).

Example 35

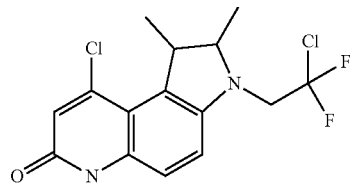 [SMILES: CC1c2c(ccc3[nH]c(=O)cc(Cl)c23)N(CC(F)(F)Cl)C1C]

(±)-9-Chloro-3-(2-chloro-2,2-difluoro-ethyl)-1,2-dimethyl-1,2,3,6-tetrahydro-pyrrolo[3,2-f]-quinolin-7-one (Compound 138, Structure 5 of Scheme I, where $R^4$=chloro, $R^1$=$R^3$=methyl, $R^5$=2-chloro-2,2-difluoroethyl)

This compound was prepared using the method described in Example 23 from compound 105 and chlorodifluoroacetic acid. Spectral data for compound 138: $^1$H NMR (500 MHz, DMSO-$d_6$) δ 11.79 (s, 1H), 7.20 (d, J=8.8 Hz, 1H), 7.08 (d, J=8.8 Hz, 1H), 6.72 (s, 1H), 4.17 (m, 1H), 4.02-3.90 (m, 2H), 3.72 (qn, J=6.7 Hz, 1H), 1.31 (d, J=6.7 Hz, 3H), 1.04 (d, J=6.7 Hz, 3H).

Example 36

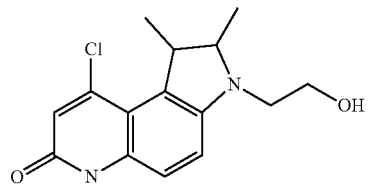 [SMILES: CC1c2c(ccc3[nH]c(=O)cc(Cl)c23)N(CCO)C1C]

(±)-9-Chloro-1,2-dimethyl-3-(2-hydroxyethyl)-1,2,3,6-tetrahydro-pyrrolo[3,2-f]-quinolin-7-one (Compound 139, Structure 5 of Scheme I, where $R^4$=chloro, $R^1$=methyl, $R^3$=methyl, $R^5$=2-hydroxyethyl)

This compound was prepared using the method described in Example 23 from compound 105 and 2-hydroxyacetic acid. Spectral data for compound 139: $^1$H NMR (500 MHz, acetone-$d_6$) δ 12.40 (s, 1H), 7.28 (d, J=8.8 Hz, 1H), 6.91 (d, J=8.8 Hz, 1H), 6.87 (s, 1H), 4.38 (dt, J=5.9, 2.0 Hz, 2H), 4.10-4.03 (dq, J=6.4, 6.8 Hz, 1H), 4.04 (s, 1H), 3.76-3.70 (dq, J=6.4, 6.8 Hz, 1H), 3.54-3.48 (dt, J=5.9, 15.6 Hz, 1H), 3.44-3.38 (dt, J=5.9, 15.6 Hz, 1H), 1.38 (d, J=6.3 Hz, 3H), 1.15 (d, J=6.3 Hz, 3H).

Example 37

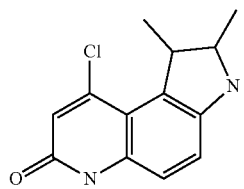 [SMILES: CC1Nc2ccc3[nH]c(=O)cc(Cl)c3c2C1C]

(±)-9-Chloro-1,2-dimethyl-1,2,3,6-tetrahydro-pyrrolo[3,2-f]quinolin-7-one (Compound 140, Structure 5 of Scheme I, where $R^A$=chloro, $R^1$=$R^3$=methyl, $R^5$=hydrogen)

This compound was prepared using the method described in Example 23 from compound 105, and isolated as a byproduct. Spectral data for compound 140: $^1$H NMR (500 MHz, CDCl$_3$) δ 10.60 (s, 1H), 7.08 (d, J=8.8 Hz, 1H), 6.99 (d, J=8.8 Hz, 1H), 6.87 (s, 1H), 4.04 (dq, J=14.2 Hz, 7.0 Hz, 1H), 1.37 (d, J=15.1 Hz, 3H), 1.13 (d, J=6.3 Hz, 3H).

Example 38

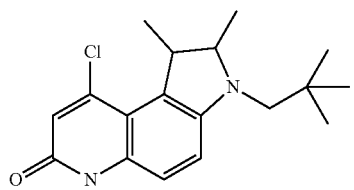 [SMILES: CC1c2c(ccc3[nH]c(=O)cc(Cl)c23)N(CC(C)(C)C)C1C]

(±)-9-Chloro-1,2-dimethyl-3-(2,2-dimethylpropyl)-1,2,3,6-tetrahydro-pyrrolo[3,2-f]quinolin-7-one (Compound 141, Structure 5 of Scheme I, where $R^A$=chloro, $R^1$=$R^3$=methyl, $R^5$=2,2-dimethylpropyl)

This compound was prepared using the method described in Example 23 from compound 105, and 2,2-dimethylpropionic acid. Spectral data for compound 141: $^1$H NMR (500 MHz, CDCl$_3$) δ (s, 1H), 7.14 (d, J=8.8 Hz, 1H), 6.93 (d, J=8.8 Hz, 1H), 6.86 (s, 1H), 4.0 (dq, J=14.2 Hz, 7.0 Hz, 1H), 3.58 (m, 1H), 2.86 (d, J=15.1 Hz, 1H), 2.78 (d, J=15.1 Hz, 1H), 1.37 (d, J=6.3 Hz, 1H), 1.22 (d, J=6.3 Hz, 3H), 1.03 (s, 9H).

Example 39

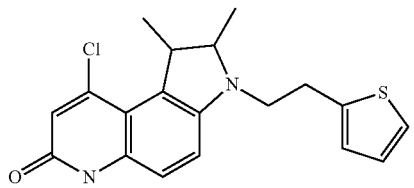 [SMILES: CC1c2c(ccc3[nH]c(=O)cc(Cl)c23)N(CCc2cccs2)C1C]

(±)-9-Chloro-1,2-dimethyl-3-(2-thien-2-yl-ethyl)-1,2,3,6-tetrahydro-pyrrolo[3,2-f]-quinolin-7-one (Compound 142, Structure 5 of Scheme I, where $R^A$=chloro, $R^1$=$R^3$=methyl, $R^5$=2-thien-2-yl-ethyl)

This compound was prepared using the method described in Example 23 from compound 105, and 2-thiophenylacetic acid. Spectral data for compound 142: $^1$H NMR (500 MHz, CDCl$_3$) δ 12.38 (s, 1H), 7.26 (d, J=8.8 Hz, 1H), 7.19 (dd, J=4.9 Hz, 1.0 Hz, 1H), 6.98 (dd, J=4.9 Hz, 2.9 Hz, 1H), 6.88 (d, J=2.9 Hz, 1H), 6.75 (s, 1H), 6.75 (d, J=8.8 Hz, 1H), 4.05 (dq, J=14.2 Hz, 7.0 Hz, 1H), 3.72 (dq, J=14.2 Hz, 7.0 Hz, 1H), 3.56-3.48 (m, 1H), 3.44-3.36 (m, 1H), 3.10-2.96 (m, 2H), 1.35 (d, J=6.8 Hz, 1H), 1.17 (d, J=6.8 Hz, 3H).

Example 40

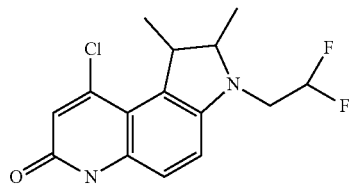 [SMILES: CC1c2c(ccc3[nH]c(=O)cc(Cl)c23)N(CC(F)F)C1C]

(±)-9-Chloro-3-(2,2-difluoroethyl)-1,2-dimethyl-1,2,3,6-tetrahydro-pyrrolo[3,2-f]quinolin-7-one (Compound 143, Structure 5 of Scheme I, where $R^A$=chloro, $R^1$=$R^3$=methyl, $R^5$=2,2-difluoroethyl)

This compound was prepared using the method described in Example 23 from compound 105, and difluoroacetic acid. Spectral data for compound 143: $^1$H NMR (500 MHz, CDCl$_3$) δ 12.20 (s, 1H), 7.27 (d, J=8.8 Hz, 1H), 6.98 (d, J=2.9 Hz, 1H), 6.92 (s, 1H), 6.09-5.78 (m, 1H), 4.12 (dq, J=14.2 Hz, 7.0 Hz, 1H), 3.79 (dq, J=14.2 Hz, 7.0 Hz, 1H), 3.54-3.45 (m, 2H), 1.41 (d, J=6.8 Hz, 1H), 1.18 (d, J=6.8 Hz, 3H).

Example 41

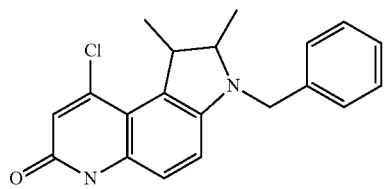 [SMILES: CC1c2c(ccc3[nH]c(=O)cc(Cl)c23)N(Cc2ccccc2)C1C]

(±)-9-Chloro-1,2-dimethyl-3-phenylmethyl-1,2,3,6-tetrahydro-pyrrolo[3,2-f]quinolin-7-one (Compound 144, Structure 5 of Scheme I, where R$^A$=chloro, R$^1$=R$^3$=methyl, R$^5$=phenylmethyl)

This compound was prepared using the method described in Example 23 from compound 105, and benzoic acid. Spectral data for compound 144: $^1$H NMR (500 MHz, CDCl$_3$) δ 11.40 (s, 1H), 7.37-7.33 (m, 3H) 7.32-7.27 (m, 1H), 7.12 (d, J=8.8 Hz, 1H), 6.83 (s, 1H), 6.77 (d, J=2.9 Hz, 1H), 4.52 (d, J=16.1 Hz, 1H), 4. (d, J=16.1 Hz, 1H), 4.08 (dq, J=14.2 Hz, 7.0 Hz, 1H), 3.70 (dq, J=14.2 Hz, 7.0 Hz, 1H), 1.36 (d, J=6.8 Hz, 1H), 1.24 (d, J=6.8 Hz, 3H).

Example 42

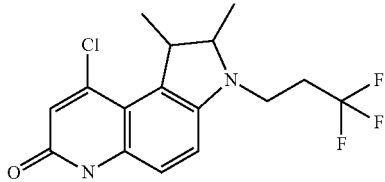 [SMILES: CC1c2c(ccc3[nH]c(=O)cc(Cl)c23)N(CCC(F)(F)F)C1C]

(±)-9-Chloro-1,2-dimethyl-3-(3,3,3-trifluoropropyl)-1,2,3,6-tetrahydro-pyrrolo[3,2-f]-quinolin-7-one (Compound 145, Structure 5 of Scheme I, where R$^A$=chloro, R$^1$=methyl, R$^3$=methyl, R$^5$=3,3,3-trifluoropropyl)

This compound was prepared using the method described in Example 23 from compound 105, and 3,3,3-trifluoropropionic acid. Spectral data for compound 145: $^1$H NMR (500 MHz, CDCl$_3$) δ 11.23 (s, 1H), 7.17 (d, J=8.5 Hz, 1H), 6.82 (s, 1H), 6.78 (d, J=8.5 Hz, 1H), 4.03 (m, 1H), 3.58 (m, 1H), 3.53 (ddd, J=15.3, 10.0, 5.4 Hz, 1H), 3.37 (ddd, J=15.3, 9.7, 5.6 Hz, 1H), 2.27 (m, 2H), 1.34 (d, J=6.5 Hz, 3H), 1.13 (d, J=7.2 Hz, 3H).

Example 43

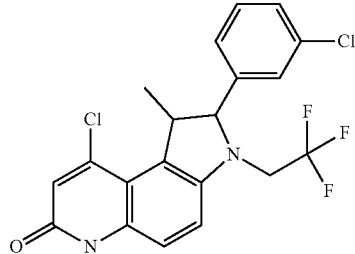 [SMILES: CC1c2c(ccc3[nH]c(=O)cc(Cl)c23)N(CC(F)(F)F)C1c1cccc(Cl)c1]

(±)-9-Chloro-2-(3-chlorophenyl)-1-methyl-3-(2,2,2-trifluoroethyl)-1,2,3,6-tetrahydro-pyrrolo[3,2-f]quinolin-7-one (Compound 146, Structure 5 of Scheme I, where R$^A$=chloro, R$^1$=methyl, R$^3$=3-chlorophenyl, R$^5$=2,2,2-trifluoroethyl)

This compound was prepared using the method described in Example 23 from 9-Chloro-2-(3-chlorophenyl)-1-methyl-3,6-dihydro-pyrrolo[3,2-f]quinolin-7-one, and trifluoroacetic acid. Spectral data for compound 146: $^1$H NMR (500 MHz, acetone-d$_6$) δ 11.02 (s, 1H), 7.63 (m, 1H), 7.56 (m, 1H), 7.53 (t, J=7.5 Hz, 1H), 7.47 (dt, J=7.5, 2.0 Hz, 1H), 7.44 (d, J=8.6 Hz, 1H), 7.36 (d, J=8.6 Hz, 1H), 6.75 (s, 1H), 5.11 (d, J=8.0 Hz, 1H), 4.41 (m, J=7.2 Hz, 1H), 4.20 (dq, J=16.5, 10.0 Hz, 1H), 3.80 (dq, J=16.5, 9.3 Hz, 1H), 0.91 (d, J=7.2 Hz, 3H).

Example 44

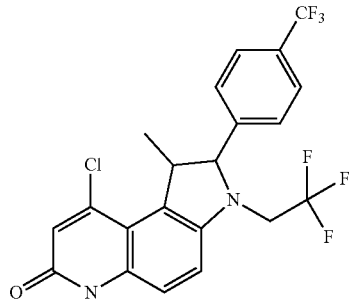 [SMILES: CC1c2c(ccc3[nH]c(=O)cc(Cl)c23)N(CC(F)(F)F)C1c1ccc(C(F)(F)F)cc1]

(±)-9-Chloro-1-methyl-2-(4-trifluoromethyl-phenyl)-3-(2,2,2-trifluoroethyl)-1,2,3,6-tetrahydro-pyrrolo[3,2-f]quinolin-7-one (Compound 147, Structure 5 of Scheme I, where R$^A$=chloro, R$^1$=methyl, R$^3$=4-trifluoromethyl-phenyl, R$^5$=2,2,2-trifluoroethyl)

This compound was prepared using the method described in Example 23 from 9-Chloro-2-(4-trifluoromethyl-phenyl)-1-methyl-3,6-dihydro-pyrrolo[3,2-f]quinolin-7-one, and trifluoroacetic acid. Spectral data for compound 147: $^1$H NMR (500 MHz, acetone-d$_6$) δ 10.75 (s, 1H), 7.44 (d, J=7.7 Hz, 2H), 7.41 (d, J=8.6 Hz, 1H), 7.33 (d, J=8.6 Hz, 1H), 7.31 (d, J=7.7 Hz, 2H), 6.72 (s, 1H), 5.03 (d, J=7.8 Hz, 1H), 4.31 (m, 1H), 4.17 (dq, J=16.5, 10.1 Hz, 1H), 3.74 (dq, J=16.5, 9.4 Hz, 1H), 2.41 (s, 3H), 0.89 (d, J=7.0 Hz, 3H).

Example 45

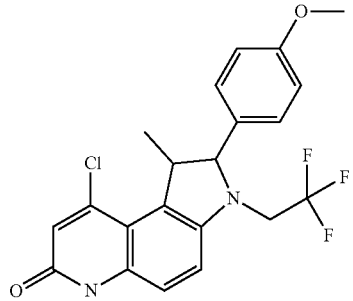 [SMILES: COc1ccc(C2C(C)c3c(ccc4[nH]c(=O)cc(Cl)c34)N2CC(F)(F)F)cc1]

(±)-9-Chloro-2-(4-methoxy-phenyl)-1-methyl-3-(2,2,2-trifluoroethyl)-1,2,3,6-tetrahydro-pyrrolo[3,2-f]quinolin-7-one (Compound 148, Structure 5 of Scheme I, where R$^A$=chloro, R$^1$=methyl, R$^3$=4-methoxy-phenyl, R$^5$=2,2,2-trifluoroethyl)

This compound was prepared using the method described in Example 23 from 9-Chloro-2-(4-methoxy-phenyl)-1-methyl-3,6-dihydro-pyrrolo[3,2-f]quinolin-7-one, and trifluoroacetic acid. Spectral data for compound 148: $^1$H NMR (500 MHz, acetone-d$_6$) δ 7.48 (d, J=8.7 Hz, 2H), 7.42 (d, J=8.8 Hz, 1H), 7.33 (d, J=8.8 Hz, 1H), 7.06 (d, J=8.7 Hz, 2H), 6.74 (s, 1H), 5.01 (d, J=8.1 Hz, 1H), 4.29 (m, 1H), 4.15 (dq, J=16.3, 10.0 Hz, 1H), 3.88 (s, 3H), 3.73 (dq, J=16.3, 9.3 Hz, 1H), 0.92 (d, J=7.2 Hz, 3H).

Example 46

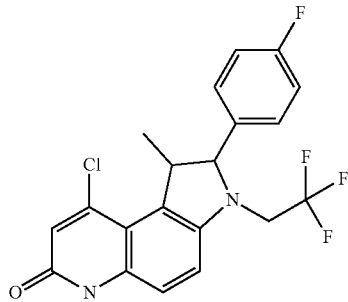 [SMILES: CC1c2c(ccc3[nH]c(=O)cc(Cl)c23)N(CC(F)(F)F)C1c1ccc(F)cc1]

(±)-9-Chloro-2-(4-fluoro-phenyl)-1-methyl-3-(2,2,2-trifluoroethyl)-1,2,3,6-tetrahydro-pyrrolo[3,2-f] quinolin-7-one (Compound 149, Structure 5 of Scheme I, where R$^4$=chloro, R$^1$=methyl, R$^3$=4-fluorophenyl, R$^5$=2,2,2-trifluoroethyl)

This compound was prepared using the method described in Example 23 from 9-Chloro-2-(4-fluorophenyl)-1-methyl-3,6-dihydro-pyrrolo[3,2-f]quinolin-7-one, and trifluoroacetic acid. Spectral data for compound 149: $^1$H NMR (500 MHz, acetone-d$_6$) δ 10.84 (s, 1H), 7.62 (dd, J=8.6, 5.5 Hz, 2H), 7.43 (d, J=8.8 Hz, 1H), 7.34 (d, J=8.8 Hz, 1H), 7.27 (t, J=8.6 Hz, 2H), 6.74 (s, 1H), 5.10 (d, J=7.8 Hz, 1H), 4.35 (m, 1H), 4.17 (dq, J=16.5, 10.1 Hz, 1H), 3.76 (dq, J=16.5, 9.4 Hz, 1H), 0.91 (d, J=7.2 Hz, 3H).

Example 47

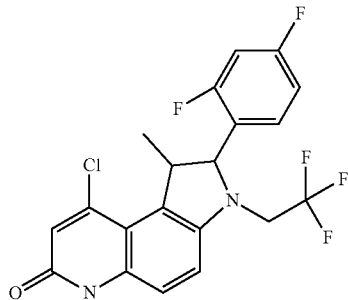 [SMILES: CC1c2c(ccc3[nH]c(=O)cc(Cl)c23)N(CC(F)(F)F)C1c1ccc(F)cc1F]

(±)-9-Chloro-2-(2,4-difluorophenyl)-1-methyl-3-(2,2,2-trifluoroethyl)-1,2,3,6-tetrahydropyrrolo-[3,2-f] quinolin-7-one (Compound 150, Structure 5 of Scheme I, where R$^4$=chloro, R$^1$=methyl, R$^3$=2,4-difluorophenyl, R$^5$=2,2,2-trifluoroethyl)

This compound was prepared using the method described in Example 23 from 9-Chloro-2-(2,4-difluorophenyl)-1-me-thyl-3,6-dihydro-pyrrolo[3,2-f]quinolin-7-one, and trifluoroacetic acid. Spectral data for compound 150: $^1$H NMR (500 MHz, acetone-d$_6$) δ 10.82 (s, 1H), 7.77 (m, 1H), 7.45 (d, J=8.8 Hz, 1H), 7.38 (d, J=8.8 Hz, 1H), 7.22-7.15 (m, 2H), 6.75 (s, 1H), 5.33 (d, J=7.9 Hz, 1H), 4.43 (m, 1H), 4.24 (dq, J=16.5, 10.1 Hz, 1H), 3.80 (dq, J=16.5, 9.4 Hz, 1H), 0.92 (d, J=7.0 Hz, 3H).

Example 48

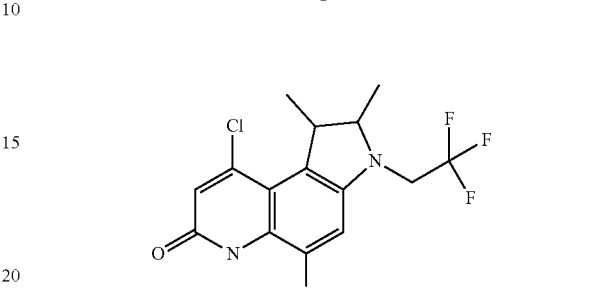

(±)-9-Chloro-1,2-dimethyl-5-fluoro-3-(2,2,2-trifluoro-ethyl)-1,2,3,6-tetrahydro-pyrrolo[3,2-f]quinolin-7-one (Compound 151, Structure 5 of Scheme I, where R$^4$=chloro, R$^1$=methyl, R$^3$=methyl, R$^5$=2,2,2-trifluoroethyl, R$^6$=fluoro)

This compound was prepared using the method described in Example 23 from 8-fluoro-6-hydrazino-4-chloroquinolin-2(1H)-one and trifluoroacetic acid. Spectral data for compound 151: $^1$H NMR (500 MHz, acetone-d$_6$) δ 10.36 (s, 1H), 7.06 (d, J=11.5 Hz, 1H), 6.78 (s, 1H), 4.11 (qn, J=6.8 Hz, 1H), 4.08 (dq, J=16.4, 9.9 Hz, 1H), 3.93 (dq, J=16.4, 9.2 Hz, 1H), 3.86 (qn, J=6.6 Hz, 1H), 1.45 (d, J=6.6 Hz, 3H), 1.17 (d, J=6.8 Hz, 3H).

Example 49

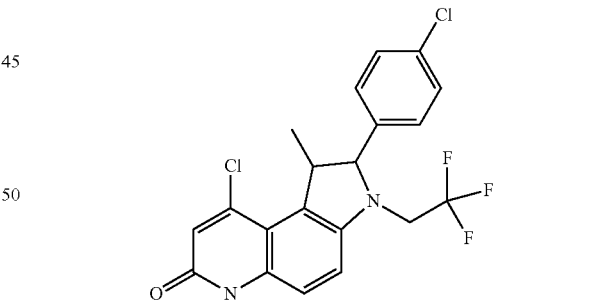

(±)-9-Chloro-2-(4-chlorophenyl)-1-methyl-3-(2,2,2-trifluoroethyl)-1,2,3,6-tetrahydro-pyrrolo[3,2-f] quinolin-7-one (Compound 152, Structure 5 of Scheme I, where R$^4$=chloro, R$^1$=methyl, R$^3$=4-chlorophenyl, R$^5$=2,2,2-trifluoroethyl)

This compound was prepared using the method described in Example 23 from 9-Chloro-2-(4-chlorophenyl)-1-methyl-3,6-dihydro-pyrrolo[3,2-f]quinolin-7-one, and trifluoroacetic acid. Spectral data for compound 152: $^1$H NMR (500 MHz, DMSO-d$_6$) δ 11.90 (s, 1H), 7.52 (d, J=8.8 Hz, 2H), 7.50

(d, J=8.8 Hz, 2H), 7.35 (d, J=8.8 Hz, 1H), 7.29 (d, J=8.8 Hz, 1H), 6.77 (s, 1H), 5.00 (d, J=7.8 Hz, 1H), 4.32-4.21 (m, 2H), 3.66 (dq, J=16.5, 9.4 Hz, 1H), 0.74 (d, J=6.8 Hz, 3H).

Example 50

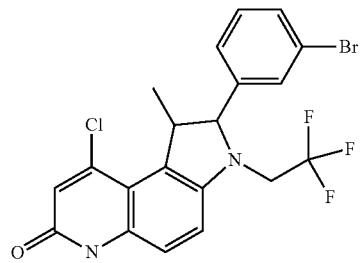 [SMILES: CC1c2c(ccc3[nH]c(=O)cc(Cl)c23)N(CC(F)(F)F)C1c1cccc(Br)c1]

(±)-2-(3-Bromophenyl)-9-chloro-1-methyl-3-(2,2,2-trifluoroethyl)-1,2,3,6-tetrahydro-pyrrolo[3,2-f]quinolin-7-one (Compound 153, Structure 5 of Scheme I, where $R^4$=chloro, $R^1$=methy, $R^3$=3-bromophenyl, $R^5$=2,2,2-trifluoroethyl)

This compound was prepared using the method as described in Example 23 from 2-(3-bromophenyl)-9-chloro-1-methyl-3,6-dihydro-pyrrolo[3,2-f]quinolin-7-one, and trifluoroacetic acid. Spectral data for compound 153: $^1$H NMR (500 MHz, DMSO-$d_6$) δ 11.91 (s, 1H), 7.69 (t, J=1.5 Hz, 1H), 7.59 (m, 1H), 7.50 (m, 1H), 7.43 (t, J=7.8 Hz, 1H), 7.34 (d, J=8.8 Hz, 1H), 7.30 (d, J=8.8 Hz, 1H), 6.78 (s, 1H), 5.00 (d, J=7.8 Hz, 1H), 4.28 (m, 1H), 4.25 (m, 1H), 3.68 (dq, J=16.4, 9.4 Hz, 1H), 0.74 (d, J=7.0 Hz, 3H).

Example 51

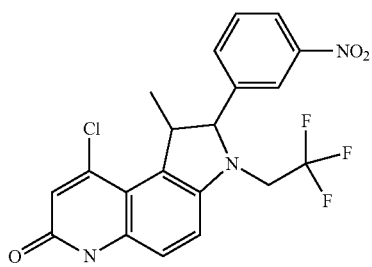 [SMILES: CC1c2c(ccc3[nH]c(=O)cc(Cl)c23)N(CC(F)(F)F)C1c1cccc([N+](=O)[O-])c1]

(±)-9-Chloro-1-methyl-2-(3-nitrophenyl)-3-(2,2,2-trifluoroethyl)-1,2,3,6-tetrahydro-pyrrolo[3,2-f]quinolin-7-one (Compound 154, Structure 5 of Scheme I, where $R^4$=chloro, $R^1$=methyl, $R^3$=3-nitrophenyl, $R^5$=2,2,2-trifluoroethyl)

This compound was prepared using the method as described in Example 23 from 9-chloro-1-methyl-2-(3-nitrophenyl)-3,6-dihydro-pyrrolo[3,2-f]quinolin-7-one, and trifluoroacetic acid. Spectral data for compound 154: $^1$H NMR (500 MHz, DMSO-$d_6$) δ 11.93 (s, 1H), 8.34 (t, J=1.8 Hz, 1H), 8.27 (ddd, J=8.0, 1.8, 0.8 Hz, 1H), 7.96 (m, 1H), 7.77 (t, J=8.0 Hz, 1H), 7.37 (d, J=8.8 Hz, 1H), 7.32 (d, J=8.8 Hz, 1H), 6.79 (d, J=1.7 Hz, 1H), 5.18 (d, J=7.7 Hz, 1H), 4.38 (m, 1H), 4.28 (dq, J=16.5, 10.0 Hz, 1H), 3.74 (dq, J=16.5, 9.4 Hz, 1H), 0.75 (d, J=7.1 Hz, 3H).

Example 52

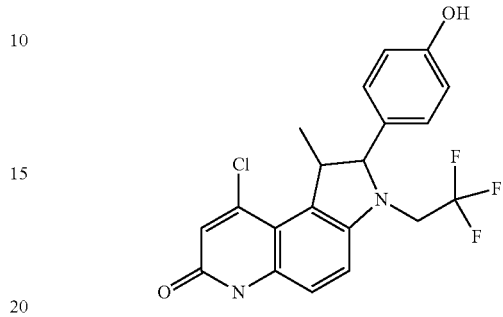

(±)-9-Chloro-2-(4-hydroxyphenyl)-1-methyl-3-(2,2,2-trifluoroethyl)-1,2,3,6-tetrahydro-pyrrolo[3,2-f]quinolin-7-one (Compound 155, Structure 5 of Scheme I, where $R^4$=chloro, $R^1$=methyl, $R^3$=4-hydroxyphenyl, $R^5$=2,2,2-trifluoroethyl)

This compound was prepared using the method described in Example 23 from 9-chloro-2-(4-hydroxyphenyl)-1-methyl-3,6-dihydro-pyrrolo[3,2-f]quinolin-7-one, and trifluoroacetic acid. Spectral data for compound 155: $^1$H NMR (500 MHz, acetone-$d_6$) δ 11.00 (s, 1H), 8.58 (s, 1H), 7.41 (d, J=8.8 Hz, 1H), 7.38 (d, J=8.5 Hz, 2H), 7.32 (d, J=8.8 Hz, 1H), 6.96 (d, J=8.5 Hz, 2H), 6.75 (s, 1H), 4.97 (d, J=7.8 Hz, 1H), 4.26 (m, 1H), 4.14 (dq, J=16.3, 10.0 Hz, 1H), 3.73 (dq, J=16.3, 9.4 Hz, 1H), 0.92 (d, J=7.1 Hz, 3H).

Example 53

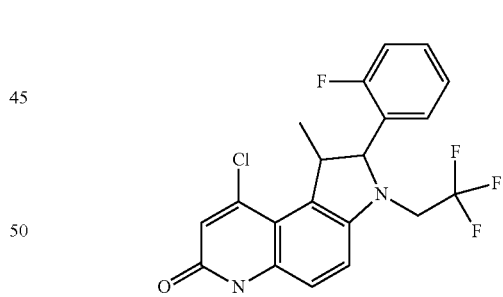

(±)-9-Chloro-2-(2-fluorophenyl)-1-methyl-3-(2,2,2-trifluoroethyl)-1,2,3,6-tetrahydro-pyrrolo[3,2-f]quinolin-7-one (Compound 156, Structure 5 of Scheme I, where $R^4$=chloro, $R^1$=methyl, $R^3$=2-fluorophenyl, $R^5$=2,2,2-trifluoroethyl)

This compound was prepared using the method described in Example 23 from 9-chloro-2-(2-fluorophenyl)-1-methyl-3,6-dihydro-pyrrolo[3,2-f]quinolin-7-one, and trifluoroacetic acid. Spectral data for compound 156: $^1$H NMR (500 MHz, DMSO-$d_6$) δ 11.91 (s, 1H), 7.58 (m, 1H), 7.46 (m, 1H), 7.39 (d, J=8.8 Hz, 1H), 7.34-7.29 (m, 3H), 6.78 (s, 1H), 5.23

(m, 1H), 4.37 (dq, J=16.7, 10.2 Hz, 1H), 4.29 (qn, J=6.8 Hz, 1H), 3.68 (dq, J=16.7, 9.6 Hz, 1H), 0.76 (d, J=6.8 Hz, 3H).

Example 54

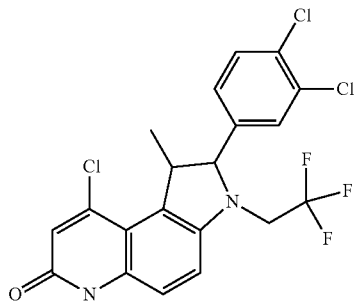 [SMILES: CC1c2c(ccc3[nH]c(=O)cc(Cl)c23)N(CC(F)(F)F)C1c1ccc(Cl)c(Cl)c1]

(±)-9-Chloro-2-(3,4-dichlorophenyl)-1-methyl-3-(2,2,2-trifluoroethyl)-1,2,3,6-tetrahydropyrrolo[3,2-f]quinolin-7-one (Compound 157, Structure 5 of Scheme I, where $R^4$=chloro, $R^1$=methyl, $R^3$=3,4-dichlorophenyl, $R^5$=2,2,2-trifluoroethyl)

This compound was prepared using the method described in Example 23 from 9-chloro-2-(3,4-dichlorophenyl)-1-methyl-3,6-dihydro-pyrrolo[3,2-f]quinolin-7-one, and trifluoroacetic acid. Spectral data for compound 157: $^1$H NMR (500 MHz, DMSO-$d_6$) δ 11.91 (s, 1H), 7.75 (d, J=1.9 Hz, 1H), 7.73 (d, J=8.3 Hz, 1H), 7.49 (dd, J=8.3, 1.9 Hz, 1H), 7.34 (d, J=8.8 Hz, 1H), 7.30 (d, J=8.8 Hz, 1H), 6.78 (d, J=1.7 Hz, 1H), 5.02 (d, J=7.0 Hz, 1H), 4.30 (qn, J=7.0 Hz, 1H), 4.25 (dq, J=16.5, 10.2 Hz, 1H), 3.71 (dq, J=16.5, 9.2 Hz, 1H), 0.76 (d, J=7.0 Hz, 3H).

Example 55

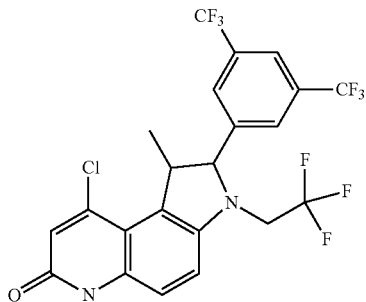 [SMILES: CC1c2c(ccc3[nH]c(=O)cc(Cl)c23)N(CC(F)(F)F)C1c1cc(C(F)(F)F)cc(C(F)(F)F)c1]

(±)-9-Chloro-2-(3,5-bis(trifluoromethyl)phenyl)-1-methyl-3-(2,2,2-trifluoroethyl)-1,2,3,6-tetrahydropyrrolo[3,2-f]quinolin-7-one (Compound 158, Structure 5 of Scheme I, where $R^4$=chloro, $R^1$=methyl, $R^3$=3,5-bistrifluoromethylphenyl, $R^5$=2,2,2-trifluoroethyl)

This compound was prepared using the method described in Example 23 from 9-chloro-2-(3,5-bis(trifluoromethyl)phenyl)-1-methyl-3,6-dihydro-pyrrolo[3,2-f]quinolin-7-one, and trifluoroacetic acid. Spectral data for compound 158: $^1$H NMR (500 MHz, DMSO-$d_6$) δ 11.94 (s, 1H), 8.20 (s, 2H), 8.16 (s, 1H), 7.34 (d, J=9.0 Hz, 1H), 7.32 (d, J=9.0 Hz, 1H), 6.80 (s, 1H), 5.21 (d, J=7.7 Hz, 1H), 4.43 (m, 1H), 4.15 (dq, J=16.7, 10.1 Hz, 1H), 3.77 (dq, J=16.7, 9.5 Hz, 1H), 0.74 (d, J=6.8 Hz, 3H).

Example 56

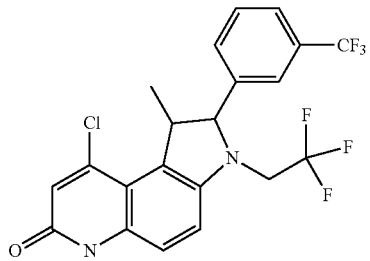 [SMILES: CC1c2c(ccc3[nH]c(=O)cc(Cl)c23)N(CC(F)(F)F)C1c1cccc(C(F)(F)F)c1]

(±)-9-Chloro-1-methyl-3-(2,2,2-trifluoroethyl)-2-(3-trifluoromethylphenyl)-1,2,3,6-tetrahydropyrrolo[3,2-f]quinolin-7-one (Compound 159, Structure 5 of Scheme I, where $R^4$=chloro, $R^1$=methyl, $R^3$=3-trifluoromethylphenyl, $R^5$=2,2,2-trifluoroethyl)

This compound was prepared using the method described in Example 23 from 9-chloro-1-methyl-2-(3-trifluoromethylphenyl)-3,6-dihydro-pyrrolo[3,2-f]quinolin-7-one, and trifluoroacetic acid. Spectral data for compound 159: $^1$H NMR (500 MHz, DMSO-$d_6$) δ 11.92 (s, 1H), 7.85 (s, 1H), 7.81 (d, J=7.5 Hz, 1H), 7.77 (d, J=7.5 Hz, 1H), 7.70 (t, J=7.5 Hz, 1H), 7.35 (d, J=8.8 Hz, 1H), 7.31 (d, J=8.8 Hz, 1H), 6.78 (d, J=2.0 Hz, 1H), 5.11 (d, J=7.8 Hz, 1H), 4.33 (m, 1H), 4.21 (dq, J=16.5, 9.9 Hz, 1H), 3.70 (dq, J=16.5, 9.5 Hz, 1H), 0.74 (d, J=7.3 Hz, 3H).

Example 57

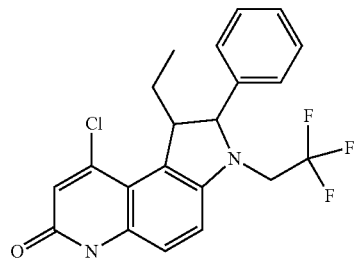 [SMILES: CCC1c2c(ccc3[nH]c(=O)cc(Cl)c23)N(CC(F)(F)F)C1c1ccccc1]

(±)-9-Chloro-1-ethyl-2-phenyl-3-(2,2,2-trifluoroethyl)-1,2,3,6-tetrahydro-pyrrolo[3,2-f]-quinolin-7-one (Compound 160, Structure 5 of Scheme I, where $R^4$=chloro, $R^1$=ethyl, $R^3$=phenyl, $R^5$=2,2,2-trifluoroethyl)

This compound was prepared using the method described in Example 23 from 9-chloro-1-ethyl-2-phenyl-3,6-dihydro-pyrrolo[3,2-f]quinolin-7-one, and trifluoroacetic acid. Spectral data for compound 160: $^1$H NMR (500 MHz, DMSO-$d_6$) δ 11.89 (s, 1H), 7.54 (d, J=7.3 Hz, 2H), 7.47 (t, J=7.3 Hz, 2H), 7.41 (t, J=7.3 Hz, 1H), 7.33 (d, J=8.8 Hz, 1H), 7.29 (d, J=8.8 Hz, 1H), 6.76 (s, 1H), 5.02 (d, J=8.1 Hz, 1H), 4.27 (dq, J=16.5, 10.2 Hz, 1H), 4.08 (m, 1H), 3.65 (dq, J=16.5, 9.5 Hz, 1H), 1.63 (m, 1H), 1.19 (m, 1H), 0.14 (t, J=7.3 Hz, 3H).

Example 58

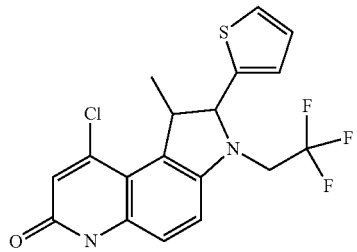 [SMILES: CC1c2c(ccc3[nH]c(=O)cc(Cl)c23)N(CC(F)(F)F)C1c1cccs1]

(±)-9-Chloro-1-methyl-2-(thien-2-yl)-3-(2,2,2-trifluoroethyl)-1,2,3,6-tetrahydro-pyrrolo[3,2-f]quinolin-7-one (Compound 161, Structure 5 of Scheme I, where $R^4$=chloro, $R^1$=methyl, $R^3$=thien-2-yl, $R^5$=2,2,2-trifluoroethyl)

This compound was prepared using the method described in Example 23 from 9-chloro-1-ethyl-2-(thien-2-yl)-3,6-dihydro-pyrrolo[3,2-f]quinolin-7-one, and trifluoroacetic acid. Spectral data for compound 161: $^1$H NMR (500 MHz, DMSO-$d_6$) δ 11.90 (s, 1H), 7.62 (dd, J: 5.1, 1.1 Hz, 1H), 7.32 (d, J: 8.8 Hz, 1H), 7.28 (d, J: 8.8 Hz, 1H), 7.25 (dd, J: 3.5, 1.1 Hz, 1H), 7.15 (dd, J: 5.1, 3.5 Hz, 1H), 6.78 (d, J: 1.7 Hz, 1H), 5.28 (d, J: 7.5 Hz, 1H), 4.32 (dq, J: 16.5, 9.9 Hz, 1H), 4.24 (m, 1H), 3.72 (dq, J: 16.5, 9.4 Hz, 1H), 0.93 (d, J: 7.2 Hz, 3H).

Example 59

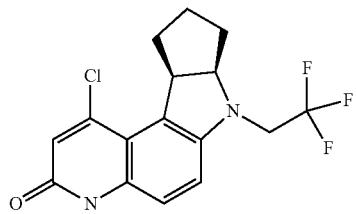 [SMILES: O=c1cc(Cl)c2c3c(ccc2[nH]1)N(CC(F)(F)F)[C@@H]1CCC[C@H]31]

(+)-9-Chloro-3-(2,2,2-trifluoroethyl)-1,2-trimethylene-1,2,3,6-tetrahydropyrrolo[3,2-f]quinolin-7-one (Compound 162, Structure 5 of Scheme I, where $R^4$=chloro, $R^1$, $R^3$=—(CH$_2$)$_3$—, $R^5$=2,2,2-trifluoroethyl)

This compound was obtained by chiral HPLC separation of the racemic compound 126. Spectral data for compound 162: $^1$H NMR (500 MHz, acetone-$d_6$) δ 11.71 (s, 1H), 7.13 (d, J=8.8 Hz, 1H), 6.94 (d, J=8.8 Hz, 1H), 6.67 (s, 1H), 4.38 (td, J=8.9, 3.2 Hz, 1H), 4.28 (m, 1H), 4.02 (dq, J=16.4, 10.0 Hz, 1H), 3.94 (dq, J=16.4, 9.6 Hz, 1H), 2.14 (m, 1H), 2.01 (m, 1H), 1.73-1.58 (m, 3H), 1.44 (m, 1H).

Example 60

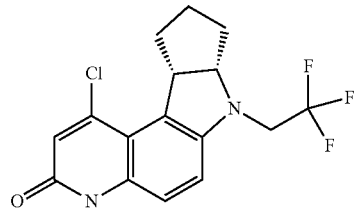 [SMILES: O=c1cc(Cl)c2c3c(ccc2[nH]1)N(CC(F)(F)F)[C@H]1CCC[C@@H]31]

(−)-9-Chloro-3-(2,2,2-trifluoroethyl)-1,2-trimethylene-1,2,3,6-tetrahydropyrrolo[3,2-f]-quinolin-7-one (Compound 163, Structure 5 of Scheme I, where $R^4$=chloro, $R^1$, $R^3$=—(CH$_2$)$_3$—, $R^5$=2,2,2-trifluoroethyl)

This compound was obtained by chiral HPLC separation of the racemic compound 126. Spectral data for compound 163: $^1$H NMR (500 MHz, acetone-$d_6$) δ 11.71 (s, 1H), 7.13 (d, J=8.8 Hz, 1H), 6.94 (d, J=8.8 Hz, 1H), 6.67 (s, 1H), 4.38 (td, J=8.9, 3.2 Hz, 1H), 4.28 (m, 1H), 4.02 (dq, J=16.4, 10.0 Hz, 1H), 3.94 (dq, J=16.4, 9.6 Hz, 1H), 2.14 (m, 1H), 2.01 (m, 1H), 1.73-1.58 (m, 3H), 1.44 (m, 1H).

Example 61

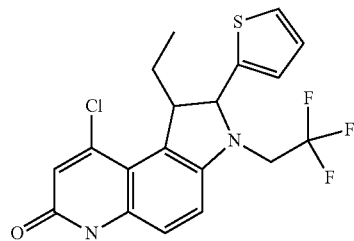 [SMILES: CCC1c2c(ccc3[nH]c(=O)cc(Cl)c23)N(CC(F)(F)F)C1c1cccs1]

(±)-9-Chloro-1-ethyl-2-(thien-2-yl)-3-(2,2,2-trifluoroethyl)-1,2,3,6-tetrahydro-pyrrolo[3,2-f]-quinolin-7-one (Compound 164, Structure 5 of Scheme I, where $R^4$=chloro, $R^1$=ethyl, $R^3$=thien-2-yl, $R^5$=2,2,2-trifluoroethyl)

This compound was prepared using the method described in Example 23 from 9-chloro-1-ethyl-2-(thien-2-yl)-3,6-dihydro-pyrrolo[3,2-f]quinolin-7-one, and trifluoroacetic acid. Spectral data for compound 164: $^1$H NMR (500 MHz, acetone-$d_6$) δ 10.96 (s, 1H), 7.56 (dd, J=5.1, 1.0 Hz, 1H), 7.38 (d, J=8.7 Hz, 1H), 7.33 (dt, J=3.4, 1.0 Hz, 1H), 7.26 (d, J=8.7 Hz, 1H), 7.14 (dd, J=5.1, 3.4 Hz, 1H), 6.72 (s, 1H), 5.35 (d, J=7.8 Hz, 1H), 4.18 (dq, J=16.4, 10.0 Hz, 1H), 4.14 (dd, J=9.5, 7.8 Hz, 1H), 3.77 (dq, J=16.4, 9.3 Hz, 1H), 1.93 (m, 1H), 1.42 (m, 1H), 0.40 (t, J=7.5 Hz, 3H).

Example 62

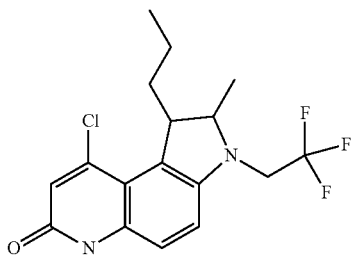 [SMILES: CCCC1c2c(ccc3[nH]c(=O)cc(Cl)c23)N(CC(F)(F)F)C1C]

(±)-9-Chloro-2-methyl-1-propyl-3-(2,2,2-trifluoroethyl)-1,2,3,6-tetrahydro-pyrrolo[3,2-f]-quinolin-7-one (Compound 165, Structure 5 of Scheme I, where $R^4$=chloro, $R^1$=propyl, $R^3$=methyl, $R^5$=2,2,2-trifluoroethyl)

This compound was prepared using the method described in Example 23 from 9-chloro-2-methyl-1-propyl-3,6-dihydro-pyrrolo[3,2-f]quinolin-7-one, and trifluoroacetic acid. Spectral data for compound 165: $^1$H NMR (500 MHz, DMSO-$d_6$) δ 11.79 (s, 1H), 7.20 (d, J=8.9 Hz, 1H), 7.03 (d, J=8.9 Hz, 1H), 6.72 (s, 1H), 4.02 (dq, J=16.3, 9.9 Hz, 1H), 3.93 (m, 1H), 3.80 (dq, J=16.3, 9.3 Hz, 1H), 3.70 (qn, J=6.6 Hz, 1H), 1.69 (m, 1H), 1.36 (d, J=6.6 Hz, 3H), 1.35 (m, 2H), 1.12 (m, 1H), 0.75 (t, J=7.3 Hz, 3H).

Example 63

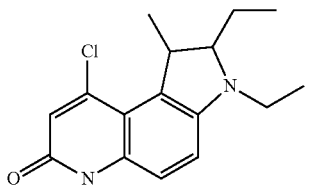 [SMILES: CCC1C(C)c2c(ccc3[nH]c(=O)cc(Cl)c23)N1CC]

(±)-9-Chloro-2,3-diethyl-1-methyl-1,2,3,6-tetrahydro-pyrrolo[3,2-f]quinolin-7-one (Compound 166, Structure 5 of Scheme I, where $R^4$=chloro, $R^1$=methyl, $R^3$=ethyl, $R^5$=ethyl)

This compound was prepared using the method described in Example 23 from 9-chloro-2-ethyl-1-methyl-3,6-dihydro-pyrrolo[3,2-f]quinolin-7-one, and acetic acid. Spectral data for compound 166: $^1$H NMR (500 MHz, DMSO-$d_6$) δ 11.71 (s, 1H), 7.16 (d, J=8.7 Hz, 1H), 6.95 (d, J=8.7 Hz, 1H), 6.67 (s, 1H), 3.98 (qn, J=6.9 Hz, 1H), 3.35 (m, 2H), 3.11 (m, 1H), 1.82 (m, 1H), 1.51 (m, 1H), 0.99 (d, J=6.9 Hz, 3H), 0.99 (t, J=7.4 Hz, 3H), 0.89 (t, J=7.0 Hz, 3H).

Example 64

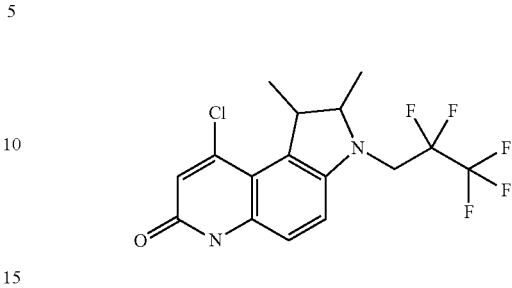

(±)-9-Chloro-1,2-dimethyl-3-(2,2,3,3,3-pentafluoropropyl)-1,2,3,6-tetrahydro-pyrrolo[3,2-f]-quinolin-7-one (Compound 167, Structure 5 of Scheme I, where $R^4$=chloro, $R^1$=methyl, $R^3$=methyl, $R^5$=2,2,3,3,3-pentafluoropropyl)

This compound was prepared using the method described in Example 23 from compound 105 and pentafluoropropionic acid. Spectral data for compound 167: $^1$H NMR (500 MHz, DMSO-$d_6$) δ 11.79 (s, 1H), 7.21 (d, J=8.7 Hz, 1H), 6.95 (d, J=8.7 Hz, 1H), 6.54 (s, 1H), 4.02 (m, 1H), 3.98 (qn, J=6.8 Hz, 1H), 3.82 (m, 1H), 3.68 (qn, J=6.8 Hz, 1H), 1.28 (d, J=6.8 Hz, 3H), 1.04 (d, J=6.8 Hz, 3H).

Example 65

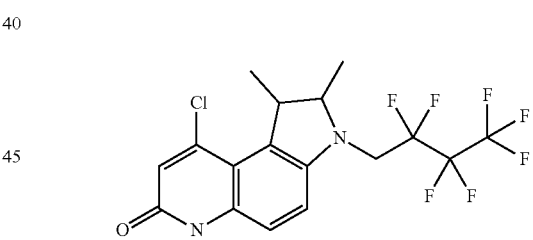

(±)-9-Chloro-1,2-dimethyl-3-(2,2,3,3,4,4,4-heptafluorobutyl)-1,2,3,6-tetrahydro-pyrrolo[3,2-f]quinolin-7-one (Compound 168, Structure 5 of Scheme I, where $R^4$=chloro, $R^1$=methyl, $R^3$=methyl, $R^5$=2,2,3,3,4,4,4-heptafluorobutyl)

This compound was prepared using the method described in Example 23 from compound 105 and heptafluorobutyric acid. Spectral data for compound 168: $^1$H NMR (500 MHz, DMSO-$d_6$) δ 11.80 (s, 1H), 7.23 (d, J=8.8 Hz, 1H), 6.94 (d, J=8.8 Hz, 1H), 6.73 (s, 1H), 4.07 (m, 1H), 4.01 (qn, J=6.6 Hz, 1H), 3.86 (m, 1H), 3.72 (qn, J=6.6 Hz, 1H), 1.29 (d, J=6.6 Hz, 3H), 1.05 (d, J=6.6 Hz, 3H).

Example 66

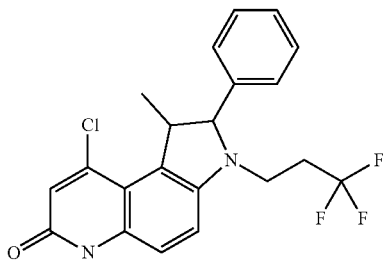 [SMILES: CC1c2c(ccc3[nH]c(=O)cc(Cl)c23)N(CCC(F)(F)F)C1c1ccccc1]

(±)-9-Chloro-1-methyl-2-phenyl-3-(3,3,3-trifluoropropyl)-1,2,3,6-tetrahydro-pyrrolo[3,2-f]quinolin-7-one (Compound 169, Structure 5 of Scheme I, where $R^4$=chloro, $R^1$=methyl, $R^3$=phenyl, $R^5$=3,3,3-trifluoropropyl)

This compound was prepared using the method described in Example 23 from compound 110 and 3,3,3-trifluoropropionic acid. Spectral data for compound 169: $^1$H NMR (500 MHz, DMSO-$d_6$) δ 11.84 (s, 1H), 7.48-7.41 (m, 4H), 7.36 (tt, J=6.9, 1.7 Hz, 1H), 7.29 (d, J=8.7 Hz, 1H), 7.18 (d, J=8.7 Hz, 1H), 6.73 (s, 1H), 4.83 (d, J=7.6 Hz, 1H), 4.17 (dq, J=7.6, 7.0 Hz, 1H), 3.64 (ddd, J=14.8, 10.7, 5.6 Hz, 1H), 3.10 (ddd, J=14.8, 10.6, 4.8 Hz, 1H), 2.51 (m, 1H), 2.37 (m, 1H), 0.70 (d, J=7.0 Hz, 3H).

Example 67

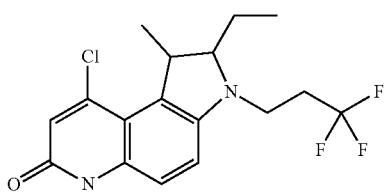 [SMILES: CCC1C(C)c2c(ccc3[nH]c(=O)cc(Cl)c23)N1CCC(F)(F)F]

(±)-9-Chloro-2-ethyl-1-methyl-3-(3,3,3-trifluoropropyl)-1,2,3,6-tetrahydro-pyrrolo[3,2-f]quinolin-7-one (Compound 170, Structure 5 of Scheme I, where $R^4$=chloro, $R^1$=methyl, $R^3$=ethyl, $R^5$=3,3,3-trifluoropropyl)

This compound was prepared using the method described in Example 23 from compound 106 and 3,3,3-trifluoropropionic acid. Spectral data for compound 170: $^1$H NMR (500 MHz, DMSO-$d_6$) δ 11.76 (s, 1H), 7.20 (d, J=8.5 Hz, 1H), 6.98 (d, J=8.5 Hz, 1H), 6.71 (s, 1H), 4.01 (qn, J=6.9 Hz, 1H), 3.55 (m, 1H), 3.29 (m, 2H), 2.52 (m, 1H), 2.33 (m, 1H), 1.84 (m, 1H), 1.55 (m, 1H), 1.01 (t, J=7.4 Hz, 3H), 1.01 (d, J=6.9 Hz, 3H).

Example 68

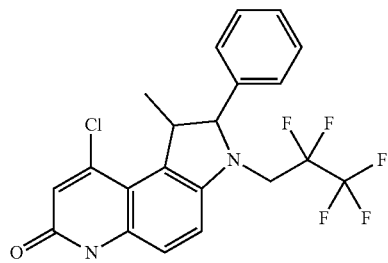 [SMILES: CC1c2c(ccc3[nH]c(=O)cc(Cl)c23)N(CC(F)(F)C(F)(F)F)C1c1ccccc1]

(±)-9-Chloro-1-methyl-3-(2,2,3,3,3-pentafluoropropyl)-2-phenyl-1,2,3,6-tetrahydro-pyrrolo[3,2-f]quinolin-7-one (Compound 171, Structure 5 of Scheme I, where $R^4$=chloro, $R^1$=methyl, $R^3$=phenyl, $R^5$=2,2,3,3,3-pentafluoropropyl)

This compound was prepared using the method described in Example 23 from compound 110 and pentafluoropropionic acid. Spectral data for compound 171: $^1$H NMR (500 MHz, acetone-$d_6$) δ 11.00 (s, 1H), 7.53 (d, J=7.6 Hz, 2H), 7.46 (td, J=7.6, 1.4 Hz, 2H), 7.39 (d, J=8.7 Hz, 1H), 7.39 (tt, J=7.6, 1.4 Hz, 1H), 7.22 (d, J=8.7 Hz, 1H), 6.71 (s, 1H), 5.11 (d, J=7.7 Hz, 1H), 4.32 (dq, J=7.7, 7.1 Hz, 1H), 4.19 (ddd, J=30.0, 16.8, 6.4 Hz, 1H), 3.75 (ddd, J=26.8, 16.8, 7.0 Hz, 1H), 0.86 (d, J=7.1 Hz, 3H).

Example 69

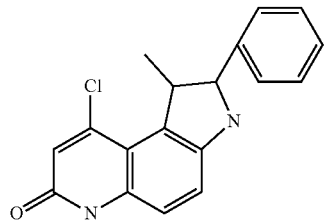 [SMILES: CC1c2c(ccc3[nH]c(=O)cc(Cl)c23)NC1c1ccccc1]

(±)-9-Chloro-1-methyl-2-phenyl-1,2,3,6-tetrahydro-pyrrolo[3,2-f]quinolin-7-one (Compound 172, Structure 5 of Scheme I, where $R^4$=chloro, $R^1$=methyl, $R^3$=phenyl, $R^5$=hydrogen)

This compound was isolated as a byproduct from the reaction described in Example 23 from compound 110 and pentafluoropropionic acid. Spectral data for compound 172: $^1$H NMR (500 MHz, acetone-$d_6$) δ 10.87 (s, 1H), 7.57 (d, J=7.5 Hz, 2H), 7.39 (td, J=7.5, 1.3 Hz, 2H), 7.29 (tt, J=7.5, 1.3 Hz, 1H), 7.27 (d, J=8.5 Hz, 1H), 7.15 (d, J=8.5 Hz, 1H), 6.66 (s, 1H), 5.42 (d, J=3.1 Hz, 1H), 5.14 (dd, J=7.0, 3.1 Hz, 1H), 4.29 (qn, J=7.0 Hz, 1H), 0.76 (d, J=7.0 Hz, 3H).

Example 70

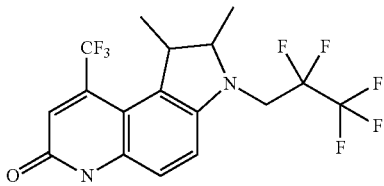

(±)-1,2-Dimethyl-3-(2,2,3,3,3-pentafluoropropyl)-9-trifluoromethyl-1,2,3,6-tetrahydro-pyrrolo[3,2-f]quinolin-7-one (Compound 173, Structure 5 of Scheme I, where $R^4$=trifluoromethyl, $R^1$=methyl, $R^3$=methyl, $R^5$=2,2,3,3,3-pentafluoropropyl)

This compound was prepared using the method described in Example 23 from 6-hydrazino-4-trifluoromethylquinolin-2(1H)-one and pentafluoropropionic acid. Spectral data for compound 173: $^1$H NMR (500 MHz, CDCl$_3$) δ 11.34 (s, 1H) 7.23 (d, J=8.6 Hz, 1H) 7.19 (s, 1H) 6.92 (d, J=8.6 Hz, 1H) 3.75-3.62 (m, 3H) 3.56 (m, 1H) 1.37 (d, J=6.6 Hz, 3H) 0.99 (d, J=6.6 Hz, 3H)

Example 71

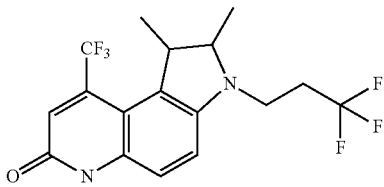 [SMILES: CC1c2c(ccc3[nH]c(=O)cc(C(F)(F)F)c23)N(CCC(F)(F)F)C1C]

(±)-1,2-Dimethyl-9-trifluoromethyl-3-(3,3,3-trifluoropropyl)-1,2,3,6-tetrahdro-pyrrolo[3,2-f]quinolin-7-one (Compound 174, Structure 5 of Scheme I, where $R^4$=trifluoromethyl, $R^1$=methyl, $R^3$=methyl, $R^5$=3,3,3-trifluoropropyl)

This compound was prepared using the method described in Example 23 from 6-hydrazino-4-trifluoromethylquinolin-2(1H)-one and 3,3,3-trifluoropropionic acid. Spectral data for compound 174: $^1$H NMR (500 MHz, CDCl$_3$) δ 11.65 (s, 1H), 7.25 (d, J=8.5 Hz, 1H), 7.18 (s, 1H), 6.85 (d, J=8.5 Hz, 1H), 3.60-3.48 (m, 3H), 3.40 (m, 1H), 2.27 (m, 2H), 1.33 (d, J=6.3 Hz, 3H), 0.96 (d, J=6.3 Hz, 3H).

Example 72

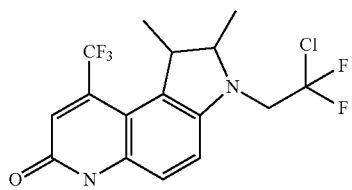 [SMILES: CC1c2c(ccc3[nH]c(=O)cc(C(F)(F)F)c23)N(CC(F)(F)Cl)C1C]

(±)-3-(2-Chloro-2,2-difluoroethyl)-1,2-dimethyl-9-trifluoromethyl-1,2,3,6-tetrahydro-pyrrolo[3,2-f]quinolin-7-one (Compound 175, Structure 5 of Scheme I, where $R^4$=trifluoromethyl, $R^1$=methyl, $R^3$=methyl, $R^5$=2-chloro-2,2-difluoroethyl)

This compound was prepared using the method described in Example 23 from 6-hydrazino-4-trifluoromethylquinolin-2(1H)-one and chlorodifluoroacetic acid. Spectral data for compound 175: $^1$H NMR (500 MHz, CDCl$_3$) δ 12.47 (s, 1H) 7.32 (d, J=8.8 Hz, 1H) 7.21 (s, 1H) 7.00 (d, J=8.8 Hz, 1H) 3.90-3.74 (m, 3H) 3.55 (qn, J=6.5 Hz, 1H) 1.39 (d, J=6.6 Hz, 3H) 0.98 (d, J=6.6 Hz, 3H).

Example 73

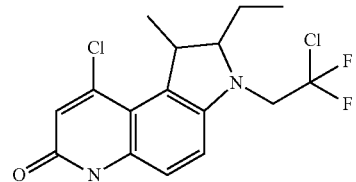 [SMILES: CCC1C(C)c2c(ccc3[nH]c(=O)cc(Cl)c23)N1CC(F)(F)Cl]

(±)-9-Chloro-3-(2-Chloro-2,2-difluoroethyl)-2-ethyl-1-methyl-1,2,3,6-tetrahydro-pyrrolo[3,2-f]quinolin-7-one (Compound 176, Structure 5 of Scheme I, where $R^4$=chloro, $R^1$=methyl, $R^3$=ethyl, $R^5$=2-chloro-2,2-difluoroethyl)

This compound was prepared using the method described in Example 23 from compound 106 and chlorodifluoroacetic acid. Spectral data for compound 176: $^1$H NMR (500 MHz, acetone-d$_6$) δ 10.73 (s, 1H), 7.31 (d, J=8.6 Hz, 1H), 7.11 (d, J=8.6 Hz, 1H), 6.68 (s, 1H), 4.18 (qn, J=6.8 Hz, 1H), 4.10 (td, J=16.5, 9.3 Hz, 1H), 3.95 (td, J=16.5, 8.5 Hz, 1H), 3.50 (m, 1H), 1.99 (m, 1H), 1.75 (m, 1H), 1.13 (d, J=6.8 Hz, 3H), 1.06 (t, J=7.4 Hz, 3H).

Example 74

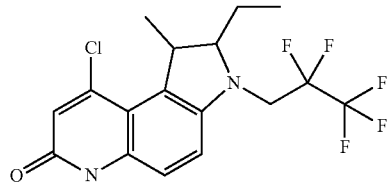 [SMILES: CCC1C(C)c2c(ccc3[nH]c(=O)cc(Cl)c23)N1CC(F)(F)C(F)(F)F]

(±)-9-Chloro-2-ethyl-1-methyl-3-(2,2,3,3,3-pentafluoropropyl)-1,2,3,6-tetrahydro-pyrrolo[3,2-f]quinolin-7-one (Compound 177, Structure 5 of Scheme I, where $R^4$=chloro, $R^1$=methyl, $R^3$=ethyl, $R^5$=2,2,3,3,3-pentafluoropropyl)

This compound was prepared using the method described in Example 23 from compound 106 and pentafluoropropionic acid. Spectral data for compound 177: $^1$H NMR (500 MHz, acetone-d$_6$) δ 10.73 (s, 1H), 7.32 (d, J=8.8 Hz, 1H), 7.01 (d, J=8.8 Hz, 1H), 6.68 (s, 1H), 4.20 (qn, J=6.8 Hz, 1H), 4.01

(ddd, J=24.7, 16.5, 10.4 Hz, 1H), 3.83 (ddd, J=22.5, 16.5, 9.0 Hz, 1H), 3.47 (m, 1H), 1.94 (m, 1H), 1.76 (m, 1H), 1.15 (d, J=6.8 Hz, 3H), 1.06 (t, J=7.3 Hz, 3H).

Example 75

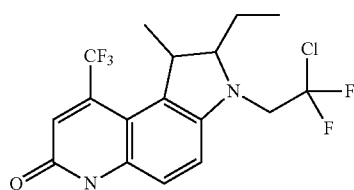 [SMILES: CCC1C(C)c2c(ccc3[nH]c(=O)cc(C(F)(F)F)c23)N1CC(F)(F)Cl]

(±)-3-(2-Chloro-2,2-difluoroethyl)-2-ethyl-1-methyl-9-trifluoromethyl-1,2,3,6-tetrahydro-pyrrolo[3,2-f]quinolin-7-one (Compound 178, Structure 5 of Scheme I, where $R^4$=trifluoromethyl, $R^1$=methyl, $R^3$=ethyl, $R^5$=2-chloro-2,2-difluoroethyl)

This compound was prepared using the method described in Example 23 from 6-hydrazino-4-trifluoromethylquinolin-2(1H)-one and chlorodifluoroacetic acid. Spectral data for compound 178: $^1$H NMR (500 MHz, CDCl$_3$) δ 12.11 (s, 1H), 7.30 (d, J=8.5 Hz, 1H), 7.21 (s, 1H), 7.00 (d, J=8.5 Hz, 1H), 3.89-3.74 (m, 2H), 3.64 (qn, J=6.4 Hz, 1H), 3.46 (m, 1H), 1.88 (m, 1H), 1.77 (m, 1H), 1.06 (t, J=7.4 Hz, 3H), 0.97 (d, J=6.4 Hz, 3H).

Example 76

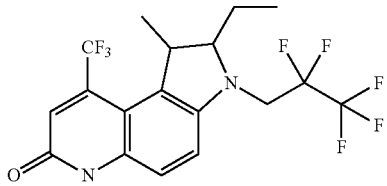 [SMILES: CCC1C(C)c2c(ccc3[nH]c(=O)cc(C(F)(F)F)c23)N1CC(F)(F)C(F)(F)F]

(±)-2-Ethyl-1-methyl-3-(2,2,3,3,3-pentafluoropropyl)-9-trifluoromethyl-1,2,3,6-tetrahydro-pyrrolo[3,2-f]quinolin-7-one (Compound 179, Structure 5 of Scheme I, where $R^4$=trifluoromethyl, $R^1$=methyl, $R^3$=ethyl, $R^5$=2,2,3,3,3-pentafluoropropyl)

This compound was prepared using the method described in Example 23 from 2-ethyl-1-methyl-9-trifluoromethyl-3,6-dihydro-pyrrolo[3,2-f]quinolin-7-one and penta-fluoropropionic acid. Spectral data for compound 179: $^1$H NMR (500 MHz, CDCl$_3$) δ 12.32 (s, 1H), 7.32 (d, J=8.8 Hz, 1H), 7.21 (s, 1H), 6.93 (d, J=8.8 Hz, 1H), 3.75-3.59 (m, 3H), 3.41 (m, 1H), 1.87-1.72 (m, 2H), 1.06 (t, J=7.3 Hz, 3H), 0.98 (d, J=6.6 Hz, 3H).

Example 77

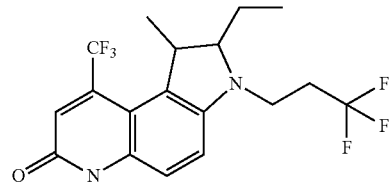 [SMILES: CCC1C(C)c2c(ccc3[nH]c(=O)cc(C(F)(F)F)c23)N1CCC(F)(F)F]

(±)-2-Ethyl-1-methyl-9-trifluoromethyl-3-(3,3,3-trifluoropropyl)-1,2,3,6-tetrahydro-pyrrolo[3,2-f]quinolin-7-one (Compound 180, Structure 5 of Scheme I, where $R^4$=trifluoromethyl, $R^1$=methyl, $R^3$=ethyl, $R^5$=3,3,3-trifluoropropyl)

This compound was prepared using the method described in Example 23 from 2-ethyl-1-methyl-9-trifluoromethyl-3,6-dihydro-pyrrolo[3,2-f]quinolin-7-one and 3,3,3-trifluoropropionic acid. Spectral data for compound 180: $^1$H NMR (500 MHz, CDCl$_3$) δ 11.22 (s, 1H), 7.21 (d, J=8.5 Hz, 1H), 7.18 (s, 1H), 6.85 (d, J=8.5 Hz, 1H), 3.60 (qn, J=6.4 Hz, 1H), 3.54 (ddd, J=15.3, 9.9, 5.2 Hz, 1H), 3.41 (ddd, J=15.3, 9.8, 5.6 Hz, 1H), 3.28 (ddd, J=11.1, 6.4, 4.1 Hz, 1H), 2.35-2.18 (m, 2H), 1.83 (m, 1H), 1.69 (m, 1H), 1.07 (t, J=7.4 Hz, 3H), 0.94 (d, J=6.4 Hz, 3H).

Example 78

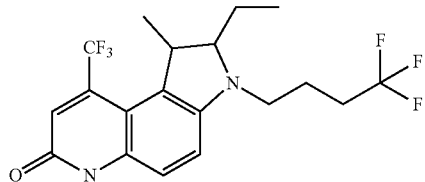 [SMILES: CCC1C(C)c2c(ccc3[nH]c(=O)cc(C(F)(F)F)c23)N1CCCC(F)(F)F]

(±)-2-Ethyl-1-methyl-3-(4,4,4-trifluorobutyl)-9-trifluoromethyl-1,2,3,6-tetrahydro-pyrrolo[3,2-f]quinolin-7-one (Compound 181, Structure 5 of Scheme I, where $R^4$=trifluoromethyl, $R^1$=methyl, $R^3$=ethyl, $R^5$=4,4,4-trifluorobutyl)

This compound was prepared using the method as described in Example 23 from 2-ethyl-1-methyl-9-trifluoromethyl-3,6-dihydro-pyrrolo[3,2-f]quinolin-7-one and 4,4,4-trifluorobutyric acid. Spectral data for compound 181: $^1$H NMR (500 MHz, acetone-d$_6$) δ 12.11 (s, 1H), 7.27 (d, J=8.6 Hz, 1H), 7.19 (s, 1H), 6.83 (d, J=8.6 Hz, 1H), 3.59 (qn, J=6.4 Hz, 1H), 3.32 (ddd, J=11.2, 6.4, 4.0 Hz, 1H), 3.25 (ddd, J=15.2, 8.1, 7.2 Hz, 1H), 3.17 (ddd, J=15.2, 8.3, 6.5 Hz, 1H), 2.25-2.08 (m, 2H), 1.86-1.74 (m, 3H), 1.68 (m, 1H), 1.07 (t, J=7.4 Hz, 3H), 0.94 (d, J=6.4 Hz, 3H).

Example 79

(±)-1,2-Dimethyl-3-(4,4,4-trifluorobutyl)-9-trifluoromethyl-1,2,3,6-tetrahydro-pyrrolo[3,2-f]quinolin-7-one (Compound 182, Structure 5 of Scheme I, where $R^4$=trifluoromethyl, $R^1$=methyl, $R^3$=methyl, $R^5$=4,4,4-trifluorobutyl)

This compound was prepared using the method as described in Example 23 from 1,2-dimethyl-9-trifluoromethyl-3,6-dihydro-pyrrolo[3,2-f]quinolin-7-one and 4,4,4-trifluorobutyric acid. Spectral data for compound 182: $^1$H NMR (500 MHz, CDCl$_3$) δ 11.76 (s, 1H), 7.24 (d, J=8.5 Hz, 1H), 7.18 (s, 1H), 6.83 (d, J=8.5 Hz, 1H), 3.60 (qn, J=6.6 Hz, 1H), 3.50 (qn, J=6.6 Hz, 1H), 3.26 (ddd, J=14.8, 8.2, 7.0 Hz, 1H), 3.17 (ddd, J=14.8, 8.1, 6.6 Hz, 1H), 2.24-2.09 (m, 2H), 1.84-1.74 (m, 2H), 1.32 (d, J=6.6 Hz, 3H), 0.96 (d, J=6.6 Hz, 3H).

Example 80

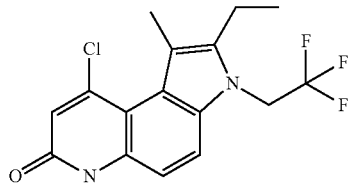 [SMILES: CCc1c(C)c2c3c(Cl)cc(=O)[nH]c3ccc2n1CC(F)(F)F]

9-Chloro-2-ethyl-1-methyl-3-(2,2,2-trifluoro-ethyl)-3,6-dihydro-pyrrolo[3,2-f]quinolin-7-one (Compound 183, Structure 6 of Scheme I, where $R^4$=chloro, $R^1$=methyl, $R^3$=ethyl, $R^5$=2,2,2-trifluoroethyl)

To a solution of Compound 128 (Example 25) (0.34 g, 1.0 mmol) in 30 mL EtOAc was added DDQ (0.35 g, 1.5 mmol, 1.5 eq) in small portions. The resulting green mixture was stirred at rt for about 30 min until almost no more starting material was visible on TLC. Then 5% aq. NaHCO$_3$ (30 mL) was added and the mixture was extracted with EtOAc (3×50 mL) and the combined organic layers were washed with 5% aq. NaHCO$_3$ (30 mL) and brine, dried over MgSO$_4$ and concentrated. Purification by chromatography (Silica gel, hexane:EtOAc 2:1 to 0:1 gradient) afforded Compound 182 (0.21 g, 62%) as a slightly yellow solid. Spectral data for compound 183: $^1$H NMR (500 MHz, DMSO-d$_6$) δ 11.96 (s, 1H), 7.90 (d, J=8.9 Hz, 1H), 7.17 (d, J=8.9 Hz, 1H), 6.68 (s, 1H), 5.27 (q, J=9.1 Hz, 2H), 2.85 (q, J=7.5 Hz, 2H), 2.47 (s, 3H), 1.15 (t, J=7.5 Hz, 3H).

Example 81

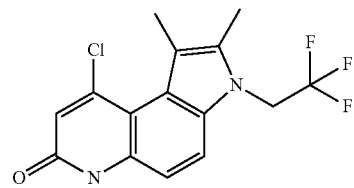 [SMILES: Cc1c(C)n(CC(F)(F)F)c2ccc3[nH]c(=O)cc(Cl)c3c12]

9-Chloro-1,2-dimethyl-3-(2,2,2-trifluoroethyl)-3,6-dihydro-pyrrolo[3,2-f]quinolin-7-one (Compound 184, Structure 6 of Scheme I, where $R^4$=chloro, $R^1$=methyl, $R^3$=methyl, $R^5$=2,2,2-trifluoroethyl)

This compound was prepared using the method described in Example 80 from compound 127. Spectral data for compound 184: $^1$H NMR (500 MHz, DMSO-d$_6$) δ 11.97 (s, 1H), 7.89 (d, J=8.9 Hz, 1H), 7.15 (d, J=8.9 Hz, 1H), 6.66 (s, 1H), 5.27 (q, J=9.1 Hz, 2H), 2.44 (s, 3H), 2.40 (s, 3H).

Example 82

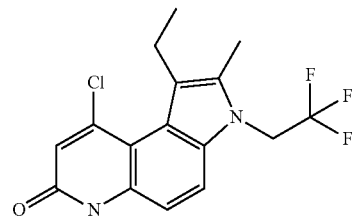 [SMILES: CCc1c(C)n(CC(F)(F)F)c2ccc3[nH]c(=O)cc(Cl)c3c12]

9-Chloro-1-ethyl-2-methyl-3-(2,2,2-trifluoroethyl)-3,6-dihydro-pyrrolo[3,2-f]quinolin-7-one (Compound 185, Structure 6 of Scheme I, where $R^4$=chloro, $R^1$=ethyl, $R^3$=methyl, $R^5$=2,2,2-trifluoroethyl)

This compound was prepared using the method described in Example 80 from compound 129. Spectral data for compound 185: $^1$H NMR (500 MHz, DMSO-d$_6$) δ 11.95 (s, 1H), 7.91 (d, J=8.9 Hz, 1H), 7.17 (d, J=8.9 Hz, 1H), 6.70 (s, 1H), 5.28 (q, J=9.2 Hz, 2H), 3.04 (q, J=7.3 Hz, 2H), 2.44 (s, 3H), 1.09 (t, J=7.3 Hz, 3H).

Example 83

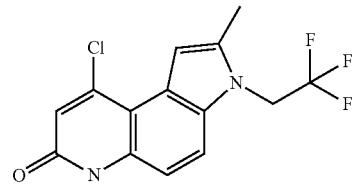 [SMILES: Cc1cc2c3c(Cl)cc(=O)[nH]c3ccc2n1CC(F)(F)F]

9-Chloro-2-methyl-3-(2,2,2-trifluoroethyl)-3,6-dihydro-pyrrolo[3,2-f]quinolin-7-one (Compound 186, Structure 6 of Scheme I, where $R^4$=chloro, $R^1$=hydrogen, $R^3$=methyl, $R^5$=2,2,2-trifluoroethyl)

This compound was prepared using the method described in Example 80 from compound 131. Spectral data for compound 186: $^1$H NMR (500 MHz, DMSO-d$_6$) δ 11.94 (s, 1H), 7.90 (d, J=9.3 Hz, 1H), 7.36 (d, J=9.3 Hz, 1H), 7.35 (s, 1H), 6.72 (s, 1H), 5.22 (q, J=9.1 Hz, 2H), 2.62 (s, 3H).

Example 84

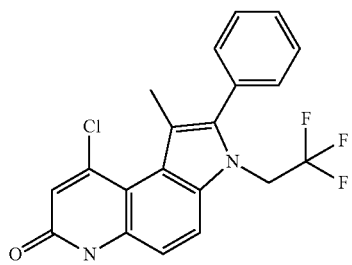 [SMILES: Cc1c(-c2ccccc2)n(CC(F)(F)F)c2ccc3[nH]c(=O)cc(Cl)c3c12]

9-Chloro-1-methyl-2-phenyl-3-(2,2,2-trifluoroethyl)-3,6-dihydro-pyrrolo[3,2-f]quinolin-7-one (Compound 187, Structure 6 of Scheme I, where $R^4$=chloro, $R^1$=methyl, $R^3$=phenyl, $R^5$=2,2,2-trifluoroethyl)

This compound was prepared using the method described in Example 80 from compound 130. Spectral data for compound 187: $^1$H NMR (500 MHz, DMSO-d$_6$) δ 12.09 (s, 1H), 8.07 (d, J=9.0 Hz, 1H), 7.58 (td, J=7.5, 1.4 Hz, 2H), 7.52 (tt, J=7.5, 1.4 Hz, 1H), 7.44 (dd, J=7.5, 1.4 Hz, 2H), 7.29 (d, J=9.0 Hz, 1H), 6.73 (s, 1H), 5.06 (q, J=8.7 Hz, 2H), 2.33 (s, 3H).

Example 85

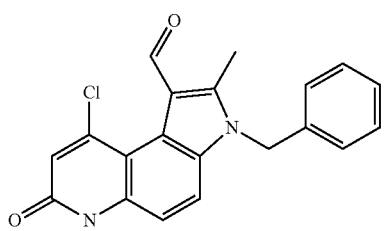 [SMILES: Cc1c(C=O)c2c3c(Cl)cc(=O)[nH]c3ccc2n1Cc1ccccc1]

3-Benzyl-9-chloro-2-methyl-7-oxo-6,7-dihydro-3H-pyrrolo[3,2-f]quinoline-1-carbaldehyde (Compound 188, Structure 6 of Scheme I, where $R^4$=chloro, $R^1$=formyl, $R^3$=methyl, $R^5$=phenylmethyl)

This compound was prepared using the method described in Example 80 from compound 144. Spectral data for compound 188: $^1$H NMR (500 MHz, DMSO-d$_6$) δ 12.18 (s, 1H), 10.55 (s, 1H), 7.94 (d, J=8.8 Hz, 1H), 7.38-7.26 (m, 5H), 7.05 (d, J=2.9 Hz, 1H), 6.80 (s, 1H), 5.65 (s, 2H), 2.68 (s, 3H).

Example 86

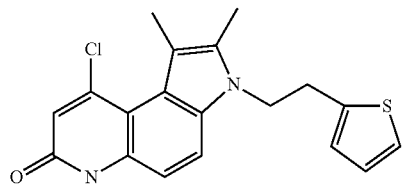 [SMILES: Cc1c(C)n(CCc2cccs2)c2ccc3[nH]c(=O)cc(Cl)c3c12]

9-Chloro-1,2-dimethyl-3-(2-thien-2-yl-ethyl)-3,6-dihydro-pyrrolo[3,2-f]quinolin-7-one (Compound 189, Structure 6 of Scheme I, where $R^4$=chloro, $R^1$=methyl, $R^3$=methyl, $R^5$=2-thien-2-ylethyl)

This compound was prepared using the method described in Example 80 from compound 142. Spectral data for compound 189: $^1$H NMR (500 MHz, acetone-d$_6$) δ 10.08 (s, 1H), 7.78 (d, J=8.8 Hz, 1H), 7.31 (dd, J=4.9 Hz, 1.0 Hz, 1H), 7.28 (d, J=8.8 Hz, 1H), 7.18 (s, 1H), 6.95 (dd, J=4.9 Hz, 2.9 Hz, 1H), 6.78 (d, J=2.9 Hz, 1H), 6.68 (s, 1H), 4.56 (t, J=6.8 Hz, 2H), 3.37 (t, J=6.8 Hz, 2H), 2.34 (s, 3H), 2.13 (s, 3H).

Example 87

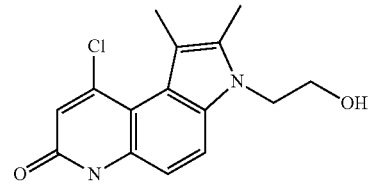 [SMILES: Cc1c(C)n(CCO)c2ccc3[nH]c(=O)cc(Cl)c3c12]

9-Chloro-3-(2-hydroxy-ethyl)-1,2-dimethyl-3,6-dihydro-pyrrolo[3,2-f]quinolin-7-one (Compound 190, Structure 6 of Scheme I, where $R^4$=chloro, $R^1$=methyl, $R^3$=methyl, $R^5$=2-hydroxy-ethyl)

This compound was prepared using the method described in Example 80 from compound 139. Spectral data for compound 190: $^1$H NMR (500 MHz, CDCl$_3$) δ 11.96 (s, 1H), 7.59 (d, J=8.8 Hz, 1H), 7.22 (d, J=8.8 Hz, 1H), 6.93 (s, 1H), 4.54-4.47 (m, 4H), 4.01 (s, 1H), 2.59 (s, 3H), 2.51 (s, 3H).

Example 88

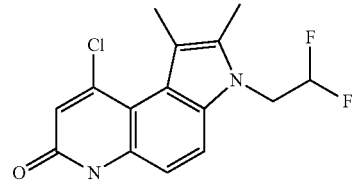 [SMILES: Cc1c(C)n(CC(F)F)c2ccc3[nH]c(=O)cc(Cl)c3c12]

9-Chloro-3-(2,2-difluoroethyl)-1,2-dimethyl-3,6-dihydro-pyrrolo[3,2-f]quinolin-7-one (Compound 191, Structure 6 of Scheme I, where $R^4$=chloro, $R^1$=methyl, $R^3$=methyl, $R^5$=2,2-difluoroethyl)

This compound was prepared using the method described in Example 80 from compound 143. Spectral data for compound 191: $^1$H NMR (500 MHz, CDCl$_3$) δ 11.35 (s, 1H), 7.56 (d, J=8.8 Hz, 1H), 7.18 (d, J=8.8 Hz, 1H), 6.92 (s, 1H), 6.02 (tt, J=54.7 Hz, 3.4 Hz, 1H), 4.56 (dt, J=13.7 Hz, 3.9 Hz, 2H), 2.60 (s, 3H), 2.48 (s, 3H).

Example 89

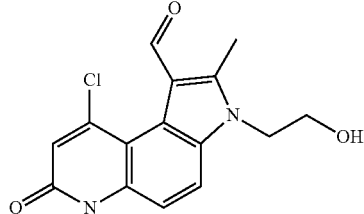 [SMILES: Cc1c(C=O)c2c3c(Cl)cc(=O)[nH]c3ccc2n1CCO]

9-Chloro-3-(2-hydroxy-ethyl)-2-methyl-7-oxo-6,7-dihydro-3H-pyrrolo[3,2-f]quinoline-1-carbaldehyde (Compound 192, Structure 6 of Scheme I, where $R^4$=chloro, $R^1$=formyl, $R^3$=methyl, $R^5$=2-hydroxyethyl)

This compound was isolated as a byproduct from the oxidation of compound 139. Spectral data for compound 192: $^1$H NMR (500 MHz, CDCl$_3$) δ 11.94 (s, 1H), 10.30 (s, 1H), 7.84 (d, J=8.8 Hz, 1H), 7.14 (d, J=8.8 Hz, 1H), 6.66 (s, 1H), 4.87 (d, J=4.4 Hz, 1H), 4.56 (t, J=5.7 Hz, 1H), 4.49 (t, J=5.7 Hz, 1H), 4.44-4.39 (m, 1H), 4.32 (s, 1H), 2.519 (s, 3H).

Example 90

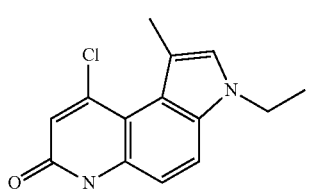 [SMILES: CCn1cc(C)c2c3c(Cl)cc(=O)[nH]c3ccc21]

9-Chloro-3-ethyl-1-methyl-3,6-dihydro-pyrrolo[3,2-f]quinolin-7-one (Compound 193, Structure 6 of Scheme I, where $R^4$=chloro, $R^1$=methyl, $R^3$=hydrogen, $R^5$=ethyl)

This compound was a prepared using the method described in Example 80 from compound 134. Spectral data for compound 193: $^1$H NMR (500 MHz, CD$_3$OD) δ 7.78 (d, J=8.9 Hz, 1H), 7.28 (m, 1H), 7.22 (d, J=8.9 Hz, 1H), 6.78 (s, 1H), 4.25 (q, J=7.2 Hz, 2H), 2.63 (d, J=1.0 Hz, 3H), 1.43 (t, J=7.2 Hz, 3H).

Examle 91

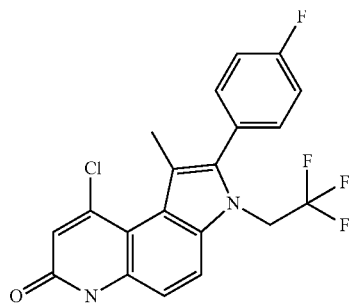 [SMILES: Cc1c(-c2ccc(F)cc2)n(CC(F)(F)F)c2ccc3[nH]c(=O)cc(Cl)c3c12]

9-Chloro-2-(4-fluorophenyl)-1-methyl-3-(2,2,2-trifluoroethyl)-3,6-dihydro-pyrrolo[3,2-f]quinolin-7-one (Compound 194, Structure 6 of Scheme I, where $R^4$=chloro, $R^1$=methyl, $R^3$=4-fluorophenyl, $R^5$=2,2,2-trifluoroethyl)

This compound was a prepared using the method described in Example 80 from compound 149. Spectral data for compound 194: $^1$H NMR (500 MHz, acetone-d$_6$) δ 11.77 (s, 1H), 8.08 (d, J=8.9 Hz, 1H), 7.62 (dd, J=8.8, 5.4 Hz, 2H), 7.48 (d, J=8.9 Hz, 1H), 7.42 (t, J=8.8 Hz, 2H), 6.81 (s, 1H), 5.09 (q, J=8.7 Hz, 2H), 2.47 (s, 3H).

Example 92

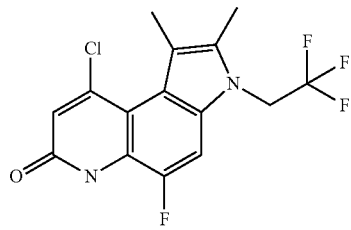 [SMILES: Cc1c(C)n(CC(F)(F)F)c2cc(F)c3[nH]c(=O)cc(Cl)c3c12]

9-Chloro-1,2-dimethyl-5-fluoro-3-(2,2,2-trifluoroethyl)-3,6-dihydro-pyrrolo[3,2-f]quinolin-7-one (Compound 195, Structure 6 of Scheme I, where $R^4$=chloro, $R^1$=methyl, $R^3$=methyl, $R^5$=2,2,2-trifluoroethyl, $R^6$=fluoro)

This compound was prepared using the method described in Example 80 from compound 151. Spectral data for compound 195: $^1$H NMR (500 MHz, acetone-d$_6$) δ 10.44 (s, 1H), 7.94 (d, J=11.0 Hz, 1H), 6.79 (s, 1H), 5.25 (q, J=8.9 Hz, 2H), 2.58 (s, 3H), 2.54 (s, 3H).

Example 93

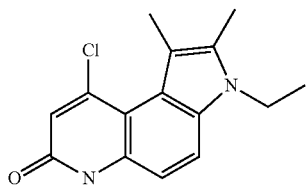 [SMILES: CCn1c(C)c(C)c2c3c(Cl)cc(=O)[nH]c3ccc21]

9-Chloro-1,2-dimethyl-3-ethyl-3,6-dihydro-pyrrolo[3,2-f]quinolin-7-one (Compound 196, Structure 6 of Scheme I, where $R^4$=chloro, $R^1$=methyl, $R^3$=methyl, $R^5$=ethyl)

This compound was prepared using the method described in Example 80 from compound 135. Spectral data for compound 196: $^1$H NMR (500 MHz, DMSO-$d_6$) δ 11.94 (s, 1H), 7.80 (d, J=8.8 Hz, 1H), 7.13 (d, J=8.8 Hz, 1H), 6.65 (s, 1H), 4.27 (q, J=7.1 Hz, 2H), 2.47 (s, 3H), 2.42 (s, 3H), 1.24 (t, J=7.1 Hz, 3H).

Example 94

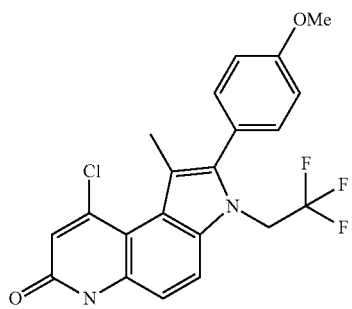 [SMILES: COc1ccc(-c2c(C)c3c4c(Cl)cc(=O)[nH]c4ccc3n2CC(F)(F)F)cc1]

9-Chloro-2-(4-methoxyphenyl)-1-methyl-3-(2,2,2-trifluoroethyl)-3,6-dihydro-pyrrolo[3,2-f]-quinolin-7-one (Compound 197, Structure 6 of Scheme I, where $R^4$=chloro, $R^1$=methyl, $R^3$=4-methoxyphenyl, $R^5$=2,2,2-trifluoroethyl)

This compound was prepared using the method described in Example 80 from compound 148. Spectral data for compound 197: $^1$H NMR (500 MHz, acetone-$d_6$) δ 11.11 (s, 1H), 8.04 (d, J=8.8 Hz, 1H), 7.45 (d, J=8.6 Hz, 2H), 7.45 (d, J=8.8 Hz, 1H), 7.19 (d, J=8.6 Hz, 2H), 6.76 (s, 1H), 5.06 (q, J=8.8 Hz, 2H), 3.95 (s, 3H), 2.46 (s, 3H).

Example 95

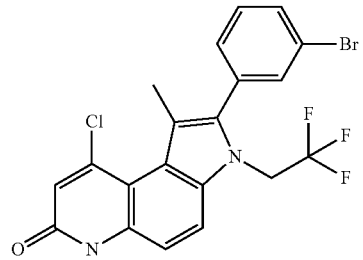 [SMILES: Cc1c(-c2cccc(Br)c2)n(CC(F)(F)F)c2ccc3[nH]c(=O)cc(Cl)c3c12]

2-(3-Bromophenyl)-9-Chloro-1-methyl-3-(2,2,2-trifluoroethyl)-3,6-dihydro-pyrrolo[3,2-f]-quinolin-7-one (Compound 198, Structure 6 of Scheme I, where $R^4$=chloro, $R^1$=methyl, $R^3$=3-bromophenyl, $R^5$=2,2,2-trifluoroethyl)

This compound was prepared using the method described in Example 80 from compound 153. Spectral data for compound 198: $^1$H NMR (500 MHz, DMSO-$d_6$) δ 8.11 (d, J=8.9 Hz, 1H), 7.76 (m, 1H), 7.70 (t, J=1.5 Hz, 1H), 7.56 (t, J=7.8 Hz, 1H), 7.50 (m, 1H), 7.35 (d, J=8.9 Hz, 1H), 6.75 (s, 1H), 5.10 (q, J=8.6 Hz, 2H), 2.37 (s, 3H).

Example 96

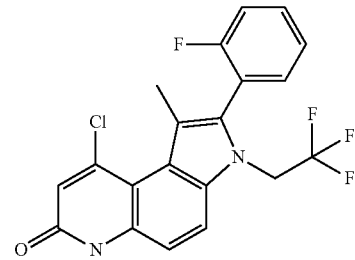 [SMILES: Cc1c(-c2ccccc2F)n(CC(F)(F)F)c2ccc3[nH]c(=O)cc(Cl)c3c12]

9-Chloro-2-(2-fluorophenyl)-1-methyl-3-(2,2,2-trifluoroethyl)-3,6-dihydro-pyrrolo[3,2-f]quinolin-7-one (Compound 199, Structure 6 of Scheme I, where $R^4$=chloro, $R^1$=methyl, $R^3$=2-fluorophenyl, $R^5$=2,2,2-trifluoroethyl)

This compound was prepared using the method described in Example 80 from compound 156. Spectral data for compound 199: $^1$H NMR (500 MHz, CD$_3$OD) δ 7.99 (d, J=9.0 Hz, 1H), 7.65 (m, 1H), 7.49 (td, J=7.4, 1.5 Hz, 1H), 7.44 (td, J=7.4, 1.5 Hz, 1H), 7.39 (d, J=9.0 Hz, 1H), 7.37 (m, 1H), 6.87 (s, 1H), 5.04 (dq, J=16.4, 8.5 Hz, 1H), 4.81 (dq, J=16.4, 8.6 Hz, 1H), 2.46 (s, 3H).

Example 97

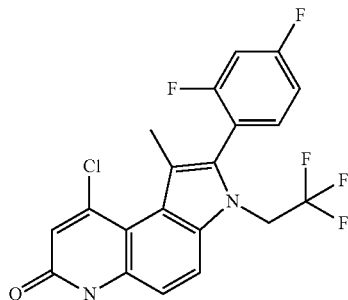 [SMILES: Cc1c(-c2ccc(F)cc2F)n(CC(F)(F)F)c2ccc3[nH]c(=O)cc(Cl)c3c12]

9-Chloro-2-(2,4-difluorophenyl)-1-methyl-3-(2,2,2-trifluoroethyl)-3,6-dihydro-pyrrolo[3,2-f]-quinolin-7-one (Compound 200, Structure 6 of Scheme I, where $R^4$=chloro, $R^1$=methyl, $R^3$=2,4-difluorophenyl, $R^5$=2,2,2-trifluoroethyl)

This compound was prepared using the method described in Example 80 from compound 150. Spectral data for compound 200: $^1$H NMR (500 MHz, acetone-$d_6$) δ 11.49 (s, 1H), 8.09 (d, J=9.0 Hz, 1H), 7.67 (dt, J=8.9, 7.4 Hz, 1H), 7.54 (d, J=9.0 Hz, 1H), 7.37-7.30 (m, 2H), 6.80 (s, 1H), 5.15 (dq, J=16.4, 8.7 Hz, 1H), 5.01 (dq, J=16.4, 8.7 Hz, 1H), 2.47 (s, 3H).

Example 98

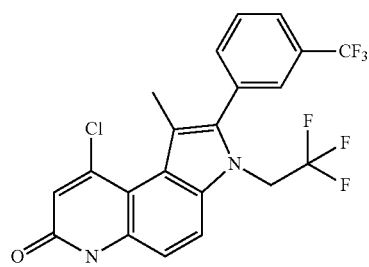 [SMILES: Cc1c(-c2cccc(C(F)(F)F)c2)n(CC(F)(F)F)c2ccc3[nH]c(=O)cc(Cl)c3c12]

9-Chloro-1-methyl-2-(3-trifluoromethylphenyl)-3-(2,2,2-trifluoroethyl)-3,6-dihydro-pyrrolo[3,2-f]-quinolin-7-one (Compound 201, Structure 6 of Scheme I, where $R^4$=chloro, $R^1$=methyl, $R^3$=3-trifluoromethylphenyl, $R^5$=2,2,2-trifluoroethyl)

This compound was prepared using the method described in Example 80 from compound 159. Spectral data for compound 201: $^1$H NMR (500 MHz, acetone-$d_6$) δ 11.14 (s, 1H), 8.10 (d, J=8.9 Hz, 1H), 7.97 (m, 1H), 7.93-7.87 (m, 3H), 7.51 (d, J=8.9 Hz, 1H), 6.78 (s, 1H), 5.12 (q, J=8.8 Hz, 2H), 2.48 (s, 3H).

Example 99

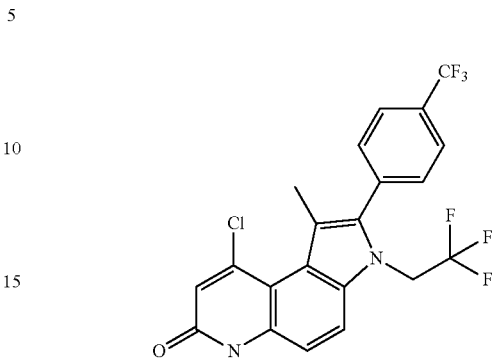

9-Chloro-1-methyl-2-(4-trifluoromethylphenyl)-3-(2,2,2-trifluoroethyl)-3,6-dihydro-pyrrolo[3,2-f]-quinolin-7-one (Compound 202, Structure 6 of Scheme I, where $R^4$=chloro, $R^1$=methyl, $R^3$=4-trifluoromethylphenyl, $R^5$=2,2,2-trifluoroethyl)

This compound was prepared using the method described in Example 80 from compound 147. Spectral data for compound 202: $^1$H NMR (500 MHz, acetone-$d_6$) δ 11.15 (s, 1H), 8.10 (d, J=9.0 Hz, 1H), 8.00 (d, J=8.1 Hz, 2H), 7.82 (d, J=8.1 Hz, 2H), 7.51 (d, J=9.0 Hz, 1H), 6.78 (s, 1H), 5.15 (q, J=8.7 Hz, 2H), 2.49 (s, 3H).

Example 100

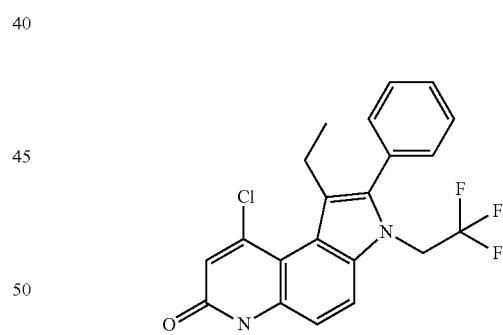

9-Chloro-1-ethyl-2-phenyl-3-(2,2,2-trifluoroethyl)-3,6-dihydro-pyrrolo[3,2-f]quinolin-7-one (Compound 203, Structure 6 of Scheme I, where $R^4$=chloro, $R^1$=ethyl, $R^3$=phenyl, $R^5$=2,2,2-trifluoroethyl)

This compound was prepared using the method described in Example 80 from compound 160. Spectral data for compound 203: $^1$H NMR (500 MHz, acetone-$d_6$) δ 11.21 (s, 1H), 8.05 (d, J=9.0 Hz, 1H), 7.67-7.59 (m, 3H), 7.53 (dd, J=7.8, 1.5 Hz, 2H), 7.48 (d, J=9.0 Hz, 1H), 6.80 (s, 1H), 5.01 (q, J=8.8 Hz, 2H), 3.04 (q, J=7.4 Hz, 2H), 1.03 (t, J=7.4 Hz, 3H).

Example 101

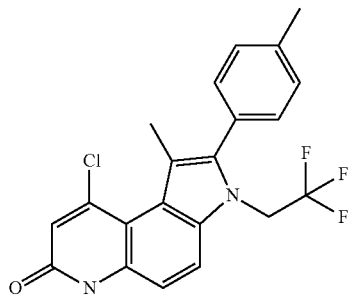 [SMILES: Cc1ccc(-c2c(C)c3c4c(Cl)cc(=O)[nH]c4ccc3n2CC(F)(F)F)cc1]

9-Chloro-1-methyl-2-(4-methylphenyl)-3-(2,2,2-trifluoroethyl)-3,6-dihydro-pyrrolo[3,2-f]-quinolin-7-one (Compound 204, Structure 6 of Scheme I, where $R^4$=chloro, $R^1$=methyl, $R^3$=4-methylphenyl, $R^5$=2,2,2-trifluoroethyl)

This compound was prepared using the method described in Example 80 from compound 147. Spectral data for compound 204: $^1$H NMR (500 MHz, acetone-$d_6$) δ 11.10 (s, 1H), 8.04 (d, J=8.9 Hz, 1H), 7.46 (d, J=8.9 Hz, 1H), 7.46 (d, J=8.1 Hz, 2H), 7.41 (d, J=8.1 Hz, 2H), 6.76 (s, 1H), 5.07 (q, J=8.7 Hz, 2H), 2.49 (s, 3H), 2.47 (s, 3H).

Example 102

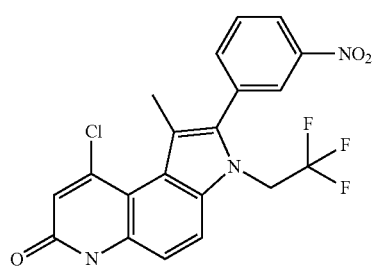 [SMILES: Cc1c(-c2cccc([N+](=O)[O-])c2)n(CC(F)(F)F)c2ccc3[nH]c(=O)cc(Cl)c3c12]

9-Chloro-1-methyl-2-(3-nitrophenyl)-3-(2,2,2-trifluoroethyl)-3,6-dihydro-pyrrolo[3,2-f]quinolin-7-one (Compound 205, Structure 6 of Scheme I, where $R^4$=chloro, $R^1$=methyl, $R^3$=3-nitrophenyl, $R^5$=2,2,2-trifluoroethyl)

This compound was prepared using the method described in Example 80 from compound 154. Spectral data for compound 205: $^1$H NMR (500 MHz, acetone-$d_6$) δ 8.47 (m, 1H), 8.43 (t, J=1.5 Hz, 1H), 8.12 (d, J=8.8 Hz, 1H), 8.05 (m, 1H), 7.97 (t, J=7.9 Hz, 1H), 7.54 (d, J=8.8 Hz, 1H), 6.81 (s, 1H), 5.17 (q, J=8.6 Hz, 2H), 2.50 (s, 3H).

Example 103

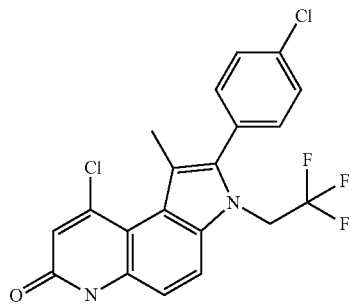

9-Chloro-2(4-chlorophenyl)-1-methyl-3-(2,2,2-trifluoroethyl)-3,6-dihydro-pyrrolo[3,2-f]quinolin-7-one (Compound 206, Structure 6 of Scheme I, where $R^4$=chloro, $R^1$=methyl, $R^3$=4-chlorophenyl, $R^5$=2,2,2-trifluoroethyl)

This compound was prepared using the method described in Example 80 from compound 152. Spectral data for compound 206: $^1$H NMR (500 MHz, acetone-$d_6$) δ 11.19 (s, 1H), 8.07 (d, J=8.9 Hz, 1H), 7.68 (d, J=8.5 Hz, 2H), 7.58 (d, J=8.5 Hz, 2H), 7.49 (d, J=8.9 Hz, 1H), 6.78 (s, 1H), 5.11 (q, J=8.8 Hz, 2H), 2.47 (s, 3H).

Example 104

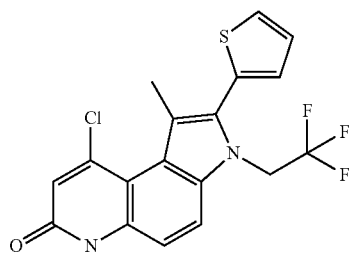 [SMILES: Cc1c(-c2cccs2)n(CC(F)(F)F)c2ccc3[nH]c(=O)cc(Cl)c3c12]

9-Chloro-1-methyl-2-thien-2-yl-3-(2,2,2-trifluoroethyl)-3,6-dihydro-pyrrolo[3,2-f]quinolin-7-one (Compound 207, Structure 6 of Scheme I, where $R^4$=chloro, $R^1$=methyl, $R^3$=thien-2-yl, $R^5$=2,2,2-trifluoroethyl)

This compound was prepared using the method described in Example 80 from compound 161. Spectral data for compound 207: $^1$H NMR (500 MHz, acetone-$d_6$) δ 11.20 (s, 1H), 8.01 (d, J=8.8 Hz, 1H), 7.83 (dd, J=3.4, 3.0 Hz, 1H), 7.46 (d, J=8.8 Hz, 1H), 7.31 (d, J=3.0 Hz, 1H), 7.31 (d, J=3.4 Hz, 1H), 6.74 (s, 1H), 5.10 (q, J=8.8 Hz, 2H), 2.51 (s, 3H).

Example 105

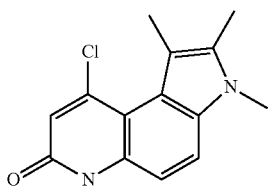 [SMILES: Cc1c(C)n(C)c2ccc3[nH]c(=O)cc(Cl)c3c12]

9-Chloro-1,2,3-trimethyl-3,6-dihydro-pyrrolo[3,2-f]
quinolin-7-one (Compound 208, Structure 6 of
Scheme I, where $R^4$=chloro, $R^1$=methyl, $R^3$=methyl,
$R^5$=methyl)

This compound was prepared using the method described in Example 80 from compound 136. Spectral data for compound 208: $^1$H NMR (500 MHz, acetone-d$_6$) δ 10.90 (s, 1H), 7.75 (d, J=8.8 Hz, 1H), 7.26 (d, J=8.8 Hz, 1H), 6.66 (s, 1H), 3.85 (s, 3H), 2.57 (s, 3H), 2.48 (s, 3H).

Example 106

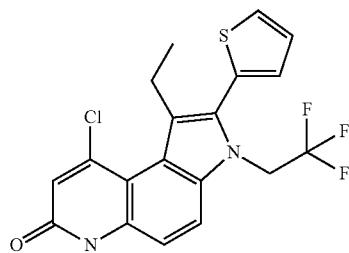 [SMILES: CCc1c(-c2cccs2)n(CC(F)(F)F)c2ccc3[nH]c(=O)cc(Cl)c3c12]

9-Chloro-1-ethyl-2-thien-2-yl-3-(2,2,2-trifluoroethyl)-3,6-dihydro-pyrrolo[3,2-f]quinolin-7-one (Compound 209, Structure 6 of Scheme I, where
$R^4$=chloro, $R^1$=ethyl, $R^3$=thien-2-yl, $R^5$=2,2,2-trifluoroethyl)

This compound was prepared using the method described in Example 80 from compound 164. Spectral data for compound 209: $^1$H NMR (500 MHz, acetone-d$_6$) δ 11.24 (s, 1H), 8.01 (d, J=9.0 Hz, 1H), 7.83 (dd, J=4.3, 2.4 Hz, 1H), 7.46 (d, J=9.0 Hz, 1H), 7.32-7.30 (m, 2H), 6.77 (s, 1H), 5.04 (q, J=8.8 Hz, 2H), 3.08 (q, J=7.4 Hz, 2H), 1.03 (t, J=7.4 Hz, 3H).

Example 107

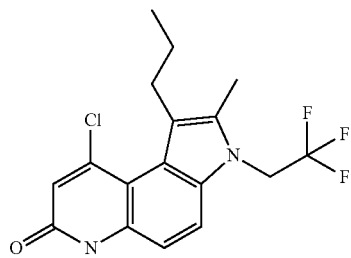 [SMILES: CCCc1c(C)n(CC(F)(F)F)c2ccc3[nH]c(=O)cc(Cl)c3c12]

9-Chloro-2-methyl-1-propyl-3-(2,2,2-trifluoroethyl)-
3,6-dihydro-pyrrolo[3,2-f]quinolin-7-one (Compound 210, Structure 6 of Scheme I, where
$R^4$=chloro, $R^1$=propyl, $R^3$=methyl, $R^5$=2,2,2-trifluoroethyl)

This compound was prepared using the method described in Example 80 from compound 165. Spectral data for compound 210: $^1$H NMR (500 MHz, DMSO-d$_6$) δ 11.98 (s, 1H), 7.90 (d, J=8.8 Hz, 1H), 7.16 (d, J=8.8 Hz, 1H), 6.69 (s, 1H), 5.27 (q, J=9.0 Hz, 2H), 2.97 (t, J=7.3 Hz, 2H), 2.42 (s, 3H), 1.46 (sext, J=7.3 Hz, 2H), 0.81 (t, J=7.3 Hz, 3H).

Example 108

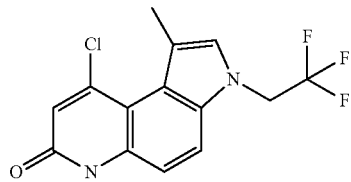 [SMILES: Cc1cn(CC(F)(F)F)c2ccc3[nH]c(=O)cc(Cl)c3c12]

9-Chloro-1-methyl-3-(2,2,2-trifluoroethyl)-3,6-dihydro-pyrrolo[3,2-f]quinolin-7-one (Compound 211,
Structure 6 of Scheme I, where $R^4$=chloro,
$R^1$=methyl, $R^3$=hydrogen, $R^5$=2,2,2-trifluoroethyl)

This compound was prepared using the method described in Example 80 from compound 132. Spectral data for compound 211: $^1$H NMR (500 MHz, DMSO-d$_6$) δ 12.07 (s, 1H), 7.98 (d, J=9.0 Hz, 1H), 7.44 (s, 1H), 7.29 (d, J=9.0 Hz, 1H), 6.75 (s, 1H), 5.27 (q, J=9.2 Hz, 2H), 2.58 (s, 3H).

Example 109

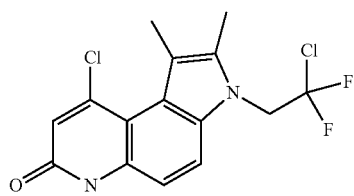 [SMILES: Cc1c(C)n(CC(F)(F)Cl)c2ccc3[nH]c(=O)cc(Cl)c3c12]

9-Chloro-3-(2-chloro-2,2-difluoroethyl)-1,2-dimethyl-3,6-dihydro-pyrrolo[3,2-f]quinolin-7-one (Compound 212, Structure 6 of Scheme I, where $R^4$=chloro, $R^1$=methyl, $R^3$=methyl, $R^5$=2-chloro-2,2-trifluoroethyl)

This compound was prepared using the method described in Example 80 from compound 138. Spectral data for compound 212: $^1$H NMR (500 MHz, DMSO-$d_6$) δ 11.96 (s, 1H), 7.90 (d, J=8.9 Hz, 1H), 7.15 (d, J=8.9 Hz, 1H), 6.66 (s, 1H), 5.36 (t, J=12.0 Hz, 2H), 2.44 (s, 3H), 2.41 (s, 3H).

Example 110

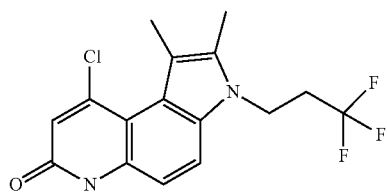 [SMILES: Cc1c(C)n(CCC(F)(F)F)c2ccc3[nH]c(=O)cc(Cl)c3c12]

9-Chloro-1,2-dimethyl-3-(3,3,3-trifluoropropyl)-3,6-dihydro-pyrrolo[3,2-f]quinolin-7-one (Compound 213, Structure 6 of Scheme I, where $R^4$=chloro, $R^1$=methyl, $R^3$=methyl, $R^5$=3,3,3-trifluoropropyl)

This compound was prepared using the method described in Example 80 from compound 145. Spectral data for compound 213: $^1$H NMR (500 MHz, acetone-$d_6$) δ 7.77 (d, J=8.8 Hz, 1H), 7.26 (d, J=8.8 Hz, 1H), 6.64 (s, 1H), 4.59 (t, J=7.4 Hz, 2H), 2.78 (m, 2H), 2.52 (s, 3H), 2.49 (s, 3H).

Example 111

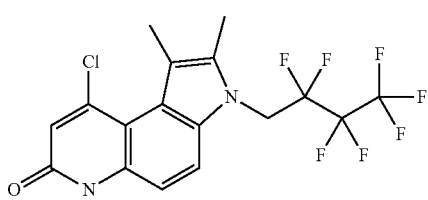 [SMILES: Cc1c(C)n(CC(F)(F)C(F)(F)C(F)(F)F)c2ccc3[nH]c(=O)cc(Cl)c3c12]

9-Chloro-1,2-dimethyl-3-(2,2,3,3,4,4,4-heptafluorobutyl)-3,6-dihydro-pyrrolo[3,2-f]-quinolin-7-one (Compound 214, Structure 6 of Scheme I, where $R^4$=chloro, $R^1$=methyl, $R^3$=methyl, $R^5$=2,2,3,3,4,4,4-heptafluorobutyl)

This compound was prepared using the method described in Example 80 from compound 168. Spectral data for compound 214: $^1$H NMR (500 MHz, DMSO-$d_6$) δ 11.98 (s, 1H), 7.82 (d, J=9.0 Hz, 1H), 7.18 (d, J=9.0 Hz, 1H), 6.68 (s, 1H), 5.33 (t, J=17.2 Hz, 2H); 2.46 (s, 3H), 2.40 (s, 3H).

Example 112

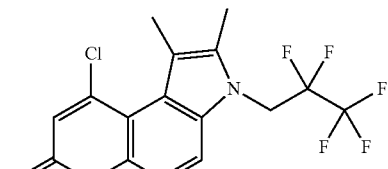

9-Chloro-1,2-dimethyl-3-(2,2,3,3,3-pentafluoropropyl)-3,6-dihydro-pyrrolo[3,2-f]-quinolin-7-one (Compound 215, Structure 6 of Scheme I, where $R^4$=chloro, $R^1$=methyl, $R^3$=methyl, $R^5$=2,2,3,3,3-pentafluoropropyl)

This compound was prepared using the method described in Example 80 from compound 167. Spectral data for compound 215: $^1$H NMR (500 MHz, DMSO-$d_6$) δ 11.98 (s, 1H), 7.83 (d, J=8.9 Hz, 1H), 7.17 (d, J=8.9 Hz, 1H), 6.68 (s, 1H), 5.32 (t, J=16.5 Hz, 2H), 2.46 (s, 3H), 2.40 (s, 3H).

Example 113

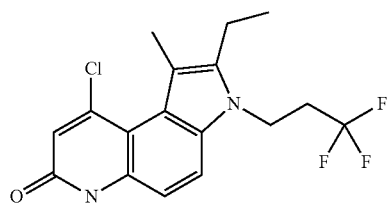 [SMILES: CCc1c(C)c2c3c(Cl)cc(=O)[nH]c3ccc2n1CCC(F)(F)F]

9-Chloro-2-ethyl-1-methyl-3-(3,3,3-trifluoropropyl)-3,6-dihydro-pyrrolo[3,2-f]quinolin-7-one (Compound 216, Structure 6 of Scheme I, where $R^4$=chloro, $R^1$=methyl, $R^3$=ethyl, $R^5$=3,3,3-trifluoropropyl)

This compound was prepared using the method described in Example 80 from compound 170. Spectral data for compound 216: $^1$H NMR (500 MHz, DMSO-$d_6$) δ 11.95 (s, 1H), 7.77 (d, J=8.9 Hz, 1H), 7.16 (d, J=8.9 Hz, 1H), 6.65 (s, 1H), 4.48 (dd, J=7.7, 6.6 Hz, 2H), 2.82 (q, J=7.6 Hz, 2H), 2.74 (m, 2H), 2.46 (s, 3H), 1.17 (t, J=7.6 Hz, 3H).

Example 114

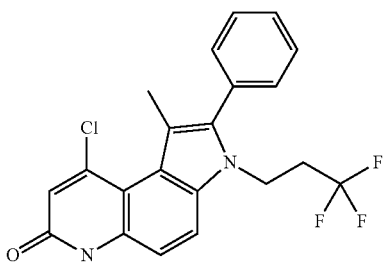 [SMILES: Cc1c(-c2ccccc2)n(CCC(F)(F)F)c2ccc3[nH]c(=O)cc(Cl)c3c12]

9-Chloro-1-methyl-2-phenyl-3-(3,3,3-trifluorouro-pyl)-3,6-dihydro-pyrrolo[3,2-f]quinolin-7-one (Compound 217, Structure 6 of Scheme I, where $R^4$=chloro, $R^1$=methyl, $R^3$=phenyl, $R^5$=3,3,3-trifluoropropyl)

This compound was prepared using the method described in Example 80 from compound 169. Spectral data for compound 217: $^1$H NMR (500 MHz, DMSO-$d_6$) δ 12.06 (s, 1H), 7.94 (d, J=9.0 Hz, 1H), 7.58 (td, J=7.0, 1.6 Hz, 2H), 7.54 (tt, J=7.0, 1.6 Hz, 1H), 7.48 (dd, J=7.0, 1.6 Hz, 2H), 7.29 (d, J=9.0 Hz, 1H), 6.71 (s, 1H), 4.37 (dd, J=7.9, 6.5 Hz, 2H), 2.55 (m, 2H), 2.36 (s, 3H).

Example 115

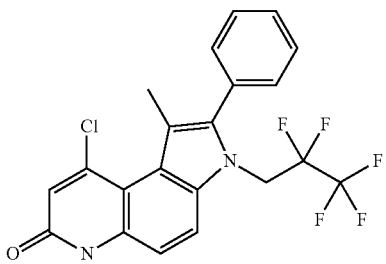 [SMILES: Cc1c(-c2ccccc2)n(CC(F)(F)C(F)(F)F)c2ccc3[nH]c(=O)cc(Cl)c3c12]

9-Chloro-1-methyl-3-(2,2,3,3,3-pentafluoropropyl)-2-phenyl-3,6-dihydro-pyrrolo[3,2-f]quinolin-7-one (Compound 218, Structure 6 of Scheme I, where $R^4$=chloro, $R^1$=methyl, $R^3$=phenyl, $R^5$=2,2,3,3,3-pentafluoropropyl)

This compound was prepared using the method described in Example 80 from compound 171. Spectral data for compound 218: $^1$H NMR (500 MHz, CDCl$_3$) δ 13.11 (s, 1H), 7.65 (d, J=8.9 Hz, 1H), 7.56-7.50 (m, 3H), 7.45 (d, J=8.9 Hz, 1H), 7.38 (m, 2H), 6.97 (s, 1H), 4.68 (t, J=14.8 Hz, 2H), 1.25 (s, 3H).

Example 116

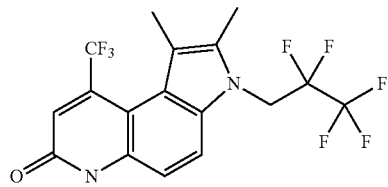 [SMILES: Cc1c(C)n(CC(F)(F)C(F)(F)F)c2ccc3[nH]c(=O)cc(C(F)(F)F)c3c12]

1,2-Dimethyl-3-(2,2,3,3,3-pentafluoropropyl)-9-trifluoromethyl-3,6-dihydro-pyrrolo[3,2-f]-quinolin-7-one (Compound 219, Structure 6 of Scheme I, where $R^4$=trifluoromethyl, $R^1$=methyl, $R^3$=methyl, $R^5$=2,2,3,3,3-pentafluoropropyl)

This compound was prepared using the method described in Example 80 from compound 173. Spectral data for compound 219: $^1$H NMR (500 MHz, acetone-$d_6$) δ 11.12 (s, 1H) 7.83 (d, J=8.8 Hz, 1H) 7.32 (d, J=8.8 Hz, 1H) 6.96 (s, 1H) 5.22 (t, J=16.0 Hz, 2H) 2.47 (s, 3H) 2.32 (q, J=1.9 Hz, 3H).

Example 117

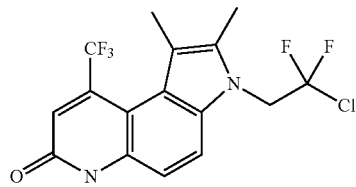 [SMILES: Cc1c(C)n(CC(F)(F)Cl)c2ccc3[nH]c(=O)cc(C(F)(F)F)c3c12]

1,2-Dimethyl-3-(2-chloro-2,2-difluoroethyl)-9-trifluoromethyl-3,6-dihydro-pyrrolo[3,2-f]-quinolin-7-one (Compound 220, Structure 6 of Scheme I, where $R^4$=trifluoromethyl, $R^1$=methyl, $R^3$=methyl, $R^5$=2-chloro-2,2-difluoroethyl)

This compound was prepared using the method described in Example 80 from compound 175. Spectral data for compound 220: $^1$H NMR (500 MHz, acetone-$d_6$) δ 11.13 (s, 1H) 7.91 (dt, J=9.0, 0.9 Hz, 1H) 7.31 (d, J=9.0 Hz, 1H) 6.96 (s, 1H) 5.28 (t, J=12.2 Hz, 2H) 2.49 (s, 3H) 2.31 (q, J=1.9 Hz, 3H).

Example 118

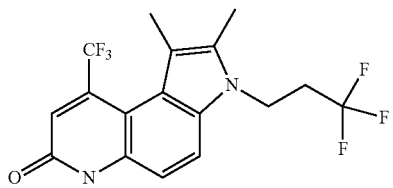 [SMILES: Cc1c(C)n(CCC(F)(F)F)c2ccc3[nH]c(=O)cc(C(F)(F)F)c3c12]

1,2-Dimethyl-9-trifluoromethyl-3-(3,3,3-trifluoropropyl)-3,6-dihydro-pyrrolo[3,2-f]-quinolin-7-one (Compound 221, Structure 6 of Scheme I, where $R^A$=trifluoromethyl, $R^1$=methyl, $R^3$=methyl, $R^5$=3,3,3-trifluoropropyl)

This compound was prepared using the method described in Example 80 from compound 174. Spectral data for compound 221: $^1$H NMR (500 MHz, acetone-d$_6$) δ 11.29 (s, 1H), 7.80 (d, J=8.8 Hz, 1H), 7.29 (d, J=8.8 Hz, 1H), 6.95 (s, 1H), 4.59 (m, 2H), 2.83-2.74 (m, 2H), 2.48 (s, 3H), 2.30 (q, J=2.0 Hz, 3H).

Example 119

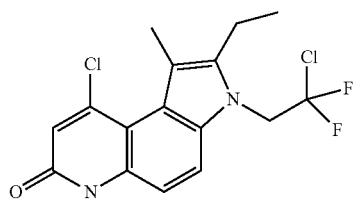 [SMILES: CCc1c(C)c2c3c(Cl)cc(=O)[nH]c3ccc2n1CC(F)(F)Cl]

9-Chloro-3-(2-chloro-2,2-difluoroethyl)-2-ethyl-1-methyl-3,6-dihydro-pyrrolo[3,2-f]-quinolin-7-one (Compound 222, Structure 6 of Scheme I, where $R^A$=chloro, $R^1$=methyl, $R^3$=ethyl, $R^5$=2-chloro-2,2-trifluoroethyl)

This compound was prepared using the method described in Example 80 from compound 176. Spectral data for compound 222: $^1$H NMR (500 MHz, CDCl$_3$) δ 10.61 (s, 1H), 7.56 (dt, J=8.8, 1.2 Hz, 1H), 7.09 (d, J=8.8 Hz, 1H), 6.87 (s, 1H), 4.86 (t, J=11.6 Hz, 2H), 2.89 (q, J=7.6 Hz, 2H), 2.57 (s, 3H), 1.23 (t, J=7.6 Hz, 3H).

Example 120

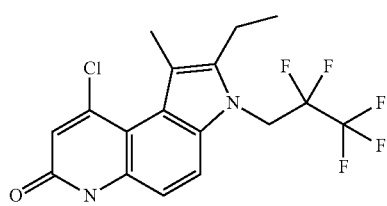 [SMILES: CCc1c(C)c2c3c(Cl)cc(=O)[nH]c3ccc2n1CC(F)(F)C(F)(F)F]

9-Chloro-2-ethyl-1-methyl-3-(2,2,3,3,3-pentafluoropropyl)-3,6-dihydro-pyrrolo[3,2-f]-quinolin-7-one (Compound 223, Structure 6 of Scheme I, where $R^A$=chloro, $R^1$=methyl, $R^3$=ethyl, $R^5$=2,2,3,3,3-pentafluoropropyl)

This compound was prepared using the method described in Example 80 from compound 177. Spectral data for compound 223: $^1$H NMR (500 MHz, acetone-d$_6$) δ 10.85 (s, 1H), 7.81 (dt, J=8.9, 1.3 Hz, 1H), 7.30 (d, J=8.9 Hz, 1H), 6.66 (s, 1H), 5.23 (t, J=16.0 Hz, 2H), 2.97 (q, J=7.6 Hz, 2H), 2.57 (s, 3H), 1.24 (t, J=7.6 Hz, 3H).

Example 121

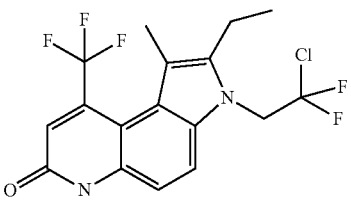 [SMILES: CCc1c(C)c2c3c(C(F)(F)F)cc(=O)[nH]c3ccc2n1CC(F)(F)Cl]

3-(2-Chloro-2,2-difluoroethyl)-2-ethyl-1-methyl-9-trifluoromethyl-3,6-dihydro-pyrrolo[3,2-f]-quinolin-7-one (Compound 224, Structure 6 of Scheme I, where $R^A$=trifluoromethyl, $R^1$=methyl, $R^3$=ethyl, $R^5$=2-chloro-2,2-difluoroethyl)

This compound was prepared using the method described in Example 80 from compound 178. Spectral data for compound 224: $^1$H NMR (500 MHz, acetone-d$_6$) δ 11.43 (s, 1H), 7.93 (dt, J=8.8, 1.1 Hz, 1H), 7.33 (d, J=8.8 Hz, 1H), 6.98 (s, 1H), 5.30 (t, J=12.2 Hz, 2H), 2.96 (q, J=7.6 Hz, 2H), 2.34 (q, J=2.0 Hz, 3H), 1.23 (t, J=7.6 Hz, 3H).

Example 122

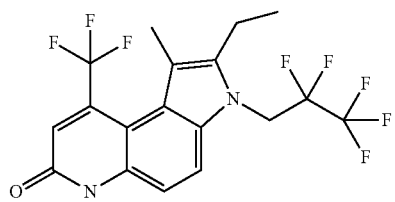 [SMILES: CCc1c(C)c2c3c(C(F)(F)F)cc(=O)[nH]c3ccc2n1CC(F)(F)C(F)(F)F]

2-Ethyl-1-methyl-3-(2,2,3,3,3-pentafluoropropyl)-9-trifluoromethyl-3,6-dihydro-pyrrolo[3,2-f]-quinolin-7-one (Compound 225, Structure 6 of Scheme I, where $R^A$=trifluoromethyl, $R^1$=methyl, $R^3$=ethyl, $R^5$=2,2,3,3,3-pentafluoropropyl)

This compound was prepared using the method described in Example 80 from compound 179. Spectral data for compound 225: $^1$H NMR (500 MHz, acetone-d$_6$) δ 11.25 (s, 1H), 7.84 (dt, J=8.8, 1.2 Hz, 1H), 7.33 (d, J=8.8 Hz, 1H), 6.97 (s, 1H), 5.23 (t, J=16.0 Hz, 2H), 2.91 (q, J=7.6 Hz, 2H), 2.34 (q, J=2.0 Hz, 3H), 1.24 (t, J=7.6 Hz, 3H).

Example 123

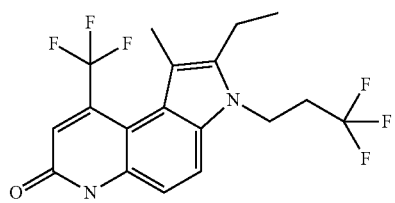 [SMILES: CCc1c(C)c2c3c(C(F)(F)F)cc(=O)[nH]c3ccc2n1CCC(F)(F)F]

2-Ethyl-1-methyl-9-trifluoromethyl-3-(3,3,3-trifluoropropyl)-3,6-dihydro-pyrrolo[3,2-f]-quinolin-7-one (Compound 226, Structure 6 of Scheme I, where $R^A$=trifluoromethyl, $R^1$=methyl, $R^3$=ethyl, $R_5$=3,3,3-trifluoropropyl)

This compound was prepared using the method described in Example 80 from compound 180. Spectral data for compound 226: $^1$H NMR (500 MHz, acetone-$d_6$) δ 11.26 (s, 1H), 7.80 (d, J=8.8 Hz, 1H), 7.30 (d, J=8.8 Hz, 1H), 6.95 (s, 1H), 4.60 (m, 2H), 2.91 (q, J=7.6 Hz, 2H), 2.81 (m, 2H), 2.32 (q, J=2.0 Hz, 3H), 1.25 (t, J=7.6 Hz, 3H).

Example 124

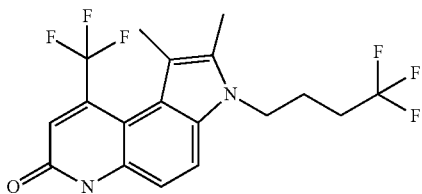 [SMILES: Cc1c(C)n(CCCC(F)(F)F)c2ccc3[nH]c(=O)cc(C(F)(F)F)c3c12]

1,2-Dimethyl-3-(4,4,4-trifluorobutyl)-9-trifluoromethyl-3,6-dihydro-pyrrolo[3,2-f]-quinolin-7-one (Compound 227, Structure 6 of Scheme I, where $R^A$=trifluoromethyl, $R^1$=methyl, $R^3$=methyl, $R^5$=4,4,4-trifluorobutyl)

This compound was prepared using the method described in Example 80 from compound 182. Spectral data for compound 227: $^1$H NMR (500 MHz, acetone-$d_6$) δ 11.17 (s, 1H), 7.83 (d, J=8.8 Hz, 1H), 7.26 (d, J=8.8 Hz, 1H), 6.93 (s, 1H), 4.42 (t, J=7.6 Hz, 2H), 2.46 (s, 3H), 2.44-2.33 (m, 2H), 2.30 (q, J=1.9 Hz, 3H), 2.04 (m, 2H).

Example 125

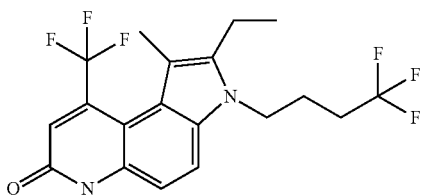 [SMILES: CCc1c(C)c2c3c(C(F)(F)F)cc(=O)[nH]c3ccc2n1CCCC(F)(F)F]

2-Ethyl-1-methyl-3-(4,4,4-trifluorobutyl)-9-trifluoromethyl-3,6-dihydro-pyrrolo quinolin-7-one (Compound 228, Structure 6 of Scheme I, where $R^A$=trifluoromethyl, $R^1$=methyl, $R^3$=ethyl, $R^5$=4,4,4-trifluorobutyl)

This compound was prepared using the method described in Example 80 from compound 181. Spectral data for compound 228: $^1$H NMR (500 MHz, acetone-$d_6$) δ 11.22 (s, 1H), 7.84 (d, J=8.8 Hz, 1H), 7.27 (d, J=8.8 Hz, 1H), 6.93 (s, 1H), 4.44 (t, J=7.7 Hz, 2H), 2.91 (q, J=7.6 Hz, 2H), 2.47-2.36 (m, 2H), 2.32 (q, J=2.0 Hz, 3H), 2.06 (m, 2H), 1.23 (t, J=7.6 Hz, 3H).

Example 126

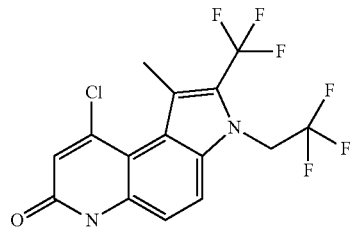 [SMILES: Cc1c(C(F)(F)F)n(CC(F)(F)F)c2ccc3[nH]c(=O)cc(Cl)c3c12]

9-Chloro-1-methyl-3-(2,2,2-trifluoromethyl)-2-trifluoromethyl-3,6-dihydro-pyrrolo[3,2-f]-quinolin-7-one (Compound 229, Structure 12 of Scheme II, where $R^A$=chloro, $R^1$=methyl, $R^3$=trifluoromethyl, $R^5$=2,2,2-trifluoroethyl)

To a mixture of compound 7 ($R^A$=chloro, $R^B$=2-propyl) in trifluoroacetic acid at 0° C. was added trifluoroacetaldehyde ethyl hemiacetal, followed by NaBH$_4$. After 2.5 hrs the reaction mixture was poured into ice/water. Solid was filtered and washed with water, then dried. Compound 8 ($R^A$=chloro, $R^5$=2,2,2-trifluoroethyl, $R^B$=2-propyl) was obtained as a yellow solid. To a mixture of compound 8 and sodium nitrite in DMF at 0° C. was added slowly 2N HCl. After 30 min., water was added. Solid was filtered and washed with water. Compound 9 ($R^A$=chloro, $R^5$=2,2,2-trifluoroethyl, $R^B$=2-propyl) was obtained as a white solid. To a mixture of compound 9 in dry THF at 0° C. was added slowly lithium aluminumhydride (1.0 M in THF). That reaction mixture was then stirred at room temperature for 1 hour. EtOAc was added slowly at 0° C. The mixture was filtered through celite. After removal of solvent, crude compound 10 ($R^A$=chloro, $R^5$=2,2,2-trifluoroethyl, $R^B$=2-propyl) was used directly in the next step without further purification.

Compound 10, 1,1,1-trifluoro-2-butanone, EtOH and conc. HCl were heated at 80° C. in a sealed tube for 18 hrs. The mixture was then poured into water. Solid was filtered and purified by chromatography. Compound 229 was obtained as a white solid. $^1$H NMR (500 MHz, acetone-$d_6$) 11.13 (s, 1H), 8.08 (d, J=9.1 Hz, 1H), 7.58 (d, J=9.1 Hz, 1H), 6.78 (s, 1H), 5.35 (q, J=8.5 Hz, 2H), 2.70 (q, J=2.6 Hz, 2H).

Example 127

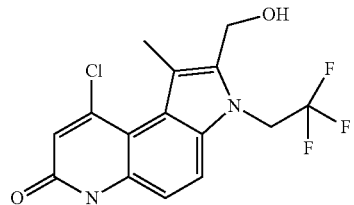 [SMILES: Cc1c(CO)n(CC(F)(F)F)c2ccc3[nH]c(=O)cc(Cl)c3c12]

9-Chloro-2-hydroxymethyl-1-methyl-3-(2,2,2-trifluoro-ethyl)-3,6-dihydro-pyrrolo[3,2-f]-quinolin-7-one (Compound 230, structure 12 of Scheme II, where $R^4$=chloro, $R^1$=methyl, $R^3$=hydroxymethyl, $R^5$=2,2,2-trifluoroethyl)

Compound 10 ($R^4$=chloro, $R^5$=2,2,2-trifluoroethyl, $R^B$=2-propyl), 2-oxo-butanoic acid ethyl ester, EtOH and conc. HCl were heated at 95° C. for 18 hrs. The mixture was then poured into water. Solid was filtered and purified by chromatography. Compound 12 ($R^4$=chloro, $R^1$=methyl, $R^3$=ethylcarboxylate, $R^5$=2,2,2-trifluoroethyl, $R^B$=2-propyl) was obtained as a white solid.

To the mixture of Compound 12 ($R^4$=chloro, $R^1$=methyl, $R^3$=ethylcarboxylate, $R^5$=2,2,2-trifluoroethyl, $R^B$=2-propyl) in dry THF at 0° C. was added lithium aluminumhydride (1.0 M in THF). The reaction mixture was stirred at 0° C. for 1 hr. MeOH was added slowly at 0° C. The mixture was then filtered through celite. After removal of the solvent, crude product was purified by chromatography. Compound 230 was obtained as a white solid. $^1$H NMR (500 MHz, acetone-$d_6$) δ 7.92 (d, J=9.1 Hz, 1H), 7.38 (d, J=9.1 Hz, 1H), 6.68 (s, 1H), 5.35 (q, J=9.0 Hz, 2H), 4.93 (s, 2H), 2.61 (s, 3H).

Example 128

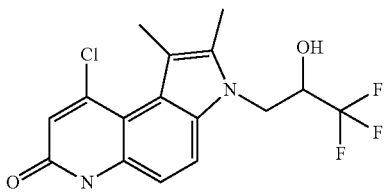 [SMILES: Cc1c(C)n(CC(O)C(F)(F)F)c2ccc3[nH]c(=O)cc(Cl)c3c12]

(±)-9-Chloro-1,2-dimethyl-3-(3,3,3-trifluoro-2-hydroxy-propyl)-3,6-dihydro-pyrrolo[3,2-f]-quinolin-7-one (Compound 231, Structure 12 of Scheme II, where $R^4$=chloro, $R^1$=methyl, $R^3$=methyl, $R^5$=2-hydroxy-3,3,3-trifluoropropyl)

To a mixture of compound 7 ($R^4$=chloro, $R^B$=2-propyl) and 1,1,1-trifluoro-2,3-epoxypropane in acetonitrile, Ca(OTf)$_2$ was added and the reaction mixture was stirred at rt for 5 days. After removal of the solvent, water and dichloromethane were added. Organic layer was separated. Aqueous layer was extracted with dichloromethane. Combined organic layers were dried (Na$_2$SO$_4$). After removal of the solvent, crude product was purified by chromatography to afford compound 8 ($R^4$=chloro, $R^5$=2-hydroxy-3,3,3-trifluoropropyl, $R^B$=2-propyl) as an oil.

To a mixture of compound 8 ($R^4$=chloro, $R^5$=2-hydroxy-3,3,3-trifluoropropyl, $R^B$=2-propyl), NaNO$_2$ in DMF at 0° C. was added slowly 2N HCl. Then kept at 0° C. for 1 hr. Then water was added. The mixture was extracted with EtOAc. Combined organic layers were washed with water, saturated NaHCO$_3$ and brine, then dried (Na$_2$SO$_4$). After removal of the solvent, the crude product was dissolved in dry THF and at 0° C. was added slowly lithium aluminum hydride (1.0 M solution in THF). After 1 hr stirring at rt, EtOAc was added slowly at 0° C. followed by MeOH. The mixture was filtered through celite. After removal of the solvent, crude product 10 ($R^4$=chloro, $R^5$=2-hydroxy-3,3,3-trifluoropropyl, $R^B$=2-propyl) was used directly in the next step without purification.

A mixture of compound 10 ($R^4$=chloro, $R^5$=2-hydroxy-3,3,3-trifluoropropyl, $R^B$=2-propyl), 2-butanone, ethanol and concentrated HCl was heated at 95° C. for 30 hrs. Then cooled to rt, and water was added. Solid was filtered, and washed with water. Chromatography afforded compound 231 as a pale green solid. $^1$H NMR (500 MHz, acetone-$d_6$) δ 10.81 (s, 1H), 7.75 (d, J=8.8 Hz, 1H), 7.22 (d, J=8.8 Hz, 1H), 6.61 (s, 1H), 5.84 (d, J=5.9 Hz, 1H), 4.60 (m, 1H), 4.54-4.46 (m, 2H), 2.53 (s, 3H), 2.51 (s, 3H).

Example 129

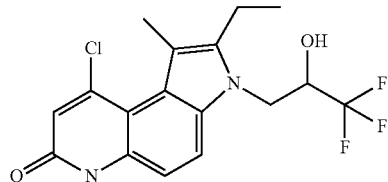 [SMILES: CCc1c(C)c2c3c(Cl)cc(=O)[nH]c3ccc2n1CC(O)C(F)(F)F]

(±)-9-Chloro-2-ethyl-1-methyl-3-(3,3,3-trifluoro-2-hydroxy-propyl)-3,6-dihydro-pyrrolo[3,2-f]quinolin-7-one (Compound 232, Structure 12 of Scheme II, where $R^4$=chloro, $R^1$=methyl, $R^3$=ethyl, $R^5$=2-hydroxy-3,3,3-trifluoropropyl)

This compound was prepared using the method that described in Example 128. Spectral data for compound 232: $^1$H NMR (500 MHz, acetone-$d_6$) δ 10.98 (s, 1H), 7.75 (d, J=8.8 Hz, 1H), 7.22 (d, J=8.8 Hz, 1H), 6.58 (s, 1H), 5.94 (d, J=5.9 Hz, 1H), 4.62 (m, 1H), 4.56-4.44 (m, 2H), 3.04 (dq, J=15.1, 7.6 Hz, 1H), 2.91 (dq, J=15.1, 7.6 Hz, 1H), 2.56 (s, 3H), 1.25 (t, J=8.8 Hz, 3H).

Example 130

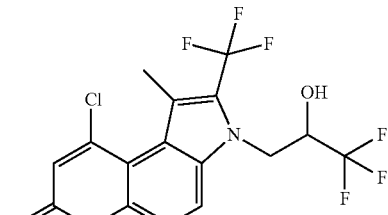

(t)-9-Chloro-1-methyl-3-(3,3,3-trifluoro-2-hydroxy-propyl)-2-trifluoromethyl-3,6-dihydro-pyrrolo[3,2-f] quinolin-7-one (Compound 233, Structure 12 of Scheme II, where $R^4$=chloro, $R^1$=methyl, $R^3$=trifluoromethyl, $R^5$=2-hydroxy-3,3,3-trifluoropropyl)

This compound was prepared using the method that described in Example 128. Spectral data for compound 233: $^1$H NMR (500 MHz, acetone-$d_6$) δ 11.04 (s, 1H), 8.02 (d, J=9.0 Hz, 1H), 7.50 (d, J=9.0 Hz, 1H), 6.71 (s, 1H), 6.00 (m, 1H), 4.72 (dd, J=15.6, 9.0 Hz, 1H), 4.67 (dd, J=15.6, 3.0 Hz, 1H), 4.53 (m, 1H), 2.68 (q, J=2.7 Hz, 3H).

Example 131

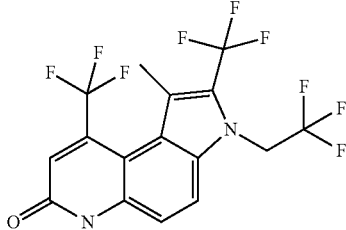 [SMILES: Cc1c(C(F)(F)F)n(CC(F)(F)F)c2ccc3[nH]c(=O)cc(C(F)(F)F)c3c12]

1-Methyl-3-(2,2,2-trifluoro-ethyl)-2,9-bis-trifluoromethyl-3,6-dihydro-pyrrolo[3,2-f]-quinolin-7-one (Compound 234, Structure 12 of Scheme II, where $R^4$=trifluoromethyl, $R^1$=methyl, $R^3$=trifluoromethyl, $R^5$=2,2,2-trifluoroethyl)

This compound was prepared using the method that described in Example 126. Spectral data for compound 234: $^1$H NMR (500 MHz, acetone-$d_6$) δ 11.1 (bs, 1H) 8.10 (d, J=9.0 Hz, 1H), 7.62 (d, J=9.0 Hz, 1H), 7.09 (s, 1H), 5.34 (q, J=8.5 Hz, 2H), 2.49 (sept, J=2.2 Hz, 3H).

Example 132

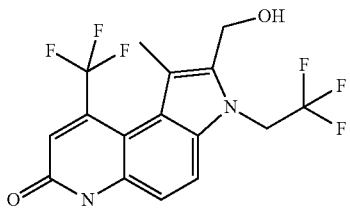 [SMILES: Cc1c(CO)n(CC(F)(F)F)c2ccc3[nH]c(=O)cc(C(F)(F)F)c3c12]

2-Hydroxymethyl-1-methyl-3-(2,2,2-trifluoro-ethyl)-9-trifluoromethyl-3,6-dihydro-pyrrolo[3,2-f]-quinolin-7-one (Compound 235, Structure 12 of Scheme II, where $R^4$=trifluoromethyl, $R^1$=methyl, $R^3$=hydroxymethyl, $R^5$=2,2,2-trifluoroethyl)

This compound was prepared using the method that described in Example 127. Spectral data for compound 235: $^1$H NMR (500 MHz, acetone-$d_6$) δ 11.1 (bs, 1H) 7.94 (d, J=8.9 Hz, 1H), 7.40 (d, J=8.9 Hz, 1H), 6.98 (s, 1H), 5.34 (q, J=9.0 Hz, 2H), 4.92 (d, J=4.9 Hz, 2H), 4.45 (t, J=4.9 Hz, 1H), 2.38 (q, j=2.1 Hz, 3H).

Example 133

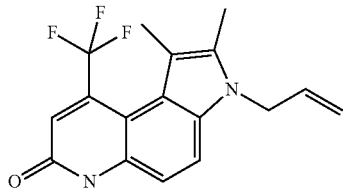 [SMILES: C=CCn1c(C)c(C)c2c3c(C(F)(F)F)cc(=O)[nH]c3ccc21]

3-Allyl-1,2-dimethyl-9-trifluoromethyl-3,6-dihydro-pyrrolo[3,2-f]quinolin-7-one (Compound 236, Structure 12 of Scheme III, where $R^4$=trifluoromethyl, $R^1$=methyl, $R^3$=methyl, $R^5$=allyl)

A mixture of compound 4 ($R^4$=trifluoromethyl, $R^1$=methyl, $R^3$=methyl) and POCl$_3$ was stirred at 90° C. for 2 h. The dark blue mixture was slowly added to 200 mL water with stirring. The aqueous layer was extracted with ethylacetate. Combined organic layers were washed with brine and dried over Na$_2$SO$_4$. After removal of the solvent the crude product was purified by chromatography to afford compound 13 ($R^4$=trifluoromethyl, $R^1$=methyl, $R^3$=methyl) as a yellow solid.

To a solution of compound 13 ($R^4$=trifluoromethyl, $R^1$=methyl, $R^3$=methyl) in DMSO was added KOH followed by allylbromide. The mixture was stirred at rt for 15 min. until complete conversion by TLC. Water was added and the precipitate was filtered and washed with water to give 14 ($R^4$=trifluoromethyl, $R^1$-methyl, $R^3$=methyl, $R^5$=allyl) as a yellow solid. This was dissolved in 10 mL HOAc and 2 mL concentrated HCl was added and the mixture was heated at 95° C. for 24 hrs. Then cooled to rt, and water was added. Solid was filtered, and washed with water. Crystallization from MeOH/water afforded compound 236 as a yellow solid. NMR (500 MHz, acetone-$d_6$) δ 11.20 (s, 1H), 7.75 (d, J=8.8 Hz, 1H), 7.28 (d, J=8.8 Hz, 1H), 6.97 (s, 1H), 6.06 (ddt, J=17.0, 10.3, 4.6 Hz, 1H), 5.14 (ddt, J=10.3, 1.9, 1.6 Hz, 1H), 4.96 (dt, J=4.6, 1.6 Hz, 2H), 4.78 (ddt, J=17.0, 1.9, 1.6 Hz, 1H), 2.45 (s, 3H), 2.36 (q, J=1.9 Hz, 3H).

Example 134

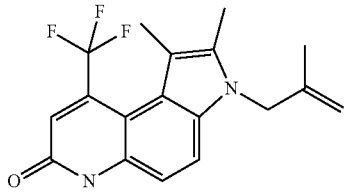 [SMILES: C=C(C)Cn1c(C)c(C)c2c3c(C(F)(F)F)cc(=O)[nH]c3ccc21]

1,2-Dimethyl-3-(2-methyl-allyl)-9-trifluoromethyl-3,6-dihydro-pyrrolo[3,2-f]quinolin-7-one (Compound 237, Structure 12 of Scheme III, where $R^4$=trifluoromethyl, $R^1$=methyl, $R^3$=methyl, $R^5$=2-methylallyl)

This compound was prepared using the method that described in Example 133. Spectral data for compound 237:

¹H NMR (500 MHz, CDCl₃) δ 11.45 (s, 1H) 7.48 (d, J=8.7 Hz, 1H) 7.13 (s, 1H) 7.08 (d, J=8.7 Hz, 1H) 4.84 (m, 1H) 4.65 (s, 2H) 4.24 (m, 1H) 2.36 (s, 3H) 2.33 (, J=1.9 Hz, 3H) 1.75 (s, 3H).

Example 135

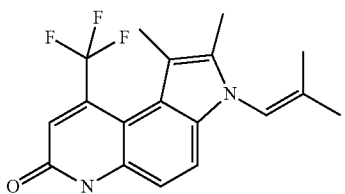 [SMILES: CC(C)=Cn1c(C)c(C)c2c3c(C(F)(F)F)cc(=O)[nH]c3ccc21]

1,2-Dimethyl-3-(2-methylprop-1-enyl)-9-trifluoromethyl-3,6-dihydro-pyrrolo[3,2-f]-quinolin-7-one (Compound 238, Structure 12 of Scheme III, where R$^A$=trifluoromethyl, R¹=methyl, R³=methyl, R⁵=2-methylprop-1-enyl)

This compound was isolated as a byproduct from the synthesis of compound 237. Spectral data for compound 237: ¹H NMR (500 MHz, CDCl₃) δ 11.07 (s, 1H) 7.38 (d, J=8.6 Hz, 1H) 7.13 (s, 1H) 7.03 (d, J=8.6 Hz, 1H) 6.36 (m, 1H) 2.33 (q, J=1.9 Hz, 3H) 2.30 (s, 3H) 2.01 (d, J=1.2 Hz, 3H) 1.49 (d, J=1.0 Hz, 3H).

Example 136

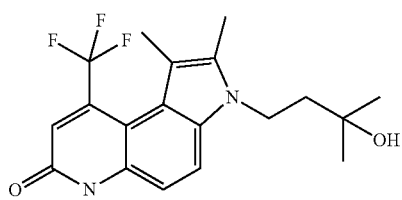 [SMILES: Cc1c(C)n(CCC(C)(C)O)c2ccc3[nH]c(=O)cc(C(F)(F)F)c3c12]

3-(3-Hydroxy-3-methyl-butyl)-1,2-dimethyl-9-trifluoromethyl-3,6-dihydro-pyrrolo[3,2-f]-quinolin-7-one (Compound 239, Structure 12 of Scheme III, where R$^A$=trifluoromethyl, R¹=methyl, R³=methyl, R⁵=3-hydroxy-3-methylbutyl)

This compound was prepared using the method that described in Example 133. Spectral data for compound 239: ¹H NMR (500 MHz, CDCl₃) δ 11.99 (s, 1H) 7.60 (d, J=8.8 Hz, 1H) 7.16 (d, J=8.8 Hz, 1H) 7.13 (s, 1H) 4.32 (m, 2H) 2.43 (s, 3H) 2.32 (q, J=1.9 Hz, 3H) 1.84 (m, 2H) 1.36 (s, 6H).

Example 137

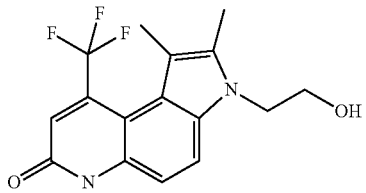 [SMILES: Cc1c(C)n(CCO)c2ccc3[nH]c(=O)cc(C(F)(F)F)c3c12]

1,2-Dimethyl-3-(2-hydroxyethyl)-9-trifluoromethyl-3,6-dihydro-pyrrolo[3,2-f]quinolin-7-one (Compound 240, Structure 12 of Scheme III, where R$^A$=trifluoromethyl, R¹=methyl, R³=methyl, R⁵=2-hydroxyethyl)

This compound was prepared using the method that described in Example 133. Spectral data for compound 240: ¹H NMR (500 MHz, acetone-d₆) δ 11.06 (s, 1H) 7.79 (d, J=8.8 Hz, 1H) 7.22 (d, J=8.8 Hz, 1H) 6.90 (s, 1H) 4.38 (t, J=5.7 Hz, 2H) 4.07 (t, J=5.7 Hz, 1H) 3.88 (q, J=5.7 Hz, 2H) 2.46 (s, 3H) 2.29 (q, J=1.9 Hz, 3H).

Example 138

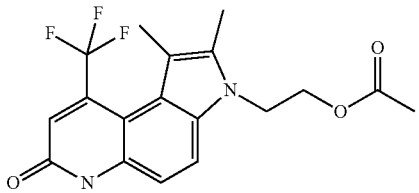 [SMILES: CC(=O)OCCn1c(C)c(C)c2c3c(C(F)(F)F)cc(=O)[nH]c3ccc21]

3-(2-Acetoxyethyl)-1,2-Dimethyl-9-trifluoromethyl-3,6-dihydro-pyrrolo[3,2-f]quinolin-7-one (Compound 241, Structure 12 of Scheme III, where R$^A$=trifluoromethyl, R¹=methyl, R³=methyl, R⁵=2-acetoxyethyl)

This compound was isolated as a byproduct from the synthesis of compound 240. Spectral data for compound 241: ¹H NMR (500 MHz, acetone-d₆) δ 11.07 (s, 1H) 7.82 (d, J=8.8 Hz, 1H) 7.27 (d, J=8.8 Hz, 1H) 6.92 (s, 1H) 4.55 (t, J=5.7 Hz, 2H) 4.37 (t, J=5.7 Hz, 2H) 2.47 (s, 3H) 2.30 (q, J=2.0 Hz, 3H) 1.93 (s, 3H).

Example 139

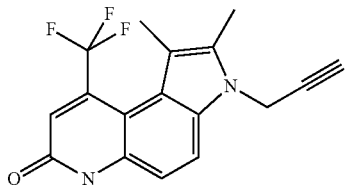 [SMILES: C#CCn1c(C)c(C)c2c3c(C(F)(F)F)cc(=O)[nH]c3ccc21]

1,2-Dimethyl-3-(prop-2-ynyl)-9-trifluoromethyl-3,6-dihydro-pyrrolo[3,2-f]quinolin-7-one (Compound 242, Structure 12 of Scheme III, where $R^A$=trifluoromethyl, $R^1$=methyl, $R^3$=methyl, $R^5$=prop-2-ynyl)

This compound was prepared using the method that described in Example 133. Spectral data for compound 242: $^1$H NMR (500 MHz, acetone-$d_6$) δ 11.13 (s, 1H) 7.84 (d, J=8.8 Hz, 1H) 7.30 (d, J=8.8 Hz, 1H) 6.93 (s, 1H) 5.13 (d, J=2.5 Hz, 2H) 2.87 (t, J=2.5 Hz, 1H) 2.50 (s, 3H) 2.30 (q, J=1.9 Hz, 3H).

Example 140

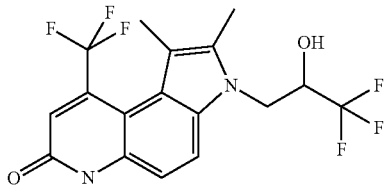 [SMILES: Cc1c(C)n(CC(O)C(F)(F)F)c2ccc3[nH]c(=O)cc(C(F)(F)F)c3c12]

(±)-1,2-Dimethyl-3-(3,3,3-trifluoro-2-hydroxy-propyl)-9-trifluoromethyl-3,6-dihydro-pyrrolo[3,2-f]-quinolin-7-one (Compound 243, Structure 12 of Scheme II, where $R^A$=trifluoromethyl, $R^1$=methyl, $R^3$=methyl, $R^5$=2-hydroxy-3,3,3-trifluoropropyl)

This compound was prepared using the method that described in Example 127. Spectral data for compound 243: $^1$H NMR (500 MHz, acetone-$d_6$) δ 11.05 (s, 1H) 7.78 (d, J=8.8 Hz, 1H) 7.27 (d, J=8.8 Hz, 1H) 6.93 (s, 1H) 4.60 (d, J=12.4 Hz, 1H) 4.50 (m, 1H) 4.49 (d, J=12.4 Hz, 1H) 2.49 (s, 3H) 2.30 (q, J=1.9 Hz, 3H)

Example 141

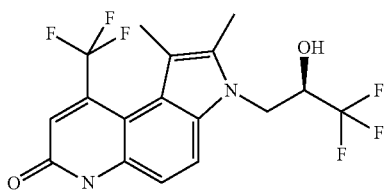 [SMILES: Cc1c(C)n(C[C@@H](O)C(F)(F)F)c2ccc3[nH]c(=O)cc(C(F)(F)F)c3c12]

(+)-1,2-Dimethyl-3-(3,3,3-trifluoro-2-hydroxy-propyl)-9-trifluoromethyl-3,6-dihydro-pyrrolo[3,2-f]-quinolin-7-one (Compound 244, Structure 12 of Scheme II, where $R^A$=trifluoromethyl, $R^1$=methyl, $R^3$=methyl, $R^5$=2-hydroxy-3,3,3-trifluoropropyl)

This compound was prepared by separation of the racemic mixture of 243 by chiral HPLC. Spectral data for compound 244: $^1$H NMR (500 MHz, acetone-$d_6$) δ 11.05 (s, 1H) 7.78 (d, J=8.8 Hz, 1H) 7.27 (d, J=8.8 Hz, 1H) 6.93 (s, 1H) 4.60 (d, J=12.4 Hz, 1H) 4.50 (m, 1H) 4.49 (d, J=12.4 Hz, 1H) 2.49 (s, 3H) 2.30 (q, J=1.9 Hz, 3H).

Example 142

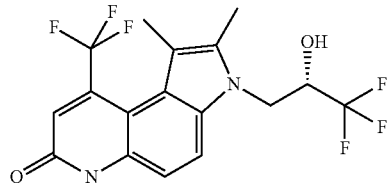

(−)-1,2-Dimethyl-3-(3,3,3-trifluoro-2-hydroxy-propyl)-9-trifluoromethyl-3,6-dihydro-pyrrolo[3,2-f]-quinolin-7-one (Compound 245, Structure 12 of Scheme II where $R^A$=trifluoromethyl, $R^1$=methyl, $R^3$=methyl, $R^5$=2-hydroxy-3,3,3-trifluoropropyl)

This compound was prepared by separation of the racemic mixture of 243 by chiral HPLC. Spectral data for compound 245: $^1$H NMR (500 MHz, acetone-$d_6$) δ 11.05 (s, 1H) 7.78 (d, J=8.8 Hz, 1H) 7.27 (d, J=8.8 Hz, 1H) 6.93 (s, 1H) 4.60 (d, J=12.4 Hz, 1H) 4.50 (m, 1H) 4.49 (d, J=12.4 Hz, 1H) 2.49 (s, 3H) 2.30 (q, J=1.9 Hz, 3H).

Example 143

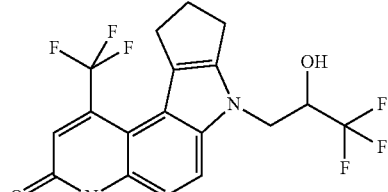

(±)-3-(3,3,3-Trifluoro-2-hydroxy-propyl)-9-trifluoromethyl-1,2-trimethylene-3,6-dihydro-pyrrolo[3,2-f]quinolin-7-one (Compound 246, Structure 12 of Scheme II, where $R^A$=trifluoromethyl, $R^1$, $R^3$=—CH$_2$CH$_2$CH$_2$—, $R^5$=2-hydroxy-3,3,3-trifluoropropyl)

This compound was prepared using the method that described in Example 128. Spectral data for compound 246: $^1$H NMR (500 MHz, acetone-$d_6$) δ 7.82 (d, J=8.9 Hz, 1H) 7.32 (d, J=8.9 Hz, 1H) 6.93 (s, 1H) 5.86 (d, J=6.3 Hz, 1H) 4.59 (dd, J=14.9, 2.7 Hz, 1H) 4.53 (m, 1H) 4.39 (dd, J=14.9, 9.2 Hz, 1H) 3.00 (m, 4H) 2.44 (m, 2H).

Example 144

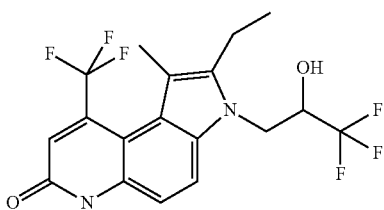 [SMILES: CCc1c(C)c2c3c(C(F)(F)F)cc(=O)[nH]c3ccc2n1CC(O)C(F)(F)F]

(±)-2-Ethyl-1-methyl-3-(3,3,3-Trifluoro-2-hydroxy-propyl)-9-trifluoromethyl-3,6-dihydro-pyrrolo[3,2-f]quinolin-7-one (Compound 247, Structure 12 of Scheme II, where $R^A$=trifluoromethyl, $R^1$=methyl $R^3$=ethyl, $R^5$=2-hydroxy-3,3,3-trifluoropropyl)

This compound was prepared using the method that described in Example 128. Spectral data for compound 247: $^1$H NMR (500 MHz, acetone-$d_6$) δ 11.11 (s, 1H) 7.78 (d, J=8.8 Hz, 1H) 7.27 (d, J=8.8 Hz, 1H) 6.92 (s, 1H) 5.86 (d, J=6.1 Hz, 1H) 4.62 (m, 1H) 4.53-4.44 (m, 2H) 3.02 (dq, J=15.1, 7.6 Hz, 1H) 2.88 (dq, J=15.1, 7.6 Hz, 1H) 2.32 (q, J=2.0 Hz, 3H) 1.24 (t, J=7.6 Hz, 3H).

Example 145

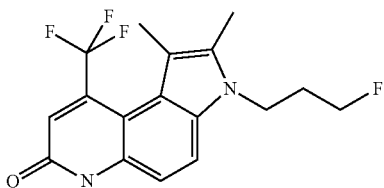 [SMILES: Cc1c(C)n(CCCF)c2ccc3[nH]c(=O)cc(C(F)(F)F)c3c12]

1,2-Dimethyl-3-(3-fluoropropyl)-9-trifluoromethyl-3,6-dihydro-pyrrolo[3,2-f]quinolin-7-one (Compound 248, Structure 12 of Scheme III, where $R^A$=trifluoromethyl, $R^1$=methyl, $R^3$=methyl, $R^5$=3-fluoropropyl)

This compound was prepared using the method that described in Example 133. Spectral data for compound 248: $^1$H NMR (500 MHz, acetone-$d_6$) δ 11.1 (bs, 1H) 7.77 (d, J=8.9 Hz, 1H) 7.25 (d, J=8.9 Hz, 1H) 6.92 (s, 1H) 4.54 (t, J=5.5 Hz, 1H) 4.44 (t, J=5.6 Hz, 1H) 4.41 (m, 2H) 2.45 (s, 1H) 2.30 (q, J=1.9 Hz, 3H) 2.21-2.10 (m, 2H).

Example 146

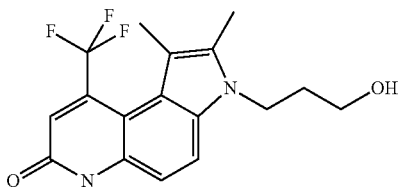 [SMILES: Cc1c(C)n(CCCO)c2ccc3[nH]c(=O)cc(C(F)(F)F)c3c12]

1,2-Dimethyl-3-(3-hydroxypropyl)-9-trifluoromethyl-3,6-dihydro-pyrrolo[3,2-f]quinolin-7-one (Compound 249, Structure 12 of Scheme III, where $R^A$=trifluoromethyl $R^1$=methyl, $R^3$=methyl, $R^5$=3-hydroxypropyl)

This compound was prepared using the method that described in Example 133. Spectral data for compound 249: $^1$H NMR (500 MHz, acetone-$d_6$) δ 11.1 (bs, 1H) 7.81 (d, J=8.8 Hz, 1H) 7.24 (d, J=8.8 Hz, 1H) 6.91 (s, 1H) 4.37 (t, J=7.2 Hz, 2H) 3.85 (m, 1H) 3.58 (m, 2H) 2.45 (s, 3H) 2.29 (q, J=2.0 Hz, 3H) 1.94 (m, 2H).

Example 147

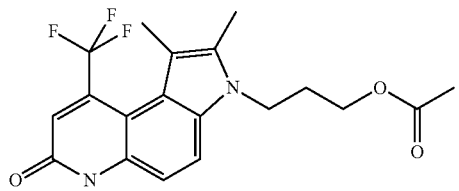 [SMILES: CC(=O)OCCCn1c(C)c(C)c2c3c(C(F)(F)F)cc(=O)[nH]c3ccc21]

3-(3-Acetoxypropyl)-1,2-dimethyl-9-trifluoromethyl-3,6-dihydro-pyrrolo[3,2-f]quinolin-7-one (Compound 250, Structure 12 of Scheme III, where $R^A$=trifluoromethyl, $R^1$=methyl, $R^3$=methyl, $R^5$=3-acetoxypropyl)

This compound was isolated as a byproduct from the synthesis of compound 249. Spectral data for compound 250: $^1$H NMR (500 MHz, acetone-$d_6$) δ 7.79 (d, J=8.8 Hz, 1H) 7.25 (d, J=8.8 Hz, 1H) 6.92 (s, 1H) 4.39 (t, J=7.3 Hz, 2H) 4.06 (t, J=6.1 Hz, 2H) 2.45 (s, 3H) 2.29 (q, J=1.9 Hz, 3H) 2.13-2.06 (m, 2H) 2.01 (s, 3H).

Example 148

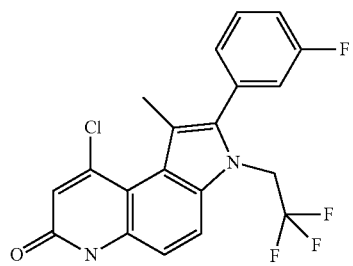 [SMILES: Cc1c(-c2cccc(F)c2)n(CC(F)(F)F)c2ccc3[nH]c(=O)cc(Cl)c3c12]

9-Chloro-2-(3-fluorophenyl)-1-methyl-3-(2,2,2-trifluoroethyl)-3,6-dihydro-pyrrolo[3,2-f]-quinolin-7-one (Compound 251, Structure 12 of Scheme II, where $R^A$=chloro, $R^1$=methyl, $R^3$=3-fluorophenyl, $R^5$=2,2,2-trifluoroethyl)

This compound was prepared using the method described in Example 126 from compound 10 by using 3-fluoropropiophenone as starting material. Spectral data for compound 251: $^1$H NMR (500 MHz, Acetone) δ 11.13 (s, 1H), 8.05 (d, J=8.9 Hz, 1H), 7.66 (td, J=7.9, 6.1 Hz, 1H), 7.45 (d, J=8.9 Hz, 1H), 7.38-7.31 (m, 3H), 6.73 (s, 1H), 5.09 (q, J=8.8 Hz, 2H), 2.45 (s, 3H).

Example 149

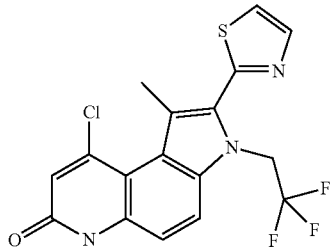 [SMILES: Cc1c(-c2nccs2)n(CC(F)(F)F)c2ccc3[nH]c(=O)cc(Cl)c3c12]

9-Chloro-1-methyl-2-(1,3-thiazol-2-yl)-3-(2,2,2-trifluoroethyl)-3,6-dihydro-pyrrolo[3,2-f]-quinolin-7-one (Compound 252, Structure 12 of Scheme II, where $R^4$=chloro, $R^1$=methyl, $R^3$=1,3-thiazol-2-yl, $R^5$=2,2,2-trifluoroethyl)

This compound was prepared using the method described in Example 126 from compound 10 by using 2-propionylthiazole as starting material. Spectral data for compound 252: $^1$H NMR (500 MHz, DMSO) δ 12.19 (s, 1H), 8.15 (d, J=3.3 Hz, 1H), 8.12 (d, J=9.0 Hz, 1H), 8.10 (d, J=3.3 Hz, 1H), 7.39 (d, J=9.0 Hz, 1H), 6.79 (s, 1H), 5.82 (q, J=8.9 Hz, 2H), 2.67 (s, 3H).

Example 150

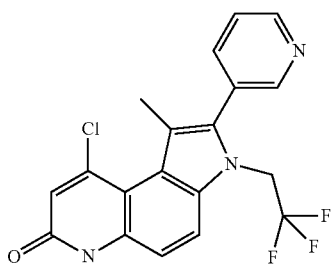 [SMILES: Cc1c(-c2cccnc2)n(CC(F)(F)F)c2ccc3[nH]c(=O)cc(Cl)c3c12]

9-Chloro-1-methyl-2-(3-pyridyl)-3-(2,2,2-trifluoroethyl)-3,6-dihydro-pyrrolo[3,2-f]-quinolin-7-one (Compound 253, Structure 12 of Scheme II, where $R^4$=chloro, $R^1$=methyl, $R^3$=3-pyridyl, $R^5$=2,2,2-trifluoroethyl)

This compound was prepared using the method described in Example 126 from compound 10 by using 3-propionylpyridine as starting material. Spectral data for compound 253: $^1$H NMR (500 MHz, DMSO) δ 12.15 (s, 1H), 8.80 (dd, J=5.0, 1.6 Hz, 1H), 8.77 (d, J=1.6 Hz, 1H), 8.15 (d, J=9.0 Hz, 1H), 8.10 (dt, J=7.8, 1.6 Hz, 1H), 7.74 (dd, J=7.8, 5.0 Hz, 1H), 7.35 (d, J=9.0 Hz, 1H), 6.77 (s, 1H), 5.14 (q, J=8.8 Hz, 2H), 2.36 (s, 3H).

Example 151

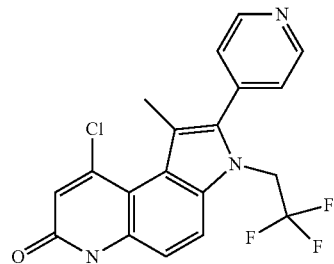 [SMILES: Cc1c(-c2ccncc2)n(CC(F)(F)F)c2ccc3[nH]c(=O)cc(Cl)c3c12]

9-Chloro-1-methyl-2-(4-pyridyl)-3-(2,2,2-trifluoroethyl)-3,6-dihydro-pyrrolo[3,2-f]-quinolin-7-one (Compound 254, Structure 12 of Scheme II, where $R^4$=chloro, $R^1$=methyl, $R^3$=4-pyridyl, $R^5$=2,2,2-trifluoroethyl)

This compound was prepared using the method described in Example 126 by using 4-propionylpyridine as starting material. Spectral data for compound 254: $^1$H NMR (500 MHz, DMSO) δ 12.18 (s, 1H), 8.87 (dd, J=4.9, 1.5 Hz, 2H), 8.18 (d, J=9.0 Hz, 1H), 7.74 (d, J=4.9 Hz, 2H), 7.36 (d, J=9.0 Hz, 1H), 6.78 (s, 1H), 5.21 (q, J=8.5 Hz, 2H), 2.41 (s, 3H).

Example 152

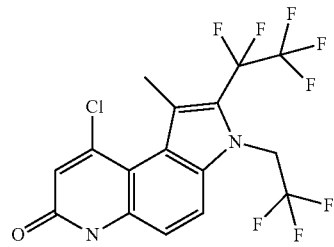 [SMILES: Cc1c(C(F)(F)C(F)(F)F)n(CC(F)(F)F)c2ccc3[nH]c(=O)cc(Cl)c3c12]

9-Chloro-1-methyl-2-(pentafluoroethyl)-3-(2,2,2-trifluoroethyl)-3,6-dihydro-pyrrolo[3,2-f]-quinolin-7-one (Compound 255, Structure 12 of Scheme II, where $R^4$=chloro, $R^1$=methyl, $R^3$=pentafluoroethyl, $R^5$=2,2,2-trifluoroethyl)

This compound was prepared using the method described in Example 126 by using pentafluoroethyl ethyl ketone as starting material. Spectral data for compound 255: $^1$H NMR (500 MHz, Acetone) δ 8.10 (dq, J=9.2, 0.7 Hz, 1H), 7.59 (d, J=9.2 Hz, 1H), 6.80 (s, 1H), 5.33 (q, J=8.1 Hz, 2H), 2.68 (t, J=3.2 Hz, 3H).

Example 153

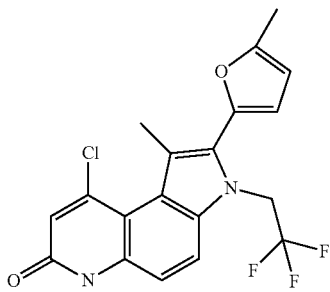

9-Chloro-1-methyl-2-(5-methyl-2-furyl)-3-(2,2,2-trifluoroethyl)-3,6-dihydro-pyrrolo[3,2-f]-quinolin-7-one (Compound 256, Structure 12 of Scheme II, where $R^1$=chloro, $R^2$=methyl, $R^3$=5-methyl-2-furyl, $R^4$=2,2,2-trifluoroethyl)

This compound was prepared using the method described in Example 126 by using (5-methyl-2-furyl)ethyl ketone as starting material. Spectral data for compound 256: $^1$H NMR (500 MHz, Acetone) δ 8.01 (d, J=9.0 Hz, 1H) 7.44 (d, J=9.0 Hz, 1H) 6.72 (d, J=3.2 Hz, 1H) 6.72 (s, 1H) 6.33 (dq, J=3.2, 1.0 Hz, 1H) 5.32 (q, J=8.9 Hz, 2H) 2.59 (s, 3H) 2.42 (d, J=1.0 Hz, 3H).

Example 154

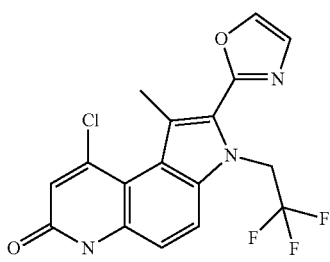 [SMILES: Cc1c(-c2ncco2)n(CC(F)(F)F)c2ccc3[nH]c(=O)cc(Cl)c3c12]

9-Chloro-1-methyl-2-(2-oxazolyl)-3-(2,2,2-trifluoroethyl)-3,6-dihydro-pyrrolo[3,2-f]-quinolin-7-one (Compound 257, Structure 12 of Scheme II, where $R^4$=chloro, $R^1$=methyl, $R^3$=2-oxazolyl, $R^5$=2,2,2-trifluoroethyl)

This compound was prepared using the method described in Example 126 by using 2-oxazolyl ethyl ketone as starting material. Spectral data for compound 257: $^1$H NMR (500 MHz, DMSO) δ 12.21 (s, 1H) 8.42 (d, J=0.8 Hz, 1H) 8.12 (d, J=9.1 Hz, 1H) 7.58 (d, J=0.8 Hz, 1H) 7.40 (d, J=9.1 Hz, 1H) 6.79 (s, 1H) 5.82 (q, J=8.9 Hz, 2H) 2.70 (s, 3H).

Example 155

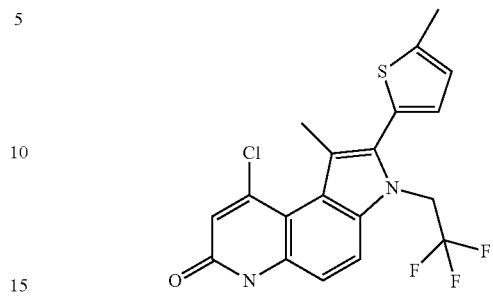

9-Chloro-1-methyl-2-(5-methyl-2-thiophenyl)-3-(2,2,2-trifluoroethyl)-3,6-dihydro-pyrrolo[3,2-f]quinolin-7-one (Compound 258, Structure 12 of Scheme II, where $R^4$=chloro, $R^1$=methyl, $R^3$=5-methyl-2-thiophenyl, $R^5$=2,2,2-trifluoroethyl)

This compound was prepared using the method described in Example 126 by using 5-methyl-2-thiophenyl ethyl ketone as starting material. Spectral data for compound 258: $^1$H NMR (300 MHz, Acetone) δ 8.00 (dq, J=9.0, 0.7 Hz, 1H) 7.45 (d, J=9.0 Hz, 1H) 7.09 (d, J=3.5 Hz, 1H) 6.98 (dq, J=3.5, 1.0 Hz, 1H) 6.73 (s, 1H) 5.12 (q, J=8.8 Hz, 2H) 2.59 (d, J=1.0 Hz, 3H) 2.52 (s, 3H).

Example 156

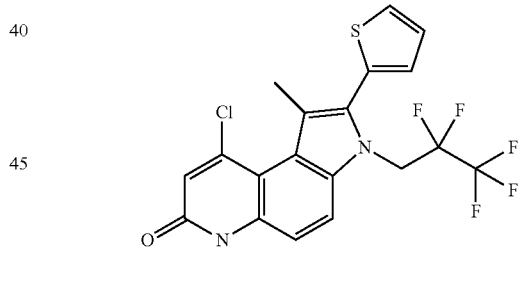

9-Chloro-1-methyl-3-(2,2,3,3,3-pentafluoropropyl)-2-thiophen-2-yl-3,6-dihydro-pyrrolo[3,2-f]quinolin-7-one (Compound 259, Structure 12 of Scheme II, where $R^4$=chloro, $R^1$=methyl, $R^3$=thiophen-2-yl, $R^5$=2,2,3,3,3-pentafluoropropyl)

This compound was prepared using the method described in Example 126 by using pentafluoropropionaldehyde hydrate and 2-propionylthiophene respectively as starting material. Spectral data for compound 259: $^1$H NMR (500 MHz, DMSO) δ 12.13 (s, 1H), 8.02 (d, J=9.0 Hz, 1H), 7.90 (dd, J=5.1, 1.2 Hz, 1H), 7.34 (d, J=9.0 Hz, 1H), 7.34 (dd, J=3.5, 1.2 Hz, 1H), 7.30 (dd, J=5.1, 3.5 Hz, 1H), 6.76 (s, 1H), 5.19 (t, J=15.7 Hz, 2H), 2.43 (s, 3H).

Example 157

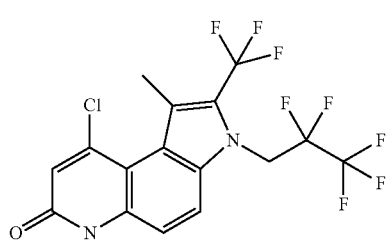 [SMILES: Cc1c(C(F)(F)F)n(CC(F)(F)C(F)(F)F)c2ccc3[nH]c(=O)cc(Cl)c3c12]

9-Chloro-1-methyl-3-(2,2,3,3,3-pentafluoropropyl)-2-(trifluoromethyl)-3,6-dihydro-pyrrolo[3,2-f]quinolin-7-one (Compound 260, Structure 12 of Scheme II, where R$^4$=chloro, R$^1$=methyl, R$^3$=trifluoromethyl, R$^5$=2,2,3,3,3-pentafluoropropyl)

This compound was prepared using the method described in Example by using pentafluoropropionaldehyde hydrate and 1,1,1-trifluoro-2-butanone respectively as starting material. Spectral data for compound 260: $^1$H NMR (500 MHz, DMSO) δ 12.26 (s, 1H), 8.08 (d, J=9.3 Hz, 1H), 7.46 (d, J=9.3 Hz, 1H), 6.82 (s, 1H), 5.44 (m, 2H), 2.62 (q, J=2.4 Hz, 3H).

Example 158

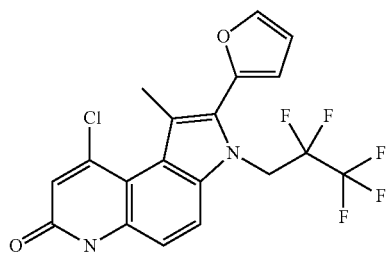 [SMILES: Cc1c(-c2ccco2)n(CC(F)(F)C(F)(F)F)c2ccc3[nH]c(=O)cc(Cl)c3c12]

9-Chloro-1-methyl-2-(2-furyl)-3-(2,2,3,3,3-pentafluoropropyl)-3,6-dihydro-pyrrolo[3,2-f]quinolin-7-one (Compound 261, Structure 12 of Scheme II, where R$^4$=chloro, R$^1$=methyl, R$^3$=2-furyl, R$^5$=2,2,3,3,3-pentafluoropropyl)

This compound was prepared using the method described in Example 126 by using pentafluoropropionaldehyde hydrate and 2-propionylfuran respectively as starting material. Spectral data for compound 261: $^1$H NMR (500 MHz, DMSO) δ 7.91 (d, J=9.0 Hz, 1H), 7.77 (dd, J=1.9, 0.7 Hz, 1H), 7.35 (d, J=9.0 Hz, 1H), 6.84 (s, 1H), 6.79 (dd, J=3.4, 0.7 Hz, 1H), 6.69 (dd, J=3.4, 1.9 Hz, 1H), 5.29 (t, J=15.4 Hz, 2H), 2.58 (s, 3H).

Example 159

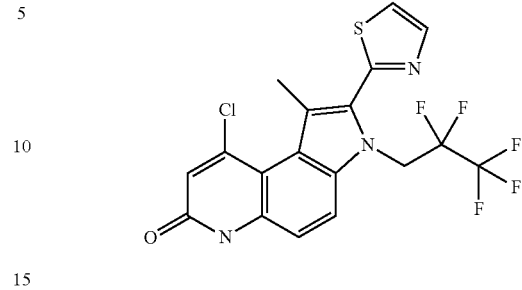

9-Chloro-1-methyl-3-(2,2,3,3,3-pentafluoropropyl)-2-(1,3-thiazol-2-yl)-3,6-dihydro-pyrrolo[3,2-f]quinolin-7-one (Compound 262, Structure 12 of Scheme II, where R$^4$=chloro, R$^1$=methyl, R$^3$=1,3-thiazol-2-yl, R$^5$=2,2,3,3,3-pentafluoropropyl)

This compound was prepared using the method described in Example 126 by using pentafluoropropionaldehyde hydrate and 2-propionylthiazole respectively as starting material. Spectral data for compound 262: $^1$H NMR (300 MHz, DMSO) δ 12.19 (s, 1H), 8.13 (d, J=3.3 Hz, 1H), 8.10 (d, J=3.3 Hz, 1H), 8.06 (d, J=9.1 Hz, 1H), 7.40 (d, J=9.1 Hz, 1H), 6.80 (s, 1H), 5.91 (d, J=15.7 Hz, 2H), 2.69 (s, 3H).

Example 160

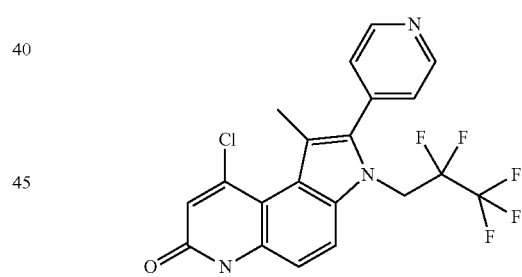

9-Chloro-1-methyl-3-(2,2,3,3,3-pentafluoropropyl)-2-(4-pyridyl)-3,6-dihydro-pyrrolo[3,2-f]quinolin-7-one (Compound 263, Structure 12 of Scheme II, where R$^4$=chloro, R$^1$=methyl, R$^3$=4-pyridyl, R$^5$=2,2,3,3,3-pentafluoropropyl)

This compound was prepared using the method described in Example 126 by using pentafluoropropionaldehyde hydrate and 4-propionylpyridine respectively as starting material. Spectral data for compound 263: $^1$H NMR (300 MHz, Acetone) δ 8.82 (dd, J=4.5, 1.6 Hz, 2H), 8.04 (d, J=9.0 Hz, 1H), 7.55 (dd, J=4.5, 1.5 Hz, 2H), 7.48 (d, J=9.0 Hz, 1H), 6.75 (s, 1H), 5.20 (t, J=15.5 Hz, 2H), 2.48 (s, 3H).

Example 161

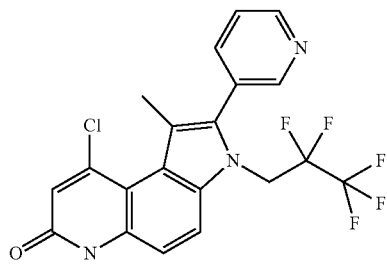 [SMILES: Cc1c(-c2cccnc2)n(CC(F)(F)C(F)(F)F)c2ccc3[nH]c(=O)cc(Cl)c3c12]

9-Chloro-1-methyl-3-(2,2,3,3,3-pentafluoropropyl)-2-(3-pyridyl)-3,6-dihydro-pyrrolo[3,2-f]quinolin-7-one (Compound 264, Structure 12 of Scheme II, where $R^4$=chloro, $R^1$=methyl, $R^3$=3-pyridyl, $R^5$=2,2,3,3,3-pentafluoropropyl)

This compound was prepared using the method described in Example 126 by using pentafluoropropionaldehyde hydrate and 3-propionylpyridine respectively as starting material. Spectral data for compound 264: $^1$H NMR (500 MHz, Acetone) δ 11.30 (s, 1H), 8.76 (dd, J=4.9, 1.9 Hz, 1H), 8.72 (d, J=1.9 Hz, 1H), 8.03 (dt, J=9.0, 1.1 Hz, 1H), 7.97 (dt, J=7.8, 1.9 Hz, 1H), 7.62 (ddd, J=7.8, 4.9, 0.9 Hz, 1H), 7.47 (d, J=9.0 Hz, 1H), 6.76 (s, 1H), 5.14 (t, J=15.6 Hz, 2H), 2.46 (s, 3H).

Example 162

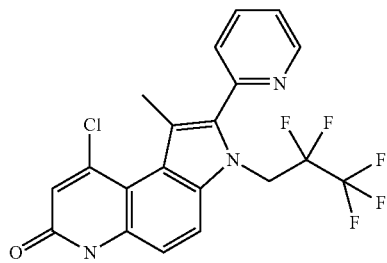 [SMILES: Cc1c(-c2ccccn2)n(CC(F)(F)C(F)(F)F)c2ccc3[nH]c(=O)cc(Cl)c3c12]

9-Chloro-1-methyl-3-(2,2,3,3,3-pentafluoropropyl)-2-(2-pyridyl)-3,6-dihydro-pyrrolo[3,2-f]quinolin-7-one (Compound 265, Structure 12 of Scheme II, where $R^4$=chloro, $R^1$=methyl, $R^3$=2-pyridyl, $R^5$=2,2,3,3,3-pentafluoropropyl)

This compound was prepared using the method described in Example 126 by using pentafluoropropionaldehyde hydrate and 2-propionylpyridine respectively as starting material. Spectral data for compound 265: $^1$H NMR (500 MHz, Acetone) δ 8.80 (ddd, J=4.9, 1.9, 1.0 Hz, 1H), 8.05 (td, J=7.7, 1.9 Hz, 1H), 8.03 (d, J=9.0 Hz, 1H), 7.83 (dt, J=7.7, 1.0 Hz, 1H), 7.49 (ddd, J=7.7, 4.9, 1.0 Hz, 1H), 7.47 (d, J=9.0 Hz, 1H), 6.74 (s, 1H), 5.81 (d, J=15.4 Hz, 2H), 2.62 (s, 3H).

Example 163

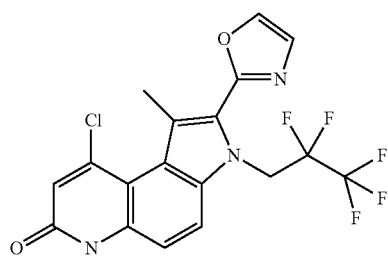 [SMILES: Cc1c(-c2ncco2)n(CC(F)(F)C(F)(F)F)c2ccc3[nH]c(=O)cc(Cl)c3c12]

9-Chloro-1-methyl-2-(oxazol-2-yl)-3-(2,2,3,3,3-pentafluoropropyl)-3,6-dihydro-pyrrolo[3,2-f]quinolin-7-one (Compound 266, Structure 12 of Scheme II, where $R^4$=chloro, $R^1$=methyl, $R^3$=2-oxazolyl, $R^5$=2,2,3,3,3-pentafluoropropyl)

This compound was prepared using the method described in Example 126 by using pentafluoropropionaldehyde hydrate and 1-oxazol-2-yl-propan-1-one respectively as starting material. Spectral data for compound 266: $^1$H NMR (300 MHz, Acetone) δ 8.26 (d, J=0.8 Hz, 1H), 8.04 (dt, J=9.0, 1.1 Hz, 1H), 7.53 (d, J=9.0 Hz, 1H), 7.50 (d, J=0.8 Hz, 1H), 6.76 (s, 1H), 5.95 (t, J=15.8 Hz, 3H), 2.79 (s, 3H).

Example 164

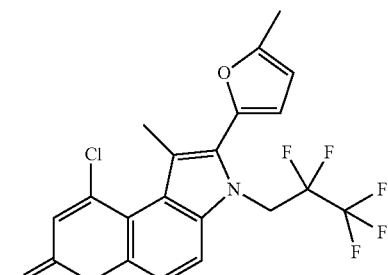

9-Chloro-1-methyl-2-(5-methylfuran-2-yl)-3-(2,2,3,3,3-pentafluoropropyl)-3,6-dihydro-pyrrolo[3,2-f]quinolin-7-one (Compound 267, Structure 12 of Scheme II, where $R^4$=chloro, $R^1$=methyl, $R^3$=5-methylfuran-2-yl, $R^5$=2,2,3,3,3-pentafluoropropyl)

This compound was prepared using the method described in Example 126 by using pentafluoropropionaldehyde hydrate and (5-methylfuran-2-yl)-propan-1-one respectively as starting material. Spectral data for compound 267: $^1$H NMR (500 MHz, Acetone) δ 7.98 (dt, J=9.0, 0.9 Hz, 1H), 7.44 (d, J=9.0 Hz, 1H), 6.73 (s, 1H), 6.72 (d, J=3.1 Hz, 1H), 6.33 (dq, J=3.1, 1.0 Hz, 1H), 5.41 (t, J=15.7 Hz, 2H), 2.61 (s, 3H), 2.41 (d, J=1.0 Hz, 3H).

Example 165

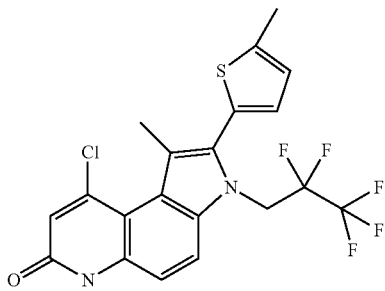 [SMILES: Cc1ccc(-c2c(C)c3c4c(Cl)cc(=O)[nH]c4ccc3n2CC(F)(F)C(F)(F)F)s1]

9-Chloro-1-methyl-2-(5-methylthiophen-2-yl)-3-(2,2,3,3,3-pentafluoropropyl)-3,6-dihydro-pyrrolo[3,2-f]quinolin-7-one (Compound 268, Structure 12 of Scheme II, where $R^4$=chloro, $R^1$=methyl, $R^3$=5-methylthiophen-2-yl, $R^5$=2,2,3,3,3-pentafluoropropyl)

This compound was prepared using the method described in Example 126 by using pentafluoropropionaldehyde hydrate and (5-methylthiophen-2-yl)-propan-1-one respectively as starting material. Spectral data for compound 268: $^1$H NMR (500 MHz, Acetone) δ 7.96 (dt, J=8.9, 1.2 Hz, 1H), 7.45 (d, J=8.9 Hz, 1H), 7.10 (d, J=3.4 Hz, 1H), 6.98 (dq, J=3.4, 1.0 Hz, 1H), 6.76 (s, 1H), 5.18 (t, J=15.8 Hz, 2H), 2.58 (d, J=1.0 Hz, 3H), 2.52 (s, 3H).

Example 166

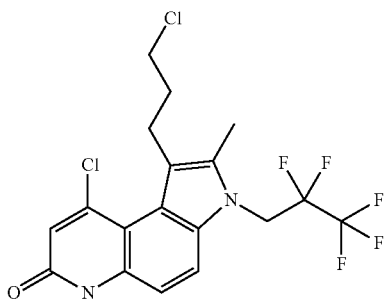

9-Chloro-1-(3-chloropropyl)-2-methyl-3-(2,2,3,3,3-pentafluoropropyl)-3,6-dihydro-pyrrolo[3,2-f]quinolin-7-one (Compound 269, Structure 12 of Scheme II, where $R^4$=chloro, $R^1$=3-chloropropyl, $R^3$=methyl, $R^4$=2,2,3,3,3-pentafluoropropyl)

This compound was prepared using the method as described in Example 126 by using pentafluoropropionaldehyde hydrate and 6-chlorohexan-2-one respectively as starting material. Spectral data for compound 269: $^1$H NMR (300 MHz, DMSO) δ 12.02 (s, 1H), 7.86 (d, J=8.8 Hz, 1H), 7.19 (d, J=8.8 Hz, 1H), 6.72 (s, 1H), 5.34 (t, J=16.4 Hz, 2H), 3.51 (t, J=6.4 Hz, 2H), 3.19 (t, J=7.5 Hz, 2H), 2.45 (s, 3H), 1.91 (m, 2H).

Example 167

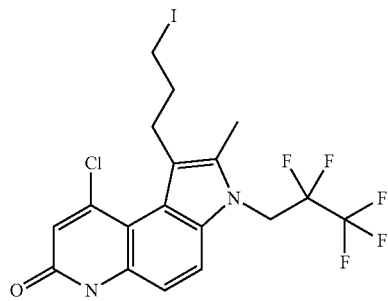 [SMILES: Cc1c(CCCI)c2c3c(Cl)cc(=O)[nH]c3ccc2n1CC(F)(F)C(F)(F)F]

9-Chloro-1-(3-iodopropyl)-2-methyl-3-(2,2,3,3,3-pentafluoropropyl)-3,6-dihydro-pyrrolo[3,2-f]quinolin-7-one (Compound 270, Structure 12 of Scheme II, where $R^4$=chloro, $R^1$=3-iodopropyl, $R^3$=methyl, $R^5$=2,2,3,3,3-pentafluoropropyl)

This compound was prepared from the compound in Example 166 by treatment with NaI in acetone. Spectral data for compound 270: $^1$H NMR (500 MHz, DMSO) δ 12.02 (s, 1H), 7.86 (d, J=8.9 Hz, 1H), 7.19 (d, J=8.9 Hz, 1H), 6.72 (s, 1H), 5.33 (t, J=16.5 Hz, 2H), 3.16 (t, J=7.0 Hz, 2H), 3.14 (m, 2H), 2.47 (s, 3H), 1.95 (qn, J=7.0 Hz, 2H).

Example 168

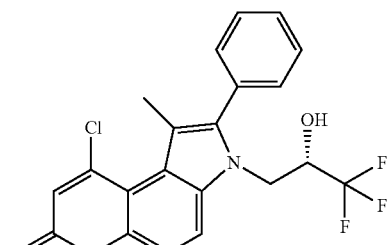

(S)-9-Chloro-1-methyl-2-phenyl-3-(3,3,3-trifluoro-2-hydroxy-propyl)-3,6-dihydro-pyrrolo[3,2-f]quinolin-7-one (Compound 271, Structure 12 of Scheme II, where $R^4$=chloro, $R^1$=methyl, $R^3$=phenyl, $R^5$=2-hydroxy-3,3,3-trifluoropropyl)

This compound was prepared using the method as described in Example 128 by using (S)-(−)-1,1,1-trifluoro-2,3-epoxypropane and propiophenone respectively as starting material. Spectral data for compound 271: $^1$H NMR (300 MHz, Acetone) δ 7.93 (d, J=8.9 Hz, 1H), 7.63-7.50 (m, 5H), 7.36 (d, J=8.9 Hz, 1H), 6.65 (s, 1H), 5.81 (d, J=6.1 Hz, 1H), 4.50-4.36 (m, 2H), 4.28 (m, 1H), 2.44 (s, 3H).

Example 169

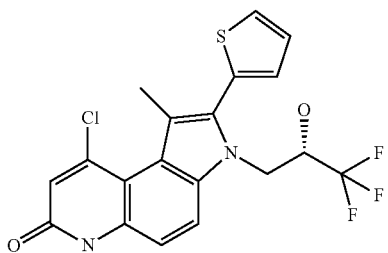 [SMILES: Cc1c(-c2cccs2)n(C[C@H](O)C(F)(F)F)c2ccc3[nH]c(=O)cc(Cl)c3c12]

(S)-9-Chloro-1-methyl-2-thiophen-2-yl-3-(3,3,3-trifluoro-2-hydroxy-propyl)-3,6-dihydro-pyrrolo[3,2-f]quinolin-7-one (Compound 272, Structure 12 of Scheme II, where $R^4$=chloro, $R^1$=methyl, $R^3$=thiophen-2-yl, $R^5$=2-hydroxy-3,3,3-trifluoropropyl)

This compound was prepared using the method as described in Example 128 by using (S)-(−)-1,1,1-trifluoro-2,3-epoxypropane and 2-propionylthiophene respectively as starting material. Spectral data for compound 272: $^1$H NMR (500 MHz, Acetone) δ 7.94 (d, J=8.8 Hz, 1H), 7.80 (dd, J=5.1, 1.2 Hz, 1H), 7.38 (d, J=8.8 Hz, 1H), 7.37 (dd, J=3.6, 1.1 Hz, 1H), 7.30 (dd, J=5.1, 3.6 Hz, 1H), 6.65 (s, 1H), 4.59-4.44 (m, 2H), 4.38 (m, 1H), 2.52 (s, 3H).

Example 170

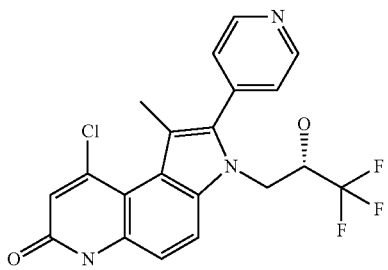 [SMILES: Cc1c(-c2ccncc2)n(C[C@H](O)C(F)(F)F)c2ccc3[nH]c(=O)cc(Cl)c3c12]

(S)-9-Chloro-1-methyl-2-(4-pyridyl)-3-(3,3,3-trifluoro-2-hydroxy-propyl)-3,6-dihydro-pyrrolo[3,2-f]quinolin-7-one (Compound 273, Structure 12 of Scheme II, where $R^4$=chloro, $R^1$=methyl, $R^3$=4-pyridyl, $R^5$=2-hydroxy-3,3,3-trifluoropropyl)

This compound was prepared by the method described in Example 128 by using (S)-(−)-1,1,1-trifluoro-2,3-epoxypropane and 4-propionylpyridine respectively as starting material. Spectral data for compound 273: $^1$H NMR (500 MHz, CD$_3$OD) δ 8.73 (d, J=6.0 Hz, 2H), 7.83 (d, J=9.0 Hz, 1H), 7.53 (d, J=6.0 Hz, 2H), 7.33 (d, J=8.9 Hz, 1H), 6.86 (s, 1H), 4.45 (dd, J=15.2, 3.1 Hz, 1H), 4.32 (dd, J=15.2, 9.0 Hz, 1H), 4.07 (m, 1H), 2.49 (s, 3H).

Example 171

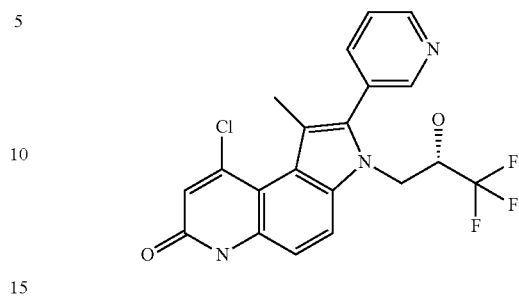

(S)-9-Chloro-1-methyl-2-(3-pyridyl)-3-(3,3,3-trifluoro-2-hydroxy-propyl)-3,6-dihydro-pyrrolo[3,2-f]quinolin-7-one (Compound 274, Structure 12 of Scheme II, where $R^4$=chloro, $R^1$=methyl, $R^3$=3-pyridyl, $R^5$=2-hydroxy-3,3,3-trifluoropropyl)

This compound was prepared by the method described in Example 128 by using (S)-(−)-1,1,1-trifluoro-2,3-epoxypropane and 3-propionylpyridine respectively as starting material. Spectral data for compound 274: $^1$H NMR (500 MHz, Acetone) δ 10.98 (s, 1H), 8.74 (m, 1H), 8.73 (dd, J=4.9, 1.7 Hz, 1H), 8.00 (dt, J=7.8, 1.7 Hz, 1H), 7.95 (d, J=8.8 Hz, 1H), 7.60 (ddd, J=7.8, 4.9, 0.9 Hz, 1H), 7.39 (d, J=8.8 Hz, 1H), 6.65 (s, 1H), 5.93 (br s, 1H), 4.51 (m, 1H), 4.41-4.34 (m, 2H), 2.45 (s, 3H).

Example 172

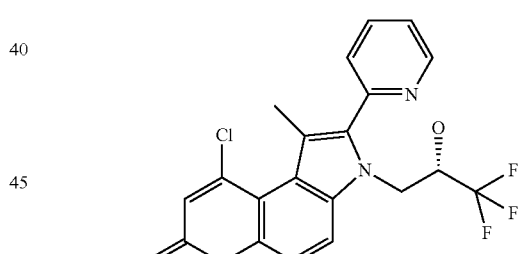

(S)-9-Chloro-1-methyl-2-(2-pyridyl)-3-(3,3,3-trifluoro-2-hydroxy-propyl)-3,6-dihydro-pyrrolo[3,2-f]quinolin-7-one (Compound 275, Structure 12 of Scheme II, where $R^4$=chloro, $R^1$=methyl, $R^3$=2-pyridyl, $R^5$=2-hydroxy-3,3,3-trifluoropropyl)

This compound was prepared by the method described in Example 128 by using (S)-(−)-1,1,1-trifluoro-2,3-epoxypropane and 2-propionylpyridine respectively as starting material. Spectral data for compound 275 $^1$H NMR (500 MHz, CD$_3$OD) δ 8.74 (ddd, j=4.9, 1.8, 1.0 Hz, 1H), 8.06 (td, J=7.7, 1.8 Hz, 1H), 7.81 (d, J=8.9 Hz, 1H), 7.80 (dt, J=7.7, 1.0 Hz, 1H), 7.53 (ddd, J=7.7, 4.9, 1.0 Hz, 1H), 7.37 (d, J=8.9 Hz, 1H), 6.87 (s, 1H), 4.65-4.59 (m, 1H), 4.54-4.46 (m, 2H), 2.64 (s, 3H).

Example 173

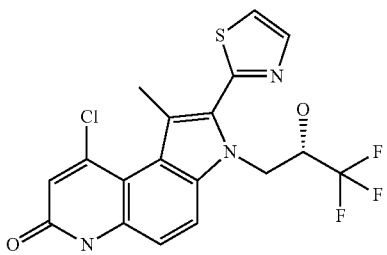 [SMILES: Cc1c(-c2nccs2)n(C[C@H](O)C(F)(F)F)c2ccc3[nH]c(=O)cc(Cl)c3c12]

(S)-9-Chloro-1-methyl-2-(1,3-thiazol-2-yl)-3-(3,3,3-trifluoro-2-hydroxy-propyl)-3,6-dihydro-pyrrolo[3,2-f]quinolin-7-one (Compound 276, Structure 12 of Scheme II, where $R^4$=chloro, $R^1$=methyl, $R^3$=1,3-thiazol-2-yl, $R^5$=2-hydroxy-3,3,3-trifluoropropyl)

This compound was prepared by the method described in Example 128 by using (S)-(−)-1,1,1-trifluoro-2,3-epoxypropane and 2-propionylthiazole respectively as starting material. Spectral data for compound 276: $^1$H NMR (500 MHz, DMSO) δ 12.14 (s, 1H), 8.12 (d, J=3.3 Hz, 1H), 8.09 (d, J=3.3 Hz, 1H), 7.96 (d, J=9.0 Hz, 1H), 7.34 (d, J=9.0 Hz, 1H), 6.75 (s, 1H), 6.59 (d, J=6.6 Hz, 1H), 4.80 (dd, J=14.9, 2.9 Hz, 1H), 4.65 (dd, J=14.9, 9.3 Hz, 1H), 4.32 (m, 1H), 2.65 (s, 3H).

Example 174

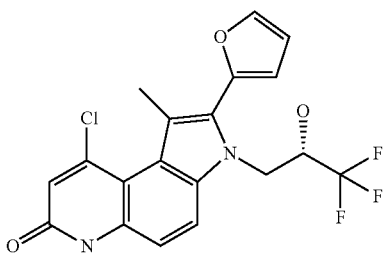 [SMILES: Cc1c(-c2ccco2)n(C[C@H](O)C(F)(F)F)c2ccc3[nH]c(=O)cc(Cl)c3c12]

(S)-9-Chloro-2-(2-furyl)-1-methyl-3-(3,3,3-trifluoro-2-hydroxy-propyl)-3,6-dihydro-pyrrolo[3,2-f]quinolin-7-one (Compound 277, Structure 12 of Scheme II, where $R^4$=chloro, $R^1$=methyl, $R^3$=2-furyl, $R^5$=2-hydroxy-3,3,3-trifluoropropyl)

This compound was prepared by the method described in Example 128 by using (S)-(−)-1,1,1-trifluoro-2,3-epoxypropane and 2-propionylfuran respectively as starting material. Spectral data for compound 277: $^1$H NMR (500 MHz, Acetone) δ 10.99 (s, 1H) 7.97 (d, J=9.0 Hz, 1H) 7.85 (dd, J=1.8, 0.8 Hz, 1H) 7.38 (d, J=9.0 Hz, 1H) 6.86 (dd, J=3.4, 0.8 Hz, 1H) 6.73 (dd, J=3.4, 1.8 Hz, 1H) 6.66 (s, 1H) 5.88 (s, 1H) 4.61-4.58 (m, 2H) 4.46 (m, 1H) 2.59 (s, 3H).

Example 175

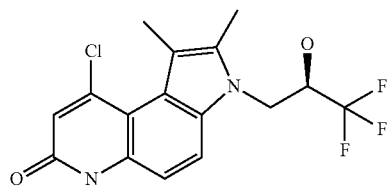 [SMILES: Cc1c(C)n(C[C@@H](O)C(F)(F)F)c2ccc3[nH]c(=O)cc(Cl)c3c12]

(R)-9-Chloro-1,2-dimethyl-3-(3,3,3-trifluoro-2-hydroxy-propyl)-3,6-dihydro-pyrrolo[3,2-f]-quinolin-7-one (Compound 278, Structure 12 of Scheme II, where $R^4$=chloro, $R^1$=methyl, $R^3$=methyl, $R^5$=2-hydroxy-3,3,3-trifluoropropyl)

This compound was prepared by the method described in Example 128 by using (R)-(+)-1,1,1-trifluoro-2,3-epoxypropane and 2-butanone respectively as starting material. Spectral data for compound 278: $^1$H NMR (500 MHz, DMSO) δ 11.94 (s, 1H), 7.71 (d, J=8.9 Hz, 1H), 7.12 (d, J=8.9 Hz, 1H), 6.64-6.61 (m, 2H), 4.48 (dd, J=15.0, 2.8 Hz, 1H), 4.33 (dd, J=15.0, 9.1 Hz, 1H), 4.25 (m, 1H), 2.43 (s, 3H), 2.40 (s, 3H).

Example 176

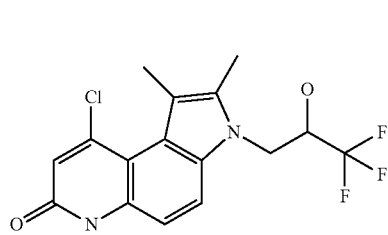 [SMILES: Cc1c(C)n(CC(O)C(F)(F)F)c2ccc3[nH]c(=O)cc(Cl)c3c12]

rac-9-Chloro-1,2-dimethyl-3-(3,3,3-trifluoro-2-hydroxy-propyl)-3,6-dihydro-pyrrolo[3,2-f]-quinolin-7-one (Compound 279, Structure 12 of Scheme II, where $R^4$=chloro, $R^1$=methyl, $R^3$=methyl, $R^5$=2-hydroxy-3,3,3-trifluoropropyl)

This compound was prepared by the method described in Example 128 by using racemic 1,1,1-trifluoro-2,3-epoxypropane and 2-butanone respectively as starting material. Spectral data for compound 279: $^1$H NMR (500 MHz, DMSO) δ 11.94 (s, 1H), 7.71 (d, J=8.8 Hz, 1H), 7.12 (d, J=8.8 Hz, 1H), 6.67 (br s, 1H), 6.63 (s, 1H), 4.48 (dd, J=15.1, 2.9 Hz, 1H), 4.33 (dd, J=15.1, 9.2 Hz, 1H), 4.25 (m, 1H), 2.43 (s, 3H), 2.40 (s, 3H).

Example 177

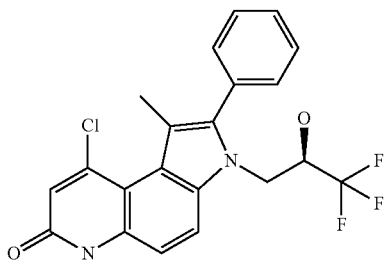 [SMILES: Cc1c(-c2ccccc2)n(C[C@@H](O)C(F)(F)F)c2ccc3[nH]c(=O)cc(Cl)c3c12]

9-Chloro-1-methyl-2-phenyl-3-(3,3,3-trifluoro-2-hydroxy-propyl)-3,6-dihydro-pyrrolo[3,2-f]quinolin-7-one (Compound 280, Structure 12 of Scheme II, where $R^4$=chloro, $R^1$=methyl, $R^3$=phenyl, $R^5$=2-hydroxy-3,3,3-trifluoropropyl)

This compound was prepared by the method described in Example 128 by using (R)-1,1,1-trifluoro-2,3-epoxypropane and propiophenone respectively as starting material. Spectral data for compound 280: $^1$H NMR (500 MHz, DMSO) δ 10.97 (s, 1H), 7.93 (d, J=8.9 Hz, 1H), 7.60 (m, 2H), 7.56-7.52 (m, 3H), 7.35 (d, J=8.9 Hz, 1H), 6.64 (s, 1H), 5.88 (d, J=6.3 Hz, 1H), 4.46 (dd, J=14.9, 3.6 Hz, 1H), 4.41 (dd, J=14.9, 8.6 Hz, 1H), 4.27 (m, 1H), 2.44 (s, 3H).

Example 178

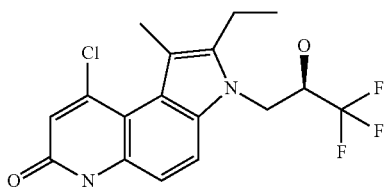 [SMILES: CCc1c(C)c2c3c(Cl)cc(=O)[nH]c3ccc2n1C[C@@H](O)C(F)(F)F]

(R)-9-Chloro-2-ethyl-1-methyl-3-(3,3,3-trifluoro-2-hydroxy-propyl)-3,6-dihydro-pyrrolo[3,2-f]quinolin-7-one (Compound 281, Structure 12 of Scheme II, where $R^4$=chloro, $R^1$=methyl, $R^3$=ethyl, $R^5$=2-hydroxy-3,3,3-trifluoropropyl)

This compound was prepared by the method described in Example 128 by using (R)-(+)-1,1,1-trifluoro-2,3-epoxypropane and 3-pentanone respectively as starting material. Spectral data for compound 281: $^1$H NMR (500 MHz, Acetone) δ 11.11 (s, 1H), 7.75 (d, j=8.8 Hz, 1H), 7.22 (d, J=8.8 Hz, 1H), 6.57 (s, 1H), 6.04 (br s, 1H), 4.61 (dd, J=14.5, 1.7 Hz, 1H), 4.52 (m, 1H), 4.47 (dd, J=14.5, 9.5 Hz, 1H), 3.04 (dq, J=15.2, 7.6 Hz, 1H), 2.91 (dq, J=15.2, 7.6 Hz, 1H), 2.56 (s, 3H), 1.25 (t, J=7.6 Hz, 3H).

Example 179

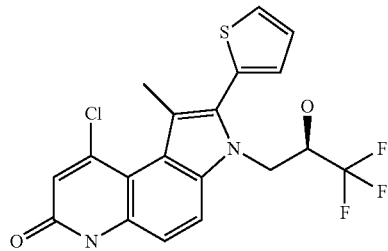 [SMILES: Cc1c(-c2cccs2)n(C[C@@H](O)C(F)(F)F)c2ccc3[nH]c(=O)cc(Cl)c3c12]

(R)-9-Chloro-1-methyl-2-thiophen-2-yl-3-(3,3,3-trifluoro-2-hydroxy-propyl)-3,6-dihydro-pyrrolo[3,2-f]quinolin-7-one (Compound 282, Structure 12 of Scheme II, where $R^4$=chloro, $R^1$=methyl, $R^3$=thiophen-2-yl, $R^5$=2-hydroxy-3,3,3-trifluoropropyl)

This compound was prepared by the method described in Example 128 by using (R)-(+)-1,1,1-trifluoro-2,3-epoxypropane and 1-(thiophen-2-yl)-propan-1-one respectively as starting material. Spectral data for compound 282: $^1$H NMR (500 MHz, Acetone) δ 11.21 (s, 1H), 7.94 (d, J=8.9 Hz, 1H), 7.80 (dd, J=5.2, 1.2 Hz, 1H), 7.38 (dd, J=3.4, 1.2 Hz, 1H), 7.35 (d, J=8.9 Hz, 1H), 7.31 (dd, J=5.2, 3.4 Hz, 1H), 6.59 (s, 1H), 6.11 (d, J=6.1 Hz, 1H), 4.51 (dd, J=14.5, 3.7 Hz, 1H), 4.45 (d, J=14.5 Hz, 1H), 4.41 (m, 1H), 2.53 (s, 3H).

Example 180

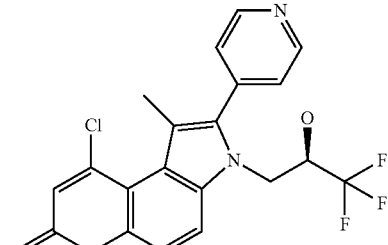

(R)-9-Chloro-1-methyl-2-(4-pyridyl)-3-(3,3,3-trifluoro-2-hydroxy-propyl)-3,6-dihydro-pyrrolo[3,2-f]quinolin-7-one (Compound 283, Structure 12 of Scheme II, where $R^4$=chloro, $R^1$=methyl, $R^3$=4-pyridyl, $R^5$=2-hydroxy-3,3,3-trifluoropropyl)

This compound was prepared by the method described in Example 128 by using (R)-(+)-1,1,1-trifluoro-2,3-epoxypropane and 1-(4-pyridyl)-propan-1-one respectively as starting material. Spectral data for compound 283: $^1$H NMR (500 MHz, CD$_3$OD) δ 8.73 (d, J=5.7 Hz, 2H), 7.93 (d, J=9.0 Hz, 1H), 7.59 (m, 2H), 7.33 (d, J=9.0 Hz, 1H), 6.82 (s, 1H), 4.53 (dd, J=15.3, 3.1 Hz, 1H), 4.36 (dd, J=15.3, 9.3 Hz, 1H), 4.07 (m, 1H), 2.48 (s, 3H).

Example 181

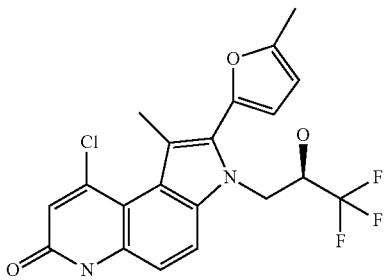 [SMILES: Cc1ccc(-c2c(C)c3c4c(Cl)cc(=O)[nH]c4ccc3n2C[C@@H](O)C(F)(F)F)o1]

(R)-9-Chloro-1-methyl-2-(5-methylfuran-2-yl)-3-(3,3,3-trifluoro-2-hydroxy-propyl)-3,6-dihydro-pyrrolo[3,2-f]quinolin-7-one (Compound 284, Structure 12 of Scheme II, where R$^4$=chloro, R$^1$=methyl, R$^3$=5-methylfuran-2-yl, R$^5$=2-hydroxy-3,3,3-trifluoropropyl)

This compound was prepared by the method described in Example 128 by using (R)-(+)-1,1,1-trifluoro-2,3-epoxypropane and 1-(5-methylfuran-2-yl)-propan-1-one respectively as starting material. Spectral data for compound 284: $^1$H NMR (500 MHz, Acetone) δ 7.97 (d, J=9.0 Hz, 1H), 7.36 (d, J=9.0 Hz, 1H), 6.71 (d, J=3.2 Hz, 1H), 6.67 (s, 1H), 6.32 (dq, J=3.2, 0.8 Hz, 1H), 4.63 (dd, J=14.9, 4.0 Hz, 1H), 4.59 (d, J=14.9 Hz, 1H), 4.51 (m, 1H), 2.60 (s, 3H), 2.40 (d, J=0.8 Hz, 3H).

Example 182

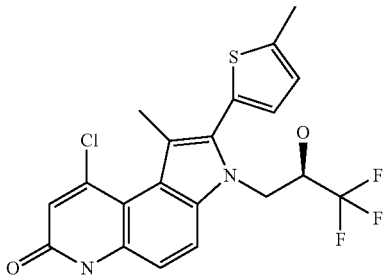

(R)-9-Chloro-1-methyl-2-(5-methylthiophen-2-yl)-3-(3,3,3-trifluoro-2-hydroxy-propyl)-3,6-dihydro-pyrrolo[3,2-f]quinolin-7-one (Compound 285, Structure 12 of Scheme II, where R$^4$=chloro, R$^1$-methyl, R$^3$=5-methylthiophen-2-yl, R$^5$=2-hydroxy-3,3,3-trifluoropropyl)

This compound was prepared by the method described in Example 128 by using (R)-(+)-1,1,1-trifluoro-2,3-epoxypropane and 1-(5-methylthiophen-2-yl)-propan-1-one respectively as starting material. Spectral data for compound 285: $^1$H NMR (500 MHz, Acetone) δ 7.92 (d, J=9.0 Hz, 1H), 7.37 (d, J=9.0 Hz, 1H), 7.13 (d, J=3.4 Hz, 1H), 6.96 (dq, J=3.4, 1.0 Hz, 1H), 6.66 (s, 1H), 5.84 (d, J=5.9 Hz, 1H), 4.54 (dd, J=14.6, 3.5 Hz, 1H), 4.49 (dd, J=14.6, 8.6 Hz, 1H), 4.39 (m, 1H), 2.58 (d, J=1.0 Hz, 3H), 2.52 (s, 3H).

Example 183

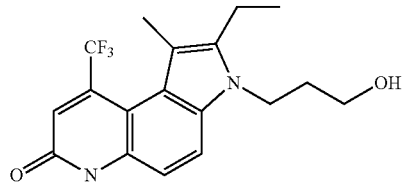 [SMILES: CCc1c(C)c2c3c(C(F)(F)F)cc(=O)[nH]c3ccc2n1CCCO]

2-Ethyl-3-(3-hydroxypropyl)-1-methyl-3,6-dihydro-pyrrolo[3,2-f]quinolin-7-one (Compound 286, Structure 12 of Scheme III, where R$^4$=trifluoromethyl, R$^1$=methyl, R$^3$=ethyl, R$^5$=3-hydroxypropyl)

This compound was prepared by the method described in Example 133 by using 3-bromopropoxy-tert-butyl dimethylsilane as starting material. Spectral data for compound 286: $^1$H NMR (500 MHz, MeOD) δ 7.81 (d, J=8.8 Hz, 1H), 7.17 (d, J=8.8 Hz, 1H), 6.99 (s, 1H), 4.36 (t, J=7.4 Hz, 2H), 3.59 (t, J=5.9 Hz, 2H), 2.90 (q, J=7.6 Hz, 2H), 2.32 (q, J=2.1 Hz, 3H), 1.95 (m, 2H), 1.24 (t, J=7.6 Hz, 3H).

Example 184

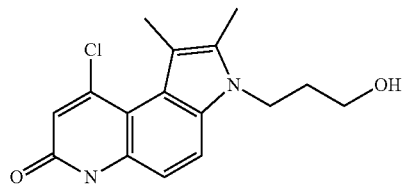 [SMILES: Cc1c(C)n(CCCO)c2ccc3[nH]c(=O)cc(Cl)c3c12]

9-Chloro-1,2-dimethyl-3-(3-hydroxypropyl)-3,6-dihydro-pyrrolo[3,2-f]quinolin-7-one (Compound 287, Structure 12 of Scheme III, where R$^4$=chloro, R$^1$-methyl, R$^3$=methyl, R$^5$=3-hydroxypropyl)

This compound was prepared by the method described in Example 133 by using 3-bromopropoxy-tert-butyl dimethylsilane as starting material. Spectral data for compound 287: $^1$H NMR (500 MHz, MeOD) δ 8.60 (br s, 2H), 7.72 (d, J=8.8 Hz, 1H), 7.13 (d, J=8.8 Hz, 1H), 6.78 (s, 1H), 4.34 (t, J=7.2 Hz, 2H), 3.60 (t, J=6.0 Hz, 3H), 2.56 (s, 3H), 2.48 (s, 3H), 1.96 (m, 2H).

Example 185

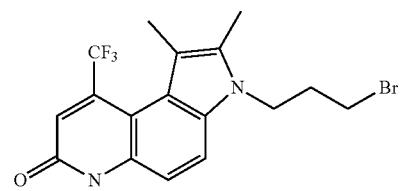 [SMILES: Cc1c(C)n(CCCBr)c2ccc3[nH]c(=O)cc(C(F)(F)F)c3c12]

3-(3-Bromopropyl)-1,2-dimethyl-9-trifluoromethyl-3,6-dihydro-pyrrolo[3,2-f]-quinolin-7-one (Compound 288, Structure 12 of Scheme III, where R$^4$=trifluoromethyl, R$^1$=methyl, R$^3$=methyl, R$^5$=3-bromopropyl)

This compound was prepared by heating compound 249 in 48% hydrobromic acid for 18 h. at 90° C. Spectral data for compound 288: $^1$H NMR (500 MHz, Acetone) δ 8.25 (d, J=9.0 Hz, 1H), 8.23 (s, 1H), 7.78 (d, J=9.0 Hz, 1H), 4.59 (t, J=7.5 Hz, 2H), 3.61 (t, J=6.4 Hz, 2H), 2.57 (s, 3H), 2.44-2.37 (m, 5H).

Example 186

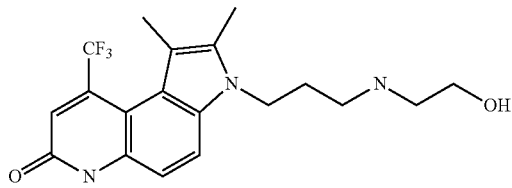 [SMILES: Cc1c(C)n(CCCNCCO)c2ccc3[nH]c(=O)cc(C(F)(F)F)c3c12]

1,2-Dimethyl-3-[3-(2-hydroxy-ethylamino)-propyl]-9-trifluoromethyl-3,6-dihydro-pyrrolo[3,2-f]quinolin-7-one (Compound 289, Structure 12 of Scheme III, where R$^4$=trifluoromethyl, R$^1$-methyl, R$^3$=methyl, R$^5$=3-(2-hydroxyethylamino)propyl This compound was prepared by treating compound 288 (from example 185) with 2-aminoethanol for 18 h. at rt. Spectral data for compound 289: $^1$H NMR (500 MHz, DMSO) δ 13.41 (s, 1H), 7.84 (d, J=9.0 Hz, 1H), 7.16 (d, J=9.0 Hz, 1H), 6.94 (s, 1H), 4.66 (m, 1H), 4.26 (t, J=7.2 Hz, 2H), 3.69-3.44 (m, 4H), 2.76 (t, J=5.5 Hz, 1H), 2.58 (t, J=5.9 Hz, 2H), 2.39 (s, 3H), 2.22 (s, 3H), 1.78 (m, 2H).

Example 187

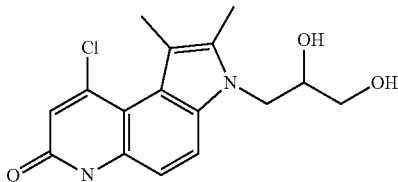

9-Chloro-3-(2,3-dihydroxypropyl)-1,2-dimethyl-3,6-dihydro-pyrrolo[3,2-f]-quinolin-7-one (Compound 290, Structure 12 of Scheme III, where R$^4$=chloro, R$^1$-methyl, R$^3$=methyl, R$^5$=2,3-dihydroxypropyl)

This compound was prepared by the method described in example 128 by using 2,2-dimethyl-1,3-dioxolan-4-ylmethyl p-toluenesulfonate as alkylating agent. Spectral data for compound 290: $^1$H NMR (500 MHz, DMSO) δ 11.90 (s, 1H), 7.74 (d, J=8.8 Hz, 1H), 7.09 (d, J=8.8 Hz, 1H), 6.62 (s, 1H), 4.97 (d, J=5.3 Hz, 1H), 4.85 (t, J=5.6 Hz, 1H), 4.33 (dd, J=14.7, 3.7 Hz, 1H), 4.07 (dd, J=14.7, 8.0 Hz, 1H), 3.69 (m, 1H), 3.44-3.33 (m, 2H), 2.45 (s, 3H), 2.41 (s, 3H).

Example 188

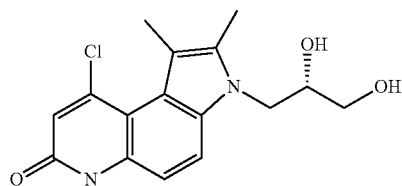 [SMILES: Cc1c(C)n(C[C@H](O)CO)c2ccc3[nH]c(=O)cc(Cl)c3c12]

(S)-9-Chloro-3-(2,3-dihydroxypropyl)-1,2-dimethyl-3,6-dihydro-pyrrolo[3,2-f]-quinolin-7-one (Compound 291, Structure 12 of Scheme III, where R$^4$=chloro, R$^1$=methyl, R$^3$=methyl, R$^5$=2,3-dihydroxypropyl)

This compound was prepared by separation of the enantiomers of example 187 by chiral HPLC. Spectral data for compound 291: $^1$H NMR (500 MHz, DMSO) δ 11.90 (s, 1H), 7.74 (d, J=8.8 Hz, 1H), 7.09 (d, J=8.8 Hz, 1H), 6.62 (s, 1H), 4.98 (m, 1H), 4.87 (m, 1H), 4.33 (dd, J=15.0, 3.7 Hz, 1H), 4.07 (dd, J=15.0, 8.1 Hz, 1H), 3.70 (m, 1H), 3.38 (m, 2H), 2.45 (s, 3H), 2.42 (s, 3H).

Example 189

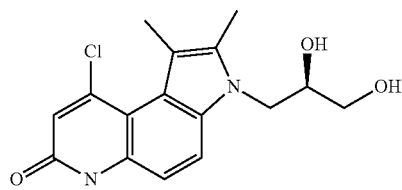 [SMILES: Cc1c(C)n(C[C@@H](O)CO)c2ccc3[nH]c(=O)cc(Cl)c3c12]

(R)-9-Chloro-3-(2,3-dihydroxypropyl)-1,2-dimethyl-3,6-dihydro-pyrrolo[3,2-f]-quinolin-7-one (Compound 292, Structure 12 of Scheme III, where R$^4$=chloro, R$^1$=methyl, R$^3$=methyl, R$^5$=2,3-dihydroxypropyl)

This compound was prepared by separation of the enantiomers of example 187 by chiral HPLC. Spectral data for compound 292: $^1$H NMR (500 MHz, DMSO) δ 11.90 (s, 1H), 7.74 (d, J=8.8 Hz, 1H), 7.09 (d, J=8.8 Hz, 1H), 6.62 (s, 1H), 4.97 (d, J=5.4 Hz, 1H), 4.86 (t, J=5.4 Hz, 1H), 4.33 (dd, J=14.9, 3.7 Hz, 1H), 4.07 (dd, J=14.9, 8.1 Hz, 1H), 3.70 (m, 1H), 3.44-3.37 (m, 2H), 2.45 (s, 3H), 2.41 (s, 3H).

Example 190

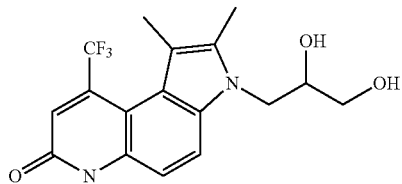 [SMILES: Cc1c(C)n(CC(O)CO)c2ccc3[nH]c(=O)cc(C(F)(F)F)c3c12]

3-(2,3-dihydroxypropyl)-1,2-dimethyl-9-trifluoromethyl-3,6-dihydro-pyrrolo[3,2-f]-quinolin-7-one (Compound 293, Structure 12 of Scheme III, where $R^4$=trifluoromethyl, $R^1$=methyl, $R^3$=methyl, $R^5$=2,3-dihydroxypropyl)

This compound was prepared by the method described in example 128 by using 2,2-dimethyl-1,3-dioxolan-4-ylmethyl p-toluenesulfonate as alkylating agent. Spectral data for compound 293: $^1$H NMR (300 MHz, DMSO) δ 12.26 (s, 1H), 7.77 (d, J=8.9 Hz, 1H), 7.12 (d, J=8.9 Hz, 1H), 6.92 (s, 1H), 4.98 (d, J=5.4 Hz, 1H), 4.87 (t, J=5.5 Hz, 1H), 4.33 (dd, J=14.9, 3.6 Hz, 1H), 4.06 (dd, J=14.9, 8.0 Hz, 1H), 3.72 (m, 1H), 3.45-3.34 (m, 2H), 2.40 (s, 3H), 2.21 (q, J=1.8 Hz, 3H).

Example 191

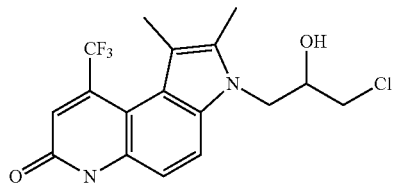 [SMILES: Cc1c(C)n(CC(O)CCl)c2ccc3[nH]c(=O)cc(C(F)(F)F)c3c12]

3-(3-chloro-2-hydroxypropyl)-1,2-dimethyl-9-trifluoromethyl-3,6-dihydro-pyrrolo[3,2-f]-quinolin-7-one (Compound 294, Structure 12 of Scheme III, where $R^4$=trifluoromethyl, $R^1$=methyl, $R^3$=methyl, $R^5$=3-chloro-2-hydroxypropyl)

This compound was isolated as a byproduct in the synthesis of compound 293 from example 190. Spectral data for compound 294: $^1$H NMR (300 MHz, DMSO) δ 12.28 (s, 1H), 7.80 (d, J=8.9 Hz, 1H), 7.14 (d, J=8.9 Hz, 1H), 6.93 (s, 1H), 5.54 (d, J=5.4 Hz, 1H), 4.35 (dd, j=15.0, 3.3 Hz, 1H), 4.19 (dd, J=15.0, 8.3 Hz, 1H), 3.96 (m, 1H), 3.71 (dd, J=11.2, 4.8 Hz, 1H), 3.65 (dd, J=11.2, 5.5 Hz, 1H), 2.40 (s, 3H), 2.21 (q, J=1.8 Hz, 3H).

Example 192

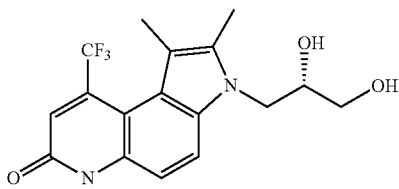 [SMILES: Cc1c(C)n(C[C@H](O)CO)c2ccc3[nH]c(=O)cc(C(F)(F)F)c3c12]

(S)-3-(2,3-dihydroxypropyl)-1,2-dimethyl-9-trifluoromethyl-3,6-dihydro-pyrrolo[3,2-f]-quinolin-7-one (Compound 295, Structure 12 of Scheme III, where $R^4$=trifluoromethyl, $R^1$=methyl, $R^3$=methyl, $R^5$=2,3-dihydroxypropyl)

This compound was prepared by separation of the enantiomers of example 190 by chiral HPLC. Spectral data for compound 295: $^1$H NMR (500 MHz, Acetone) δ 11.04 (s, 1H), 7.82 (d, J=8.8 Hz, 1H), 7.22 (d, J=8.8 Hz, 1H), 6.90 (s, 1H), 4.46 (dd, J=15.0, 4.0 Hz, 1H), 4.23 (dd, J=15.0, 7.8 Hz, 2H), 4.00 (m, 1H), 3.64-3.55 (m, 2H), 2.47 (s, 3H), 2.30 (q, J=2.2 Hz, 3H).

Example 193

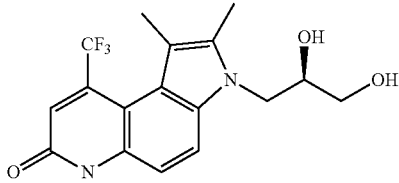 [SMILES: Cc1c(C)n(C[C@@H](O)CO)c2ccc3[nH]c(=O)cc(C(F)(F)F)c3c12]

(R)-3-(2,3-dihydroxypropyl)-1,2-dimethyl-9-trifluoromethyl-3,6-dihydro-pyrrolo[3,2-f]-quinolin-7-one (Compound 296, Structure 12 of Scheme III, where $R^4$=trifluoromethyl, $R^1$=methyl, $R^3$=methyl, $R^5$=2,3-dihydroxypropyl)

This compound was prepared by separation of the enantiomers of example 190 by chiral HPLC. Spectral data for compound 296: $^1$H NMR (500 MHz, Acetone) δ 7.82 (d, J=8.8 Hz, 1H), 7.22 (d, J=8.8 Hz, 1H), 6.90 (s, 1H), 4.46 (dd, J=15.1, 4.1 Hz, 1H), 4.23 (dd, J=15.1, 7.8 Hz, 1H), 4.00 (m, 1H), 3.64-3.57 (m, 2H), 2.47 (s, 3H), 2.30 (q, J=2.2 Hz, 3H).

Example 194

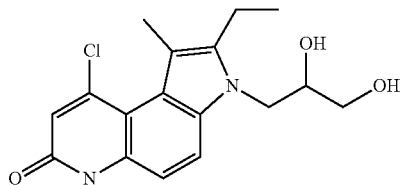 [SMILES: CCc1c(C)c2c3c(Cl)cc(=O)[nH]c3ccc2n1CC(O)CO]

9-Chloro-3-(2,3-dihydroxypropyl)-2-ethyl-1-methyl-3,6-dihydro-pyrrolo[3,2-f]-quinolin-7-one (Compound 297, Structure 12 of Scheme III, where $R^4$=chloro, $R^1$=methyl, $R^3$=ethyl, $R^5$=2,3-dihydroxypropyl)

This compound was prepared by the method described in example 128 by using 2,2-dimethyl-1,3-dioxolan-4-ylmethyl p-toluenesulfonate as alkylating agent. Spectral data for compound 297: $^1$H NMR (500 MHz, DMSO) δ 11.91 (br s, 1H), 7.75 (d, J=8.9 Hz, 1H), 7.10 (d, J=8.9 Hz, 1H), 6.62 (s, 1H), 5.04 (br s, 1H), 4.91 (br s, 1H), 4.35 (dd, J=14.9, 3.6 Hz, 1H), 4.06 (dd, J=14.9, 8.2 Hz, 1H), 3.69 (m, 1H), 3.40 (dd, J=10.9, 4.9 Hz, 1H), 3.35 (dd, J=10.9, 6.5 Hz, 1H), 2.92 (dq, J=15.0, 7.5 Hz, 1H), 2.83 (dq, J=15.0, 7.5 Hz, 1H), 2.47 (s, 3H), 1.15 (t, J=7.5 Hz, 3H).

Example 195

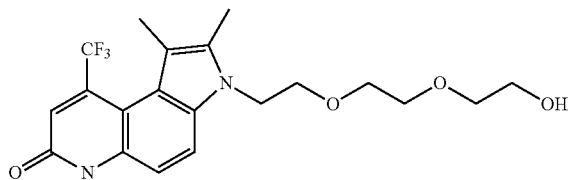 [SMILES: Cc1c(C)n(CCOCCOCCO)c2ccc3[nH]c(=O)cc(C(F)(F)F)c3c12]

3-{2-[2-(2-Hydroxy-ethoxy)-ethoxy]-ethyl}-1,2-dimethyl-9-trifluoromethyl-3,6-dihydro-pyrrolo[3,2-f]quinolin-7-one (Compound 298, Structure 12 of Scheme III, where $R^4$=trifluoromethyl, $R^1$=methyl, $R^3$=methyl, $R^5$=2-[2-(2-Hydroxy-ethoxy)-ethoxy]-ethyl This compound was prepared by the method described in Example 133 by using 2-{2-[2-Chloro-ethoxy)-ethoxy]-ethoxy}-tetrahydro-2H-pyran. as alkylating agent. Spectral data for compound 298: $^1$H NMR (500 MHz, CDCl$_3$) δ 7.75 (d, J=8.8 Hz, 1H), 7.38 (d, J=8.8 Hz, 1H), 7.22 (s, 1H), 4.35 (t, J=5.7 Hz, 2H), 3.72 (t, J=5.7 Hz, 2H), 3.64 (m, 2H), 3.52-3.44 (m, 6H), 2.80 (q, J=7.6 Hz, 2H), 2.27 (q, J=2.0 Hz, 3H), 1.17 (t, J=7.6 Hz, 3H).

Example 196

IR Binding Assay

For the whole cell binding assay, COS-1 cells in 96-well microtiter plates including DMEM-10% FBS were transfected as described above with the following plasmid DNA: pRShAR (2 ng/well), pRS-β-Gal (50 ng/well) and pGEM (48 ng/well). Six hours after transfection, media was removed, the cells were washed with PBS and fresh media was added. The next day, the media was changed to DMEM-serum free to remove any endogenous ligand that might be complexed with the receptor in the cells.

After 24 hours in serum-free media, either a saturation analysis to determine the $K_d$ for tritiated dihydrotestosterone ($^3$H-DHT) on human AR or a competitive binding assay to evaluate the ability of test compounds to compete with $^3$H-DHT for AR was performed. For the saturation analysis, media (DMEM-0.2% CA-FBS) including $^3$H-DHT (in concentrations ranging from 12 nM to 0.24 nM) in the absence (total binding) or presence (non-specific binding) of a 100-fold molar excess of unlabeled DHT were added to the cells. For the competitive binding assay, media including 1 nM $^3$H-DHT and test compounds in concentrations ranging from $10^{-10}$ to $10^{-6}$ M were added to the cells. Three replicates were used for each sample. After three hours at 37° C., an aliquot of the total binding media at each concentration of $^3$H-DHT was removed to estimate the amount of free $^3$H-DHT. The remaining media was removed, the cells were washed three times with PBS to remove unbound ligand, and cells were lysed with a Triton X-100-based buffer. The lysates were assayed for amount of bound $^3$H-DHT and β-Gal activity using a scintillation counter or spectrophotometer, respectively.

For the saturation analyses, the difference between the total binding and the nonspecific binding, normalized by the β-Gal rate, was defined as specific binding. The specific binding was evaluated by Scatchard analysis to determine the $K_d$ for $^3$H-DHT. See e.g., D. Rodbard, "Mathematics and statistics of ligand assays: an illustrated guide" In: J. Langon and J. J. Clapp, eds., *Ligand Assay*, Masson Publishing U.S.A., Inc., New York, pp. 45-99, (1981), the disclosure of which is herein incorporated by reference. For the competition studies, the data was plotted as the amount of $^3$H-DHT (% of control in the absence of test compound) remaining over the range of the dose-response curve for a given compound. The concentration of test compound that inhibited 50% of the amount of $^3$H-DHT bound in the absence of competing ligand was quantified (IC$_{50}$) after log-logit transformation. The $K_i$ values were determined by application of the Cheng-Prusoff equation to the IC$_{50}$ values, where:

$$\frac{IC_{50}}{K_i} = (1 + [^3H\text{-}DHT])/K_d \text{ for } ^3H\text{-}DHT$$

After correcting for non-specific binding, IC$_{50}$ values were determined. The IC$_{50}$ value is defined as the concentration of competing ligand needed to reduce specific binding by 50%. The IC$_{50}$ value was determined graphically from a log-logit plot of the data. The $K_i$ values were determined by application of the Cheng-Prusoff equation to the IC$_{50}$ values, the labeled ligand concentration and the $K_d$ of the labeled ligand. see e.g., Cheng, Y. C. and Prusoff, W. H. *Biochem. Pharmacol.* 22:3099 (1973). $K_i$ value ranges for certain AR binding compounds are shown in Table 1.

TABLE 1

| Binding Data | | |
|---|---|---|
| Compound Number | Example | $K_i$ (nM) |
| 105 | 2 | A |
| 106 | 3 | B |

TABLE 1-continued

Binding Data

| Compound Number | Example | $K_i$ (nM) |
|---|---|---|
| 107 | 4 | C |
| 108 | 5 | A |
| 109 | 6 | C |
| 110 | 7 | A |
| 111 | 8 | C |
| 112 | 9 | C |
| 113 | 10 | C |
| 114 | 11 | C |
| 115 | 12 | C |
| 116 | 13 | A |
| 117 | 14 | A |
| 118 | 15 | A |
| 119 | 16 | A |
| 120 | 17 | C |
| 121 | 18 | C |
| 122 | 19 | A |
| 123 | 20 | B |
| 124 | 21 | C |
| 125 | 22 | C |
| 126 | 23 | A |
| 127 | 24 | B |
| 128 | 25 | C |
| 129 | 26 | C |
| 130 | 27 | B |
| 131 | 28 | C |
| 132 | 29 | A |
| 133 | 30 | A |
| 134 | 31 | A |
| 135 | 32 | B |
| 136 | 33 | C |
| 137 | 34 | A |
| 138 | 35 | A |
| 139 | 36 | C |
| 140 | 37 | C |
| 141 | 38 | B |
| 142 | 39 | A |
| 143 | 40 | B |
| 144 | 41 | B |
| 145 | 42 | A |
| 146 | 43 | C |
| 147 | 44 | C |
| 148 | 45 | B |
| 149 | 46 | B |
| 150 | 47 | C |
| 151 | 48 | A |
| 152 | 49 | C |
| 153 | 50 | C |
| 154 | 51 | C |
| 155 | 52 | C |
| 156 | 53 | A |
| 157 | 54 | A |
| 158 | 55 | A |
| 159 | 56 | C |
| 160 | 57 | C |
| 161 | 58 | A |
| 162 | 59 | A |
| 163 | 60 | C |
| 164 | 61 | A |
| 165 | 62 | A |
| 166 | 63 | C |
| 167 | 64 | A |
| 168 | 65 | C |
| 169 | 66 | A |
| 170 | 67 | A |
| 171 | 68 | C |
| 172 | 69 | C |
| 173 | 70 | A |
| 174 | 71 | A |
| 175 | 72 | A |
| 176 | 73 | A |
| 177 | 74 | A |
| 178 | 75 | A |
| 179 | 76 | A |
| 180 | 77 | A |
| 181 | 78 | B |
| 182 | 79 | A |
| 183 | 80 | A |
| 184 | 81 | A |
| 185 | 82 | A |
| 186 | 83 | B |
| 187 | 84 | A |
| 188 | 85 | A |
| 189 | 86 | C |
| 190 | 87 | C |
| 191 | 88 | A |
| 192 | 89 | C |
| 193 | 90 | B |
| 194 | 91 | A |
| 195 | 92 | A |
| 196 | 93 | A |
| 197 | 94 | A |
| 198 | 95 | C |
| 199 | 96 | A |
| 200 | 97 | A |
| 201 | 98 | C |
| 202 | 99 | C |
| 203 | 100 | A |
| 204 | 101 | A |
| 205 | 102 | B |
| 206 | 103 | C |
| 207 | 104 | A |
| 208 | 105 | B |
| 209 | 106 | A |
| 210 | 107 | A |
| 211 | 108 | B |
| 212 | 109 | A |
| 213 | 110 | A |
| 214 | 111 | C |
| 215 | 112 | A |
| 216 | 113 | A |
| 217 | 114 | A |
| 218 | 115 | A |
| 219 | 116 | A |
| 220 | 117 | A |
| 221 | 118 | A |
| 222 | 119 | A |
| 223 | 120 | A |
| 224 | 121 | A |
| 225 | 122 | A |
| 226 | 123 | A |
| 227 | 124 | A |
| 228 | 125 | A |
| 229 | 126 | A |
| 230 | 127 | C |
| 231 | 128 | A |
| 232 | 129 | A |
| 233 | 130 | A |
| 234 | 131 | A |
| 235 | 132 | C |
| 236 | 133 | A |
| 237 | 134 | A |
| 238 | 135 | A |
| 239 | 136 | C |
| 240 | 137 | C |
| 241 | 138 | B |
| 242 | 139 | A |
| 243 | 140 | A |
| 244 | 141 | C |
| 245 | 142 | C |
| 246 | 143 | B |
| 247 | 144 | A |
| 248 | 145 | A |
| 249 | 146 | A |
| 250 | 147 | A |
| 251 | 148 | A |
| 252 | 149 | A |
| 253 | 150 | C |
| 254 | 151 | C |
| 255 | 152 | A |
| 256 | 153 | A |

TABLE 1-continued

Binding Data

| Compound Number | Example | $K_i$ (nM) |
|---|---|---|
| 257 | 154 | A |
| 258 | 155 | A |
| 259 | 156 | C |
| 260 | 157 | C |
| 261 | 158 | A |
| 262 | 159 | B |
| 263 | 160 | A |
| 264 | 161 | A |
| 265 | 162 | A |
| 266 | 163 | A |
| 267 | 164 | B |
| 268 | 165 | A |
| 269 | 166 | C |
| 270 | 167 | C |
| 271 | 168 | A |
| 272 | 169 | A |
| 273 | 170 | C |
| 274 | 171 | C |
| 275 | 172 | B |
| 276 | 173 | C |
| 277 | 174 | A |
| 278 | 175 | A |
| 279 | 176 | A |
| 280 | 177 | C |
| 281 | 178 | A |
| 282 | 179 | A |
| 283 | 180 | B |
| 284 | 181 | A |
| 285 | 182 | A |
| 286 | 183 | A |
| 287 | 184 | C |
| 288 | 185 | A |
| 289 | 186 | C |
| 290 | 187 | C |
| 291 | 188 | C |
| 292 | 189 | C |
| 293 | 190 | C |
| 294 | 191 | A |
| 295 | 192 | C |
| 296 | 193 | C |
| 297 | 194 | C |
| 298 | 195 | C |

A: <5 nM,
B: 5-10 nM,
C: >10 nM.

Since modifications will be apparent to those of skill in this art, it is intended that this invention be limited only by the scope of the appended claims.

We claim:

1. A method of treating a patient having a condition susceptible to treatment with an androgen receptor modulator, wherein the condition is selected from acne, male-pattern baldness, cancer cachexia, hirsutism, hypogonadism, osteoporosis, impotence, breast cancer, prostate cancer and prostatic hyperplasia, comprising administering to the patient a compound having a structure of Formula I:

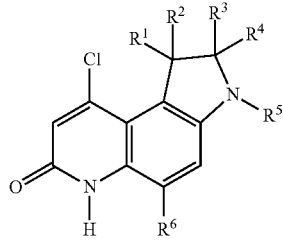

(I)

wherein:
$R^1$ and $R^3$ are each independently selected from hydrogen, optionally substituted $C_1$-$C_4$ alkyl, $C_1$-$C_4$ heteroalkyl, $C_1$-$C_4$ haloalkyl, optionally substituted heteroaryl, and optionally substituted aryl; or
$R^1$ and $R^3$ taken together to form a $C_3$-$C_8$ carbocyclic ring;
$R^2$ and $R^4$ are each hydrogen; or
$R^2$ and $R^4$ taken together to form a bond;
$R^5$ is selected from hydrogen, $C_1$-$C_8$ alkyl, $C_1$-$C_8$ haloalkyl, $C_1$-$C_8$ heteroalkyl, $C_7$-$C_{10}$ arylalkyl, and $C_2$-$C_8$ heteroarylalkyl; and
$R^6$ is hydrogen or F;
or a pharmaceutically acceptable salt thereof.

2. The method of claim 1, wherein $R^1$ and $R^3$ each independently is selected from among fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl.

3. The method of claim 1, wherein $R^1$ is selected from among hydrogen, fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl; and $R^3$ is selected from $C_1$-$C_4$ alkyl, $C_1$-$C_4$ heteroalkyl, $C_1$-$C_4$ haloalkyl, heteroaryl, and optionally substituted aryl.

4. The method of claim 1, wherein $R^1$ is selected from among hydrogen, $C_1$-$C_4$ alkyl, $C_1$-$C_4$ heteroalkyl, $C_1$-$C_4$ haloalkyl, optionally substituted heteroaryl, and optionally substituted aryl; and $R^3$ is selected from hydrogen, fully saturated $C_1$-$C_4$ alkyl, fully saturated $C_r$-$C_4$ heteroalkyl, fully saturated $C_1$-$C_4$ haloalkyl, optionally substituted heteroaryl, and optionally substituted aryl.

5. The method of claim 1, wherein the compound is selected from among:
9-Chloro-1,2-dimethyl-3,6-dihydropyrrolo[3,2-f]quinolin-7-one;
9-Chloro-2-ethyl-1-methyl-3,6-dihydropyrrolo[3,2-f]quinolin-7-one;
9-Chloro-1,2-trimethylene-3,6-dihydropyrrolo[3,2-f]quinolin-7-one;
9-Chloro-1-methyl-2-trifluoromethyl-3,6-dihydropyrrolo[3,2-f]quinolin-7-one;
9-Chloro-2-methyl-1-ethyl-3,6-dihydropyrrolo[3,2-f]quinolin-7-one;
9-Chloro-1-methyl-2-phenyl-3,6-dihydropyrrolo[3,2-f]quinolin-7-one;
9-Chloro-2-methyl-3,6-dihydropyrrolo[3,2-f]quinolin-7-one;
9-Chloro-1,2-tetramethylene-3,6-dihydropyrrolo[3,2-f]quinolin-7-one;
9-Chloro-1-methyl-3,6-dihydropyrrolo[3,2-f]quinolin-7-one;
9-Chloro-2-(4-methoxy-phenyl)-1-methyl-3,6-dihydropyrrolo[3,2-f]quinolin-7-one;

9-Chloro-2-(4-fluorophenyl)-1-methyl-3,6-dihydropyrrolo[3,2-f]quinolin-7-one;
9-Chloro-2-(2,4-difluorophenyl)-1-methyl-3,6-dihydropyrrolo[3,2-f]quinolin-7-one;
9-Chloro-2-(4-chlorophenyl)-1-methyl-3,6-dihydropyrrolo[3,2-f]quinolin-7-one;
9-Chloro-2-(2-fluorophenyl)-1-methyl-3,6-dihydropyrrolo[3,2-f]quinolin-7-one;
9-Chloro-1methyl-2-thien-2-yl-3,6-dihydropyrrolo[3,2-f]quinolin-7-one;
9-Chloro-1-ethyl-2-thien-2-yl-3,6-dihydropyrrolo[3,2-f]quinolin-7-one;
9-Chloro-2-methyl-1-propyl-3,6-dihydropyrrolo[3,2-f]quinolin-7-one;
9-Chloro-1-ethyl-2-phenyl-3,6-dihydropyrrolo[3,2-f]quinolin-7-one;
(±)-9-Chloro-3-(2,2,2-trifluoroethyl)-1,2-trimethylene-1,2,3,6-tetrahydro-pyrrolo[3,2-f]-quinolin-7-one;
(±)-9-Chloro-1,2-dimethyl-3-(2,2,2-trifluoroethyl)-1,2,3,6-tetrahydro-pyrrolo[3,2-f]-quinolin-7-one;
(±)-9-Chloro-2-ethyl-1-methyl-3-(2,2,2-trifluoroethyl)-1,2,3,6-tetrahydro-pyrrolo[3,2-f]-quinolin-7-one;
(±)-9-Chloro-1-ethyl-2-methyl-3-(2,2,2-trifluoroethyl)-1,2,3,6-tetrahydro-pyrrolo[3,2-f]-quinolin-7-one;
(±)-9-Chloro-1-methyl-2-phenyl-3-(2,2,2-trifluoroethyl)-1,2,3,6-tetrahydro-pyrrolo[3,2-f]-quinolin-7-one;
(±)-9-Chloro-2-methyl-3-(2,2,2-trifluoroethyl)-1,2,3,6-tetrahydro-pyrrolo[3,2-f]-quinolin-7-one;
(±)-9-Chloro-1-methyl-3-(2,2,2-trifluoroethyl)-1,2,3,6-tetrahydropyrrolo[3,2-f]-quinolin-7-one;
(±)-9-Chloro-1,2-tetramethylene-3-(2,2,2-trifluoroethyl)-1,2,3,6-tetrahydro-pyrrolo[3,2-f]-quinolin-7-one;
(±)-9-Chloro-3-ethyl-1-methyl-1,2,3,6-tetrahydro-pyrrolo[3,2-f]quinolin-7-one;
(±)-9-Chloro-1,2-dimethyl-3-ethyl-1,2,3,6-tetrahydro-pyrrolo[3,2-f]quinolin-7-one;
(±)-9-Chloro-1,2,3-trimethyl-1,2,3,6-tetrahydro-pyrrolo[3,2-f]quinolin-7-one;
(±)-9-Chloro-1,2-dimethyl-3-propyl-1,2,3,6-tetrahydro-pyrrolo[3,2-f]quinolin-7-one;
(±)-9-Chloro-3-(2-chloro-2,2-difluoro-ethyl)-1,2-dimethyl-1,2,3,6-tetrahydro-pyrrolo[3,2-f]-quinolin-7-one;
(±)-9-Chloro-1,2-dimethyl-1,2,3,6-tetrahydro-pyrrolo[3,2-f]quinolin-7-one;
(±)-9-Chloro-1,2-dimethyl-3-(2,2-dimethylpropyl)-1,2,3,6-tetrahydro-pyrrolo[3,2-f]quinolin-7-one;
(±)-9-Chloro-1,2-dimethyl-3-(2-thien-2-yl-ethyl)-1,2,3,6-tetrahydro-pyrrolo[3,2-f]quinolin-7-one;
(±)-9-Chloro-3-(2,2-difluoroethyl)-1,2-dimethyl-1,2,3,6-tetrahydro-pyrrolo[3,2-f]quinolin-7-one;
(±)-9-Chloro-1,2-dimethyl-3-phenylmethyl-1,2,3,6-tetrahydro-pyrrolo[3,2-f]quinolin-7-one;
(±)-9-Chloro-1,2-dimethyl-3-(3,3,3-trifluoropropyl)-1,2,3,6-tetrahydro-pyrrolo[3,2-f]-quinolin-7-one;
(±)-9-Chloro-2-(3-chlorophenyl)-1-methyl-3-(2,2,2-trifluoroethyl)-1,2,3,6-tetrahydro-pyrrolo[3,2-f]quinolin-7-one;
(±)-9-Chloro-2-(4-methoxy-phenyl)-1-methyl-3-(2,2,2-trifluoroethyl)-1,2,3,6-tetrahydro-pyrrolo[3,2-f]quinolin-7-one;
(±)-9-Chloro-2-(4-fluoro-phenyl)-1-methyl-3-(2,2,2-trifluoroethyl)-1,2,3,6-tetrahydro-pyrrolo[3,2-f]quinolin-7-one;
(±)-9-Chloro-2-(2,4-difluorophenyl)-1-methyl-3-(2,2,2-trifluoroethyl)-1,2,3,6-tetrahydro-pyrrolo[3,2-f]quinolin-7-one;
(±)-9-Chloro-1,2-dimethyl-5-fluoro-3-(2,2,2-trifluoroethyl)-1,2,3,6-tetrahydro-pyrrolo[3,2-f]quinolin-7-one;
(±)-9-Chloro-2-(4-chlorophenyl)-1-methyl-3-(2,2,2-trifluoroethyl)-1,2,3,6-tetrahydro-pyrrolo[3,2-f]quinolin-7-one;
(±)-2-(3-Bromophenyl)-9-chloro-1-methyl-3-(2,2,2-trifluoroethyl)-1,2,3,6-tetrahydro-pyrrolo[3,2-f]quinolin-7-one;
(±)-9-Chloro-1-methyl-2-(3-nitrophenyl)-3-(2,2,2-trifluoroethyl)-1,2,3,6-tetrahydro-pyrrolo[3,2-f]quinolin-7-one;
(±)-9-Chloro-2-(4-hydroxyphenyl)-1-methyl-3-(2,2,2-trifluoroethyl)-1,2,3,6-tetrahydro-pyrrolo[3,2-f]quinolin-7-one;
(±)-9-Chloro-2-(2-fluorophenyl)-1-methyl-3-(2,2,2-trifluoroethyl)-1,2,3,6-tetrahydro-pyrrolo[3,2-f]quinolin-7-one;
(±)-9-Chloro-2-(3,4-dichlorophenyl)-1-methyl-3-(2,2,2-trifluoroethyl)-1,2,3,6-tetrahydro-pyrrolo[3,2-f]quinolin-7-one;
(±)-9-Chloro-1-ethyl-2-phenyl-3-(2,2,2-trifluoroethyl)-1,2,3,6-tetrahydro-pyrrolo[3,2-f]-quinolin-7-one;
(±)-9-Chloro-1-methyl-2-(thien-2-yl)-3-(2,2,2-trifluoroethyl)-1,2,3,6-tetrahydro-pyrrolo[3,2-f]quinolin-7-one;
(+)-9-Chloro-3-(2,2,2-trifluoro-ethyl)-1,2-trimethylene-1,2,3,6-tetrahydro-pyrrolo[3,2-f]-quinolin-7-one;
(−)-9-Chloro-3-(2,2,2-trifluoro-ethyl)-1,2-trimethylene-1,2,3,6-tetrahydro-pyrrolo[3,2-f]-quinolin-7-one;
(±)-9-Chloro-1-ethyl-2-(thien-2-yl)-3-(2,2,2-trifluoroethyl)-1,2,3,6-tetrahydro-pyrrolo[3,2-f]quinolin-7-one;
(±)-9-Chloro-2-methyl-1-propyl-3-(2,2,2-trifluoroethyl)-1,2,3,6-tetrahydro-pyrrolo[3,2-f]-quinolin-7-one;
(±)-9-Chloro-2,3-diethyl-1-methyl-1,2,3,6-tetrahydro-pyrrolo[3,2-f]quinolin-7-one;
(±)-9-Chloro-1,2-dimethyl-3-(2,2,3,3,3-pentafluoropropyl)-1,2,3,6-tetrahydro-pyrrolo[3,2-f]quinolin-7-one;
(±)-9-Chloro-1,2-dimethyl-3-(2,2,3,3,4,4,4-heptafluorobutyl)-1,2,3,6-tetrahydro-pyrrolo[3,2-f]quinolin-7-one;
(±)-9-Chloro-1-methyl-2-phenyl-3-(3,3,3-trifluoropropyl)-1,2,3,6-tetrahydro-pyrrolo[3,2-f]-quinolin-7-one;
(±)-9-Chloro-2-ethyl-1-methyl-3-(3,3,3-trifluoropropyl)-1,2,3,6-tetrahydro-pyrrolo[3,2-f]-quinolin-7-one;
(±)-9-Chloro-1-methyl-3-(2,2,3,3,3-pentafluoropropyl)-2-phenyl-1,2,3,6-tetrahydro-pyrrolo[3,2-f]quinolin-7-one;
(±)-9-Chloro-1-methyl-2-phenyl-1,2,3,6-tetrahydro-pyrrolo[3,2-f]quinolin-7-one;
(±)-9-Chloro-3-(2-Chloro-2,2-difluoroethyl)-2-ethyl-1-methyl-1,2,3,6-tetrahydro-pyrrolo[3,2-f]quinolin-7-one;
(±)-9-Chloro-2-ethyl-1-methyl-3-(2,2,3,3,3-pentafluoropropyl)-1,2,3,6-tetrahydro-pyrrolo[3,2-f]quinolin-7-one;
9-Chloro-2-ethyl-1-methyl-3-(2,2,2-trifluoroethyl)-3,6-dihydro-pyrrolo[3,2-f]-quinolin-7-one;
9-Chloro-1,2-dimethyl-3-(2,2,2-trifluoroethyl)-3,6-dihydropyrrolo[3,2-f]quinolin-7-one;
9-Chloro-1-ethyl-2-methyl-3-(2,2,2-trifluoroethyl)-3,6-dihydro-pyrrolo[3,2-f]-quinolin-7-one;
9-Chloro-2-methyl-3-(2,2,2-trifluoroethyl)-3,6-dihydropyrrolo[3,2-f]quinolin-7-one;
9-Chloro-1-methyl-2-phenyl-3-(2,2,2-trifluoroethyl)-3,6-dihydro-pyrrolo[3,2-f]-quinolin-7-one;
9-Chloro-1,2-dimethyl-3-(2-thien-2-yl-ethyl)-3,6-dihydro-pyrrolo[3,2-f]quinolin-7-one;

9-Chloro-3-(2,2-difluoroethyl)-1,2-dimethyl-3,6-dihydro-pyrrolo[3,2-f]quinolin-7-one;
9-Chloro-3-ethyl-1-methyl-3,6-dihydro-pyrrolo[3,2-f]quinolin-7-one;
9-Chloro-2-(4-fluorophenyl)-1-methyl-3-(2,2,2-trifluoroethyl)-3,6-dihydro-pyrrolo[3,2-f]-quinolin-7-one;
9-Chloro-1,2-dimethyl-5-fluoro-3-(2,2,2-trifluoroethyl)-3,6-dihydro-pyrrolo[3,2-f]-quinolin-7-one;
9-Chloro-1,2-dimethyl-3-ethyl-3,6-dihydro-pyrrolo[3,2-f]quinolin-7-one;
9-Chloro-2-(4-methoxyphenyl)-1-methyl-3-(2,2,2-trifluoroethyl)-3,6-dihydro-pyrrolo[3,2-f]quinolin-7-one;
2-(3-Bromophenyl)-9-Chloro-1-methyl-3-(2,2,2-trifluoroethyl)-3,6-dihydro-pyrrolo[3,2-f]-quinolin-7-one;
9-Chloro-2-(2-fluorophenyl)-1-methyl-3-(2,2,2-trifluoroethyl)-3,6-dihydro-pyrrolo[3,2-f]-quinolin-7-one;
9-Chloro-2-(2,4-difluorophenyl)-1-methyl-3-(2,2,2-trifluoroethyl)-3,6-dihydro-pyrrolo[3,2-f]quinolin-7-one;
9-Chloro-1-ethyl-2-phenyl-3-(2,2,2-trifluoroethyl)-3,6-dihydro-pyrrolo[3,2-f]-quinolin-7-one;
9-Chloro-1-methyl-2-(3-nitrophenyl)-3-(2,2,2-trifluoroethyl)-3,6-dihydro-pyrrolo[3,2-f]-quinolin-7-one;
9-Chloro-2(4-chlorophenyl)-1-methyl-3-(2,2,2-trifluoroethyl)-3,6-dihydropyrrolo-[3,2-f]-quinolin-7-one;
9-Chloro-1-methyl-2-thien-2-yl-3-(2,2,2-trifluoroethyl)-3,6-dihydro-pyrrolo[3,2-f]-quinolin-7-one;
9-Chloro-1,2,3-trimethyl-3,6-dihydro-pyrrolo[3,2-f]quinolin-7-one;
9-Chloro-1-ethyl-2-thien-2-yl-3-(2,2,2-trifluoroethyl)-3,6-dihydro-pyrrolo[3,2-f]-quinolin-7-one;
9-Chloro-2-methyl-1-propyl-3-(2,2,2-trifluoroethyl)-3,6-dihydro-pyrrolo[3,2-f]-quinolin-7-one;
9-Chloro-1-methyl-3-(2,2,2-trifluoroethyl)-3,6-dihydro-pyrrolo[3,2-f]quinolin-7-one;
9-Chloro-3-(2-chloro-2,2-difluoroethyl)-1,2-dimethyl-3,6-dihydro-pyrrolo[3,2-f]-quinolin-7-one;
9-Chloro-1,2-dimethyl-3-(3,3,3-trifluoropropyl)-3,6-dihydro-pyrrolo[3,2-f]-quinolin-7-one;
9-Chloro-1,2-dimethyl-3-(2,2,3,3,4,4,4-heptafluorobutyl)-3,6-dihydro-pyrrolo[3,2-f]-quinolin-7-one;
9-Chloro-1,2-dimethyl-3-(2,2,3,3,3-pentafluoropropyl)-3,6-dihydro-pyrrolo[3,2-f]-quinolin-7-one;
9-Chloro-2-ethyl-1-methyl-3-(3,3,3-trifluoropropyl)-3,6-dihydro-pyrrolo[3,2-f]-quinolin-7-one;
9-Chloro-1-methyl-2-phenyl-3-(3,3,3-trifluoropropyl)-3,6-dihydro-pyrrolo[3,2-f]-quinolin-7-one;
9-Chloro-1-methyl-3-(2,2,3,3,3-pentafluoropropyl)-2-phenyl-3,6-dihydro-pyrrolo[3,2-f]-quinolin-7-one;
9-Chloro-3-(2-chloro-2,2-difluoroethyl)-2-ethyl-1-methyl-3,6-dihydropyrrolo[3,2-f]-quinolin-7-one;
9-Chloro-2-ethyl-1-methyl-3-(2,2,3,3,3-pentafluoropropyl)-3,6-dihydropyrrolo[3,2-f]-quinolin-7-one;
9-Chloro-1-methyl-3-(2,2,2-trifluoro-ethyl)-2-trifluoromethyl-3,6-dihydro-pyrrolo[3,2-f]-quinolin-7-one;
9-Chloro-2-hydroxymethyl-1-methyl-3-(2,2,2-trifluoroethyl)-3,6-dihydro-pyrrolo[3,2-f]-quinolin-7-one;
9-Chloro-2-(3-fluorophenyl)-1-methyl-3-(2,2,2-trifluoroethyl)-3,6-dihydro-pyrrolo[3,2-f]-quinolin-7-one;
9-Chloro-1-methyl-2-(1,3-thiazol-2-yl)-3-(2,2,2-trifluoroethyl)-3,6-dihydro-pyrrolo[3,2-f]-quinolin-7-one;
9-Chloro-1-methyl-2-(3-pyridyl)-3-(2,2,2-trifluoroethyl)-3,6-dihydropyrrolo[3,2-f]-quinolin-7-one;
9-Chloro-1-methyl-2-(4-pyridyl)-3-(2,2,2-trifluoroethyl)-3,6-dihydropyrrolo[3,2-f]-quinolin-7-one;
9-Chloro-1-methyl-2-(pentafluoroethyl)-3-(2,2,2-trifluoroethyl)-3,6-dihydro-pyrrolo[3,2-f]-quinolin-7-one;
9-Chloro-1-methyl-2-(2-oxazolyl)-3-(2,2,2-trifluoroethyl)-3,6-dihydropyrrolo[3,2-f]-quinolin-7-one;
9-Chloro-1-methyl-3-(2,2,3,3,3-pentafluoropropyl)-2-thiophen-2-yl-3,6-dihydro-pyrrolo[3,2-f]quinolin-7-one;
9-Chloro-1-methyl-3-(2,2,3,3,3-pentafluoropropyl)-2-(trifluoromethyl)-3,6-dihydro-pyrrolo[3,2-f]quinolin-7-one;
9-Chloro-1-methyl-2-(2-furyl)-3-(2,2,3,3,3-pentafluoropropyl)-3,6-dihydro-pyrrolo-[3,2-f]-quinolin-7-one;
9-Chloro-1-methyl-3-(2,2,3,3,3-pentafluoropropyl)-2-(1,3-thiazol-2-yl)-3,6-dihydro-pyrrolo[3,2-f]-quinolin-7-one;
9-Chloro-1-methyl-3-(2,2,3,3,3-pentafluoropropyl)-2-(4-pyridyl)-3,6-dihydro-pyrrolo[3,2-f]-quinolin-7-one;
9-Chloro-1-methyl-3-(2,2,3,3,3-pentafluoropropyl)-2-(3-pyridyl)-3,6-dihydro-pyrrolo[3,2-f]-quinolin-7-one;
9-Chloro-1-methyl-3-(2,2,3,3,3-pentafluoropropyl)-2-(2-pyridyl)-3,6-dihydro-pyrrolo[3,2-f]-quinolin-7-one;
9-Chloro-1-methyl-2-(oxazol-2-yl)-3-(2,2,3,3,3-pentafluoropropyl)-3,6-dihydro-pyrrolo[3,2-f]quinolin-7-one;
9-Chloro-1-(3-chloropropyl)-2-methyl-3-(2,2,3,3,3-pentafluoropropyl)-3,6-dihydro-pyrrolo[3,2-f]quinolin-7-one; and
9-Chloro-1-(3-iodopropyl)-2-methyl-3-(2,2,3,3,3-pentafluoropropyl)-3,6-dihydro-pyrrolo[3,2-f]quinolin-7-one; or a pharmaceutically acceptable salt of any of these compounds.

6. A method for modulating an activity of an androgen receptor, comprising contacting an androgen receptor with a compound having a structure of Formula I:

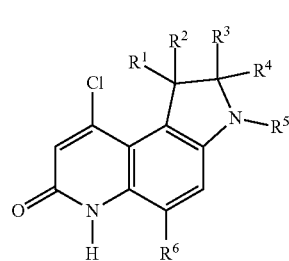

wherein:
$R^1$ and $R^3$ are each independently selected from hydrogen, optionally substituted $C_1$-$C_4$ alkyl, $C_1$-$C_4$ heteroalkyl, $C_1$-$C_4$ haloalkyl, optionally substituted heteroaryl, and optionally substituted aryl; or
$R^1$ and $R^3$ taken together to form a $C_3$-$C_8$ carbocyclic ring;
$R^2$ and $R^4$ are each hydrogen; or
$R^2$ and $R^4$ taken together to form a bond;
$R^5$ is selected from hydrogen, $C_1$-$C_8$ alkyl, $C_1$-$C_8$ haloalkyl, $C_1$-$C_8$ heteroalkyl, $C_7$-$C_{10}$ arylalkyl, and $C_2$-$C_8$ heteroarylalkyl; and
$R^6$ is hydrogen or F;
or a pharmaceutically acceptable salt thereof.

7. The method of claim 6, wherein $R^1$ and $R^3$ each independently is selected from among fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl.

8. The method of claim 6, wherein $R^1$ is selected from among hydrogen, fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl; and $R^3$ is selected from $C_1$-$C_4$ alkyl, $C_1$-$C_4$ heteroalkyl, $C_1$-$C_4$ haloalkyl, heteroaryl, and optionally substituted aryl.

9. The method of claim 6, wherein $R^1$ is selected from among hydrogen, $C_1$-$C_4$ alkyl, $C_1$-$C_4$ heteroalkyl, $C_1$-$C_4$ haloalkyl, optionally substituted heteroaryl, and optionally substituted aryl; and $R^3$ is selected from hydrogen, fully saturated $C_1$-$C_4$ alkyl, fully saturated $C_1$-$C_4$ heteroalkyl, fully saturated $C_1$-$C_4$ haloalkyl, optionally substituted heteroaryl, and optionally substituted aryl.

10. The method of claim 6, wherein the compound is selected from among:
- 9-Chloro-1,2-dimethyl-3,6-dihydropyrrolo quinolin-7-one;
- 9-Chloro-2-ethyl-1-methyl-3,6-dihydropyrrolo quinolin-7-one;
- 9-Chloro-1,2-trimethylene-3,6-dihydropyrrolo quinolin-7-one;
- 9-Chloro-1-methyl-2-trifluoromethyl-3,6-dihydropyrrolo quinolin-7-one;
- 9-Chloro-2-methyl-1-ethyl-3,6-dihydropyrrolo quinolin-7-one;
- 9-Chloro-1-methyl-2-phenyl-3,6-dihydropyrrolo quinolin-7-one;
- 9-Chloro-2-methyl-3,6-dihydropyrrolo[3,2-f]quinolin-7-one;
- 9-Chloro-1,2-tetramethylene-3,6-dihydropyrrolo[3,2-f]quinolin-7-one;
- 9-Chloro-1-methyl-3,6-dihydropyrrolo[3,2-f]quinolin-7-one;
- 9-Chloro-2-(4-methoxy-phenyl)-1-methyl-3,6-dihydropyrrolo[3,2-f]quinolin-7-one;
- 9-Chloro-2-(4-fluorophenyl)-1-methyl-3,6-dihydropyrrolo[3,2-f]quinolin-7-one;
- 9-Chloro-2-(2,4-difluorophenyl)-1-methyl-3,6-dihydropyrrolo[3,2-f]quinolin-7-one;
- 9-Chloro-2-(4-chlorophenyl)-1-methyl-3,6-dihydropyrrolo[3,2-f]quinolin-7-one;
- 9-Chloro-2-(2-fluorophenyl)-1-methyl-3,6-dihydropyrrolo[3,2-f]quinolin-7-one;
- 9-Chloro-1methyl-2-thien-2-yl-3,6-dihydropyrrolo[3,2-f]quinolin-7-one;
- 9-Chloro-1-ethyl-2-thien-2-yl-3,6-dihydropyrrolo[3,2-f]quinolin-7-one;
- 9-Chloro-2-methyl-1-propyl-3,6-dihydropyrrolo[3,2-f]quinolin-7-one;
- 9-Chloro-1-ethyl-2-phenyl-3,6-dihydropyrrolo[3,2-f]quinolin-7-one;
- (±)-9-Chloro-3-(2,2,2-trifluoroethyl)-1,2-trimethylene-1,2,3,6-tetrahydro-pyrrolo[3,2-f]-quinolin-7-one;
- (±)-9-Chloro-1,2-dimethyl-3-(2,2,2-trifluoroethyl)-1,2,3,6-tetrahydro-pyrrolo[3,2-f]-quinolin-7-one;
- (±)-9-Chloro-2-ethyl-1-methyl-3-(2,2,2-trifluoroethyl)-1,2,3,6-tetrahydro-pyrrolo[3,2-f]-quinolin-7-one;
- (±)-9-Chloro-1-ethyl-2-methyl-3-(2,2,2-trifluoroethyl)-1,2,3,6-tetrahydro-pyrrolo[3,2-f]-quinolin-7-one;
- (±)-9-Chloro-1-methyl-2-phenyl-3-(2,2,2-trifluoroethyl)-1,2,3,6-tetrahydro-pyrrolo[3,2-f]-quinolin-7-one;
- (±)-9-Chloro-2-methyl-3-(2,2,2-trifluoroethyl)-1,2,3,6-tetrahydro-pyrrolo[3,2-f]-quinolin-7-one;
- (±)-9-Chloro-1-methyl-3-(2,2,2-trifluoroethyl)-1,2,3,6-tetrahydropyrrolo[3,2-f]-quinolin-7-one;
- (±)-9-Chloro-1,2-tetramethylene-3-(2,2,2-trifluoroethyl)-1,2,3,6-tetrahydro-pyrrolo[3,2-f]-quinolin-7-one;
- (±)-9-Chloro-3-ethyl-1-methyl-1,2,3,6-tetrahydro-pyrrolo[3,2-f]quinolin-7-one;
- (±)-9-Chloro-1,2-dimethyl-3-ethyl-1,2,3,6-tetrahydro-pyrrolo[3,2-f]quinolin-7-one;
- (±)-9-Chloro-1,2,3-trimethyl-1,2,3,6-tetrahydro-pyrrolo[3,2-f]quinolin-7-one;
- (±)-9-Chloro-1,2-dimethyl-3-propyl-1,2,3,6-tetrahydro-pyrrolo[3,2-f]quinolin-7-one;
- (±)-9-Chloro-3-(2-chloro-2,2-difluoro-ethyl)-1,2-dimethyl-1,2,3,6-tetrahydro-pyrrolo[3,2-f]-quinolin-7-one;
- (±)-9-Chloro-1,2-dimethyl-1,2,3,6-tetrahydro-pyrrolo[3,2-f]quinolin-7-one;
- (±)-9-Chloro-1,2-dimethyl-3-(2,2-dimethylpropyl)-1,2,3,6-tetrahydro-pyrrolo[3,2-f]-quinolin-7-one;
- (±)-9-Chloro-1,2-dimethyl-3-(2-thien-2-yl-ethyl)-1,2,3,6-tetrahydro-pyrrolo[3,2-f]-quinolin-7-one;
- (±)-9-Chloro-3-(2,2-difluoroethyl)-1,2-dimethyl-1,2,3,6-tetrahydro-pyrrolo[3,2-f]-quinolin-7-one;
- (±)-9-Chloro-1,2-dimethyl-3-phenylmethyl-1,2,3,6-tetrahydro-pyrrolo[3,2-f]-quinolin-7-one;
- (±)-9-Chloro-1,2-dimethyl-3-(3,3,3-trifluoropropyl)-1,2,3,6-tetrahydro-pyrrolo[3,2-f]-quinolin-7-one;
- (±)-9-Chloro-2-(3-chlorophenyl)-1-methyl-3-(2,2,2-trifluoroethyl)-1,2,3,6-tetrahydro-pyrrolo[3,2-f]quinolin-7-one;
- (±)-9-Chloro-2-(4-methoxy-phenyl)-1-methyl-3-(2,2,2-trifluoroethyl)-1,2,3,6-tetrahydro-pyrrolo[3,2-f]quinolin-7-one;
- (±)-9-Chloro-2-(4-fluoro-phenyl)-1-methyl-3-(2,2,2-trifluoroethyl)-1,2,3,6-tetrahydro-pyrrolo[3,2-f]quinolin-7-one;
- (±)-9-Chloro-2-(2,4-difluorophenyl)-1-methyl-3-(2,2,2-trifluoroethyl)-1,2,3,6-tetrahydro-pyrrolo[3,2-f]quinolin-7-one;
- (±)-9-Chloro-1,2-dimethyl-5-fluoro-3-(2,2,2-trifluoroethyl)-1,2,3,6-tetrahydro-pyrrolo[3,2-f]-quinolin-7-one;
- (±)-9-Chloro-2-(4-chlorophenyl)-1-methyl-3-(2,2,2-trifluoroethyl)-1,2,3,6-tetrahydro-pyrrolo[3,2-f]quinolin-7-one;
- (±)-2-(3-Bromophenyl)-9-chloro-1-methyl-3-(2,2,2-trifluoroethyl)-1,2,3,6-tetrahydro-pyrrolo[3,2-f]quinolin-7-one;
- (±)-9-Chloro-1-methyl-2-(3-nitrophenyl)-3-(2,2,2-trifluoroethyl)-1,2,3,6-tetrahydro-pyrrolo[3,2-f]quinolin-7-one;
- (±)-9-Chloro-2-(4-hydroxyphenyl)-1-methyl-3-(2,2,2-trifluoroethyl)-1,2,3,6-tetrahydro-pyrrolo[3,2-f]quinolin-7-one;
- (±)-9-Chloro-2-(2-fluorophenyl)-1-methyl-3-(2,2,2-trifluoroethyl)-1,2,3,6-tetrahydro-pyrrolo[3,2-f]quinolin-7-one;
- (±)-9-Chloro-2-(3,4-dichlorophenyl)-1-methyl-3-(2,2,2-trifluoroethyl)-1,2,3,6-tetrahydro-pyrrolo[3,2-f]quinolin-7-one;
- (±)-9-Chloro-1-ethyl-2-phenyl-3-(2,2,2-trifluoroethyl)-1,2,3,6-tetrahydro-pyrrolo[3,2-f]-quinolin-7-one;
- (±)-9-Chloro-1-methyl-2-(thien-2-yl)-3-(2,2,2-trifluoroethyl)-1,2,3,6-tetrahydro-pyrrolo[3,2-f]-quinolin-7-one;
- (+)-9-Chloro-3-(2,2,2-trifluoro-ethyl)-1,2-trimethylene-1,2,3,6-tetrahydro-pyrrolo[3,2-f]-quinolin-7-one;
- (−)-9-Chloro-3-(2,2,2-trifluoro-ethyl)-1,2-trimethylene-1,2,3,6-tetrahydro-pyrrolo[3,2-f]-quinolin-7-one;
- (±)-9-Chloro-1-ethyl-2-(thien-2-yl)-3-(2,2,2-trifluoroethyl)-1,2,3,6-tetrahydro-pyrrolo[3,2-f]-quinolin-7-one;
- (±)-9-Chloro-2-methyl-1-propyl-3-(2,2,2-trifluoroethyl)-1,2,3,6-tetrahydro-pyrrolo[3,2-f]-quinolin-7-one;
- (±)-9-Chloro-2,3-diethyl-1-methyl-1,2,3,6-tetrahydro-pyrrolo[3,2-f]quinolin-7-one;

(±)-9-Chloro-1,2-dimethyl-3-(2,2,3,3,3-pentafluoropropyl)-1,2,3,6-tetrahydro-pyrrolo[3,2-f]quinolin-7-one;
(±)-9-Chloro-1,2-dimethyl-3-(2,2,3,3,4,4,4-heptafluorobutyl)-1,2,3,6-tetrahydro-pyrrolo[3,2-f]quinolin-7-one;
(±)-9-Chloro-1-methyl-2-phenyl-3-(3,3,3-trifluoropropyl)-1,2,3,6-tetrahydro-pyrrolo[3,2-f]-quinolin-7-one;
(±)-9-Chloro-2-ethyl-1-methyl-3-(3,3,3-trifluoropropyl)-1,2,3,6-tetrahydro-pyrrolo[3,2-f]-quinolin-7-one;
(±)-9-Chloro-1-methyl-3-(2,2,3,3,3-pentafluoropropyl)-2-phenyl-1,2,3,6-tetrahydro-pyrrolo[3,2-f]quinolin-7-one;
(±)-9-Chloro-1-methyl-2-phenyl-1,2,3,6-tetrahydro-pyrrolo[3,2-f]quinolin-7-one;
(±)-9-Chloro-3-(2-Chloro-2,2-difluoroethyl)-2-ethyl-1-methyl-1,2,3,6-tetrahydro-pyrrolo[3,2-f]quinolin-7-one;
(±)-9-Chloro-2-ethyl-1-methyl-3-(2,2,3,3,3-pentafluoropropyl)-1,2,3,6-tetrahydro-pyrrolo[3,2-f]quinolin-7-one;
9-Chloro-2-ethyl-1-methyl-3-(2,2,2-trifluoroethyl)-3,6-dihydro-pyrrolo[3,2-f]-quinolin-7-one;
9-Chloro-1,2-dimethyl-3-(2,2,2-trifluoroethyl)-3,6-dihydropyrrolo[3,2-f]quinolin-7-one;
9-Chloro-1-ethyl-2-methyl-3-(2,2,2-trifluoroethyl)-3,6-dihydro-pyrrolo[3,2-f]-quinolin-7-one;
9-Chloro-2-methyl-3-(2,2,2-trifluoroethyl)-3,6-dihydro-pyrrolo[3,2-f]quinolin-7-one;
9-Chloro-1-methyl-2-phenyl-3-(2,2,2-trifluoroethyl)-3,6-dihydro-pyrrolo[3,2-f]-quinolin-7-one;
9-Chloro-1,2-dimethyl-3-(2-thien-2-yl-ethyl)-3,6-dihydro-pyrrolo[3,2-f]quinolin-7-one;
9-Chloro-3-(2,2-difluoroethyl)-1,2-dimethyl-3,6-dihydro-pyrrolo[3,2-f]quinolin-7-one;
9-Chloro-3-ethyl-1-methyl-3,6-dihydro-pyrrolo quinolin-7-one;
9-Chloro-2-(4-fluorophenyl)-1-methyl-3-(2,2,2-trifluoroethyl)-3,6-dihydro-pyrrolo-quinolin-7-one;
9-Chloro-1,2-dimethyl-5-fluoro-3-(2,2,2-trifluoroethyl)-3,6-dihydro-pyrrolo-quinolin-7-one;
9-Chloro-1,2-dimethyl-3-ethyl-3,6-dihydro-pyrrolo quinolin-7-one;
9-Chloro-2-(4-methoxyphenyl)-1-methyl-3-(2,2,2-trifluoroethyl)-3,6-dihydro-pyrrolo quinolin-7-one;
2-(3-Bromophenyl)-9-Chloro-1-methyl-3-(2,2,2-trifluoroethyl)-3,6-dihydro-pyrrolo-quinolin-7-one;
9-Chloro-2-(2-fluorophenyl)-1-methyl-3-(2,2,2-trifluoroethyl)-3,6-dihydro-pyrrolo-quinolin-7-one;
9-Chloro-2-(2,4-difluorophenyl)-1-methyl-3-(2,2,2-trifluoroethyl)-3,6-dihydro-pyrrolo quinolin-7-one;
9-Chloro-1-ethyl-2-phenyl-3-(2,2,2-trifluoroethyl)-3,6-dihydro-pyrrolo-quinolin-7-one;
9-Chloro-1-methyl-2-(3-nitrophenyl)-3-(2,2,2-trifluoroethyl)-3,6-dihydro-pyrrolo-quinolin-7-one;
9-Chloro-2(4-chlorophenyl)-1-methyl-3-(2,2,2-trifluoroethyl)-3,6-dihydropyrrolo-[3,2-f]-quinolin-7-one;
9-Chloro-1-methyl-2-thien-2-yl-3-(2,2,2-trifluoroethyl)-3,6-dihydro-pyrrolo-quinolin-7-one;
9-Chloro-1,2,3-trimethyl-3,6-dihydro-pyrrolo quinolin-7-one;
9-Chloro-1-ethyl-2-thien-2-yl-3-(2,2,2-trifluoroethyl)-3,6-dihydro-pyrrolo[3,2-f]-quinolin-7-one;
9-Chloro-2-methyl-1-propyl-3-(2,2,2-trifluoroethyl)-3,6-dihydro-pyrrolo[3,2-f]-quinolin-7-one;
9-Chloro-1-methyl-3-(2,2,2-trifluoroethyl)-3,6-dihydro-pyrrolo[3,2-f]quinolin-7-one;
9-Chloro-3-(2-chloro-2,2-difluoroethyl)-1,2-dimethyl-3,6-dihydro-pyrrolo[3,2-f]-quinolin-7-one;
9-Chloro-1,2-dimethyl-3-(3,3,3-trifluoropropyl)-3,6-dihydro-pyrrolo[3,2-f]-quinolin-7-one;
9-Chloro-1,2-dimethyl-3-(2,2,3,3,4,4,4-heptafluorobutyl)-3,6-dihydro-pyrrolo[3,2-f]-quinolin-7-one;
9-Chloro-1,2-dimethyl-3-(2,2,3,3,3-pentafluoropropyl)-3,6-dihydro-pyrrolo[3,2-f]-quinolin-7-one;
9-Chloro-2-ethyl-1-methyl-3-(3,3,3-trifluoropropyl)-3,6-dihydro-pyrrolo[3,2-f]-quinolin-7-one;
9-Chloro-1-methyl-2-phenyl-3-(3,3,3-trifluoropropyl)-3,6-dihydro-pyrrolo[3,2-f]-quinolin-7-one;
9-Chloro-1-methyl-3-(2,2,3,3,3-pentafluoropropyl)-2-phenyl-3,6-dihydro-pyrrolo[3,2-f]-quinolin-7-one;
9-Chloro-3-(2-chloro-2,2-difluoroethyl)-2-ethyl-1-methyl-3,6-dihydropyrrolo[3,2-f]-quinolin-7-one;
9-Chloro-2-ethyl-1-methyl-3-(2,2,3,3,3-pentafluoropropyl)-3,6-dihydropyrrolo[3,2-f]-quinolin-7-one;
9-Chloro-1-methyl-3-(2,2,2-trifluoro-ethyl)-2-trifluoromethyl-3,6-dihydro-pyrrolo[3,2-f]-quinolin-7-one;
9-Chloro-2-hydroxymethyl-1-methyl-3-(2,2,2-trifluoroethyl)-3,6-dihydro-pyrrolo[3,2-f]-quinolin-7-one;
9-Chloro-2-(3-fluorophenyl)-1-methyl-3-(2,2,2-trifluoroethyl)-3,6-dihydro-pyrrolo[3,2-f]-quinolin-7-one;
9-Chloro-1-methyl-2-(1,3-thiazol-2-yl)-3-(2,2,2-trifluoroethyl)-3,6-dihydro-pyrrolo[3,2-f]-quinolin-7-one;
9-Chloro-1-methyl-2-(3-pyridyl)-3-(2,2,2-trifluoroethyl)-3,6-dihydropyrrolo[3,2-f]-quinolin-7-one;
9-Chloro-1-methyl-2-(4-pyridyl)-3-(2,2,2-trifluoroethyl)-3,6-dihydropyrrolo[3,2-f]-quinolin-7-one;
9-Chloro-1-methyl-2-(pentafluoroethyl)-3-(2,2,2-trifluoroethyl)-3,6-dihydro-pyrrolo[3,2-f]-quinolin-7-one;
9-Chloro-1-methyl-2-(2-oxazolyl)-3-(2,2,2-trifluoroethyl)-3,6-dihydropyrrolo[3,2-f]-quinolin-7-one;
9-Chloro-1-methyl-3-(2,2,3,3,3-pentafluoropropyl)-2-thiophen-2-yl-3,6-dihydro-pyrrolo[3,2-f]quinolin-7-one;
9-Chloro-1-methyl-3-(2,2,3,3,3-pentafluoropropyl)-2-(trifluoromethyl)-3,6-dihydro-pyrrolo[3,2-f]quinolin-7-one;
9-Chloro-1-methyl-2-(2-furyl)-3-(2,2,3,3,3-pentafluoropropyl)-3,6-dihydro-pyrrolo-[3,2-f]-quinolin-7-one;
9-Chloro-1-methyl-3-(2,2,3,3,3-pentafluoropropyl)-2-(1,3-thiazol-2-yl)-3,6-dihydro-pyrrolo[3,2-f]quinolin-7-one;
9-Chloro-1-methyl-3-(2,2,3,3,3-pentafluoropropyl)-2-(4-pyridyl)-3,6-dihydro-pyrrolo[3,2-f]-quinolin-7-one;
9-Chloro-1-methyl-3-(2,2,3,3,3-pentafluoropropyl)-2-(3-pyridyl)-3,6-dihydro-pyrrolo[3,2-f]-quinolin-7-one;
9-Chloro-1-methyl-3-(2,2,3,3,3-pentafluoropropyl)-2-(2-pyridyl)-3,6-dihydro-pyrrolo[3,2-f]-quinolin-7-one;
9-Chloro-1-methyl-2-(oxazol-2-yl)-3-(2,2,3,3,3-pentafluoropropyl)-3,6-dihydro-pyrrolo[3,2-f]quinolin-7-one;
9-Chloro-1-(3-chloropropyl)-2-methyl-3-(2,2,3,3,3-pentafluoropropyl)-3,6-dihydro-pyrrolo[3,2-f]quinolin-7-one; and
9-Chloro-1-(3-iodopropyl)-2-methyl-3-(2,2,3,3,3-pentafluoropropyl)-3,6-dihydro-pyrrolo[3,2-f]quinolin-7-one; or
a pharmaceutically acceptable salt of any of these compounds.

11. The method of claim 1, wherein the compound is selected from among:
9-Chloro-1-methyl-7-oxo-6,7-dihydro-3H-pyrrolo[3,2-f]quinoline-2-carboxylic acid ethyl ester;

2-Acetyl-9-chloro-1-methyl-3,6-dihydropyrrolo[3,2-f] quinolin-7-one;
(9-Chloro-2-methyl-7-oxo-6,7-dihydro-3H-pyrrolo[3,2-f] quinolin-1-yl)-acetic acid;
(±)-9-Chloro-1-methyl--2-(4-trifluoromethyl-phenyl)-3-(2,2,2-trifluoroethyl)-1,2,3,6-tetrahydro-pyrrolo [3,2-f]quinolin-7-one;
(±)-9-Chloro-2-(3,5-bis(trifluoromethyl)phenyl)-1-methyl-3-(2,2,2-trifluoroethyl)-1,2,3,6-tetrahydro-pyrrolo [3,2-f]quinolin-7-one;
(±)-9-Chloro-1-methyl-3-(2,2,2-trifluoroethyl)-2-(3-trifluoromethylphenyl)-1,2,3,6-tetrahydro-pyrrolo [3,2-f] quinolin-7-one;
3-Benzyl-9-chloro-2-methyl-7-oxo-6,7-dihydro-3H-pyrrolo[3,2-f]quinoline-1-carbaldehyde;
9-Chloro-1-methyl-2-(3-trifluoromethylphenyl)-3-(2,2,2-trifluoroethyl)-3,6-dihydro-pyrrolo [3,2-f]quinolin-7-one;
9-Chloro-1-methyl-2-(4-trifluoromethylphenyl)-3-(2,2,2-trifluoroethyl)-3,6-dihydro-pyrrolo [3,2-f]quinolin-7-one;
9-Chloro-1-methyl-2-(4-methylphenyl)-3-(2,2,2-trifluoroethyl)-3,6-dihydro-pyrrolo [3,2-f]-quinolin-7-one;
9-Chloro-1-methyl-2-(5-methyl-2-furyl)-3-(2,2,2-trifluoroethyl)-3,6-dihydro-pyrrolo [3,2-f]-quinolin-7-one;
9-Chloro-1-methyl-2-(5-methyl-2-thiophenyl)-3-(2,2,2-trifluoroethyl)-3,6-dihydro-pyrrolo[3,2-f]quinolin-7-one;
9-Chloro-1-methyl-2-(5-methylfuran-2-yl)-3-(2,2,3,3,3-pentafluoropropyl)-3,6-dihydro-pyrrolo[3,2-f]quinolin-7-one; and
9-Chloro-1-methyl-2-(5-methylthiophen-2-yl)-3-(2,2,3,3,3-pentafluoropropyl)-3,6-dihydro-pyrrolo[3,2-f]quinolin-7-one; or
a pharmaceutically acceptable salt of any of these compounds.

12. The method of claim 1, wherein the compound is selected from among:
(±)-9-Chloro-1,2-dimethyl-3-(2-hydroxyethyl)-1,2,3,6-tetrahydro-pyrrolo [3,2-f]-quinolin-7-one;
9-Chloro-3-(2-hydroxy-ethyl)-1,2-dimethyl-3,6-dihydro-pyrrolo[3,2-f]quinolin-7-one;
9-Chloro-3-(2-hydroxy-ethyl)-2-methyl-7-oxo-6,7-dihydro-3H-pyrrolo [3,2-f]-quinoline-1-carbaldehyde;
9-Chloro-1,2-dimethyl-3-(3-hydroxypropyl)-3,6-dihydro-pyrrolo[3,2-f]quinolin-7-one;
9-Chloro-3-(2,3-dihydroxypropyl)-1,2-dimethyl-3,6-dihydro-pyrrolo[3,2-f]-quinolin-7-one;
(S)-9-Chloro-3-(2,3-dihydroxypropyl)-1,2-dimethyl-3,6-dihydro-pyrrolo[3,2-f]-quinolin-7-one;
(R)-9-Chloro-3-(2,3-dihydroxypropyl)-1,2-dimethyl-3,6-dihydro-pyrrolo[3,2-f]-quinolin-7-one; and
9-Chloro-3-(2,3-dihydroxypropyl)-2-ethyl-1-methyl-3,6-dihydro-pyrrolo[3,2-f]-quinolin-7-one; or
a pharmaceutically acceptable salt of any of these compounds.

13. The method of claim 6, wherein the compound is selected from among:
9-Chloro-1-methyl-7-oxo-6,7-dihydro-3H-pyrrolo[3,2-f] quinoline-2-carboxylic acid ethyl ester;
2-Acetyl-9-chloro-1-methyl-3,6-dihydropyrrolo[3,2-f] quinolin-7-one;
(9-Chloro-2-methyl-7-oxo-6,7-dihydro-3H-pyrrolo[3,2-f] quinolin-1-yl)-acetic acid;
(±)-9-Chloro-1-methyl-2-(4-trifluoromethyl-phenyl)-3-(2,2,2-trifluoroethyl)-1, 2,3,6-tetrahydro-pyrrolo[3,2-f] quinolin-7-one;
(±)-9-Chloro-2-(3,5-bis(trifluoromethyl)phenyl)-1-methyl-3-(2,2,2-trifluoroethyl)-1, 2,3,6-tetrahydro-pyrrolo [3,2-f]quinolin-7-one;
(±)-9-Chloro-1-methyl-3-(2,2,2-trifluoroethyl)-2-(3-trifluoromethylphenyl)-1, 2,3,6-tetrahydro-pyrrolo[3,2-f] quinolin-7-one;
3-Benzyl-9-chloro-2-methyl-7-oxo-6,7-dihydro-3H-pyrrolo[3,2-f]quinoline-1-carbaldehyde;
9-Chloro-1-methyl-2-(3-trifluoromethylphenyl)-3-(2,2,2-trifluoroethyl)-3, 6-dihydro-pyrrolo[3,2-f]quinolin-7-one;
9-Chloro-1-methyl-2-(4-trifluoromethylphenyl)-3-(2,2,2-trifluoroethyl)-3, 6-dihydro-pyrrolo[3,2-f]quinolin-7-one;
9-Chloro-1-methyl-2-(4-methylphenyl)-3-(2,2,2-trifluoroethyl)-3,6-dihydro-pyrrolo[3,2-f]-quinolin-7-one;
9-Chloro-1-methyl-2-(5-methyl-2-furyl)-3-(2,2,2-trifluoroethyl)-3,6-dihydro-pyrrolo[3,2-f]-quinolin-7-one;
9-Chloro-1-methyl-2-(5-methyl-2-thiophenyl)-3-(2,2,2-trifluoroethyl)-3,6-dihydro-pyrrolo[3,2-f]quinolin-7-one;
9-Chloro-1-methyl-2-(5-methylfuran-2-yl)-3-(2,2,3,3,3-pentafluoropropyl)-3,6-dihydro-pyrrolo[3,2-f]quinolin-7-one; and
9-Chloro-1-methyl-2-(5-methylthiophen-2-yl)-3-(2,2,3,3,3-pentafluoropropyl)-3,6-dihydro-pyrrolo[3,2-f]quinolin-7-one; or
a pharmaceutically acceptable salt of any of these compounds.

14. The method of claim 6, wherein the compound is selected from among:
(±)-9-Chloro-1,2-dimethyl-3-(2-hydroxyethyl)-1,2,3,6-tetrahydro-pyrrolo[3,2-f]-quinolin-7-one;
9-Chloro-3-(2-hydroxy-ethyl)-1,2-dimethyl-3,6-dihydro-pyrrolo[3,2-f]quinolin-7-one;
9-Chloro-3-(2-hydroxy-ethyl)-2-methyl-7-oxo-6,7-dihydro-3H-pyrrolo[3,2-f]-quinoline-1-carbaldehyde;
9-Chloro-1,2-dimethyl-3-(3-hydroxypropyl)-3,6-dihydro-pyrrolo[3,2-f]quinolin-7-one;
9-Chloro-3-(2,3-dihydroxypropyl)-1,2-dimethyl-3,6-dihydro-pyrrolo[3,2-f]-quinolin-7-one;
(S)-9-Chloro-3-(2,3-dihydroxypropyl)-1,2-dimethyl-3,6-dihydro-pyrrolo[3,2-f]-quinolin-7-one;
(R)-9-Chloro-3-(2,3-dihydroxypropyl)-1,2-dimethyl-3,6-dihydro-pyrrolo[3,2-f]-quinolin-7-one; and
9-Chloro-3-(2,3-dihydroxypropyl)-2-ethyl-1 -methyl-3,6-dihydro-pyrrolo[3,2-f]-quinolin-7-one; or
a pharmaceutically acceptable salt of any of these compounds.

* * * * *